United States Patent
Babu et al.

(10) Patent No.: US 10,905,683 B2
(45) Date of Patent: Feb. 2, 2021

(54) COMPOSITIONS AND USES OF AMIDINE DERIVATIVES

(71) Applicant: BIOCRYST PHARMACEUTICALS, INC., Durham, NC (US)

(72) Inventors: Yarlagadda S Babu, Birmingham, AL (US); Vivekanand P Kamath, Helena, AL (US); Walter Gowan, Durham, NC (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 15/505,534

(22) PCT Filed: Aug. 24, 2015

(86) PCT No.: PCT/US2015/046578
§ 371 (c)(1),
(2) Date: Feb. 21, 2017

(87) PCT Pub. No.: WO2016/029214
PCT Pub. Date: Feb. 25, 2016

(65) Prior Publication Data
US 2017/0266172 A1    Sep. 21, 2017

Related U.S. Application Data

(60) Provisional application No. 62/040,836, filed on Aug. 22, 2014.

(51) Int. Cl.
| | |
|---|---|
| *A61K 31/4418* | (2006.01) |
| *A61K 9/00* | (2006.01) |
| *A61K 9/48* | (2006.01) |

(52) U.S. Cl.
CPC ........ *A61K 31/4418* (2013.01); *A61K 9/0053* (2013.01); *A61K 9/0095* (2013.01); *A61K 9/4858* (2013.01); *A61K 9/4866* (2013.01)

(58) Field of Classification Search
CPC ......... A61K 31/4418; A61K 9/48; A61K 9/00
See application file for complete search history.

(56) References Cited

FOREIGN PATENT DOCUMENTS

| | | |
|---|---|---|
| WO | 02/34711 | 5/2002 |
| WO | 2014/057068 | 4/2014 |

OTHER PUBLICATIONS

Pfitzner, Gabriele "International Search Report and Written Opinion—International Application No. PCT/US2015/046578" European Patent Office; dated Feb. 3, 2016; pp. 1-16.
Zhang, et al. "Discovery of Highly Potent Small Molecule Kallikrein Inhibitors" Medicinal Chemistry, 2006, 2, pp. 545-553.

*Primary Examiner* — Zohreh A Fay
(74) *Attorney, Agent, or Firm* — Thomas G. Peterson; Maynard Cooper & Gale

(57) ABSTRACT

Use of a compound of formula (I): wherein A, X, Y, $R_1$ and $R_2$ as defined herein, in treating hereditary angioedema is disclosed. A composition containing the compounds, a polar organic solvent or a mixture thereof; and optionally a co-solvent, is also disclosed.

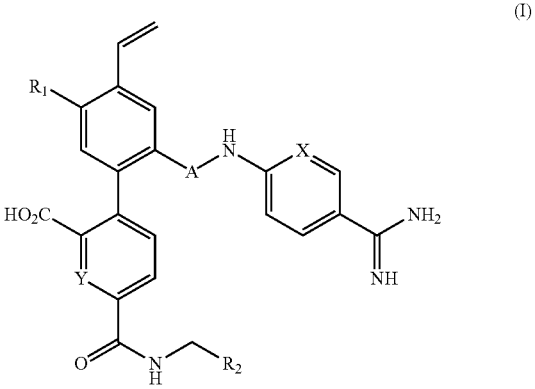

(I)

26 Claims, 11 Drawing Sheets

COMPOSITIONS AND USES OF AMIDINE DERIVATIVES

CROSS-REFERENCE TO RELATED APPLICATIONS

This application is a national stage under 35 U.S.C. 371 of International Application PCT/US2015/046578, filed on Aug. 24, 2015 (currently published). International Application no. PCT/US2015/046578 cites the priority of U.S. patent application No. 62/040,836, filed Aug. 22, 2014.

FIELD OF THE INVENTION

This invention relates to novel uses of amidine derivatives. It also relates to novel compositions containing amidine derivatives and their use in the treatment of a range of conditions.

BACKGROUND TO THE INVENTION

Hereditary angioedema (HAE) is a serious and potentially life-threatening rare genetic illness, caused by mutations in the C1-esterase inhibitor (C1INH) gene, located on chromosome 11q. HAE is inherited as an autosomal dominant condition, although one quarter of diagnosed cases arise from a new mutation. HAE has been classed as an orphan disease in Europe, with an estimated prevalence of 1 in 50,000. Individuals with HAE experience recurrent acute attacks of painful subcutaneous or submucosal edema of the face, larynx, gastrointestinal tract, limbs or genitalia which, if untreated, may last up to 5 days. Attacks vary in frequency, severity and location and can be life-threatening. Laryngeal attacks, with the potential for asphyxiation, pose the greatest risk. Abdominal attacks are especially painful, and often result in exploratory procedures or unnecessary surgery. Facial and peripheral attacks are disfiguring and debilitating.

HAE has a number of subtypes. HAE type I is defined by C1INH gene mutations which produce low levels of C1-inhibitor, whereas HAE type II is defined by mutations which produce normal levels of ineffective C1 protein. HAE type III has separate pathogenesis, being caused by mutations in the F12 gene which codes for the serine protease known as Factor XII. Diagnostic criteria for distinguishing the subtypes of HAE, and distinguishing HAE from other angioedemas, can be found in *Ann Allergy Asthma Immunol* 2008; 100(Suppl 2): S30-S40 and *J Allergy Clin Immunol* 2004; 114: 629-37, incorporated herein by reference.

Current treatments for HAE fall into two main types. Older non-specific treatments including androgens and antifibrinolytics are associated with significant side effects, particularly in females. Newer treatments are based on an understanding of the molecular pathology of the disease, namely that C1INH is the most important inhibitor of kallikrein in human plasma and that C1INH deficiency leads to unopposed activation of the kallikrein-bradykinin cascade, with bradykinin the most important mediator of the locally increased vascular permeability that is the hallmark of an attack.

Approved therapies include purified plasma-derived C1INH (Cinryze®, Berinert), the recombinant peptide kallikrein inhibitor ecallantide (Kalbitor®), and the bradykinin receptor B2 inhibitor icatibant (Firazyr®). All of the currently available targeted therapies are administered by intravenous or subcutaneous injection. There is currently no specific targeted oral chronic therapy for HAE.

There are many delivery routes for active pharmaceutical ingredients (APIs). Generally, the oral route of administration is favored. Oral administration provides a number of advantages, such as, but not limited to, patient convenience, flexibility of timing of administration, location of administration and non-invasiveness. Oral administration also provides more prolonged drug exposure compared with intermittent intravenous infusion, which may be important for drugs with schedule-dependent efficacy. For example, a drug with a short half-life can achieve a greater exposure time by either continuous infusion or by continuous oral dosing. The use of oral therapy further has the potential to reduce the cost of healthcare resources for inpatient and ambulatory patient care services.

In the pharmaceutical arts, it is known that a number of APIs cannot be administered effectively by the oral route. The main reasons why these compounds cannot be administered by the oral route are: a) rapid enzymatic and metabolic degradation; b) chemical and/or biological instability; c) low solubility in aqueous medium; and/or d) limited permeability in the gastrointestinal tract. For such compounds, non-oral routes of delivery, such as parenteral administration, mainly via intramuscular or subcutaneous injections, may be developed. However, non-oral administration poses a disadvantage for the patient as well as healthcare providers, and for this reason, it is important to develop alternative routes of administration for such compounds, such as oral routes of administration.

While the oral route of administration is the most convenient for the patient and the most economical, designing formulations for administration by the oral route involves many complications. Several methods are available to predict the ease by which an API may be formulated into a formulation suitable for administration by the oral route. Such methods include, but are not limited to, and Lipinski rule (also referred to as the Rule of Five) and the Biopharmaceutical Drug Disposition Classification System (BDDCS).

The BDDCS divides APIs into four classifications, depending on their solubility and permeability. Class I APIs have high solubility and high permeability; Class II APIs have low solubility and high permeability; Class III APIs have high solubility and low permeability; and Class IV APIs have low solubility and low permeability. APIs in higher classes in the BDDCS face greater challenges in formulating into an effective, pharmaceutically acceptable product than those in lower classes. Of the four classes, APIs falling into Class IV are the most difficult to formulate into a formulation for administration by the oral route that is capable of delivering an effective amount of the API as problems of both solubility and permeability must be addressed (note the BDDCS does not inherently address chemical stability). The role of BDDCS in drug development is described generally in L. Z. Benet *J Pharm Sci.* 2013, 102(1), 34-42.

Lipinski's rule (described in Lipinski et al. *Adv. Drug Deliv. Rev.* 46 (1-3): 3-26) states, in general, that in order to develop a successful formulation for administration by the oral route, an API can have no more than one violation of the following criteria:
  i) not more than 5 hydrogen bond donors (nitrogen or oxygen atoms with one or more hydrogen atoms)
  ii) not more than 10 hydrogen bond acceptors (nitrogen or oxygen atoms)
  iii) a molecular mass less than 500 daltons
  iv) an octanol-water partition coefficient log P not greater than 5.

J. Zhang et al. *Medicinal Chemistry*, 2006, 2, 545-553, describes a number of small molecule amidine compounds which have activity as inhibitors of kallikrein. The molecules described in this document fall into Class IV of the BDDCS as described above. The compounds are poorly soluble in aqueous and physiological fluids, and are poorly permeable as demonstrated by oral dosing in rats and in vitro experiments with Caco-2 cells. Furthermore, 3-[2-(4-carbamimidoyl-phenylcarbamoyl)-5-methoxy-4-vinyl-phenyl]-6-(cyclopropylmethyl-carbamoyl)-pyridine-2-carboxylic acid, one of the compounds described in Zhang et al., is a Class IV API and violates criteria iii) and iv) as set forth in the Lipinski Rule.

Furthermore, the compounds described in Zhang et al., including 3-[2-(4-carbamimidoyl-phenylcarbamoyl)-5-methoxy-4-vinyl-phenyl]-6-(cyclopropylmethyl-carbamoyl)-pyridine-2-carboxylic acid, exhibit poor stability with respect to oxidation in air, to light (photodegradation) and in aqueous and physiological fluids, as well as to elevated temperatures.

Therefore, the compounds described by Zhang et al. including, but not limited to, 3-[2-(4-carbamimidoyl-phenylcarbamoyl)-5-methoxy-4-vinyl-phenyl]-6-(cyclopropylmethyl-carbamoyl)-pyridine-2-carboxylic acid, not only exhibit poor solubility and permeability characteristics, but also poor stability characteristics. As a result, such compounds are predicted to be especially difficult to formulate into an effective, orally deliverable pharmaceutical composition that is capable of delivering an effective amount of the compound to a subject.

Polymorphism, the occurrence of different crystal forms, is a property of some molecules. A single molecule may give rise to a variety of polymorphs having distinct crystal structures and physical properties, such as, but not limited to, melting point, thermal behaviors (e.g. measured by thermogravimetric analysis (TGA), or differential scanning calorimetry (DSC), x-ray diffraction pattern, infrared absorption fingerprint, and solid state NMR spectrum. One or more of these techniques may be used to distinguish different polymorphic forms of a compound.

Discovering new polymorphic forms and solvates of a pharmaceutical product can provide alternate forms of the compound that display a number of desirable and advantageous properties, such as, but not limited to, ease of handling, ease of processing, ease of formulation, storage stability, and/or ease of purification. Further, new polymorphic forms and solvates of a pharmaceutically useful compound or salts thereof may further provide for improved pharmaceutical products, by providing compounds that are more soluble in a set of pharmaceutical excipients. Still further, the provision of new polymorphic forms and solvates of a pharmaceutically useful compound or salts thereof enlarges the repertoire of compounds that a formulation scientist has available for formulation optimization, for example by providing a pharmaceutical product with different properties, such as, but not limited to, improved processing characteristics, improved handling characteristics, improved solubility profiles, improved dissolution profile and/or improved shelf-life. Therefore, there is a need for additional polymorphs of pharmaceutically useful compounds, such as, but not limited to, 3-[2-(4-carbamimidoyl-phenylcarbamoyl)-5-methoxy-4-vinyl-phenyl]-6-(cyclopropylmethyl-carbamoyl)-pyridine-2-carboxylic acid and the compounds disclosed herein.

In one aspect, the present invention provides an oral formulation that is capable of delivering an effective amount of the amidine compounds described by Zhang et al. to a subject. In particular, the present invention provides an oral formulation that is capable of delivering an effective amount of 3-[2-(4-carbamimidoyl-phenylcarbamoyl)-5-methoxy-4-vinyl-phenyl]-6-(cyclopropylmethyl-carbamoyl)-pyridine-2-carboxylic acid to a subject. In one specific aspect, the 3-[2-(4-carbamimidoyl-phenylcarbamoyl)-5-methoxy-4-vinyl-phenyl]-6-(cyclopropylmethyl-carbamoyl)-pyridine-2-carboxylic acid is present in a particular crystal form designated Form A. In light of the art suggesting the difficulties in formulating such an oral formulation, this result was unexpected.

As described herein, the amidine compounds described in Zhang et al., including, but not limited to, 3-[2-(4-carbamimidoyl-phenylcarbamoyl)-5-methoxy-4-vinyl-phenyl]-6-(cyclopropylmethyl-carbamoyl)-pyridine-2-carboxylic acid (specifically including particular crystal Form A), may now be conveniently used in oral administration and further used in oral administration for the treatment of a number of diseases and conditions in a subject, such as, but not limited to, HAE, as described herein.

SUMMARY OF THE INVENTION

The present inventors have developed compositions including the small molecule compounds described in the above Shang et al. publication which overcome the problems of solubility, permeability and stability associated with the compounds, in particular, formulating these compounds for oral administration.

In addition, the present inventors have found for the first time that certain compounds described in the above publication can be used to treat HAE.

In one aspect, the invention comprises a compound of formula (I):

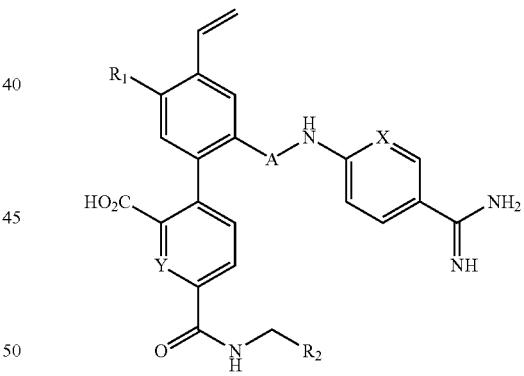

wherein:
X is CH or N;
Y is CH or N;
A is C=O or $CH_2$;
$R_1$ is hydrogen or a $C_{1-4}$ alkoxy group and $R_2$ is a $C_{1-4}$ alkyl group or a $C_{3-6}$ cycloalkyl group, optionally substituted by 1 or 2 hydroxyl groups; or a pharmaceutically acceptable salt, solvate, ester, crystalline forms or prodrug thereof; for use in treating hereditary angioedema.

In another aspect, the invention comprises compounds of formula (I'). Compounds of the formula (I') have the structure of the compounds of formula (I) as defined above, provided that when X is N, Y is CH, A is CO and $R_1$ is methoxy, $R_2$ is other than isopropyl. Therefore, in one embodiment compounds of the formula (I) are defined with the proviso that when X is N, Y is CH, A is CO and $R_1$ is methoxy, $R_2$ is other than isopropyl.

In another aspect, the invention relates to a hydrochloride salt of a compounds of the formula (I). In a particular aspect, the hydrochloride salt is 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride. In another particular aspect, the hydrochloride salt compound has a chloride content greater than 0.65 and less than or equal to 1.0 (salt to API).

In another aspect, the invention relates to specific crystalline forms of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride (the compound of formula (I) wherein X is CH, Y is N, A is CO, $R_1$ is methoxy and $R_2$ is cyclopropyl as a hydrochloride salt). Such specific crystalline forms of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride are designated as Forms A and C. Form A is also referred to as a compound of the formula (II). Such specific crystalline forms are further described herein. In one particular aspect, Form A is a variable hydrate. In another particular aspect, Form A has a chloride content greater than 0.65 and less than or equal to 1.0 (salt to API). As such, Forms A is also included within the definition of a compound of the formula (I).

In another aspect, the invention comprises use of a compound of formula (I), as defined above, or a pharmaceutically acceptable salt, solvate, ester or prodrug thereof, in the manufacture of a medicament for treating hereditary angioedema.

In another aspect, the invention comprises use of 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof, in the manufacture of a medicament for treating hereditary angioedema.

In another aspect, the invention comprises use of Form A, in the manufacture of a medicament for treating hereditary angioedema.

In another aspect, the invention comprises a method of treating hereditary angioedema in a subject in need thereof, comprising administering to said subject a compound of formula (I), as defined above, or a pharmaceutically acceptable salt, solvate, ester or prodrug thereof.

In another aspect, the invention comprises a method of treating hereditary angioedema in a subject in need thereof, comprising administering to said subject 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof.

In another aspect, the invention comprises a method of treating hereditary angioedema in a subject in need thereof, comprising administering to said subject Form A.

In another aspect, the invention comprises an oral pharmaceutical composition comprising an effective amount of a compound of formula (I), as defined herein, or a pharmaceutically acceptable salt, solvate, ester or prodrug thereof; and pharmaceutically acceptable excipients.

In another aspect, the invention comprises a liquid pharmaceutical composition comprising an effective amount of a compound of formula (I), as defined herein, or a pharmaceutically acceptable salt, solvate, ester or prodrug thereof; and pharmaceutically acceptable excipients.

In another aspect, the invention comprises a liquid oral pharmaceutical composition comprising an effective amount of a compound of formula (I), as defined herein, or a pharmaceutically acceptable salt, solvate, ester or prodrug thereof; and pharmaceutically acceptable excipients.

In another aspect, the invention comprises a solid oral dosage form comprising an effective amount of a compound of formula (I), as defined herein, or a pharmaceutically acceptable salt, solvate, ester or prodrug thereof; and pharmaceutically acceptable excipients.

In another aspect, the invention comprises a capsule, including a hard capsule or a soft capsule, comprising a pharmaceutically acceptable shell, said shell being filled with a pharmaceutical composition comprising a compound of formula (I), as defined herein, or a pharmaceutically acceptable salt, solvate, ester or prodrug thereof; and pharmaceutically acceptable excipients.

In another aspect, the invention comprises a hard gelatin capsule (as defined herein) comprising a pharmaceutically acceptable shell, said shell being filled with a pharmaceutical composition comprising a compound of formula (I), as defined herein, or a pharmaceutically acceptable salt, solvate, ester or prodrug thereof; and pharmaceutically acceptable excipients.

In another aspect, the invention comprises a soft gelatin capsule (as defined herein) comprising a pharmaceutically acceptable shell, said shell being filled with a pharmaceutical composition comprising a compound of formula (I), as defined herein, or a pharmaceutically acceptable salt, solvate, ester or prodrug thereof; and pharmaceutically acceptable excipients.

In another aspect, the invention comprises an oral pharmaceutical composition comprising 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof; and pharmaceutically acceptable excipients.

In another aspect, the invention comprises a liquid pharmaceutical composition comprising 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof; and pharmaceutically acceptable excipients.

In another aspect, the invention comprises a liquid oral pharmaceutical composition comprising 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof; and pharmaceutically acceptable excipients.

In another aspect, the invention comprises a solid oral dosage form 3-[2-(4-carbamimidoyl-phenyl carbamoyl)-5-methoxy-4-vinyl-phenyl]-6-(cyclopropylmethyl-carbamyl)-pyridine-2-carboxylic acid, or a pharmaceutically acceptable salt, solvate, ester or prodrug thereof; and pharmaceutically acceptable excipients.

In another aspect, the invention comprises a capsule, including a hard capsule or a soft capsule, comprising a pharmaceutically acceptable shell, said shell being filled with a pharmaceutical composition comprising 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof; and pharmaceutically acceptable excipients.

In another aspect, the invention comprises a hard gelatin capsule (as defined herein) comprising a pharmaceutically acceptable shell, said shell comprising gelatin and being filled with a pharmaceutical composition comprising 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof; and pharmaceutically acceptable excipients.

In another aspect, the invention comprises a soft gelatin capsule (as defined herein) comprising a pharmaceutically acceptable shell, said shell comprising gelatin and being filled with a pharmaceutical composition comprising 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof; and pharmaceutically acceptable excipients.

In another aspect, the invention comprises an oral pharmaceutical composition comprising a compound of the formula II, or a pharmaceutically acceptable salt, solvate, ester or prodrug thereof; and pharmaceutically acceptable excipients.

In another aspect, the invention comprises a liquid pharmaceutical composition comprising a compound of the formula II, or a pharmaceutically acceptable salt, solvate, ester or prodrug thereof; and pharmaceutically acceptable excipients.

In another aspect, the invention comprises a liquid oral pharmaceutical composition comprising a compound of the formula II, or a pharmaceutically acceptable salt, solvate, ester or prodrug thereof; and pharmaceutically acceptable excipients.

In another aspect, the invention comprises a solid oral dosage form a compound of the formula II, or a pharmaceutically acceptable salt, solvate, ester or prodrug thereof; and pharmaceutically acceptable excipients.

In another aspect, the invention comprises a capsule, including a hard capsule or a soft capsule, comprising a pharmaceutically acceptable shell, said shell being filled with a pharmaceutical composition comprising a compound of the formula II, or a pharmaceutically acceptable salt, solvate, ester or prodrug thereof; and pharmaceutically acceptable excipients.

In another aspect, the invention comprises a hard gelatin capsule (as defined herein) comprising a pharmaceutically acceptable shell, said shell comprising gelatin and being filled with a pharmaceutical composition comprising a compound of the formula II, or a pharmaceutically acceptable salt, solvate, ester or prodrug thereof; and pharmaceutically acceptable excipients.

In another aspect, the invention comprises a soft gelatin capsule (as defined herein) comprising a pharmaceutically acceptable shell, said shell comprising gelatin and being filled with a pharmaceutical composition comprising a compound of the formula II, or a pharmaceutically acceptable salt, solvate, ester or prodrug thereof; and pharmaceutically acceptable excipients.

In another aspect, the invention comprises an oral pharmaceutical composition comprising:
  a. a compound of formula (I), as defined herein, or a pharmaceutically acceptable salt, solvate, ester or prodrug thereof;
  b. a polar organic solvent or a mixture thereof; and optionally one or more co-solvents.

In another aspect, the invention comprises a liquid pharmaceutical composition comprising:
  a. a compound of formula (I), as defined herein, or a pharmaceutically acceptable salt, solvate, ester or prodrug thereof;
  b. a polar organic solvent or a mixture thereof; and optionally one or more co-solvents.

In another aspect, the invention comprises a liquid oral pharmaceutical composition comprising:
  a. a compound of formula (I), as defined herein, or a pharmaceutically acceptable salt, solvate, ester or prodrug thereof;
  b. a polar organic solvent or a mixture thereof; and optionally one or more co-solvents.

In another aspect, the invention comprises a solid oral dosage form comprising:
  a. a compound of formula (I), as defined herein, or a pharmaceutically acceptable salt, solvate, ester or prodrug thereof;
  b. a polar organic solvent or a mixture thereof; and optionally one or more co-solvents.

In another aspect, the invention comprises a capsule, including a hard capsule or a soft capsule, comprising a pharmaceutically acceptable shell, said shell being filled with a pharmaceutical composition comprising:
  a. a compound of formula (I), as defined herein, or a pharmaceutically acceptable salt, solvate, ester or prodrug thereof;
  b. a polar organic solvent or a mixture thereof; and optionally one or more co-solvents.

In another aspect, the invention comprises a hard gelatin capsule comprising a pharmaceutically acceptable shell, said shell comprising gelatin and being filled with a pharmaceutical composition comprising:
  a. a compound of formula (I), as defined herein, or a pharmaceutically acceptable salt, solvate, ester or prodrug thereof;
  b. a polar organic solvent or a mixture thereof; and optionally one or more co-solvents.

In another aspect, the invention comprises a soft gelatin capsule comprising a pharmaceutically acceptable shell, said shell comprising gelatin and being filled with a pharmaceutical composition comprising:
  a. a compound of formula (I), as defined herein, or a pharmaceutically acceptable salt, solvate, ester or prodrug thereof;
  b. a polar organic solvent or a mixture thereof; and optionally one or more co-solvents.

In another aspect, the invention comprises an oral pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and optionally one or more co-solvents.

In another aspect, the invention comprises a liquid pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and optionally one or more co-solvents.

In another aspect, the invention comprises a liquid oral pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and optionally one or more co-solvents.

In another aspect, the invention comprises a solid oral dosage form comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and optionally one or more co-solvents.

In another aspect, the invention comprises a capsule, including a hard capsule or a soft capsule, comprising a pharmaceutically acceptable shell, said shell being filled with a pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and optionally one or more co-solvents.

In another aspect, the invention comprises a hard gelatin capsule comprising a pharmaceutically acceptable shell, said shell comprising gelatin and being filled with a pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and optionally one or more co-solvents.

In another aspect, the invention comprises a soft gelatin capsule comprising a pharmaceutically acceptable shell, said shell comprising gelatin and being filled with a pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and optionally one or more co-solvents.

In another aspect, the invention comprises an oral pharmaceutical composition comprising:
  a. a compound of formula (I), as defined herein, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a liquid pharmaceutical composition comprising:
  a. a compound of formula (I), as defined herein, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a liquid oral pharmaceutical composition comprising:
  a. a compound of formula (I), as defined herein, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a solid oral dosage form comprising:
  a. a compound of formula (I), as defined herein, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a capsule, including a hard capsule or a soft capsule, comprising a pharmaceutically acceptable shell, said shell being filled with a pharmaceutical composition comprising:
  a. a compound of formula (I), as defined herein, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a hard gelatin capsule comprising a pharmaceutically acceptable shell, said shell comprising gelatin and being filled with a pharmaceutical composition comprising:
  a. a compound of formula (I), as defined herein, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a soft gelatin capsule comprising a pharmaceutically acceptable shell, said shell comprising gelatin and being filled with a pharmaceutical composition comprising:
  a. a compound of formula (I), as defined herein, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises an oral pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a liquid pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. a polar organic solvent or a mixture thereof; and one or more co-solvents, wherein the co-solvents function, at least in part, as a stabilizer, an absorption enhancer or a combination of the foregoing.

In another aspect, the invention comprises a liquid oral pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;

b. a polar organic solvent or a mixture thereof; and one or more co-solvents, wherein the co-solvents function, at least in part, as a stabilizer, an absorption enhancer or a combination of the foregoing.

In another aspect, the invention comprises a solid oral dosage form comprising:
   a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
   b. a polar organic solvent or a mixture thereof; and one or more co-solvents, wherein the co-solvents function, at least in part, as a stabilizer, an absorption enhancer or a combination of the foregoing.

In another aspect, the invention comprises a capsule, including a hard capsule or a soft capsule, comprising a pharmaceutically acceptable shell, said shell being filled with a pharmaceutical composition comprising:
   a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
   b. a polar organic solvent or a mixture thereof; and one or more co-solvents, wherein the co-solvents function, at least in part, as a stabilizer, an absorption enhancer or a combination of the foregoing.

In another aspect, the invention comprises a hard gelatin capsule comprising a pharmaceutically acceptable shell, said shell comprising gelatin and being filled with a pharmaceutical composition comprising:
   a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
   b. a polar organic solvent or a mixture thereof; and one or more co-solvents, wherein the co-solvents function, at least in part, as a stabilizer, an absorption enhancer or a combination of the foregoing.

In another aspect, the invention comprises a soft gelatin capsule comprising a pharmaceutically acceptable shell, said shell comprising gelatin and being filled with a pharmaceutical composition comprising:
   a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
   b. a polar organic solvent or a mixture thereof; and one or more co-solvents, wherein the co-solvents function, at least in part, as a stabilizer, an absorption enhancer or a combination of the foregoing.

In one aspect, the invention comprises an oral pharmaceutical composition, including an oral liquid pharmaceutical composition, comprising:
   a. a compound of formula (I), as defined herein, or a pharmaceutically acceptable salt, solvate, ester or prodrug thereof;
   b. 1 to 99% of at least one polar protic solvent selected from the group consisting of a $C_{3-6}$ diol, a poly($C_{2-3}$) alkylene glycol having a number average molecular weight (Mn) of 200 to 1000 and a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
   a. a compound of formula (I), as defined herein, or a pharmaceutically acceptable salt, solvate, ester or prodrug thereof;
   b. 1 to 99% of at least one polar protic solvent selected from the group consisting of a $C_{3-6}$ diol, a poly($C_{2-3}$) alkylene glycol having a number average molecular weight (Mn) of 200 to 1000 and a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 99% of at least one polar protic solvent selected from the group consisting of a $C_{3-6}$ diol, a poly($C_{2-3}$) alkylene glycol having a number average molecular weight (Mn) of 200 to 1000 and a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 99% of at least one polar protic solvent selected from the group consisting of a $C_{3-6}$ diol, a poly($C_{2-3}$) alkylene glycol having a number average molecular weight (Mn) of 200 to 1000 and a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In one aspect, the invention comprises an oral pharmaceutical composition, including an oral liquid pharmaceutical composition, comprising:
   a. a compound of formula (I), as defined herein, or a pharmaceutically acceptable salt, solvate, ester or prodrug thereof;
   b. 1 to 99% of at least one polar protic solvent selected from the group consisting of a $C_{3-6}$ diol, a poly($C_{2-3}$) alkylene glycol having a number average molecular weight (Mn) of 200 to 1000 and optionally a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
   a. a compound of formula (I), as defined herein, or a pharmaceutically acceptable salt, solvate, ester or prodrug thereof;
   b. 1 to 99% of at least one polar protic solvent selected from the group consisting of a $C_{3-6}$ diol, a poly($C_{2-3}$) alkylene glycol having a number average molecular weight (Mn) of 200 to 1000 and optionally a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 1 to 99% of at least one polar protic solvent selected from the group consisting of a $C_{3-6}$ diol, a poly($C_{2-3}$) alkylene glycol having a number average molecular weight (Mn) of 200 to 1000 and optionally a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 1 to 99% of at least one polar protic solvent selected from the group consisting of a $C_{3-6}$ diol, a poly($C_{2-3}$) alkylene glycol having a number average molecular weight (Mn) of 200 to 1000 and optionally a $C_{2-6}$ monoalcohol and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In one aspect, the invention comprises an oral pharmaceutical composition, including an oral liquid pharmaceutical composition, comprising:
- c. a compound of formula (I), as defined herein, or a pharmaceutically acceptable salt, solvate, ester or prodrug thereof;
- d. 1 to 99% of at least one polar protic solvent selected from the group consisting of a $C_{3-6}$ diol and a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
- c. a compound of formula (I), as defined herein, or a pharmaceutically acceptable salt, solvate, ester or prodrug thereof;
- d. 1 to 99% of at least one polar protic solvent selected from the group consisting of a $C_{3-6}$ diol and a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
- c. a compound of formula (I), as defined herein, or a pharmaceutically acceptable salt, solvate, ester or prodrug thereof;
- d. 1 to 99% of at least one polar protic solvent selected from the group consisting of a $C_{3-6}$ diol and a poly($C_{2-3}$) alkylene glycol having a number average molecular weight (Mn) of 200 to 1000 and and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
- c. a compound of formula (I), as defined herein, or a pharmaceutically acceptable salt, solvate, ester or prodrug thereof;
- d. 1 to 99% of at least one polar protic solvent selected from the group consisting of a $C_{3-6}$ diol and a poly($C_{2-3}$) alkylene glycol having a number average molecular weight (Mn) of 200 to 1000 and and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In one aspect, the invention comprises an oral pharmaceutical composition, including an oral liquid pharmaceutical composition, comprising:
- a. a compound of formula (I), as defined herein, or a pharmaceutically acceptable salt, solvate, ester or prodrug thereof;
- b. 1 to 99% of at least one polar protic solvent selected from the group consisting of a $C_{3-6}$ diol and a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
- e. a compound of formula (I), as defined herein, or a pharmaceutically acceptable salt, solvate, ester or prodrug thereof;
- f. 1 to 99% of at least one polar protic solvent selected from the group consisting of a $C_{3-6}$ diol and a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 1 to 99% of at least one polar protic solvent selected from the group consisting of a $C_{3-6}$ diol and a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 99% of at least one polar protic solvent selected from the group consisting of a $C_{3-6}$ diol and a poly($C_{2-3}$) alkylene glycol having a number average molecular weight (Mn) of 200 to 1000 and and at least one of a vitamin E present at 0.1% to 10% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 5-40% of a $C_{3-8}$ diol, 20-95% of a poly($C_{2-3}$) alkylene glycol having a number average molecular weight (Mn) of 200 to 1000 and at least one of a vitamin E present at 0.1% to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 5-40% of a $C_{3-8}$ diol, 20-95% of a poly($C_{2-3}$) alkylene glycol having a number average molecular weight (Mn) of 200 to 1000 and at least one of a vitamin E present at 0.1% to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 5-40% of a $C_{3-6}$ diol, 20-95% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
  a. a compound of formula (I), as defined herein, or a pharmaceutically acceptable salt, solvate, ester or prodrug thereof;
  b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10%, $C_{2-8}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 0-40% of a $C_{3-8}$ diol, 10-99% of a poly($C_{2-3}$) alkylene glycol having a number average molecular weight (Mn) of 200 to 1000 and at least one of a vitamin E present at 0.1% to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
  a. a compound of formula (I), as defined herein, or a pharmaceutically acceptable salt, solvate, ester or prodrug thereof;
  b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
- a. a compound of formula (I), as defined herein, or a pharmaceutically acceptable salt, solvate, ester or prodrug thereof;
- b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
- a. a compound of formula (I), as defined herein, or a pharmaceutically acceptable salt, solvate, ester or prodrug thereof;
- b. 0-40% of a $C_{3-6}$ diol, 10-99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 0-40% of a $C_{3-8}$ diol, 10-99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 0-40% of a $C_{3-8}$ diol, 10-99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In one aspect, the invention comprises an oral pharmaceutical composition, including an oral liquid pharmaceutical composition, comprising:
- a. a compound of formula (I), as defined herein, or a pharmaceutically acceptable salt, solvate, ester or prodrug thereof;
- b. 1 to 99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
- a. a compound of formula (I), as defined herein, or a pharmaceutically acceptable salt, solvate, ester or prodrug thereof;
- b. 1 to 99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 1 to 99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 1 to 99% of a poly($C_{2-3}$) alkylene glycol having a number average molecular weight (Mn) of 200 to 1000 and at least one of a vitamin E present at 0.1% to 10% and a vitamin E poly($C_{2-3}$)alkylene glycol dicarboxylic ester present at 0 to 50%.

In one aspect, the invention comprises an oral pharmaceutical composition, including an oral liquid pharmaceutical composition, comprising:
- a. a compound of formula (I), as defined herein, or a pharmaceutically acceptable salt, solvate, ester or prodrug thereof;
- b. 1 to 99% of a poly($C_{2-3}$) alkylene glycol having a number average molecular weight (Mn) of 200 to 1000 and a vitamin E present at 0.1% to 10% and a vitamin E poly($C_{2-3}$)alkylene glycol dicarboxylic ester present at 5 to 50%.

In another aspect, the invention comprises a capsule, including a hard capsule or a soft capsule, comprising a pharmaceutically acceptable shell, said shell containing a pharmaceutical composition comprising:
- a. a compound of formula (I), as defined herein, or a pharmaceutically acceptable salt, solvate, ester or prodrug thereof;
- b. 1 to 99% of a poly($C_{2-3}$) alkylene glycol having a number average molecular weight (Mn) of 200 to 1000 and a vitamin E present at 0.1% to 10% and a vitamin E poly($C_{2-3}$)alkylene glycol dicarboxylic ester present at 5 to 50%.

In another aspect, the invention comprises a hard gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 99% of a poly($C_{2-3}$) alkylene glycol having a number average molecular weight (Mn) of 200 to 1000 and a vitamin E present at 0.1% to 10% and a vitamin E poly($C_{2-3}$)alkylene glycol dicarboxylic ester present at 5 to 50%.

In another aspect, the invention comprises a soft gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 99% of a poly($C_{2-3}$) alkylene glycol having a number average molecular weight (Mn) of 200 to 1000 and a vitamin E present at 0.1% to 10% and a vitamin E poly($C_{2-3}$)alkylene glycol dicarboxylic ester present at 5 to 50%.

In another aspect, the invention comprises an oral pharmaceutical composition, including an oral liquid pharmaceutical composition, comprising:
   a. a compound of formula (I), as defined herein, or a pharmaceutically acceptable salt, solvate, ester or prodrug thereof;
   b. 1 to 50% of a $C_{3-8}$ diol, 1 to 90% of a poly($C_{2-3}$) alkylene glycol having a number average molecular weight (Mn) of 200 to 1000 and at least one of a vitamin E present at 0.1 to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
   a. a compound of formula (I), as defined herein, or a pharmaceutically acceptable salt, solvate, ester or prodrug thereof;
   b. 1 to 50% of a $C_{3-6}$ diol, 1 to 90% of a poly($C_{2-3}$) alkylene glycol having a number average molecular weight (Mn) of 200 to 1000 and at least one of a vitamin E present 0.1 to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 50% of a $C_{2-6}$ diol, 1 to 90% of a poly($C_{2-3}$) alkylene glycol having a number average molecular weight (Mn) of 200 to 1000 and at least one of a vitamin E present at 0.1 to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
   a. a compound of formula (I), as defined herein, or a pharmaceutically acceptable salt, solvate, ester or prodrug thereof;
   b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10%, a $C_{10-18}$ alkyl sulphate present at 0.1 to 7.5% and a vitamin E poly($C_{2-3}$) alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
   a. a compound of formula (I), as defined herein, or a pharmaceutically acceptable salt, solvate, ester or prodrug thereof;
   b. 1 to 50% of a $C_{3-8}$ diol, 1 to 90% of a poly($C_{2-3}$) alkylene glycol having a number average molecular weight (Mn) of 200 to 1000 and at least one of a vitamin E present at 0.1 to 10%, a $C_{10-18}$ alkyl sulphate present at 0.1 to 7.5% and a vitamin E poly($C_{2-3}$) alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10%, a $C_{10-18}$ alkyl sulphate present at 0.1 to 7.5% and a vitamin E poly($C_{2-3}$) alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
   a. a compound of formula (I), as defined herein, or a pharmaceutically acceptable salt, solvate, ester or prodrug thereof;
   b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10%, a $C_{10-18}$ alkyl sulphate present at 0.1 to 7.5% and a vitamin E poly($C_{2-3}$) alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol, 1 to 90% of a poly($C_{2-3}$) alkylene glycol having a number average molecular weight (Mn) of 200 to 1000 and at least one of a vitamin E present at 0.1 to 10% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 50 to 90% of a poly($C_{2-3}$) alkylene glycol having a number average molecular weight (Mn) of 200 to 1000 and at least one of a vitamin E present at 0.1 to 10% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 50 to 90% of a poly($C_{2-3}$) alkylene glycol having a number average molecular weight (Mn) of 200 to 1000 and at least one of a vitamin E present at 0.1 to 10% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of a poly($C_{2-3}$) alkylene glycol having a number average molecular weight (Mn) of 200 to 1000 and at least one of a vitamin E present at 0.1 to 10% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of polyethylene glycol having a number average molecular weight (Mn) of 200 to 1000, and at least one of a vitamin E present at 0.1 to 10% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 50 to 90% of a poly($C_{2-3}$) alkylene glycol having a number average molecular weight (Mn) of 200 to 1000, a vitamin E present at 0.1% to 10% and a vitamin E poly($C_{2-3}$)alkylene glycol dicarboxylic ester present at 1 to 40%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 50 to 90% of a poly($C_{2-3}$) alkylene glycol having a number average molecular weight (Mn) of 200 to 1000, a vitamin E present at 0.1% to 10% and a vitamin E poly($C_{2-3}$)alkylene glycol dicarboxylic ester present at 1 to 40%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of a poly($C_{2-3}$) alkylene glycol having a number average molecular weight (Mn) of 200 to 1000, a vitamin E present at 0.1% to 10% and a vitamin E poly($C_{2-3}$)alkylene glycol dicarboxylic ester present at 1 to 40%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of a poly($C_{2-3}$) alkylene glycol having a number average molecular weight (Mn) of 200 to 1000, a vitamin E present at 0.1% to 10% and a vitamin E poly($C_{2-3}$)alkylene glycol dicarboxylic ester present at 1 to 40%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000 and at least one of vitamin E present at 0.1 to 10%, a $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 1 to 50% of a $C_{3-8}$ diol and 1 to 90% of polyethylene glycol having a number average molecular weight (Mn) of 200 to 1000, and at least one of a vitamin E present at 0.1 to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10%, $C_{2-6}$ monoalcohol present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000 and at least one of vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000 and at least one of vitamin E present at 0.1 to 10% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:

a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of a $C_{3-6}$ diol and 1 to 90% of polyethylene glycol having a number average molecular weight (Mn) of 200 to 1000, and at least one of a vitamin E present at 0.1 to 10% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 50 to 90% of polyethylene glycol having a number average molecular weight (Mn) of 200 to 1000, and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 50 to 90% of polyethylene glycol having a number average molecular weight (Mn) of 200 to 1000, and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of polyethylene glycol having a number average molecular weight (Mn) of 200 to 1000, and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of polyethylene glycol having a number average molecular weight (Mn) of 200 to 1000, and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 50 to 90% of a of polyethylene glycol having a number average molecular weight (Mn) of 200 to 1000, a vitamin E present at 0.1 to 10% and a vitamin E poly($C_{2-3}$)alkylene glycol dicarboxylic ester present at 1 to 40%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 50 to 90% of a of polyethylene glycol having a number average molecular weight (Mn) of 200 to 1000, a vitamin E present at 0.1 to 10% and a vitamin E poly($C_{2-3}$)alkylene glycol dicarboxylic ester present at 1 to 40%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of a of polyethylene glycol having a number average molecular weight (Mn) of 200 to 1000, a vitamin E present at 0.1 to 10% and a vitamin E poly($C_{2-3}$)alkylene glycol dicarboxylic ester present at 1 to 40%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 50 to 90% of a of polyethylene glycol having a number average molecular weight (Mn) of 200 to 1000, a vitamin E present at 00.1 to 10% and a vitamin E poly($C_{2-3}$)alkylene glycol dicarboxylic ester present at 1 to 40%.

In another aspect, the invention comprises an oral pharmaceutical composition, including an oral liquid pharmaceutical composition, comprising:

a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000, 0 to 10% of a $C_{2-6}$ monoalcohol and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000, 0 to 10% of a $C_{2-6}$ monoalcohol and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000, 0 to 10% of a $C_{2-6}$ monoalcohol and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000, 0 to 10% of a $C_{2-6}$ monoalcohol, and at least one of a 0.1 to 10% of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000 and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000 and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000 and at least one of a vitamin E present 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000 and at least one of a vitamin E present at 0.1 to 10%, a $C_{10-18}$ alkyl sulphate present at 0.1 to 7.5% and a vitamin E poly($C_{2-3}$)alkylene glycol dicarboxylic ester present at 0 to 50%.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000 and at least one of a vitamin E present at 0.1 to 10%, and a vitamin E poly($C_{2-3}$)alkylene glycol dicarboxylic ester present at 0 to 50%.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 1 to 50% of 1,2-propanediol, 1 to 90% of polyethylene glycol having a number average molecular weight (Mn) of 200 to 1000 and at least one of a vitamin E present at 0.1 to 10%, and a vitamin E poly($C_{2-3}$)alkylene glycol dicarboxylic ester present at 0 to 50%.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;

b. 1 to 50% of 1,2-propanediol, 1 to 90% of polyethylene glycol having a number average molecular weight (Mn) of 200 to 1000 and at least one of a vitamin E present at 0.1 to 10%, and a vitamin E poly($C_{2-3}$)alkylene glycol dicarboxylic ester present at 0 to 50%.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 1 to 50% of 1,2-propanediol, 1 to 90% of polyethylene glycol having a number average molecular weight (Mn) of 200 to 1000 and at least one of a vitamin E present at 0.1 to 10%, and a vitamin E poly($C_{2-3}$)alkylene glycol dicarboxylic ester present at 0 to 50%

In another aspect, the invention comprises an oral pharmaceutical composition, including an oral liquid pharmaceutical composition, comprising:
  a. a compound of formula (I), as defined herein, or a pharmaceutically acceptable salt, solvate, ester or prodrug thereof;
  b. 30-80% of a polar protic solvent comprising a $C_{3-8}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10%, a $C_{2-6}$ monoalcohol present at 0 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10%, a $C_{2-6}$ monoalcohol present at 0 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10%, a $C_{2-6}$ monoalcohol present at 0 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-8}$ diol may be present at up to one-half the percentage of the polar protic solvent (for example up to a maximum of 40%) and at least one of a vitamin E present at 0.1% to 10%, a $C_{2-6}$ monoalcohol present at 0 to 10%, a $C_{10-18}$ alkyl sulphate present at 0.1 to 7.5% and a vitamin E poly($C_{2-3}$)alkylene glycol dicarboxylic ester present at 1 to 50%.

In another aspect, the invention comprises an oral pharmaceutical composition, including an oral liquid pharmaceutical composition, comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-8}$ diol may be present at up to one-half the percentage of the polar protic solvent (for example up to a maximum of 40%) and at least one of a vitamin E present at 0.1% to 10%, a $C_{10-18}$ alkyl sulphate present at 0.1 to 7.5% and a vitamin E poly($C_{2-3}$) alkylene glycol dicarboxylic ester present at 1 to 50%.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10%, a $C_{10-18}$ alkyl sulphate present at 0.1 to 7.5% and a vitamin E poly($C_{2-3}$) alkylene glycol dicarboxylic ester present at 1 to 50%.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10%, a $C_{10-18}$ alkyl sulphate present at 0.1 to 7.5% and a vitamin E poly($C_{2-3}$) alkylene glycol dicarboxylic ester present at 1 to 50%.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-8}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10%, a $C_{10-18}$ alkyl sulphate present at 0.1 to 7.5% and a vitamin E poly($C_{2-3}$) alkylene glycol dicarboxylic ester present at 1 to 50%.

In another aspect, the invention comprises an oral pharmaceutical composition, including an oral liquid pharmaceutical composition, comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10% and a vitamin E poly($C_{2-3}$) alkylene glycol dicarboxylic ester present at 1 to 50%.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10% and a vitamin E poly($C_{2-3}$) alkylene glycol dicarboxylic ester present at 1 to 50%.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10%, and a vitamin E poly($C_{2-3}$) alkylene glycol dicarboxylic ester present at 1 to 50%.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 30-80% of a polar protic solvent comprising a $C_{3-6}$ diol and a poly($C_{2-3}$) alkylene glycol having a number average molecular weight (Mn) of 200 to 1000, wherein the $C_{3-6}$ diol may be present at up to one-half the percentage of the polar protic solvent (for example up to a maximum of 40%) and at least one of a vitamin E present at 0.1% to 10% and a vitamin E poly($C_{2-3}$) alkylene glycol dicarboxylic ester present at 1 to 50%.

In another aspect, the invention comprises an oral pharmaceutical composition, including an oral liquid pharmaceutical composition, comprising:
  a. a compound of formula (I), as defined herein, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises an oral pharmaceutical composition, including an oral liquid pharmaceutical composition, comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, as defined herein, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, as defined herein, or a pharmaceutically acceptable salt, solvate, ester or prodrug thereof;
  b. 20% of 1,2-propanediol, 52.5% of polyethylene glycol having a number average molecular weight (Mn) of 400 or 600, 5% of ethanol, 2.5% of sodium dodecyl sulphate and 20% of D-α-tocopherol polyethylene glycol 1000 succinate.

In another aspect, the invention comprises an oral pharmaceutical composition, including an oral liquid pharmaceutical composition, comprising:
  a. a compound of formula (I), as defined herein, or a pharmaceutically acceptable salt, solvate, ester or prodrug thereof;
  b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
  a. a compound of formula (I), as defined herein, or a pharmaceutically acceptable salt, solvate, ester or prodrug thereof;
  b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
  a. a compound of formula (I), as defined herein, or a pharmaceutically acceptable salt, solvate, ester or prodrug thereof;
  b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises an oral pharmaceutical composition, including an oral liquid pharmaceutical composition, comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
  a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
  b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
a. 3-[2-(4-carbamimidoyl-phenylcarbamoyl)-5-methoxy-4-vinyl-phenyl]-6-(cyclopropylmethyl-carbamoyl)-pyridine-2-carboxylic acid, as defined herein, or a pharmaceutically acceptable salt, solvate, ester or prodrug thereof;
b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
a. 3-[2-(4-carbamimidoyl-phenylcarbamoyl)-5-methoxy-4-vinyl-phenyl]-6-(cyclopropylmethyl-carbamoyl)-pyridine-2-carboxylic acid, as defined herein, or a pharmaceutically acceptable salt, solvate, ester or prodrug thereof;
b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises an oral pharmaceutical composition, including an oral liquid pharmaceutical composition, comprising:
a. Form A, as defined herein;
b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
a. Form A, as defined herein;
b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
a. Form A, as defined herein;
b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
a. Form A, as defined herein;
b. 65 to 80% of a polar protic solvent comprising a 1,2-propanediol and a polyethylene glycol having a number average molecular weight (Mn) of 400 or 600, wherein the 1,2-propanediol may be present at up to one-half the percentage of the polar protic solvent (for example up to a maximum of 40%), 0 to 7.5% of sodium dodecyl sulphate, 0.1 to 10% D-α-tocopherol and 20 to 30% of D-α-tocopherol polyethylene glycol 1000 succinate.

In another aspect, the invention comprises an oral pharmaceutical composition, including an oral liquid pharmaceutical composition, comprising:
a. a compound of formula (I), as defined herein, or a pharmaceutically acceptable salt, solvate, ester or prodrug thereof;
b. 70 to 75% of polyethylene glycol having a number average molecular weight (Mn) of 200 to 1000, 0 to 10% of a $C_{2-6}$ monoalcohol, 0 to 5% of a $C_{10-18}$ alkyl sulphate, 0.1 to 5% of a vitamin E, citric acid or a combination thereof and 24 to 28% of a vitamin E poly($C_{2-3}$)alkylene glycol dicarboxylic ester.

In another aspect, the invention comprises a capsule, including a hard capsule or a soft capsule, comprising a pharmaceutically acceptable shell, said shell containing a pharmaceutical composition comprising:
a. a compound of formula (I), as defined herein, or a pharmaceutically acceptable salt, solvate, ester or prodrug thereof;
b. 70 to 75% of polyethylene glycol having a number average molecular weight (Mn) of 200 to 1000, 0 to 10% of a $C_{2-6}$ monoalcohol, 0 to 5% of a $C_{10-18}$ alkyl sulphate, 0.1 to 5% of a vitamin E, citric acid or a combination thereof and 24 to 28% of a vitamin E poly($C_{2-3}$)alkylene glycol dicarboxylic ester.

In another aspect, the invention comprises a hard gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 70 to 75% of polyethylene glycol having a number average molecular weight (Mn) of 200 to 1000, 0 to 10% of a $C_{2-6}$ monoalcohol, 0 to 5% of a $C_{10-18}$ alkyl sulphate, 0.1 to 5% of a vitamin E, citric acid or a combination thereof and 24 to 28% of a vitamin E poly($C_{2-3}$)alkylene glycol dicarboxylic ester.

In another aspect, the invention comprises a soft gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 200 to 1000, 0 to 10% of a $C_{2-6}$ monoalcohol, 0 to 5% of a $C_{10-18}$ alkyl sulphate, 0.1 to 5% of a vitamin E, citric acid or a combination thereof and 24 to 28% of a vitamin E poly($C_{2-3}$)alkylene glycol dicarboxylic ester.

In another aspect, the invention comprises an oral pharmaceutical composition, including an oral liquid pharmaceutical composition, comprising:
- c. a compound of formula (I), as defined herein, or a pharmaceutically acceptable salt, solvate, ester or prodrug thereof;
- a. 70 to 75% of polyethylene glycol having a number average molecular weight (Mn) of 200 to 1000, 0.1 to 5% of a vitamin E, citric acid or a combination thereof and 24 to 28% of a vitamin E poly($C_{2-3}$)alkylene glycol dicarboxylic ester.

In another aspect, the invention comprises a capsule, including a hard capsule or a soft capsule, comprising a pharmaceutically acceptable shell, said shell containing a pharmaceutical composition comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 200 to 1000, 0.1 to 5% of a vitamin E, citric acid or a combination thereof and 24 to 28% of a vitamin E poly($C_{2-3}$)alkylene glycol dicarboxylic ester.

In another aspect, the invention comprises a hard gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 200 to 1000, 0.1 to 5% of a vitamin E, citric acid or a combination thereof and 24 to 28% of a vitamin E poly($C_{2-3}$)alkylene glycol dicarboxylic ester.

In another aspect, the invention comprises a soft gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 200 to 1000, 0.1 to 5% of a vitamin E, citric acid or a combination thereof and 24 to 28% of a vitamin E poly($C_{2-3}$)alkylene glycol dicarboxylic ester.

In another aspect, the invention comprises an oral pharmaceutical composition, including an oral liquid pharmaceutical composition, comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 400 to 600, 0.1 to 5% of a D-α-tocopherol, citric acid or a combination thereof, and 24 to 28% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 400 to 600, 0.1 to 5% of a D-α-tocopherol, citric acid or a combination thereof, and 24 to 28% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 400 to 600, 0.1 to 5% of a D-α-tocopherol, citric acid or a combination thereof, and 24 to 28% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
- a. a compound of formula (I), as defined herein, or a pharmaceutically acceptable salt, solvate, ester or prodrug thereof;
- b. 70 to 75% of polyethylene glycol having a number average molecular weight (Mn) of 400 to 600, 0.1 to 5% of a D-α-tocopherol, citric acid or a combination thereof, and 24 to 28% of D-α-tocopherol polyethylene glycol 1000 succinate.

In another aspect, the invention comprises an oral pharmaceutical composition, including an oral liquid pharmaceutical composition, comprising:
- a. a compound of formula (I), as defined herein, or a pharmaceutically acceptable salt, solvate, ester or prodrug thereof;
- b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
- a. a compound of formula (I), as defined herein, or a pharmaceutically acceptable salt, solvate, ester or prodrug thereof;
- b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:

a. a compound of formula (I), as defined herein, or a pharmaceutically acceptable salt, solvate, ester or prodrug thereof;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
a. a compound of formula (I), as defined herein, or a pharmaceutically acceptable salt, solvate, ester or prodrug thereof;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises an oral pharmaceutical composition, including an oral liquid pharmaceutical composition, comprising:
a. 3-[2-(4-carbamimidoyl-phenylcarbamoyl)-5-methoxy-4-vinyl-phenyl]-6-36(cyclopropylmethyl-carbamoyl)-pyridine-2-carboxylic acid, or a pharmaceutically acceptable salt, solvate, ester or prodrug thereof;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
a. 3-[2-(4-carbamimidoyl-phenylcarbamoyl)-5-methoxy-4-vinyl-phenyl]-6-(cyclopropylmethyl-carbamoyl)-pyridine-2-carboxylic acid, or a pharmaceutically acceptable salt, solvate, ester or prodrug thereof;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
a. 3-[2-(4-carbamimidoyl-phenylcarbamoyl)-5-methoxy-4-vinyl-phenyl]-6-(cyclopropylmethyl-carbamoyl)-pyridine-2-carboxylic acid, as defined herein, or a pharmaceutically acceptable salt, solvate, ester or prodrug thereof;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
a. 3-[2-(4-carbamimidoyl-phenylcarbamoyl)-5-methoxy-4-vinyl-phenyl]-6-(cyclopropylmethyl-carbamoyl)-pyridine-2-carboxylic acid, as defined herein, or a pharmaceutically acceptable salt, solvate, ester or prodrug thereof;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises an oral pharmaceutical composition, including an oral liquid pharmaceutical composition, comprising:
a. Form A, as defined herein;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a capsule, including a hard capsule or a soft capsule, comprising a pharmaceutically acceptable shell, said shell containing a pharmaceutical composition comprising:
a. Form A, as defined herein;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a hard gelatin capsule comprising a pharmaceutically acceptable shell, said shell comprising gelatin and containing a pharmaceutical composition comprising:
a. Form A, as defined herein;
b. 72.7% of polyethylene glycol having a number average molecular weight (Mn) of 400 or 600, 0.7% D-α-tocopherol and 26.6% of D-α-tocopherol polyethylene glycol 1000 succinate.

In another aspect, the invention comprises a soft gelatin capsule comprising a pharmaceutically acceptable shell, said shell comprising gelatin and containing a pharmaceutical composition comprising:
a. Form A, as defined herein;
b. 72.7% of polyethylene glycol having a number average molecular weight (Mn) of 400 or 600, 0.7% D-α-tocopherol and 26.6% of D-α-tocopherol polyethylene glycol 1000 succinate.

In the foregoing aspects, the percentages of various compounds are expressed as a percentage of the total weight of the mixture of excipients (i.e. excluding the active ingredient). Furthermore, when the term "number average molecular weight" appears in the specification, for the purposes of the present invention it is to be understood that the number average molecular weight was measured by osmometry, unless otherwise stated.

In any of the foregoing aspects, a compound of formula (I) includes a compound of formula (I') unless explicitly stated otherwise and/or a compound of formula (II) (Form A). In any of the foregoing aspects, a compound of the formula (I), specifically includes 3-[2-(4-carbamimidoyl-phenylcarbamoyl)-5-methoxy-4-vinyl-phenyl]-6-(cyclopropylmethyl-carbamoyl)-pyridine-2-carboxylic acid and its hydrochloride salt.

In any of the foregoing aspects, for the general ranges specified for the combinations above, the following subranges are applicable.

When the polar protic solvent is a combination of a $C_{3-6}$ diol, such as 1,2-propanediol, and a poly($C_{2-3}$) alkylene glycol having a number average molecular weight (Mn) of 200 to 1000 (or any subrange therein), such as polyethylene glycol having a number average molecular weight (Mn) of 200 to 1000 (or any subrange therein) at 1 to 99%:
  i) the vitamin E may be present at 0 to 10%, the $C_{2-6}$ monoalcohol may be present at 0 to 7.5%, the a $C_{10-18}$ alkyl sulphate may be present at 0 to 5%, and the vitamin E poly($C_{2-3}$)alkylene glycol dicarboxylic ester may be present at 0 to 5% or 5 to 30%;
  ii) the vitamin E may be present at 0.1% to 10%, the $C_{2-6}$ monoalcohol may be present at 0.1% to 7.5%, the a $C_{10-18}$ alkyl sulphate may be present at 0.1% to 5%, and the vitamin E poly($C_{2-3}$)alkylene glycol dicarboxylic ester may be present at 0 to 5% or 5 to 30%;

iii) the vitamin E may be present at 0 to 2%, the $C_{2-6}$ monoalcohol may be present at 0.1 to 6.0%, the a $C_{10-01}$ alkyl sulphate may be present at 0.1 to 3%, and the vitamin E poly($C_{2-3}$)alkylene glycol dicarboxylic ester may be present at 0 to 5% or 5 to 30%;

iv) the vitamin E may be present at 0.1 to 1%, the $C_{2-6}$ monoalcohol may be present at 2.0 to 6.0%, the a $C_{10-18}$ alkyl sulphate may be present at 1.0 to 4.0%, and the vitamin E poly($C_{2-3}$)alkylene glycol dicarboxylic ester may be present at 0 to 5% or 5 to 30%;

v) the vitamin E may be present at 0.1 to 2%, the $C_{2-6}$ monoalcohol may be present at 0.1 to 5%, the a $C_{10-18}$ alkyl sulphate may be present at 0.1 to 3%, and the vitamin E poly($C_{2-3}$)alkylene glycol dicarboxylic ester may be present at 5 to 30% or 20 to 40%;

vi) the vitamin E may be present at 0.1 to 2%, the $C_{2-6}$ monoalcohol is absent, the a $C_{10-18}$ alkyl sulphate may be present at 0.1 to 3%, and the vitamin E poly($C_{2-3}$) alkylene glycol dicarboxylic ester may be present at 5 to 30% or 20 to 40%; and vii) the vitamin E may be present at 0.1 to 2%, the $C_{2-6}$ monoalcohol is absent, the a $C_{10-18}$ alkyl sulphate is absent, and the vitamin E poly($C_{2-3}$)alkylene glycol dicarboxylic ester may be present at 5 to 30% or 20 to 40%.

When the polar protic solvent is a combination of a $C_{3-6}$ diol, such as 1,2-propanediol, at 5-40% and a poly($C_{2-3}$) alkylene glycol having a number average molecular weight (Mn) of 200 to 1000 (or any subrange therein), such as polyethylene glycol having a number average molecular weight (Mn) of 200 to 1000 (or any subrange therein) at 20 to 95%:

i) the vitamin E may be present at 0 to 10%, the $C_{2-6}$ monoalcohol may be present at 0 to 7.5%, the a $C_{10-18}$ alkyl sulphate may be present at 0 to 5%, and the vitamin E poly($C_{2-3}$)alkylene glycol dicarboxylic ester may be present at 0 to 5% or 5 to 30%;

ii) the vitamin E may be present at 0.1% to 10%, the $C_{2-6}$ monoalcohol may be present at 0.1% to 7.5%, the a $C_{10-18}$ alkyl sulphate may be present at 0.1% to 5%, and the vitamin E poly($C_{2-3}$)alkylene glycol dicarboxylic ester may be present at 0 to 5% or 5 to 30%;

iii) the vitamin E may be present at 0 to 2%, the $C_{2-6}$ monoalcohol may be present at 0.1 to 6.0%, the a $C_{10-18}$ alkyl sulphate may be present at 0.1 to 3%, and the vitamin E poly($C_{2-3}$)alkylene glycol dicarboxylic ester may be present at 0 to 5% or 5 to 30%;

iv) the vitamin E may be present at 0.1 to 1%, the $C_{2-6}$ monoalcohol may be present at 2.0 to 6.0%, the a $C_{10-18}$ alkyl sulphate may be present at 1.0 to 4.0%, and the vitamin E poly($C_{2-3}$)alkylene glycol dicarboxylic ester may be present at 0 to 5% or 5 to 30%;

v) the vitamin E may be present at 0.1 to 2%, the $C_{2-6}$ monoalcohol may be present at 0.1 to 5%, the a $C_{10-18}$ alkyl sulphate may be present at 0.1 to 3%, and the vitamin E poly($C_{2-3}$)alkylene glycol dicarboxylic ester may be present at 5 to 30% or 20 to 40%;

vi) the vitamin E may be present at 0.1 to 2%, the $C_{2-6}$ monoalcohol is absent, the a $C_{10-18}$ alkyl sulphate may be present at 0.1 to 3%, and the vitamin E poly($C_{2-3}$) alkylene glycol dicarboxylic ester may be present at 5 to 30% or 20 to 40%; and vii) the vitamin E may be present at 0.1 to 2%, the $C_{2-6}$ monoalcohol is absent, the a $C_{10-18}$ alkyl sulphate is absent, and the vitamin E poly($C_{2-3}$)alkylene glycol dicarboxylic ester may be present at 5 to 30% or 20 to 40%.

When the polar protic solvent is a combination of a $C_{3-6}$ diol, such as 1,2-propanediol, at 0 to 10% or 0 to 40% and a poly($C_{2-3}$) alkylene glycol having a number average molecular weight (Mn) of 200 to 1000 (or any subrange therein), such as polyethylene glycol having a number average molecular weight (Mn) of 200 to 1000 (or any subrange therein) at 1 to 99% (for example 10 to 99%):

i) the vitamin E may be present at 0 to 10%, the $C_{2-6}$ monoalcohol may be present at 0 to 7.5%, the a $C_{10-18}$ alkyl sulphate may be present at 0 to 5%, and the vitamin E poly($C_{2-3}$)alkylene glycol dicarboxylic ester may be present at 0 to 5% or 5 to 30%;

ii) the vitamin E may be present at 0.1% to 10%, the $C_{2-6}$ monoalcohol may be present at 0.1% to 7.5%, the a $C_{10-18}$ alkyl sulphate may be present at 0.1% to 5%, and the vitamin E poly($C_{2-3}$)alkylene glycol dicarboxylic ester may be present at 0 to 5% or 5 to 30%;

iii) the vitamin E may be present at 0 to 2%, the $C_{2-6}$ monoalcohol may be present at 0.1 to 6.0%, the a $C_{10-18}$ alkyl sulphate may be present at 0.1 to 3%, and the vitamin E poly($C_{2-3}$)alkylene glycol dicarboxylic ester may be present at 0 to 5% or 5 to 30%;

iv) the vitamin E may be present at 0.1 to 1%, the $C_{2-6}$ monoalcohol may be present at 2.0 to 6.0%, the a $C_{10-18}$ alkyl sulphate may be present at 1.0 to 4.0%, and the vitamin E poly($C_{2-3}$)alkylene glycol dicarboxylic ester may be present at 0 to 5% or 5 to 30%;

v) the vitamin E may be present at 0.1 to 2%, the $C_{2-6}$ monoalcohol may be present at 0.1 to 5%, the a $C_{10-18}$ alkyl sulphate may be present at 0.1 to 3%, and the vitamin E poly($C_{2-3}$)alkylene glycol dicarboxylic ester may be present at 5 to 30% or 20 to 40%;

vi) the vitamin E may be present at 0.1 to 2%, the $C_{2-6}$ monoalcohol is absent, the a $C_{10-18}$ alkyl sulphate may be present at 0.1 to 3%, and the vitamin E poly($C_{2-3}$) alkylene glycol dicarboxylic ester may be present at 5 to 30% or 20 to 40%; and vii) the vitamin E may be present at 0.1 to 2%, the $C_{2-6}$ monoalcohol is absent, the a $C_{10-18}$ alkyl sulphate is absent, and the vitamin E poly($C_{2-3}$)alkylene glycol dicarboxylic ester may be present at 5 to 30% or 20 to 40%.

When the polar protic solvent is a combination of a $C_{3-6}$ diol, such as 1,2-propanediol, at 1 to 50% and a poly($C_{2-3}$) alkylene glycol having a number average molecular weight (Mn) of 200 to 1000 (or any subrange therein), such as polyethylene glycol having a number average molecular weight (Mn) of 200 to 1000 (or any subrange therein) at 1 to 90%:

i) the vitamin E may be present at 0 to 10%, the $C_{2-6}$ monoalcohol may be present at 0 to 7.5%, the a $C_{10-18}$ alkyl sulphate may be present at 0 to 5%, and the vitamin E poly($C_{2-3}$)alkylene glycol dicarboxylic ester may be present at 0 to 5% or 5 to 30%;

ii) the vitamin E may be present at 0.1% to 10%, the $C_{2-6}$ monoalcohol may be present at 0.1% to 7.5%, the a $C_{10-18}$ alkyl sulphate may be present at 0.1% to 5%, and the vitamin E poly($C_{2-3}$)alkylene glycol dicarboxylic ester may be present at 0 to 5% or 5 to 30%;

iii) the vitamin E may be present at 0 to 2%, the $C_{2-6}$ monoalcohol may be present at 0.1 to 6.0%, the a $C_{10-18}$ alkyl sulphate may be present at 0.1 to 3%, and the vitamin E poly($C_{2-3}$)alkylene glycol dicarboxylic ester may be present at 0 to 5% or 5 to 30%;

iv) the vitamin E may be present at 0.1 to 1%, the $C_{2-6}$ monoalcohol may be present at 2.0 to 6.0%, the a $C_{10-18}$ alkyl sulphate may be present at 1.0 to 4.0%, and the vitamin E poly($C_{2-3}$)alkylene glycol dicarboxylic ester may be present at 0 to 5% or or 5 to 30%;

v) the vitamin E may be present at 0.1 to 2%, the $C_{2-6}$ monoalcohol may be present at 0.1 to 5%, the a $C_{10-18}$ alkyl sulphate may be present at 0.1 to 3%, and the vitamin E poly($C_{2-3}$)alkylene glycol dicarboxylic ester may be present at 5 to 30% or 20 to 40%;

vi) the vitamin E may be present at 0.1 to 2%, the $C_{2-6}$ monoalcohol is absent, the a $C_{10-18}$ alkyl sulphate may be present at 0.1 to 3%, and the vitamin E poly($C_{2-3}$) alkylene glycol dicarboxylic ester may be present at 5 to 30% or 20 to 40%; and vii) the vitamin E may be present at 0.1 to 2%, the $C_{2-6}$ monoalcohol is absent, the a $C_{10-18}$ alkyl sulphate is absent, and the vitamin E poly($C_{2-3}$)alkylene glycol dicarboxylic ester may be present at 5 to 30% or 20 to 40%.

When the polar protic solvent is a combination of a $C_{3-6}$ diol, such as 1,2-propanediol, and a poly($C_{2-3}$) alkylene glycol having a number average molecular weight (Mn) of 200 to 1000 (or any subrange therein), such as polyethylene glycol having a number average molecular weight (Mn) of 200 to 1000 (or any subrange therein) at 30 to 80%, the $C_{3-6}$ diol being present at up to one-half the percentage of the polar protic solvent (for example up to a maximum of 40%):

i) the vitamin E may be present at 0 to 10%, the $C_{2-6}$ monoalcohol may be present at 0 to 7.5%, the a $C_{10-18}$ alkyl sulphate may be present at 0 to 5%, and the vitamin E poly($C_{2-3}$)alkylene glycol dicarboxylic ester may be present at 0 to 5% or 5 to 30%;

ii) the vitamin E may be present at 0.1% to 10%, the $C_{2-6}$ monoalcohol may be present at 0.1% to 7.5%, the a $C_{10-18}$ alkyl sulphate may be present at 0.1% to 5%, and the vitamin E poly($C_{2-3}$)alkylene glycol dicarboxylic ester may be present at 0 to 5% or 5 to 30%;

iii) the vitamin E may be present at 0 to 2%, the $C_{2-6}$ monoalcohol may be present at 0.1 to 6.0%, the a $C_{10-18}$ alkyl sulphate may be present at 0.1 to 3%, and the vitamin E poly($C_{2-3}$)alkylene glycol dicarboxylic ester may be present at 0 to 5% or 5 to 30%;

iv) the vitamin E may be present at 0.1 to 1%, the $C_{2-8}$ monoalcohol may be present at 2.0 to 6.0%, the a $C_{10-18}$ alkyl sulphate may be present at 1.0 to 4.0%, and the vitamin E poly($C_{2-3}$)alkylene glycol dicarboxylic ester may be present at 0 to 5% or or 5 to 30%;

v) the vitamin E may be present at 0.1 to 2%, the $C_{2-6}$ monoalcohol may be present at 0.1 to 5%, the a $C_{10-18}$ alkyl sulphate may be present at 0.1 to 3%, and the vitamin E poly($C_{2-3}$)alkylene glycol dicarboxylic ester may be present at 5 to 30% or 20 to 40%;

vi) the vitamin E may be present at 0.1 to 2%, the $C_{2-6}$ monoalcohol is absent, the a $C_{10-18}$ alkyl sulphate may be present at 0.1 to 3%, and the vitamin E poly($C_{2-3}$) alkylene glycol dicarboxylic ester may be present at 5 to 30% or 20 to 40%; and vii) the vitamin E may be present at 0.1 to 2%, the $C_{2-6}$ monoalcohol is absent, the a $C_{10-18}$ alkyl sulphate is absent, and the vitamin E poly($C_{2-3}$)alkylene glycol dicarboxylic ester may be present at 5 to 30% or 20 to 40%.

When the polar protic solvent is a poly($C_{2-3}$) alkylene glycol having a number average molecular weight (Mn) of 200 to 1000 (or any subrange therein), such as polyethylene glycol having a number average molecular weight (Mn) of 200 to 1000 (or any subrange therein) at 1 to 99% (such as 1 to 99% or 50 to 90%):

i) the vitamin E may be present at 0.1 to 2%, the $C_{2-6}$ monoalcohol may be present at 0.1 to 5%, the a $C_{10-18}$ alkyl sulphate may be present at 0.1 to 3%, and the vitamin E poly($C_{2-3}$)alkylene glycol dicarboxylic ester may be present at 5 to 30% or 20 to 40%;

ii) the vitamin E may be present at 0.1 to 2%, the $C_{2-6}$ monoalcohol is absent, the a $C_{10-18}$ alkyl sulphate may be present at 0.1 to 3%, and the vitamin E poly($C_{2-3}$) alkylene glycol dicarboxylic ester may be present at 5 to 30% or 20 to 40%; and iii) the vitamin E may be present at 0.1 to 2%, the $C_{2-6}$ monoalcohol is absent, the a $C_{10-18}$ alkyl sulphate is absent, and the vitamin E poly($C_{2-3}$)alkylene glycol dicarboxylic ester may be present at 5 to 30% or 20 to 40%.

In the foregoing paragraphs, the percentages of various compounds are expressed as a percentage of the total weight of the mixture of excipients (i.e. excluding the active ingredient).

In any of the foregoing aspects, the polar protic solvent may be at least one of $C_{3-6}$ diol, a poly($C_{2-3}$) alkylene glycol having a number average molecular weight (Mn) of 200 to 1000 and a $C_{2-6}$ monoalcohol, where the polar protic solvent is present at 1-99%. In one embodiment of any of the foregoing aspects, the polar protic solvent is a mixture of a $C_{3-6}$ diol and a poly($C_{2-3}$) alkylene glycol having a number average molecular weight (Mn) of 200 to 1000. In one embodiment of any of the foregoing aspects, the polar protic solvent is a mixture of a $C_{3-6}$ diol and a poly($C_{2-3}$) alkylene glycol having a number average molecular weight (Mn) of 200 to 1000 wherein the $C_{3-6}$ diol may be present at up to one-half the percentage of the polar protic solvent. In one embodiment of any of the foregoing aspects, the polar protic solvent is a mixture of a $C_{3-6}$ diol, a poly($C_{2-3}$) alkylene glycol having a number average molecular weight (Mn) of 200 to 1000 and a $C_{2-6}$ monoalcohol. In one embodiment of any of the foregoing aspects, the polar protic solvent is a poly($C_{2-3}$) alkylene glycol having a number average molecular weight (Mn) of 200 to 1000.

In certain aspects, a representative $C_{3-6}$ diol includes propylene glycol, such as 1,2-propanediol ($\alpha$-propylene glycol), representative poly($C_{2-3}$) alkylene glycols include polyethylene glycol and polypropylene glycol and representative $C_{2-6}$ monoalcohols include ethanol.

In any of the foregoing aspects, the $C_{3-6}$ diol is present at 0 to 50%, 0 to 40%, 5 to 40%, 1% to 10%, 1% to 25%, 10% to 20%, 2.5% to 7.5%, 1% or 20%. In any of the foregoing aspects, the $C_{3-6}$ diol is 1,2-propanediol and the 1,2-propanediol is present 0 to 50%, 0 to 40%, 5 to 40%, 1% to 10%, 1% to 25%, 10% to 20%, 2.5% to 7.5%, 1% or 20%.

In any of the foregoing aspects, the poly($C_{2-3}$) alkylene glycol having a number average molecular weight (Mn) of 200 to 1000 is present at 1 to 99%, 1 to 90%, 10 to 99%, 50 to 90%, 90 to 99%, 10 to 90%, 30 to 70%, 20 to 95%, 40 to 60%, 45 to 55%, 65 to 75%, 70 to 75%, 72.1%, 72.7% or 52.5%. In any of the foregoing aspects, the poly($C_{2-3}$) alkylene glycol is present at 1 to 99%, 1 to 90%, 10 to 99%, 50 to 90%, 90 to 99%, 10 to 90%, 30 to 70%, to 95%, 40 to 60%, 45 to 55%, 65 to 75%, 70 to 75%, 72.1%, 72.7% or 52.5% and has a number average molecular weight (Mn) of 200 to 1000, of 200 to 800, of 400 to 800, of 400 or of 600. In any of the foregoing aspects, the poly($C_{2-3}$) alkylene glycol is polyethylene glycol or polypropylene glycol. In any of the foregoing aspects, the poly($C_{2-3}$) alkylene glycol is polyethylene glycol and is present at, 1 to 99%, 1 to 90%, 10 to 99%, 50 to 90%, 90 to 99%, 10 to 90%, 30 to 70%, 20 to 95%, 40 to 60%, 45 to 55%, 65 to 75%, 70 to 75%, 72.1%, 72.7% or 52.5% and has a number average molecular weight (Mn) of 200 to 1000, of 200 to 800, of 400 to 800, of 400 or of 600.

In any of the foregoing aspects, the $C_{2-3}$ monoalcohol is present at 0.1% to 10%, 0.1% to 1%, 0.5% to 7.5%, 0.5% to 2.5%, 2% to 6%, 3% to 5%, 2.5% or 5%. In any of the foregoing aspects, the $C_{2-6}$ monoalcohol is ethanol and is present at 0.1% to 10%, 0.1% to 1%, 0.5% to 7.5%, 0.5% to 2.5%, 2% to 6%, 3% to 5%, 2.5% or 5%. In certain embodiments, particularly when the polar protic solvent is solely a poly($C_{2-3}$) alkylene glycol having a number average molecular weight (Mn) of 200 to 1000, the $C_{2-6}$ monoalcohol, such as ethanol, may be absent.

In any of the foregoing aspects, the $C_{10-18}$ alkyl sulphate is present at 0.1% to 7.5%, 0.1% to 1%, 0.5% to 5%, 1% to 3% or 2.5%. In any of the foregoing aspects, the $C_{10-18}$ alkyl sulphate is sodium dodecyl sulphate (also known as sodium lauryl sulphate) and is present at 0.1% to 7.5%, 0.5% to 5%, 1% to 4% or 2.5%. In certain embodiments, particularly when the poloar protic solvent is solely a poly($C_{2-3}$) alkylene glycol having a number average molecular weight (Mn) of 200 to 1000, the $C_{10-18}$ alkyl sulphate, such as sodium dodecyl sulphate, may be absent or replaced with another surfactant.

In any of the foregoing aspects, the vitamin E poly($C_{2-3}$)alkylene glycol dicarboxylic ester is present at 0 to 50%, 0.1 to 50%, 0 to 5%, 0.1% to 5%, 0.1% to 1%, 5% to 30%, 20 to 40%, 10% to 25%, 15% to 20%, 20 to 30%, 1%, 27.2%, 26.6% or 20%. In any of the foregoing aspects, the vitamin E poly($C_{2-3}$)alkylene glycol dicarboxylic ester is D-α-tocopherol polyethylene glycol 1000 succinate (also known as Vitamin E polyethylene glycol 1000 succinate or vitamin E TPGS) and is present at 0 to 50%, 0 to 5%, 0.1% to 5%, 0.1% to 1%, 5% to 30%, 20 to 40%, 10% to 25%, 15% to 20%, 20 to 30%, 1%, 27.2%, 26.6% or 20%.

In any of the foregoing aspects, the vitamin E is present at 0 to 10%, 0 to 5%, 0.1% to 5%, 0.1% to 2%, 0.1% to 1%, 0.1% to 3%, 0.7%, 1% or 5%, In any of the foregoing aspects, the vitamin E is D-α-tocopherol and is present at 0 to 10%, 0 to 5%, 0.1% to 5%, 0.1% to 2%, 0.1% to 1%, 0.1% to 3%, 0.7%, 1% or 5%. In certain embodiments, the vitamin E, such as D-α-tocopherol, may be absent. %. In certain embodiments, the vitamin E, such as D-α-tocopherol, may be replaced with another stabilizer, such as, but not limited to, citric acid, or may be present with another stabilizer, such as, but not limited to, citric acid at the concentrations above.

In the foregoing aspects, the percentages of various compounds are expressed as a percentage of the total weight of the mixture of excipients (i.e. excluding the active ingredient).

In any of the foregoing aspects, a compound of formula (I) is 3-[2-(4-carbamimidoyl-phenylcarbamoyl)-5-methoxy-4-vinyl-phenyl]-6-(cyclopropylmethyl-carbamoyl)-pyridine-2-carboxylic acid, 3-(2-((4-carbamimidoylphenyl)carbamoyl)-4-vinylphenyl)-6-(isobutylcarbamoyl)-pyridine-2-carboxylic acid, 3-(2-((4-carbamimidoylphenyl)carbamoyl)-4-vinylphenyl)-6-((cyclopropylmethyl)carbamoyl)-pyridine-2-carboxylic acid, 2'-(((5-carbamimidoylpyridin-2-yl)amino)methyl)-4-(isobutylcarbamoyl)-4'-vinyl-[1,1'-biphenyl]-2-carboxylic acid, 2'-((4-carbamimidoylphenyl)carbamoyl)-4-((2,3-dihydroxypropyl)carbamoyl)-4'-vinyl-[1,1'-biphenyl]-2-carboxylic acid or a combination of the foregoing. In any of the foregoing aspects, a compound of formula (I) is 3-[2-(4-carbamimidoyl-phenylcarbamoyl)-5-methoxy-4-vinyl-phenyl]-6-(cyclopropylmethyl-carbamoyl)-pyridine-2-carboxylic acid. In any of the foregoing aspects, a compound of formula (I) is 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride. In any of the foregoing aspects, a compound of formula (I) is crystalline Form A of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride.

In another aspect, the invention comprises a composition, as defined above in any of the above aspects, for use as a medicament.

In another aspect, the invention comprises a composition, as defined above in any of the above aspects, for use in treating hereditary angioedema.

In another aspect, the invention comprises use of a composition, as defined above in any of the above aspects, in the manufacture of a medicament for treating hereditary angioedema.

In another aspect, the invention comprises a method of treating hereditary angioedema in a subject in need thereof, comprising administering to said subject a composition, as defined above in any of the above aspects.

In one embodiment, the oral compositions of the present invention contain an effective amount of a compound of the formula (I), specifically including 3-[2-(4-carbamimidoyl-phenylcarbamoyl)-5-methoxy-4-vinyl-phenyl]-6-(cyclopropylmethyl-carbamoyl)-pyridine-2-carboxylic acid, its hydrochloride salt and Form A. As used in the present disclosure, the term "effective amount" or "therapeutically effective amount" means an amount of a compound that, when administered to a subject for treating a condition, is sufficient to effect such treatment. The "effective amount" or "therapeutically effective amount" will vary depending on the compound, the disease and its severity and the age, weight, physical condition and responsiveness of the subject to be treated.

In one aspect, the effective amount or therapeutically effective amount is an amount that will result in a plasma level of a compound of the formula (I), specifically including 3-[2-(4-carbamimidoyl-phenylcarbamoyl)-5-methoxy-4-vinyl-phenyl]-6-(cyclopropylmethyl-carbamoyl)-pyridine-2-carboxylic acid, its hydrochloride salt and Form A., of at least 10 ng/ml, at least 15 ng/ml or at least 25 ng/ml for a period of at least from two hours to four hours after administration to a subject.

In one aspect, the condition is hereditary angioedema and the effective amount or therapeutically effective amount is an amount that will result in a plasma level of a compound of the formula (I), specifically including 3-[2-(4-carbamimidoyl-phenylcarbamoyl)-5-methoxy-4-vinyl-phenyl]-6-(cyclopropylmethyl-carbamoyl)-pyridine-2-carboxylic acid, its hydrochloride salt and Form A., of at least 10 ng/ml, at least 15 ng/ml or at least 25 ng/ml for a period of at least from two hours to four hours after administration to a subject.

As used in the present disclosure, the term "treat" or "treating" means a course of action that i) prevents or delays the appearance of clinical symptoms of the condition in a subject that may be afflicted with or predisposed to the condition but does not yet experience or display clinical or subclinical symptoms of the condition; ii) inhibits (i.e., arrests or reduces) the development of at least one clinical or subclinical symptom of the condition; or iii) relieves (i.e., causing regression or a decrease in) at least one clinical or subclinical symptom of the condition. The benefit to a subject being treated or to be treated may either be statistically significant or perceptible to the subject or to physician directing treatment.

DETAILED DESCRIPTION

Compounds

Figure 1:
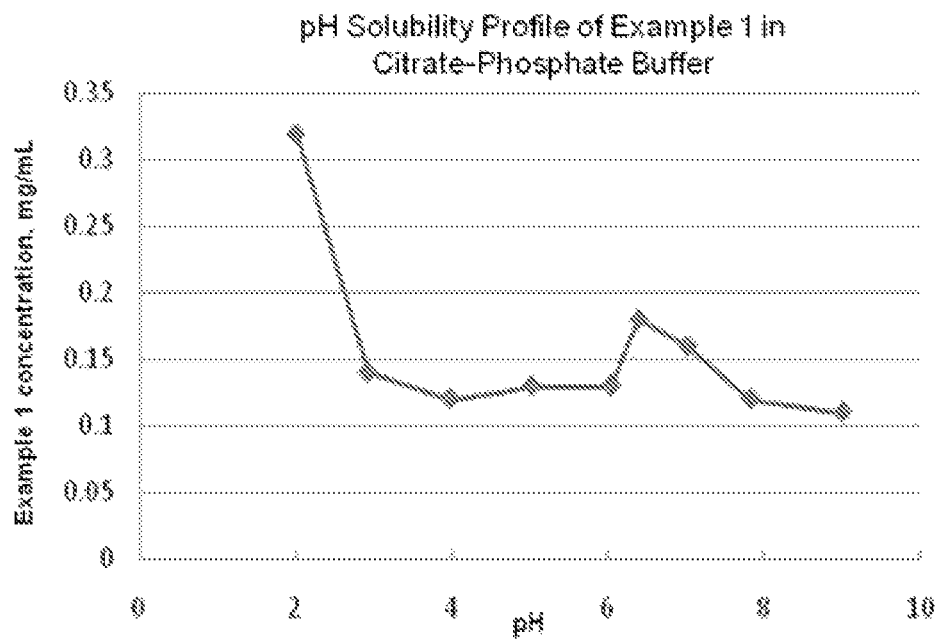
FIG. 1 illustrates the pH solubility profile of the compound of Example 1 in phosphate-citrate buffers.

The compounds used in the present invention are of the formula (I):

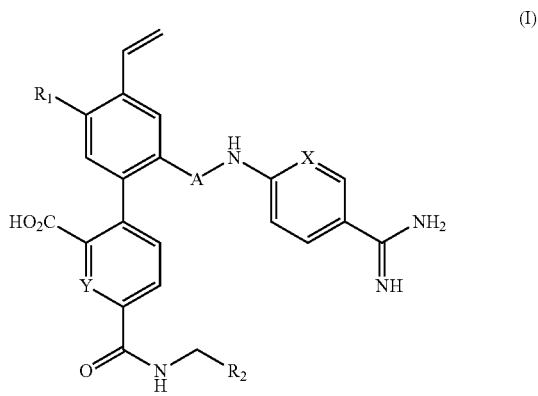

wherein:
X is CH or N;
Y is CH or N;
A is C=O or $CH_2$;
$R_1$ is hydrogen or a $C_{1-4}$ alkoxy group and
$R_2$ is a $C_{1-4}$ alkyl group or a $C_{3-6}$ cycloalkyl group, optionally substituted by 1 or 2 hydroxyl groups;
and pharmaceutically acceptable salts, solvates, esters, crystalline forms and prodrugs thereof.

In this specification "alkyl" means a straight or branched, aliphatic radical having a chain of carbon atoms. $(C_{1-4})$alkyl means alkyl groups that have a chain of between 1 and 4 carbons such as methyl, ethyl, n-propyl, isopropyl, butyl, sec-butyl, isobutyl and tert-butyl.

"Alkoxy" means an oxygen atom bonded to an alkyl group, wherein alkyl is as defined above. $(C_{1-4})$alkoxy means alkoxy groups that have a chain of between 1 and 4 carbons such as methoxy, 1-ethoxy, 2-ethoxy, 1-propyloxy, 2-propyloxy, 3-propyloxy, isopropoxy, 1-butyloxy, 2-butyloxy, 3-butyloxy, 4-butyloxy, sec-butyloxy, isobutyloxy and tert-butyloxy.

"Cycloalkyl" means a saturated monocyclic ring of carbon atoms. $(C_{3-3})$cycloalkyl includes cyclopropyl, cyclobutyl, cyclopentyl and cyclohexyl.

"Hydroxyl" means the group —OH.

In one embodiment, X is CH. In another embodiment, X is N.

In one embodiment, Y is CH. In another embodiment, Y is N.

In one embodiment, A is C=O. In another embodiment, A is $CH_2$.

In one embodiment, $R_1$ is hydrogen. In one embodiment, $R_1$ is a $C_{1-4}$ alkoxy group.

In one embodiment, $R_1$ is a methoxy group.

In one embodiment, $R_2$ is a $C_{1-4}$ alkyl group optionally substituted by 1 or 2 hydroxyl groups.

In one embodiment, $R_2$ is a $C_{2-3}$ alkyl group optionally substituted by 1 or 2 hydroxyl groups.

In one embodiment, $R_2$ is an isopropyl group or a 1,2-dihydroxyethyl group.

In one embodiment, $R_2$ is a $(C_{3-6})$cycloalkyl group. In one embodiment, $R_2$ is a $(C_{3-4})$cycloalkyl group. In one embodiment, $R_2$ is a cyclopropyl group.

In one embodiment, $R_1$ is hydrogen or methoxy, and $R_2$ is cyclopropyl, isopropyl or 1,2-dihydroxyethyl.

In one embodiment, the compounds used in the present invention are compounds of formula (I), as defined above, provided that when X is N, Y is CH, A is CO and $R_1$ is methoxy, $R_2$ is other than isopropyl. Such compounds are referred to herein as compounds of formula (I'). Therefore, in one embodiment compounds of the formula (I) are defined with the proviso that when X is N, Y is CH, A is CO and $R_1$ is methoxy, $R_2$ is other than isopropyl.

In one embodiment, X is CH, Y is N, A is C=O, $R_1$ is hydrogen or methoxy, and $R_2$ is a $(C_{3-4})$cycloalkyl group, a $C_{2-3}$ alkyl group or a $C_{2-3}$ alkyl group optionally substituted by 1 or 2 hydroxyl groups In one embodiment, X is CH, Y is N, A is C=O, $R_1$ is hydrogen or methoxy, and $R_2$ is a cyclopropyl group, an isopropyl group or a 1,2-dihydroxyethyl.

In one embodiment, X is CH, Y is N, A is C=O, $R_1$ is methoxy, and $R_2$ is a cyclopropyl group.

In one embodiment, X is N, Y is CH, A is CH, $R_1$ is hydrogen, and $R_2$ is a $C_{2-3}$ alkyl group or an isopropyl group.

Specific compounds used in the present invention include the following compounds listed in Table 1 below:

TABLE 1

| Structure | Name |
|---|---|
| 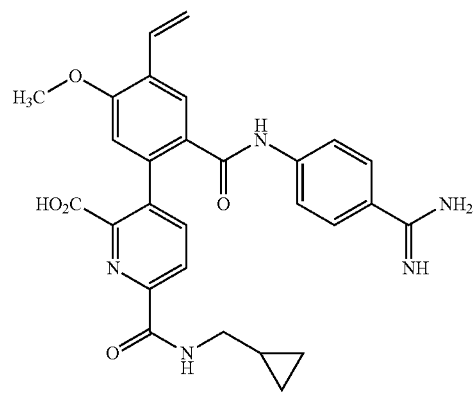 [SMILES: C=Cc1cc(C(=O)Nc2ccc(C(=N)N)cc2)c(-c2ccc(C(=O)NCC3CC3)nc2C(=O)O)cc1OC] | 3-[2-(4-carbamimidoyl-phenylcarbamoyl)-5-methoxy-4-vinyl-phenyl]-6-(cyclopropylmethyl-carbamoyl)-pyridine-2-carboxylic acid |
| 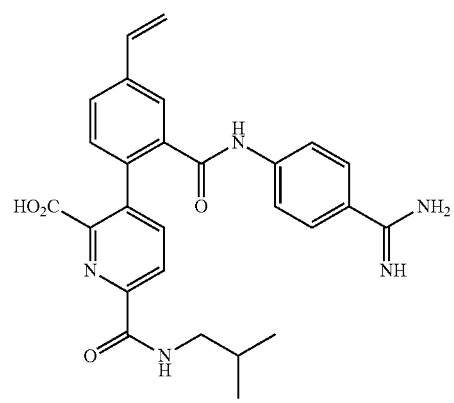 [SMILES: C=Cc1ccc(-c2ccc(C(=O)NCC(C)C)nc2C(=O)O)c(C(=O)Nc2ccc(C(=N)N)cc2)c1] | 3-(2-((4-carbamimidoylphenyl)carbamoyl)-4-vinylphenyl)-6-(isobutylcarbamoyl)-pyridine-2-carboxylic acid |
| 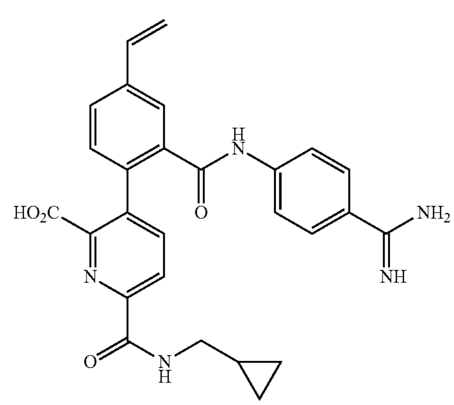 [SMILES: C=Cc1ccc(-c2ccc(C(=O)NCC3CC3)nc2C(=O)O)c(C(=O)Nc2ccc(C(=N)N)cc2)c1] | 3-(2-((4-carbamimidoylphenyl)carbamoyl)-4-vinylphenyl)-6-((cyclopropylmethyl)carbamoyl)-pyridine-2-carboxylic acid |

TABLE 1-continued

| Structure | Name |
| --- | --- |
| 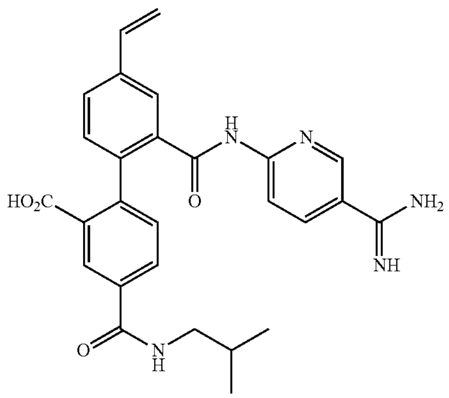 | 2'-(((5-carbamimidoylpyridin-2-yl)amino)methyl)-4-(isobutylcarbamoyl)-4'-vinyl-[1,1'-biphenyl]-2-carboxylic acid |
| 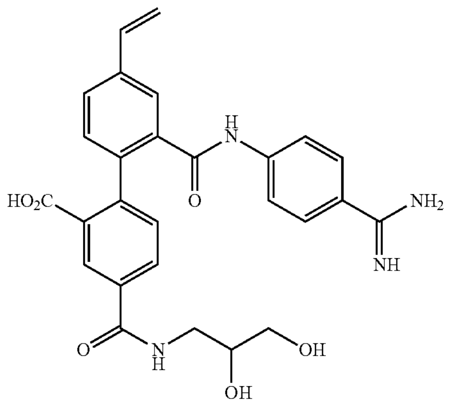 [SMILES: C=Cc1ccc(-c2ccc(C(=O)NCC(O)CO)cc2C(=O)O)c(C(=O)Nc2ccc(C(=N)N)cc2)c1] | 2'-((4-carbamimidoylphenyl)carbamoyl)-4-((2,3-dihydroxypropyl)carbamoyl)-4'-vinyl-[1,1'-biphenyl]-2-carboxylic acid |

The structures of the above specific compounds are shown in J. Zhang et al. *Medicinal Chemistry,* 2006, 2, 545-553, incorporated herein by reference for such teaching. Their synthesis is described generally in P. L. Kotian et al. Abstract for 18th International Symposium on Medicinal Chemistry, Copenhagen, Aug. 16, 2004, incorporated herein by reference for such teaching. Synthesis of similar compounds is described generally in in U.S. Pat. No. 6,699,994, incorporated herein by reference for such teaching.

In another aspect, the invention relates to a hydrochloride salt of a compounds of the formula (I). In a particular aspect, the hydrochloride salt is 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride. In another particular aspect, the hydrochloride salt compound has a chloride content greater than 0.65 and less than or equal to 1.0 (salt to API).

Crystalline Forms

The present disclosure also specific crystalline forms of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride. Such specific crystalline forms of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride are designated as Forms A and C. Further, pharmaceutical compositions of Forms A and C are also provided.

A crystal form may be referred to herein to be characterized "as depicted in" a Figure. Such data include powder X-ray diffractograms (PXRD), differential scanning calorimetry (DSC), thermogravimetric analysis (TG) and scanning electron microscopy. The skilled person will understand that the data as depicted in the Figures may be subject to variations (for example, variations in peak intensity and/or exact peak positions) due to variations on instrument parameters, sample concentration, and sample purity. The skilled person will be able to compare the Figures herein and the data for an unknown crystalline form and determine whether the data characterize the crystalline form (s) disclosed or different crystalline forms.

A crystalline form (polymorph) may be referred to herein as substantially free of any other crystalline (polymorphic) forms. As used herein in this context, the expressions "substantially free of any other forms" means that the crystalline form contains, 20% or less (w/w), 10% or less (w/w), 5% or less (w/w), 2% or less (w/w), or 1% or less (w/w) of other crystalline (polymorphic) forms of the subject compound as measured, for example, by PXRD.

Furthermore, a crystalline form of 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride contains greater than 80% (w/w), greater than 90% (w/w), greater than 95% (w/w), greater than 98% (w/w), or greater than 99% (w/w) of the subject polymorphic form of 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride.

The present disclosure provides two crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride, namely Form A (also referred to as compound of the formula (II)) and Form C.

In one embodiment, the present disclosure provides crystalline Form A of 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride. In one embodiment, Form A is characterized by data selected from a group consisting of: i) a PXRD pattern having peaks at 7.3, 9.5, 18.5 and 21.9° 2θ±0.2°2θ; ii) a PXRD pattern having peaks at 7.31, 9.52, 18.54 and 21.85° 2θ±0.2°2θ; iii) a PXRD pattern as depicted in FIG. 13; and iv) any combination thereof.

Figure 14:
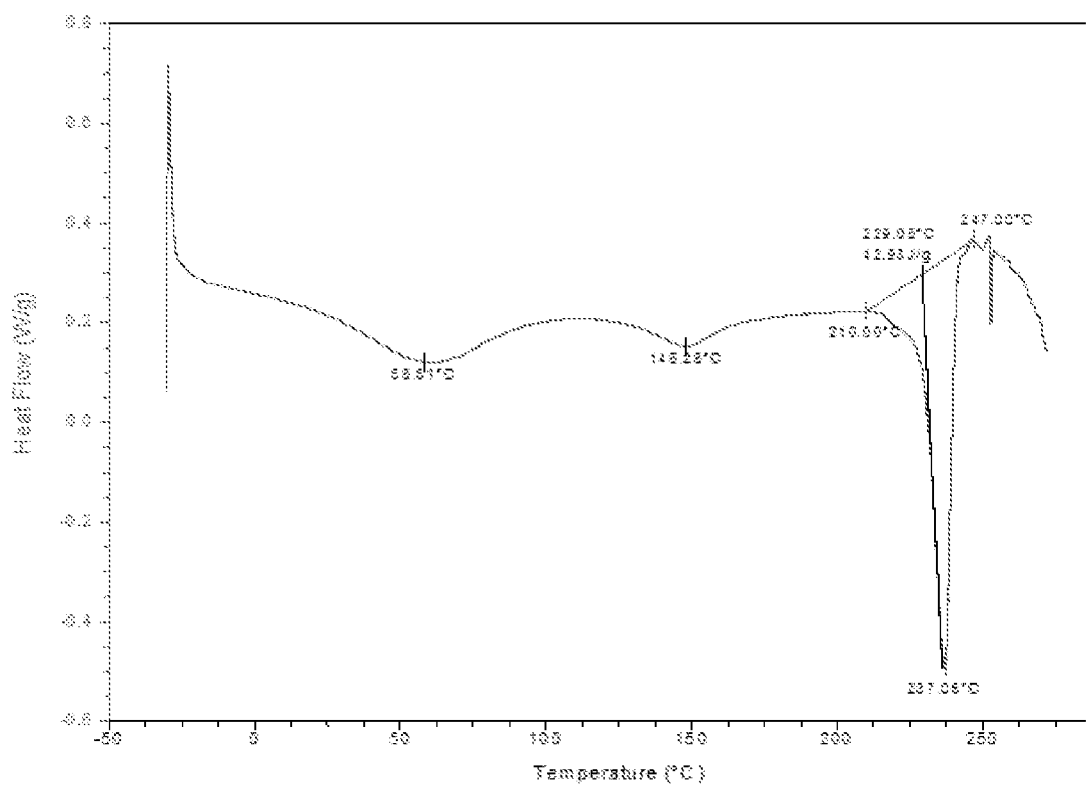
FIG. 14 illustrates the DSC thermogram of crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride designated Form A.
Figure 15:
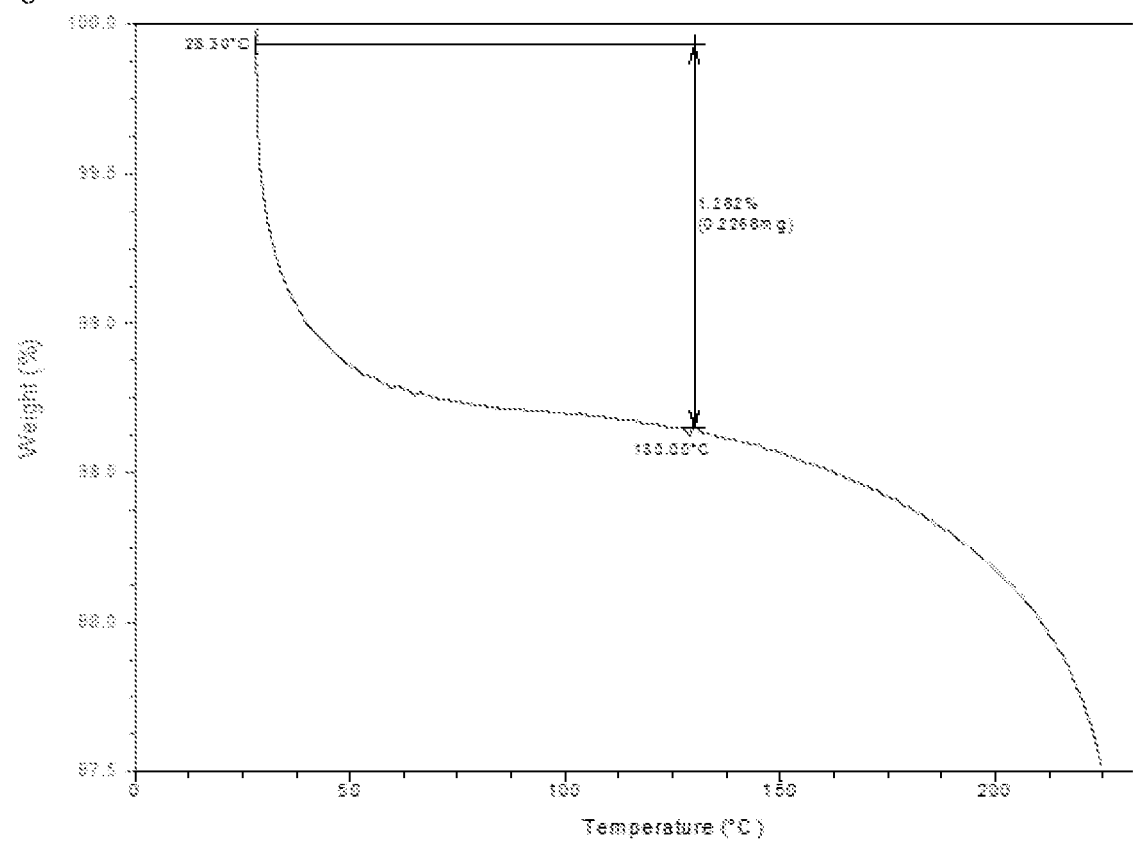
FIG. 15 illustrates the TG thermogram of crystalline 3-[2-(4-carbamimidoyl-phenylcarbamoyl)-5-methoxy-4-vinylphenyl]-6-(cycl propylmethyl-carbamoyl)-pyridine-2-carboxylic acid hydrochloride designated Form A.
Figure 16:
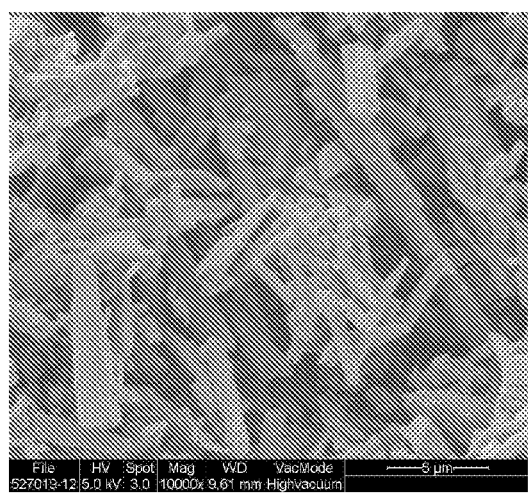
FIG. 16 illustrates scanning electron microscopy of crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride designated Form A.

In still another embodiment, Form A is characterized by data selected from a group consisting of: i) a PXRD pattern having peaks at 14.7, 20.3, 22.5, 22.7, 26.1, and 26.7° 2θ±0.2° 2θ; ii) a PXRD pattern having peaks at 14.65, 20.28, 22.51, 22.96, 26.14, and 26.72° 2θ+0.2° 2θ; iii) a differential scanning calorimetry (DSC) thermogram as depicted in FIG. 14; iv) a thermogravimetric (TG) thermogram as depicted in FIG. 15; v) a crystal structure as determined by scanning electron microscopy (SEM) as depicted in FIG. 16; and vi) any combination of the foregoing.

Figure 13:
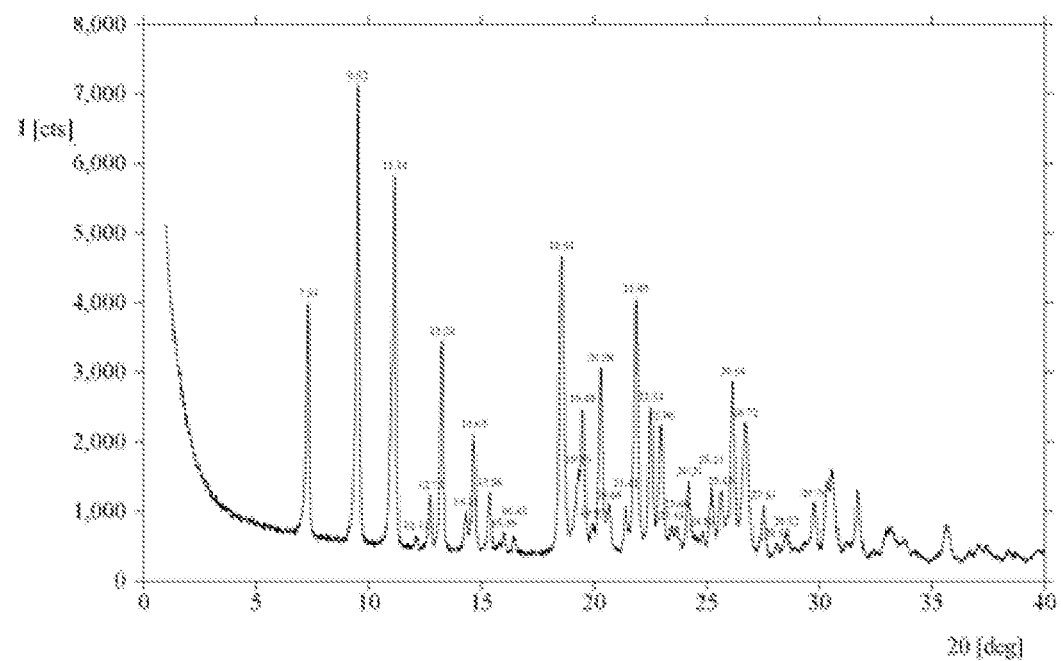
FIG. 13 illustrates a powder XRD pattern of crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride designated Form A.

In still another embodiment, Form A is characterized by data selected from a group consisting of: i) a PXRD pattern having peaks at 7.3, 9.5, 18.5 and 21.9° 2θ±0.2°2θ; ii) a PXRD pattern having peaks at 7.31, 9.52, 18.54 and 21.85° 2θ+0.2°2θ; iii) a PXRD pattern as depicted in FIG. 13; iv) a PXRD pattern having peaks at 14.7, 20.3, 22.5, 22.7, 26.1, and 26.7° 2θ±0.2° 2θ; v) a PXRD pattern having peaks at 14.65, 20.28, 22.51, 22.96, 26.14, and 26.72° 2θ±0.2° 2θ; vi) a DSC thermogram as depicted in FIG. 14; vii) a TG thermogram as depicted in FIG. 15; viii) a crystal structure as determined by SEM as depicted in FIG. 16; and ix) any combination of the foregoing.

The above crystalline Form A as described above is a variable hydrate. As used herein, and unless stated otherwise, the term "variable hydrate" in relation to crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride means that the water content is dependent on relative humidity ("RH") conditions. At about room temperature and 30% RH, Form A shows water content consistent with a monohydrate (estimated at about 1.2 mole of water per mole of crystalline Form A).

Form A is present as a hydrochloride salt, wherein the chloride content of the Form A is greater than or equal to 0.65 and less than or equal to 1.0 (salt to API). In one embodiment, the chloride content of Form A is greater than 0.65 (salt to API). In another embodiment, the chloride content of Form A is greater than 0.75 (salt to API). In another embodiment, the chloride content of Form A is greater than 0.85 (salt to API). In another embodiment, the chloride content of Form A is greater than 0.95 (salt to API). In another embodiment, the chloride content of Form A is 1.0 (salt to API).

In one embodiment, Form A has the advantageous property of superior solubility in the pharmaceutical compositions, in particular the oral pharmaceutical compositions described herein. In another embodiment, pharmaceutical compositions of Form A, in particular the oral pharmaceutical compositions described herein, when administered to a subject provide for increased bioavailability of the compound as compared to amorphous 3-[2-(4-carbamimidoyl-phenylcarbamoyl)-5-methoxy-4-vinylphenyl]-6-(cyclopropylmethyl-carbamoyl)-pyridine-2-carboxylic acid and salts thereof and other crystalline forms. In another embodiment, pharmaceutical compositions of Form A, in particular the oral pharmaceutical compositions described herein, when administered to a subject for treating a condition, is sufficient to affect such treatment. In another embodiment, pharmaceutical compositions of Form A, in particular the oral pharmaceutical compositions described herein, when administered to a subject for treating a condition, is sufficient to affect such treatment when dosed 1 to 3 times per day or less (such as 1 to 2 times). In another embodiment, pharmaceutical compositions of Form A, in particular the oral pharmaceutical compositions described wherein when administered to a subject provide for a therapeutically effective amount of the compound of at least 10 ng/ml, at least 15 ng/ml or at least 25 ng/ml in the blood of the subject for a period of at least from two hours to four hours after administration to a subject. In another embodiment, Form A, has the advantageous property of being solubilized at a concentration of greater than 140 mg/ml in the pharmaceutical compositions, in particular the oral pharmaceutical compositions described herein. In another embodiment, Form A, has the advantageous property of stability to polymorphic conversion. In particular, conversion to other polymorphic forms was not observed for Form A in RH conditions of 43%, 75%, and 100%, at room temperature.

In a particular embodiment, Form A is advantageously solubilized and provided in a liquid pharmaceutical composition comprising 72.7% of polyethylene glycol having a number average molecular weight (Mn) of 600, 0.7% D-α-tocopherol and 26.6% of D-α-tocopherol polyethylene glycol 1000 succinate (the percentages of compounds expressed as a percentage of the total weight of the mixture of excipients and excluding the active ingredient). In a particular embodiment, Form A is advantageously solubilized and provided in a pharmaceutical composition at concentrations greater than 140 mg/ml, the composition comprising 72.7% of polyethylene glycol having a number average molecular weight (Mn) of 600, 0.7% D-α-tocopherol and 26.6% of D-α-tocopherol polyethylene glycol 1000 succinate (the percentages of compounds expressed as a percentage of the total weight of the mixture of excipients and excluding the active ingredient). In a particular embodiment, Form A is advantageously solubilized and provided in a pharmaceutical composition comprising 72.7% of polyethylene glycol having a number average molecular weight (Mn) of 600, 0.7% D-α-tocopherol and 26.6% of D-α-tocopherol polyethylene glycol 1000 succinate (the percentages of compounds expressed as a percentage of the total weight of the mixture of excipients and excluding the active ingredient) wherein when administered to a subject provide for a therapeutically effective amount of the compound when dosed 1 to 3 times per day or less (such as 1 to 2 times). In a particular embodiment, Form A is advantageously solubilized and provided in a pharmaceutical composition comprising 72.7% of polyethylene glycol having a number average molecular weight (Mn) of 600, 0.7% D-α-tocopherol and 26.6% of D-α-tocopherol polyethylene glycol 1000 succinate (the percentages of compounds expressed as a percentage of the total weight of the mixture of excipients and excluding the active ingredient) wherein when administered to a subject provide for a therapeutically effective amount of the compound of at least 10 ng/ml, at least 15 ng/ml or at least 25 ng/ml in the blood of the subject for a period of at least from two hours to four hours after administration to a subject. In all of the above, the pharmaceutical composition may be a liquid pharmaceutical composition. In all of the above, the pharmaceutical composition may be a liquid pharmaceutical composition contained in a capsule as described herein, including a soft gelatin capsule or a hard gelatin capsule.

A representative formulation includes, but is not limited to: i) 100.01 mg of Form A; ii) 545.9 mg of polyethylene glycol having a number average molecular weight (Mn) of 600; iii) 5.0 mg of D-α-tocopherol; and iv) 200.0 mg of D-α-tocopherol polyethylene glycol 1000 succinate.

Preferably, Form A of crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride is substantially free of any other polymorphic forms.

Methods for the manufacture of Form A are disclosed herein. Form A may be obtainable by treatment of 3-[2-(4-carbamimidoyl-phenylcarbamoyl)-5-methoxy-4-vinylphenyl]-6-(cyclopropylmethyl-carbamoyl)-pyridine-2-carboxylic acid in aqueous acetonitrile with base followed by hydrochloric acid, precipitation of 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride, and washing of the 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride with methyl tert-butyl ether. Thus there is provided 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride in the form obtainable by this method.

In one embodiment, the present disclosure provides crystalline Form C of 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride. In one embodiment, Form C is characterized by data selected from a group consisting of: i) a PXRD pattern having peaks at 4.2, 7.9, and 10.8° 2θ±0.2°2θ; ii) a PXRD pattern having peaks 4.15, 7.94, and 10.79° 2θ±0.2°2θ; iii) a PXRD pattern as depicted in FIG. 17; and iv) any combination thereof.

Figure 18:
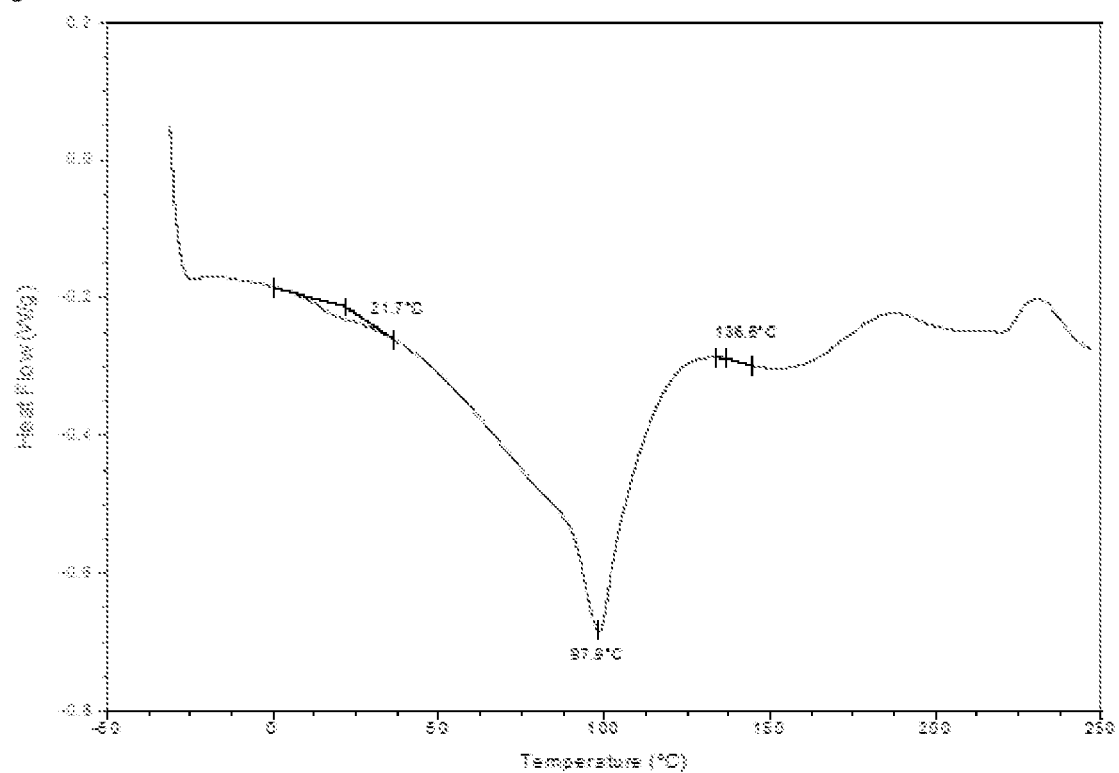
FIG. 18 illustrates the DSC thermogram of crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride designated Form C.
Figure 19:
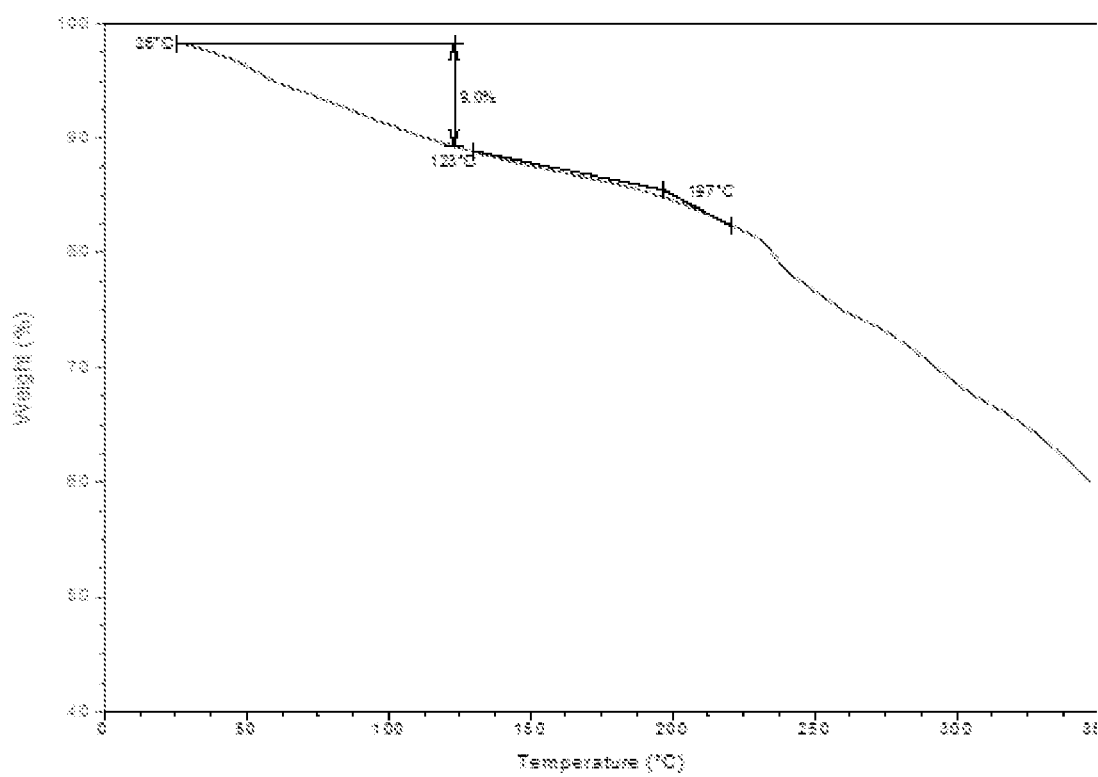
FIG. 19 illustrates the TG thermogram of crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride designated Form C.

In still another embodiment, Form C is characterized by data selected from a group consisting of: i) a PXRD pattern having peaks at 12.6, 20.9, 21.3, 23.8, 24.5, 27.0, and 28.4° 2θ±0.2°2θ; ii) a PXRD pattern having peaks at 12.57, 20.90, 21.31, 23.97, 24.45, 27.02, and 28.36° 2θ±0.2°2θ; iii) a DSC thermogram as depicted in FIG. 18; iv) a TG thermogram as depicted in FIG. 19; and v) any combination of the foregoing.

Figure 17:
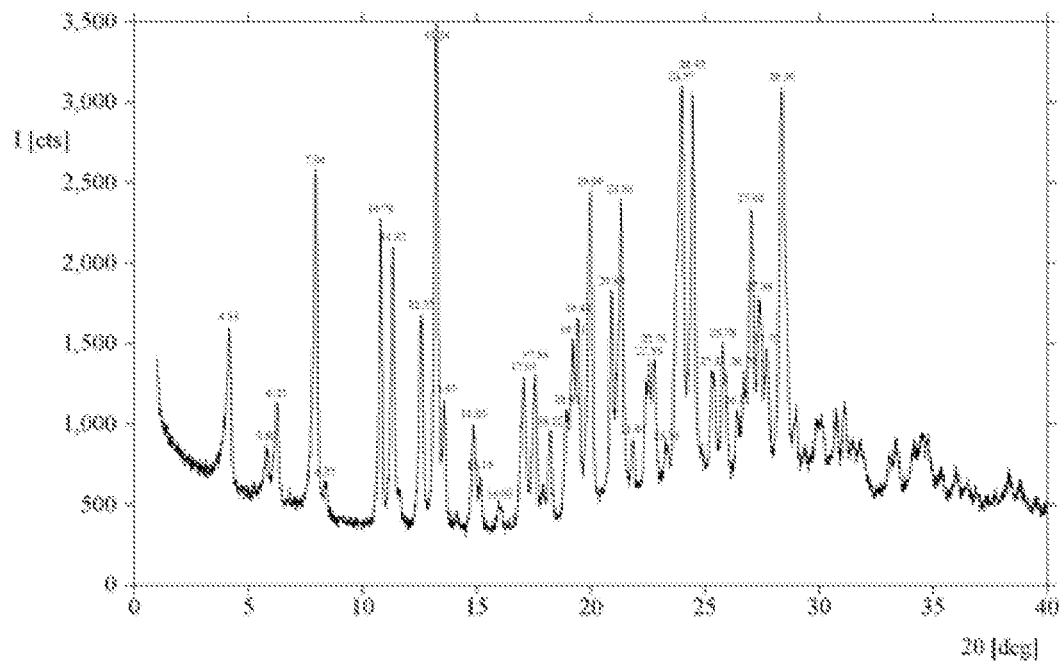
FIG. 17 illustrates a powder XRD pattern of crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride designated Form C.

In still another embodiment, Form C is characterized by data selected from a group consisting of: i) a PXRD pattern having peaks at 4.2, 7.9, and 10.8° 2θ±0.2°2θ; ii) a PXRD pattern having peaks 4.15, 7.94, and 10.79° 2θ±0.2°2θ; iii) a PXRD as depicted in FIG. 17; iv) a PXRD pattern having peaks at 12.6, 20.9, 21.3, 23.8, 24.5, 27.0, and 28.4° 2θ±0.2°2θ; v) a PXRD pattern having peaks at 12.57, 20.90, 21.31, 23.97, 24.45, 27.02, and 28.36° 2θ35 0.2°2θ; vi) a DSC thermogram as depicted in FIG. 18; vii) a TG thermogram as depicted in FIG. 19; and viii) any combination of the foregoing.

The above 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride crystalline Form C is a variable hydrate.

As used herein, the term "variable hydrate" in relation to crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride Form C means that the water content is dependent on relative humidity ("RH") conditions. At about room temperature and 34% RH, Form C shows water content close to a monohydrate (estimated at about 1.4 mole of water per mole of crystalline Form C).

Preferably, the crystalline 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride Form C of the invention is substantially free of any other polymorph forms.

Methods for the manufacture of Form C are described herein. Form C may be obtainable by treatment of 3-[2-(4-carbamimidoyl-phenylcarbamoyl)-5-methoxy-4-vinylphenyl]-6-(cyclopropylmethyl-carbamoyl)-pyridine-2-carboxylic acid in aqueous acetonitrile with base followed by hydrochloric acid, precipitation of 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride, and washing of the 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride with water. Thus there is provided 3-[2-(4-carbamimidoyl-phenylcarbamoyl)-5-methoxy-4-vinylphenyl]-6-(cyclopropylmethyl-carbamoyl)-pyridine-2-carboxylic acid hydrochloride in the form obtainable by this method.

Salts, Hydrates, Esters and Prodrugs

The compounds of formula (I) used in the present invention may be present and optionally administered in the form of salts, hydrates, esters and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

Therefore, in a further aspect, the invention provides a pharmaceutically acceptable salt of a compound of formula (I) as defined herein, either in its broadest aspect or a preferred aspect. In one embodiment, the invention provides a pharmaceutically acceptable salt of 3-[2-(4-carbamimidoyl-phenylcarbamoyl)-5-methoxy-4-vinyl-phenyl]-6-(cyclopropylmethyl-carbamoyl)-pyridine-2-carboxylic acid.

The compound of formula (I) used in the present invention possess at least one basic nitrogen atom, and may be present as a free base form. Alternatively, the compounds can be prepared as a pharmaceutically acceptable acid addition salt by reacting the free base form of the compound with a pharmaceutically acceptable inorganic or organic acid.

Therefore, in a further aspect, the invention provides a pharmaceutically acceptable acid addition salt of a compound of formula (I) as defined herein, either in its broadest aspect or a preferred aspect. In one embodiment, the invention provides a pharmaceutically acceptable acid addition salt of 3-[2-(4-carbamimidoyl-phenylcarbamoyl)-5-methoxy-4-vinyl-phenyl]-6-(cyclopropylmethyl-carbamoyl)-pyridine-2-carboxylic acid.

Examples of pharmaceutically acceptable acid addition salts include hydrohalides such as hydrochloride, hydrobromide, hydroiodide; other mineral acids and their corresponding salts such as sulfate, nitrate, phosphate, etc.; alkyl and monoarylsulfonates such as methanesulfonate, ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, butyrate, camphorate, camphorsulfonate, caprylate, chlorobenzoate, cyclopentanepropionate, digluconate, dihydrogenphosphate, dinitrobenzoate, dodecylsulfate, 1,2-ethanedisulfonate (edisylate), fumarate, galacterate (from mucic acid), galacturonate, gentisate, glucoheptonate, gluconate, glutamate, glycerophosphate, glycolate, hemisuccinate, hemisulfate, heptanoate, hexanoate, hippurate, 2-hydroxyethanesulfonate, isethionate, iso-butyrate, lactate, lactobionate, malate, malonate, mandelate, metaphosphate, methylbenzoate, monohydrogenphosphate, 2-naphthalenesulfonate, nicotinate, oxalate, oleate, pamoate, pectinate, persulfate, phenylacetate, 3-phenylpropionate, phosphonate, phthalate, and vanillate. In one embodiment, the acid addition salt is a hydrochloride salt.

In one embodiment, the acid addition salt is a hydrochloride salt of the compound of formula (I) wherein the chloride content of the salt is greater than 0.65 (salt to API). In another embodiment, the acid addition salt is a hydrochloride salt of the compound of formula (I) wherein the chloride content of the salt is greater than 0.75 (salt to API). In another embodiment, the acid addition salt is a hydrochloride salt of the compound of formula (I) wherein the chloride content of the salt is greater than 0.85 (salt to API). In another embodiment, the acid addition salt is a hydrochloride salt of the compound of formula (I) wherein the chloride content of the salt is greater than 0.95 (salt to API). In another embodiment, the acid addition salt is a hydrochloride salt of the compound of formula (I) wherein the chloride content of the salt is 1.0 (salt to API).

In one embodiment, the acid addition salt is a hydrochloride salt of 3-[2-(4-carbamimidoyl-phenylcarbamoyl)-5-methoxy-4-vinyl-phenyl]-6-(cyclopropylmethyl-carbamoyl)-pyridine-2-carboxylic acid wherein the chloride content of the salt is greater than 0.65 (salt to API). In another embodiment, the acid addition salt is a hydrochloride salt of the compound of 3-[2-(4-carbamimidoyl-phenylcarbamoyl)-5-methoxy-4-vinyl-phenyl]-6-(cyclopropylmethyl-carbamoyl)-pyridine-2-carboxylic acid wherein the chloride content of the salt is greater than 0.75 (salt to API). In another embodiment, the acid addition salt is a hydrochloride salt of 3-[2-(4-carbamimidoyl-phenylcarbamoyl)-5-methoxy-4-vinyl-phenyl]-6-(cyclopropylmethyl-carbamoyl)-pyridine-2-carboxylic acid wherein the chloride content of the salt is greater than 0.85 (salt to API). In another embodiment, the acid addition salt is a hydrochloride salt of 3-[2-(4-carbamimidoyl-phenylcarbamoyl)-5-methoxy-4-vinyl-phenyl]-6-(cyclopropylmethyl-carbamoyl)-pyridine-2-carboxylic acid wherein the chloride content of the salt is 1.0 (salt to API).

The compounds of formula (I) used in the present invention also possess a free carboxylic acid group, and may be present as free acids. Alternatively a pharmaceutically acceptable base addition salt can be prepared by reacting the free acid form of the compound with a pharmaceutically acceptable inorganic or organic base.

Therefore, in a further aspect, the invention provides a pharmaceutically acceptable base addition salt of a compound of formula (I) as defined herein, either in its broadest aspect or a preferred aspect. In one embodiment, the invention provides a pharmaceutically acceptable base addition salt of 3-[2-(4-carbamimidoyl-phenylcarbamoyl)-5-methoxy-4-vinyl-phenyl]-6-(cyclopropylmethyl-carbamoyl)-pyridine-2-carboxylic acid.

Examples of such base addition salts are alkali metal salts, such as lithium, sodium and potassium salts, typically formed by reaction with alkali metal hydroxides such as potassium, sodium and lithium hydroxides or alkali metal alkoxides, such as potassium ethanolate and sodium propanolate; alkaline earth metal salts, such as magnesium, calcium and barium salts typically formed by reaction with alkaline earth metal hydroxides such as and calcium hydroxides; salts of other metal ions such as aluminium, copper, ferric ($Fe^{3+}$), ferrous ($Fe^{2+}$) and zinc salts; ammonium ($NH_4^+$) salts; organic base salts including, but not limited to, salts of primary, secondary and tertiary amines including, as primary amines, methylamine, ethylamine, propylamine, benzylamine, aniline and butylamine, as secondary amines dimethylamine, and diethylamine, and as tertiary amines trimethylamine and triethylamine, quaternary ammonium salts such as tetramethylammonium salts, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine).

The compounds used in the present invention may exist in the form of solvates. Such solvates include solvent molecules in their crystal structure. Therefore, in a further aspect, the invention provides a pharmaceutically acceptable solvate of a compound of formula (I) as defined herein, either in its broadest aspect or a preferred aspect. In one embodiment, the invention provides a pharmaceutically acceptable solvate of 3-[2-(4-carbamimidoyl-phenylcarbamoyl)-5-methoxy-4-vinyl-phenyl]-6-(cyclopropylmethyl-carbamoyl)-pyridine-2-carboxylic acid. Examples of solvates include hydrates and alcoholates.

Prodrug derivatives of the compounds used in the present invention can be prepared by modifying substituents of compounds of the present invention that are then converted in vivo to a different substituent. In particular, the compounds of the present invention possess both carboxylic acid ($-CO_2H$) and amidine ($-C(=NH)NH_2$) functional groups, either of which can be derivatised to form prodrugs of the compounds of the invention.

Esters of the compounds used in the present invention can be formed by reacting the compounds with a suitable compound containing a hydroxyl group. Therefore, in a further aspect, the invention provides a pharmaceutically acceptable ester of a compound of formula (I) as defined herein, either in its broadest aspect or a preferred aspect. In one embodiment, the invention provides a pharmaceutically acceptable ester of 3-[2-(4-carbamimidoyl-phenylcarbamoyl)-5-methoxy-4-vinyl-phenyl]-6-(cyclopropylmethyl-carbamoyl)-pyridine-2-carboxylic acid.

Examples of suitable esters include alkyl esters, in particular $C_{1-4}$ alkyl esters such as methyl, ethyl, propyl, isopropyl, butyl, isobutyl, sec-butyl and tert-butyl esters, and longer-chain alkyl esters such as $C_{5-30}$ alkyl esters including pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl and triacontyl esters.

Other examples of suitable esters include substituted $C_{1-4}$ alkyl esters (preferably substituted methyl or ethyl esters) wherein the substituent is selected from the group consisting of:

a hydroxyl group; examples of such substituted groups include 2-hydroxyethyl; an alkoxy group, in particular $C_{1-4}$ alkoxy; examples of such substituted groups include methoxymethyl or 2-ethoxyethyl;

an acyloxy group, wherein the acyl moiety is a group R—C(=O)— wherein R is a hydrocarbon group, including but not limited to an alkyl group (such as a $C_{1-4}$ or $C_{5-30}$ alkyl group as defined and exemplified above) or a benzyl group; examples of such substituted groups include acetyloxyethyl, pivaloyloxymethyl, 2-(pivaloyloxy)ethyl and 2-methyl-1-(pivaloyloxy)propyl;

a carbonate group, wherein the carbonate group attached is a moiety of formula RO—C(=O)—O— wherein R is $C_{1-8}$ alkyl; examples of such substituted groups include isopropyl methyl carbonate wherein the ester moiety has the formula

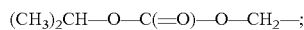

(CH$_3$)$_2$CH—O—C(=O)—O—CH$_2$—;

a 5-methyl-2-oxo-1,3-dioxolene-4-yl group; examples of such substituted groups include (5-methyl-2-oxo-1,3-dioxolene-4-yl)methyl;

an amino acid residue, including but not limited to Gly (glycine), Ala (alanine; CH$_3$CH(NH$_2$)CO—), Arg (arginine), Asn (asparagine), Asp (aspartic acid), Cys (cysteine), Glu (glutamic acid), His (histidine), Ile (isoleucine), Leu (leucine; (CH$_3$)$_2$CHCH$_2$CH(NH$_2$)CO—), Lys (lysine), Met (methionine), Phe (phenylalanine), Pro (proline), Ser (serine), Thr (threonine), Trp (tryptophan), Tyr (tyrosine), Val (valine). The amino acid residue may be attached via its amine terminus, its carboxylic acid terminus or a side chain; examples of such substituted groups include valinemethyl, 2-(valine)ethyl, 2-(valine)propyl, 2-(phenylalanine)ethyl, 2-(isoleucine)ethyl;

a saturated heterocyclic group having 3-8 ring atoms, of which at least one ring atom (preferably 1, 2 or 3; more preferably 1 or 2) is a heteroatom selected from nitrogen, oxygen and sulphur; including but not limited to aziridinyl; azetidinyl; piperidyl, morpholinyl, piperazinyl, pyrrolidinyl, azepinyl, azocinyl, 1,3-dioxanyl, 1,4-dioxanyl; examples of such substituted groups include 2-(morpholino)ethyl.

Amide prodrugs of the compounds can be formed by reacting the compounds with a suitable compound containing a primary or secondary amine group, such that the carboxylic acid group forms an amide bond with the amine, eliminating a molecule of water. Therefore, in a further aspect, the invention provides a pharmaceutically acceptable amide prodrug of a compound of formula (I) as defined herein, either in its broadest aspect or a preferred aspect. In one embodiment, the invention provides a pharmaceutically acceptable amide prodrug of 3-[2-(4-carbamimidoyl-phenylcarbamoyl)-5-methoxy-4-vinyl-phenyl]-6-(cyclopropylmethyl-carbamoyl)-pyridine-2-carboxylic acid.

Examples of such amide prodrugs include those formed by reaction with the following:

ammonia;

hydroxylamine (—NH$_2$OH)

alkylamines, in particular $C_1$ alkyl amines such as methylamine, ethylamine, propylamine, isopropylamine, butylamine, isobutylamines, sec-butylamine and tert-butylamine; dialkylamines, in particular di($C_{1-4}$ alkyl) amines such as dimethylamine, diethylamine, N-methylethylamine, dipropylamine, N-methylpropylamine, N-methylisopropylamine, N-ethylisopropylamine, diisopropylamine, dibutylamine, diisobutylamine, di(sec-butyl)amine and di(tert-butyl)amine;

arylalkylamines and diarylalkylamines, such as benzylamine and benzhydrylamine; amino acid residues, such as those defined and exemplified above in relation to amino acid substituted alkyl esters;

saturated nitrogen-containing heterocyclic amines having 3-8 ring atoms, of which at least one ring atom is a nitrogen atom and other heteroatoms are selected from nitrogen, oxygen and sulphur; including but not limited to aziridine; azetidine; pyrrolidine; piperidine, morpholine, piperazine, azepine and azocine.

Amidine prodrugs of the compounds used in the present invention can be formed by reacting the compounds with a compound capable of reacting with an amidine functional group. Therefore, in a further aspect, the invention provides a pharmaceutically acceptable amidine prodrug of a compound of formula (I) as defined herein, either in its broadest aspect or a preferred aspect. In one embodiment, the invention provides a pharmaceutically acceptable amidine prodrug of 3-[2-(4-carbamimidoyl-phenylcarbamoyl)-5-methoxy-4-vinyl-phenyl]-6-(cyclopropylmethyl-carbamoyl)-pyridine-2-carboxylic acid.

Examples of amidine prodrugs include the following:

prodrugs wherein the amidine is bonded to a hydroxyl group;

prodrugs wherein the amidine is bonded to an alkyl group; such as those defined and exemplified above;

prodrugs with amino acid residues, where the amino acid residue is as defined and exemplified above in relation to amino acid substituted alkyl esters; examples of such prodrugs include valine amides; and carbamates, in particular alkyl carbamates, such as $C_{1-6}$ alkyl carbamates such as methyl, ethyl, propyl, isopropyl, butyl, isobutyl, sec-butyl, tert-butyl, pentyl or hexyl carbamates.

The prodrugs may themselves form salts and solvates. Examples of suitable salts and solvates include as those listed above in relation to pharmaceutically acceptable salts and solvates of the compounds of formula (I).

Particular examples of prodrugs of 3-[2-(4-carbamimidoyl-phenylcarbamoyl)-5-methoxy-4-vinyl-phenyl]-6-(cyclopropylmethyl-carbamoyl)-pyridine-2-carboxylic acid, including salts thereof, include those listed in Table 2 below.

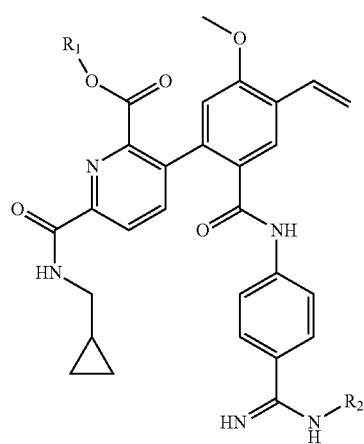

TABLE 2

| R₁ | R₂ | Salt form |
|---|---|---|
| H | H | HCl salt |
| Methyl (—CH₃) | H | HCl and MSA salt |
| Propyl (—CH₂CH₂CH₃) | H | HCl salt |
| 2-Hydroxyethyl (—CH₂CH₂OH) | H | HCl salt |
| Ethyl (—CH₂CH₃) | H | HCl salt |
| 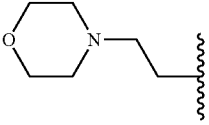<br>morpholinoethyl | H | HCl salt |
| 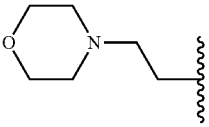<br>morpholinoethyl | 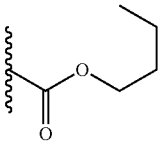<br>hexyl carbamate | HCl salt |
| Ethyl (—CH₂CH₃) | 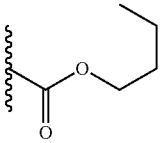<br>hexyl carbamate | Free base |
| H | —OH | Free base |
| 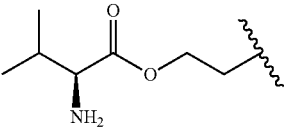<br>2-(Valine)ethyl | H | TFA salt |
| 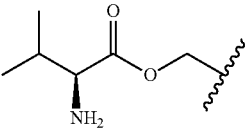<br>Valine methyl | H | TFA salt |
| 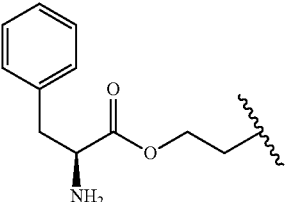<br>2-(phenylalanine)ethyl | H | TFA salt |
| 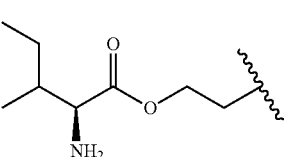<br>2-(isoluecine)ethyl | H | TFA salt |

TABLE 2-continued

| R₁ | R₂ | Salt form |
|---|---|---|
| 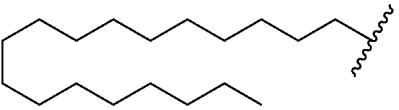<br>nonadecane<br>18-carbon fatty acid | H | HCl salt |
| 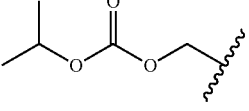<br>Isopropyl methyl carbonate | H | HCl salt |
| 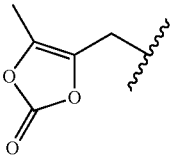<br>(5-methyl-2-oxo-1,3-dioxolene-4-yl) methyl | H | HCl salt |
|  | H | HCl salt |
|  | H | HCl salt |
| 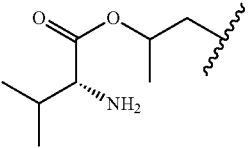<br>2-(Valine)propyl | H | HCl salt |
| Methyl (—CH₃) | 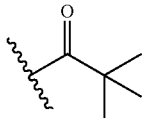<br>t-butyl amide | Free Base |
| Methyl (—CH₃) | 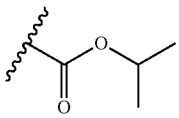<br>Isopropylcarbamate | Free Base |
| 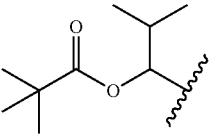<br>2-methyl-1-(pivaloyloxy)propyl | H | HCl salt |
| Methyl (—CH₃) | 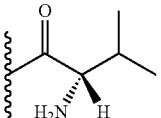<br>Valine amide | Free Base |

TABLE 2-continued

| R$_1$ | R$_2$ | Salt form |
|---|---|---|
| 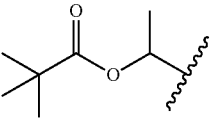<br>1-(pivaloyloxy)ethyl | H | HCl salt |
| 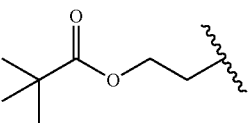<br>2-(pivaloyloxy)ethyl | H | HCl salt |

Compositions

The pharmaceutical compositions of the invention contain as the active ingredient a compound of formula (I), as defined herein, either in its broadest aspect or a preferred aspect, or a pharmaceutically acceptable salt, solvate, ester or prodrug thereof. In a particular aspect, the pharmaceutical compositions of the invention contain as the active ingredient a compound of formula (I). In another particular aspect, the pharmaceutical compositions of the invention contain as the active ingredient 3-[2-(4-carbamimidoyl-phenylcarbamoyl)-5-methoxy-4-vinyl-phenyl]-6-(cyclopropylmethyl-carbamoyl)-pyridine-2-carboxylic acid. In another particular aspect, the pharmaceutical compositions of the invention contain as the active ingredient 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride. In another particular aspect, the pharmaceutical compositions of the invention contain as the active ingredient crystalline Form A of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride. These compounds are described in this specification as "active ingredients", "APIs", or "active pharmaceutical ingredients".

The pharmaceutical compositions of the invention also contain excipients. In this specification the term 'excipient' is defined generally as meaning a pharmacologically inactive substance formulated with the active pharmaceutical ingredient. The nature of the excipients varies depending on various factors such as the nature and concentration of the active ingredient, the subject to be treated, and the intended mode of administration. As discussed above, the APIs of the present disclosure exhibit poor solubility and permeability characteristics, as well as poor stability characteristics. As a result, such compounds are predicted to be especially difficult to formulate into an effective, oral pharmaceutical composition that is capable of delivering a therapeutically effective amount of the API to a subject.

The present invention provides an oral formulation comprising the API and defined excipients that produce an oral formulation that is capable of delivering an effective amount of the API to a subject. In particular, the present provides an oral formulation that is capable of delivering an effective amount of 3-[2-(4-carbamimidoyl-phenylcarbamoyl)-5-methoxy-4-vinyl-phenyl]-6-(cyclopropylmethyl-carbamoyl)-pyridine-2-carboxylic acid or crystalline Form A of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride to a subject. In light of the art suggesting the difficulties in formulating such an oral formulation, this result was unexpected.

The pharmaceutical composition of the present invention may take a number of forms. In one aspect the pharmaceutical composition of the present invention is an oral composition.

In one aspect the pharmaceutical composition of the present invention is a liquid composition. In one aspect the pharmaceutical composition of the present invention is a liquid oral composition (i.e. a liquid composition suitable for oral delivery, containing the active ingredient and excipients suitable for administration by ingestion). In this specification the term 'liquid composition' includes any composition in which the active pharmaceutical ingredient is dispersed in a liquid matrix. The term 'liquid' is defined according to its usual meaning in the art, i.e. the state of matter with a definite volume but no fixed shape and typically capable of flowing under pressure. It is therefore envisaged within the scope of the present invention that the term 'liquid composition' includes suspensions, emulsions and solutions.

In one aspect the liquid pharmaceutical composition of the present invention is a solution. A solution is a homogeneous mixture composed of only one phase, in which the substance being dissolved (a solute) is dissolved in a liquid solvent. In particular, the liquid pharmaceutical composition of the present invention may be an oral solution (i.e. a solution containing the active ingredient and excipients suitable for administration by ingestion).

In one aspect the liquid pharmaceutical composition of the present invention is an emulsion. An emulsion is a mixture of two or more liquids that are normally immiscible, in which one liquid (the dispersed phase) is dispersed in the other (the continuous phase).

In one aspect the liquid pharmaceutical composition of the present invention is a suspension. A suspension is a heterogeneous mixture containing insoluble solid particles dispersed throughout a liquid (fluid), and in which the solid ultimately settles.

In one aspect the pharmaceutical composition of the present invention is a solid or semisolid composition. In one aspect the pharmaceutical composition of the present invention is a solid or semisolid oral composition (i.e. a solid or semisolid composition suitable for oral delivery). In this specification the term 'solid composition' includes any composition in which the active pharmaceutical ingredient is dispersed in a solid matrix. Similarly, the term 'semisolid composition' includes any composition in which the active pharmaceutical ingredient is dispersed in a semisolid matrix. The term 'solid' is defined as the state of matter with a fixed volume and fixed shape. Semi-solids are similar to solids in some respects (it can support its own weight and hold its shape), but also share some properties of liquids, such as shape conformity to something applying pressure to it, or the ability to flow under pressure.

Examples of solid compositions include solid dispersions (also known as solid solutions), in which the active pharmaceutical ingredient is dispersed either as a particulate or at the molecular level in a solid matrix—the matrix can be in the form of a semisolid or solid. Other examples include glasses and hot melt solutions, in which the product is dispersed in the molten state before cooling.

In one aspect the pharmaceutical composition of the present invention is a solid oral dosage form. In one aspect, the solid oral dosage form comprises a shell or housing (typically of pharmaceutically acceptable materials as described and exemplified below) containing a liquid composition of the present invention (as described and exemplified herein, particularly in the form of a solution, suspension or emulsion).

In another aspect, the solid oral dosage form comprises a shell or housing containing a solid composition of the present invention. Such solid dosage forms may contain, for example, solid dispersions of the active pharmaceutical ingredient and excipients.

In one aspect, the solid oral dosage form of the present invention is enteric coated.

An enteric coating is a barrier applied to oral medication that controls the location in the digestive system where it is absorbed. Most enteric coatings work by presenting a surface that is stable at the highly acidic pH found in the stomach, but breaks down rapidly at a less acidic (relatively more basic) pH. For example, enteric coatings will not dissolve in the acidic juices of the stomach (pH ~3), but will in the alkaline (pH 7-9) environment present in the small intestine. Materials used for enteric coatings include fatty acids, waxes, shellac, plastics, and plant fibres. Particular examples of materials used to form enteric coatings include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, and sodium alginate and stearic acid.

In one aspect, the pharmaceutical composition of the present invention is a capsule. Capsules are well known to those skilled in the art and typically comprise a shell capable of housing a solid or liquid composition, the shell comprising a material capable of being dissolved or degraded in vivo (in the gastrointestinal tract) to liberate the active ingredient.

The capsules may be hard capsules (also known as hard-shelled capsules) or soft capsules (also called beads or soft-shelled capsules). The shells of both hard and soft of capsules are typically made from materials capable of being dissolved or degraded in vivo (in the gastrointestinal tract) to liberate the active ingredient.

The material used to form the shell may be a gelling agent, in particular animal proteins such as gelatin; plant polysaccharides or their derivatives like carrageenans; natural or modified forms of starch and cellulose (in particular amylopectin, hydroxypropyl starch or hydroxypropylmethyl cellulose, HPMC); and polymers (in particular polyvinyl alcohol, PVA). Other ingredients can be added to the shell material solution like plasticizers such as glycerin and/or sorbitol to decrease the capsule's hardness, opacifying agents, flavourings, sweeteners, colouring agents, preservatives, disintegrants, lubricants and surface treatment.

In one aspect, the material used to form the shell comprises or consists of gelatin. Gelatin is a mixture of peptides and proteins typically produced by partial hydrolysis of collagen, a protein typically extracted from the skin, boiled crushed horn, hoof and bones, connective tissues, organs and some intestines of animals such as domesticated cattle, fish, chicken, pigs, and horses. The gelatin may also be modified as is known in the art to provide desired properties to the gelatin (for example, succinylated gelatin for use with reactive fill ingredients).

In another aspect, the material used to form the shell comprises or consists of a material other than gelatin. Examples of hard capsules formed from non-gelatin shells include EcoCaps™ from Banner, the plant-derived VegiCaps™ from Catalent and Vegisoft™ from EuroCaps, and LiCaps™ from Capsugel. Examples of soft capsules formed from non-gelatin shells include Enteric softgels from Banner.

In one embodiment, the capsule is a hard capsule (especially a hard gelatin capsule). Typically, such hard capsules comprise empty upper and lower shells formed of rigid shell material. The formation of such capsules is a separate process and requires separate equipment from capsule filling. Typically, the bottom capsule shell is filled with the drug formulation, then the top capsule shell is placed over the lower filled shell.

In one aspect, the material used to form the capsule can be defined by its "Bloom" value (or Bloom strength). Bloom is a test to measure the strength of a gel or gelatin. The test was originally developed and patented in 1925 by O. T. Bloom (U.S. Pat. No. 1,540,979). This value is a measure of the force, expressed in grams, necessary to depress by 4 mm the surface of a gelatin or gel with a standard plunger, which typically has a diameter of 1.27 cm (0.5 inch). To perform the Bloom test on gelatin, a 6.67% gelatin solution is typically kept for 17-18 hours at 10° C. prior to being tested. Higher Bloom gelatins form stronger gels than lower Bloom gelatins (at the same concentration).

In one aspect, the Bloom strength of gelatin used in hard capsules is in the range of 200-270 bloom-grams (as typically measured according to the test described above).

In another aspect, the material used to form the capsule can be defined by its moisture level. The moisture level is typically measured with a Karl Fischer titration. This is a technique to determine the concentration of a substance in solution by adding to it a standard reagent of known concentration in carefully measured amounts until a reaction of definite and known proportion is completed, as shown by a colour change or by electrical measurement, and then calculating the unknown concentration. The technique was first described in K. Fischer *Angew. Chem.* (1935) 48 (26): 394-396. In one aspect, the moisture level in capsule of such hard capsules is in the range 12% to 16% (as typically measured according to the test described above).

In one embodiment, the capsule is a soft capsule (especially a soft gelatin capsule). Typically, such a capsule takes the form of a single sealed flexible shell that contains the drug. In contrast to hard capsules, the process of forming soft capsules, comprising forming the shell and filling the shell with the drug formulation, can be achieved in a single process step. Typically this is carried out by forming sheets of the shell material, running the sheet through a mold to form a cavity, filling the cavity with the drug formulation, sealing the filled cavity, cutting/clipping the capsule from the gelatin ribbon, and drying. The formation of soft gelatin capsules is described in more detail by G. Reich in "Formulation and physical properties of soft capsules", Pharmaceutical Capsules, Chapter 11, page 201, Pharmaceutical Press, Second Edition, 2004.

In one aspect, the Bloom strength of gelatin used in soft capsules is in the range of 150-180 bloom-grams (as typically measured according to the test described above). In one aspect, the moisture level in capsule of such soft capsules is in the range 6% to 10% (typically measured with a Karl Fischer titration as described above).

The materials used to form the shells of soft capsules may comprise or consist of gelatin, as described above. Alternatively, the materials used to form the shells of soft capsules may comprise or consist of non-gelatin materials, which may be natural, semi-synthetic or synthetic; examples of such materials include carrageenan, starch, modified starches, and polyvinyl alcohol.

Excipients

The compositions of the present disclosure, including the forms described above, comprise one or more excipients. The excipients may serve to solubilize the API, provide for increased permeability of the API and/or provide for increased stability of the API. In one aspect, the excipients may serve to solubilize the API, provide for increased permeability of the API and provide for increased stability of the API. In another aspect, the excipients may serve to solubilize the API and provide for increased permeability of the API. In another aspect, the excipients may serve to solubilize the API and provide for increased stability of the API.

As discussed above, the compounds of the present disclosure are difficult to formulate into a composition/formulation suitable for oral delivery in which an effective amount or a therapeutically effective amount of the compound will be delivered to a subject. Through the use of the excipients described herein, the problem of a formulation suitable for oral delivery in which an effective amount or a therapeutically effective amount of the compound will be delivered to a subject has been solved.

In particular, it has been unexpectedly found that use of the excipients according to the present invention enables the API used in the present invention to dissolve at a concentration sufficient to produce an oral formulation that is capable of being contained in a dosage form (particularly although not exclusively a capsule, such as a hard gel or soft gel capsule) which on administration to a subject can achieve therapeutic plasma levels when dosed at 1 to 4 times per day, or once or twice daily. This is considered unexpected in view of the fact the APIs of the present disclosure were predicted to be difficult to formulate based on the BDDCS (Class IV with low solubility and low permeability) and the Lipinski Rule. Therefore, the excipients described herein provide a novel solution to the technical problem of formulating the APIs described into an oral formulation that is capable of being contained in a dosage form (particularly although not exclusively a capsule, such as a hard gel or soft gel capsule) which on delivery to a subject can achieve therapeutic plasma levels when dosed at 1 to 4 times per day, or once or twice daily. The prior art generally delivers such APIs via parenteral administration.

In initial formulation work for the amidine compounds described herein, in particular 3-[2-(4-carbamimidoyl-phenylcarbamoyl)-5-methoxy-4-vinyl-phenyl]-6-(cyclopropylmethyl-carbamoyl)-pyridine-2-carboxylic acid, extensive studies were carried out to identify a suitable mixture of excipients to produce the oral formulation described herein.

Specifically, a variety of approaches were taken to develop suitable oral formulations of 3-[2-(4-carbamimidoyl-phenylcarbamyl)-5-methoxy-4-vinyl-phenyl]-6-(cyclopropylmethyl-carbamoyl)-pyridine-2-carboxylic acid. The approaches taken included use of a variety of hydrophilic polymers, including α-cyclodextrin and a polyanionic β-cyclodextrin derivative with a sodium sulfonate salt separated from the lipophilic cavity by a butyl ether or sulfobutylether spacer group in combination with a variety of co-solvents. In addition, the compound was evaluated in formulations created by a number of different technologies (such as dry blends, nanosuspensions, solid dispersion and emulsions) using a variety of approaches.

In each case, the results of these initial evaluations resulted in formulations in which the concentrations of 3-[2-(4-carbamimidoyl-phenylcarbamoyl)-5-methoxy-4-vinyl-phenyl]-6-(cyclopropylmethyl-carbamoyl)-pyridine-2-carboxylic acid were less than 10.5 mg/ml. Furthermore, there was significant variability from animal to animal in initial pharmacokinetic studies.

In contrast, the novel excipient mixtures of the present invention allow 3-[2-(4-carbamimidoyl-phenylcarbamoyl)-5-methoxy-4-vinyl-phenyl]-6-(cyclopropylmethyl-carbamoyl)-pyridine-2-carboxylic acid to achieve concentrations of at least 100 mg/ml and pharmacokinetic variability was reduced in both animal and human studies (as described herein). As a result, through the use of the excipient mixtures described herein, oral formulations of 3-[2-(4-carbamimidoyl-phenylcarbamoyl)-5-methoxy-4-vinyl-phenyl]-6-(cyclopropylmethyl-carbamoyl)-pyridine-2-carboxylic acid and generally compounds of the formula (I), (I') or (II) can be produced which on delivery to a subject can achieve therapeutic plasma levels of the compounds.

In one embodiment, the invention comprises an oral pharmaceutical composition, including an oral liquid pharmaceutical composition, comprising i) an effective amount of a compound of formula (I), as defined herein, or a pharmaceutically acceptable salt, solvate, ester or prodrug thereof and ii) a mixture of excipients. Such a mixture of excipients are described below and produce an oral formulation, including an oral liquid formulation, capable of being contained in a dosage form (particularly although not exclusively a capsule, such as a hard gel or soft gel capsule) which on delivery to a subject can achieve therapeutic plasma levels when dosed at 1 to 4 times per day, 1 to 3 times per day or once or twice daily. The oral pharmaceutical composition can be any of the forms described above or herein. In a particular aspect, the oral pharmaceutical composition comprises an effective amount of the compounds of formula (I). In another particular aspect, the oral pharmaceutical composition comprises an effective amount of 3-[2-(4-carbamimidoyl-phenylcarbamoyl)-5-methoxy-4-vinyl-phenyl]-6-(cyclopropylmethyl-carbamoyl)-pyridine-2-carboxylic acid. In another particular aspect, the oral pharmaceutical composition comprises an effective amount of 3-[2-(4-carbamimidoyl-phenylcarbamoyl)-5-methoxy-4-vinyl-phenyl]-6-(cyclopropylmethyl-carbamoyl)-pyridine-2-carboxylic acid hydrochloride. In a further particular aspect, the oral pharmaceutical composition comprises an effective amount of Form A.

In one embodiment, the mixture of excipients comprises 1 to 99% of at least one polar protic solvent selected from the group consisting of a $C_{3-6}$ diol, a poly($C_{2-3}$) alkylene glycol having a number average molecular weight (Mn) of 200 to 1000 and a $C_{2-6}$ monoalcohol and 1-50% of at least one co-solvent (as defined herein). In one embodiment, the mixture of excipients comprises 1 to 99% of at least one polar protic solvent selected from the group consisting of a $C_{3-6}$ diol and a poly($C_{2-3}$) alkylene glycol having a number average molecular weight (Mn) of 200 to 1000 and 1-50% of at least one co-solvent (as defined herein). In one aspect, the co-solvent is a vitamin E, citric acid or a substituted phenol (i.e. a benzene ring substituted with 1 to 3 hydroxyl groups) which is further substituted with at least one tertiary alkyl group (preferably a tert-butyl group) or an alkyl ester (preferably a propyl ester) and, optionally, a ($C_{1-4}$) alkyl and/or a ($C_{1-4}$) alkoxy group present at 0.1 to 10%, a $C_{10-18}$ alkyl sulphate present at 0.1 to 7.5%, a vitamin E poly($C_{2-3}$)alkylene glycol dicarboxylic ester present at 1 to 50%. In one aspect, the co-solvent is a vitamin E present at 0.1 to 10% and a vitamin E poly($C_{2-3}$)alkylene glycol dicarboxylic ester present at 1 to 50%.

The foregoing are expressed as a percentage of the total weight of the mixture of excipients (i.e., excluding the active ingredient).

Solvents

In particular, it has been unexpectedly found by the present inventors that use of a polar organic solvent according to the present invention enables the active pharmaceutical ingredients used in the present invention to dissolve at a concentration sufficient such that the resulting liquid composition is capable of being contained in a dosage form (particularly although not exclusively a capsule, such as a hard gel or soft gel capsule) which can achieve therapeutic plasma levels when dosed at 1 to 4 times per day or 1 to 3 times per day, and potentially even once or twice daily. This is considered unexpected in view of the low solubility and permeability of APIs in Class IV of the BDDCS, which are very difficult to formulate into oral dosage forms and are as a result generally administered parenterally.

In one aspect, the polar organic solvent is a polar protic solvent. A polar protic solvent is a solvent that has a hydrogen atom bound to an oxygen or a nitrogen atom. In one aspect, the polar protic solvent contains one or more functional groups capable of hydrogen-bonding. Such functional groups include O—H and/or N—H groups. Examples of classes of hydrophilic organic solvents include alcohols (including glycols, diols and polyols) and amides. In one embodiment the polar organic solvent is not dimethyl sulfoxide.

In one embodiment, the polar organic solvent is present in an amount of 0.1% to 99.9% by weight of the total weight of the composition. In certain aspects, the polar organic solvent is present in an amount of 1% to 99%, 50% to 90%, 50% to 99%, 70% to 99%, 80% to 99%, 90% to 99%, 95% to 99%, 20% to 80%, 50% to 80%, 65% to 85% or 70% to 75% expressed as a percentage of the total weight of the mixture of excipients (i.e., excluding the active ingredient). In one embodiment, the polar organic solvent is present in an amount of 65% to 85% expressed as a percentage of the total weight of the mixture of excipients (i.e., excluding the active ingredient). In one embodiment, the polar organic solvent is present in an amount of 70% to 75% expressed as a percentage of the total weight of the mixture of excipients (i.e., excluding the active ingredient). In one embodiment, the polar organic solvent is present in an amount of 72.7% expressed as a percentage of the total weight of the mixture of excipients (i.e., excluding the active ingredient).

In one embodiment, the polar protic solvent may be at least one of $C_{3-6}$ diol, a poly($C_{2-3}$) alkylene glycol having a number average molecular weight (Mn) of 200 to 1000 and a $C_{2-6}$ monoalcohol, where the polar protic solvent is present at 1-99% (or any of the subranges disclosed in the preceding paragraph) expressed as a percentage of the total weight of the mixture of excipients (i.e. excluding the active ingredient). In one embodiment, the polar protic solvent lacks a $C_{2-6}$ monoalcohol. In one embodiment of any of the foregoing, the polar protic solvent is a mixture of a $C_{3-6}$ diol and a poly($C_{2-3}$) alkylene glycol having a number average molecular weight (Mn) of 200 to 1000. In one embodiment of any of the foregoing, the polar protic solvent is a poly($C_{2-3}$) alkylene glycol having a number average molecular weight (Mn) of 200 to 1000. In one embodiment of any of the foregoing, the polar protic solvent is a mixture of a $C_{3-6}$ diol, a poly($C_{2-3}$) alkylene glycol having a number average molecular weight (Mn) of 200 to 1000 and a $C_{2-6}$ monoalcohol. In certain aspects the polar protic solvent is present from 1% to 99%, 50% to 90%, 50% to 99%, 70% to 99%, 80% to 99%, 90% to 99%, 95% to 99%, 20% to 80%, 50% to 80%, 65% to 80% or 70% to 75% (expressed as a percentage of the total weight of the mixture of excipients, i.e. excluding the active ingredient). In one embodiment, the polar protic solvent is present in an amount of 65% to 85% expressed as a percentage of the total weight of the mixture of excipients (i.e., excluding the active ingredient). In one embodiment, the polar protic solvent is present in an amount of 70% to 75% expressed as a percentage of the total weight of the mixture of excipients (i.e., excluding the active ingredient). In one embodiment, the polar protic solvent is present in an amount of 72.7% expressed as a percentage of the total weight of the mixture of excipients (i.e., excluding the active ingredient).

In certain aspects, a representative $C_{3-6}$ diol includes propylene glycol, such as 1,2-propanediol (α-propylene glycol), representative poly($C_{2-3}$) alkylene glycols include polyethylene glycol and polypropylene glycol and representative $C_{2-6}$ monoalcohols include ethanol.

Alcohols

In one embodiment, the polar organic solvent comprises an alcohol or a mixture thereof. In one embodiment, the polar organic solvent comprises a pharmaceutically acceptable alcohol or a mixture thereof. Pharmaceutically acceptable alcohols are those considered non-toxic when consumed in normal daily amounts and in normal pharmaceutical dosage forms, and include, but are not limited to, those alcohols generally recognized as safe (GRAS) by the Food & Drug Administration. In certain embodiment, the alcohol, particularly $C_{2-6}$ monoalcohols, are also considered co-solvents and may be described as such, for example, in certain embodiments where the mixture of excipients is expressed as percentages by weight based on the total weight of the excipient mixture (excluding the active ingredient).

In one embodiment, the alcohol comprises or consists of a $C_{2-6}$ monoalcohol or a mixture thereof. $C_{2-6}$ monoalcohols are advantageous in the present invention in that they are both capable of solubilizing the compounds used therein and are themselves soluble in physiological fluids, thus having the potential to addressing both the solubility and absorption problems associated with these compounds. Examples of $C_{2-6}$ monoalcohols include ethanol, 1-propanol; 2-propanol, 1-butanol, 2-butanol, isobutanol, sec-butanol, tert-butanol, 1-pentanol, 2-pentanol, 3-pentanol, 1-hexanol, 2-hexanol and 3-hexanol. Suitably, the alcohol comprises or consists of a $C_{2-4}$ monoalcohol or a mixture thereof, especially ethanol, 1-propanol, 2-propanol, or a mixture thereof.

When the $C_{2-6}$ monoalcohol, such as ethanol, is present as part of a mixture of polar organic solvents (especially a mixture of polar protic solvents), the $C_{2-6}$ monoalcohol may comprise from 0.01% to 99.99%, such as 0.05 to 50%, such as 0.1 to 25%, such as 0.5 to 2.5%, such as 2 to 6%, such as 2.5 to 5%, such as 0.2 to 10%, such as 0.5 to 5%. These percentages are expressed by weight as a proportion of the total weight of all of the polar protic solvents present in the mixture (excluding the active ingredient and any other excipients).

Furthermore, when the $C_{2-6}$ monoalcohol, such as ethanol, is present as part of a mixture of polar organic solvents (especially a mixture of polar protic solvents), the $C_{2-6}$ monoalcohol may comprise from 0.1 to 10%, 0.1 to 1%, 0.5 to 7.5%, 0.5 to 2.5%, 2 to 6%, 3 to 5%, 2.5% or 5%. In one aspect, the $C_{2-6}$ monoalcohol may comprise from 2.5 to 5%, or 2.5% or 5%. The above percentages are expressed by weight as a proportion of the total weight of all of the mixture of excipients (excluding the active ingredient).

In one particular embodiment, the monoalcohol is ethanol. Ethanol, especially when part of a mixture of polar protic solvents, is capable of dissolving the compound 3-[2-(4-carbamimidoyl-phenylcarbamoyl)-5-methoxy-4-vinyl-phenyl]-6-(cyclopropylmethyl-carbamoyl)-pyridine-2-carboxylic acid at high concentrations which enable the compound to be included in single unit doses (such as filled gelatin capsules). Ethanol is also non-toxic when consumed in amounts typical in pharmaceutical compositions.

When ethanol is present as part of a mixture of polar organic solvents (especially a mixture of polar protic solvents) used to form liquid oral formulations (particularly oral solutions), the ethanol may comprise up to 50% of the mixture, such as up to 25%, such as up to 10%, such as up to 7.5%, such as up to 5%, such as up to 4%, such as up to 3.5%, such as up to 3%, such as up to 2.5%, such as up to 2%, such as up to 1.5%, such as up to 1%, such as up to 0.5%. These percentages are expressed by weight as a proportion of the total weight of all of the polar protic solvents present in the mixture (excluding the active ingredient and any other excipients).

When ethanol is present as part of a mixture of polar organic solvents (especially a mixture of polar protic solvents) for liquid formulations contained in solid oral dosage forms (especially capsules, such as hard or soft gel capsules), the ethanol may comprise up to 10%, such as up to 7.5%, such as up to 6%, such as up to 5%, such as up to 4%, such as up to 3.5%, such as up to 3%, such as up to 2.5%, such as up to 2%, such as up to 1.5%, such as up to 1%, such as up to 0.5% of the mixture. These percentages are expressed by weight as a proportion of the total weight of all of the polar protic solvents present in the mixture (excluding the active ingredient and any other excipients). In particular, ethanol in a proportion of up to 2.5% or 7.5% of a mixture of solvents is suitable for a solution for filling soft gelatin capsules. In some embodiments, the ethanol may comprise 0.01 to 10%, such as 0.02 to 7.5%, such as 0.05 to 5% of the mixture of solvents. In one embodiment, the mixture of polar organic solvents comprises 1 to 10% ethanol. In one embodiment, the mixture of polar organic solvents comprises 0.5 to 2% ethanol. In one embodiment, the mixture of polar organic solvents comprises 3 to 7% ethanol. These percentages are expressed by weight as a proportion of the total weight of excipients present in the mixture (excluding the active ingredient).

Polyol and Diol

In one embodiment, the polar organic solvent comprises, consists essentially of or consists of a $C_{3-6}$ polyol or a mixture thereof other than a diol. In one embodiment, the polar organic solvent comprises, consists essentially of or consists of a $C_{3-6}$ diol or a mixture thereof. In one embodiment, the polar organic solvent comprises, consists essentially of or consists of a pharmaceutically acceptable $C_{3-6}$ polyol or a mixture thereof. In one embodiment, the polar organic solvent comprises, consists essentially of or consists of a pharmaceutically acceptable $C_{3-6}$ diol or a mixture thereof. Pharmaceutically acceptable $C_{3-6}$ polyols and diols are those considered non-toxic when consumed in normal daily amounts and in normal pharmaceutical dosage forms, and include, but are not limited to, those alcohols generally recognized as safe (GRAS) by the Food & Drug Administration. $C_{3-6}$ polyols and diols are also advantageous in the present invention in that they are both capable of solubilizing the compounds used therein and are themselves soluble in physiological fluids, thus having the potential to address both the solubility and permeability problems associated with these compounds. Examples of $C_{3-6}$ diols include but not limited to 1,2-propanediol (α-propylene glycol), 1,3-propanediol (β-propylene glycol), 1,2-butanediol, 2,3-butanediol, 1,3-butanediol, 1,4-butanediol, 1,2-pentanediol, 1,5-pentanediol, 1,2-hexanediol and 1,6-hexanediol. Examples of $C_{3-6}$ polyols include $C_{3-6}$ triols including but not limited to glycerol. Mixtures of any of the foregoing may also be used. In one embodiment the polar organic solvent comprises, consists essentially of or consists of a $C_{3-6}$ polyols and a $C_{3-6}$ diol, such as 1,2-propanediol, glycerol, or a mixture thereof.

In one particular embodiment, the $C_{3-6}$ diol is 1,2-propanediol (α-propylene glycol). It has surprisingly been found by the present inventors that 1,2-propanediol, especially when part of a mixture of polar protic solvents, is capable of dissolving the compound 3-[2-(4-carbamimidoyl-phenylcarbamoyl)-5-methoxy-4-vinyl-phenyl]-6-(cyclopropylmethyl-carbamoyl)-pyridine-2-carboxylic acid at concentrations of up to 140 mg/ml. Dissolution at such high concentrations enables the compound to be formulated as a solution in single unit dosage forms (in particular but not limited to a solution for filling hard or soft gelatin capsules). 1,2-propanediol is also soluble in physiological fluids. These properties of the solvent address both the solubility and absorption problems faced by this particular compound. 1,2-propanediol is also non-toxic when consumed in amounts typical in pharmaceutical compositions.

In the described formulations, the $C_{3-6}$ diol, such as 1,2-propanediol, may be present at 0% to 40%, 0.1% to 10%, 1% to 25%, 10% to 20%, 2.5% to 7.5%, 1% or 20%. In one aspect, the $C_{3-6}$ diol may be present at 0.1% to 10%, 2.5% to 25%, 20% to 40%, 5% or 20%. The above percentages are expressed by weight as a proportion of the total weight of all of the mixture of excipients (excluding the active ingredient).

In one embodiment, 1,2-propanediol may be the sole polar organic solvent present in the composition. In another embodiment 1,2-propanediol may be present as part of a mixture of polar organic solvents (especially a mixture of polar protic solvents). In particular, 1,2-propanediol may be present as part of a mixture with a poly($C_{2-3}$) alkylene glycol having a number average molecular weight (Mn) of 200 to 1000. In this embodiment, the 1,2-propanediol may comprise up to 99%, such as up to 98%, such as up to 97%, such as up to 96%, such as up to 95%, such as up to 90%, such as up to 85%, such as up to 80%, such as up to 75%, such as up to 70%, such as up to 65%, such as up to 60%, such as up to 55%, such as up to 50%, such as up to 45%, such as up to 40%, such as up to 35%, such as up to 30%, such as up to 25%, such as up to 20%, such as up to 15%, such as up to 10%, such as up to 5%, such as up to 4%, such as up to 3%, such as up to 2%, such as up to 1% of the mixture of polar organic solvents. In this embodiment, the 1,2-propanediol may comprise at least 1%, such as at least 2%, such as at least 3%, at least 4%, such as at least 5%, such as at least 10%, such at least 15%, such as at least 20%, such as at least 25%, such as at least 30%, such as at least 35%, such as at least 40%, such as at least 45%, such as at least 50%, such at least 55%, such as at least 60%, such as at least 65%, such as at least 70%, such as at least 75%, such as at least 80%, such as at least 85%, such as at least 90%, such at least 95%, such as at least 97%, such as at least 98%, such as at least 99% of the mixture of polar protic solvents. In one embodiment, the mixture of polar organic solvents comprises 0.1% to 10%, 20% to 50% or 5% to 25% of 1,2-propanediol. In one embodiment, the mixture of polar organic solvents comprises 10% to 25% of 1,2-propanediol. In one embodiment, the mixture of polar organic solvents comprises 0.1 to 5% of 1,2-propanediol. In one embodiment, the mixture of polar organic solvents comprises 25% to 50% of 1,2-propanediol. These percentages are expressed by weight as a proportion of the total weight of all of the polar protic solvents present in the mixture (excluding the active ingredient and any other excipients).

When 1,2-propanediol is present as part of a mixture of polar organic solvents (especially a mixture of polar protic solvents) used to form liquid oral formulations (particularly oral solutions), it has been found that 1,2-propanediol in a proportion of up to 75% of a mixture of solvents is particularly suitable for use in an oral solution formulation of the active compounds used in the present invention. In this embodiment, the 1,2-propanediol may comprise 0.01% to 75%, such as 0.05% to 70%, such as 0.1% to 65%, such as 0.2% to 60%, such as 0.5% to 55%, such as 1% to 50%, such as 10% to 75%, such as 20% to 65%, such as 30% to 50% or such as 50% to 75%, of the mixture of polar organic solvents. These percentages are expressed by weight as a proportion of the total weight of all of the polar protic solvents present in the mixture (excluding the active ingredient and any other excipients).

When 1,2-propanediol is present as part of a mixture of polar organic solvents (especially a mixture of polar protic solvents) for liquid formulations contained in solid oral dosage forms (especially capsules, such as hard or soft gel capsules), it has also been found that 1,2-propanediol in a proportion of up to 50% of a mixture of such solvents is particularly suitable for use in a solution for filling liquid filled capsules (particularly in a solution for filling soft gelatin capsules). In this embodiment, the 1,2-propanediol may comprise 0.01% to 50%, such as 5% to 25%, 25% to 50%, 30% to 40%, 10% to 21%, 0.1% to 10% or 0.1% to 5% of the mixture of polar organic solvents. These percentages are expressed by weight as a proportion of the total weight of all of the polar protic solvents present in the mixture (excluding the active ingredient and any other excipients). In particular, it has been found that, when present in these amounts, the 1,2-propanediol, in addition to its ability to dissolve the compound 3-[2-(4-carbamimidoyl-phenylcarbamoyl)-5-methoxy-4-vinyl-phenyl]-6-(cyclopropylmethyl-carbamoyl)-pyridine-2-carboxylic acid, is both compatible with a soft gel formulation and capable of acting as an absorption enhancer.

($C_{2-3}$) Alkylene Glycol

In one embodiment, the polar organic solvent comprises, consists essentially of or consists of a ($C_{2-3}$) alkylene glycol or a mixture thereof. In one embodiment, the polar organic solvent comprises, consists essentially of or consists of a pharmaceutically acceptable ($C_{2-3}$) alkylene glycol or a mixture thereof. Pharmaceutically acceptable ($C_{2-3}$) alkylene glycols are those considered non-toxic when consumed in normal daily amounts and in normal pharmaceutical dosage forms, and include, but are not limited to, those ($C_{2-3}$) alkylene glycols generally recognized as safe (GRAS) by the Food & Drug Administration. In this specification the term "poly($C_{2-3}$)alkylene glycol" generally means a compound having the general formula:

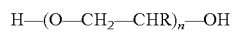

wherein R is H or methyl, and n is at least 2. When R is H, the compound is a polyethylene glycol. When R is methyl, the compound is a polypropylene glycol.

In one embodiment, the polar organic solvent comprises or consists of a poly($C_{2-3}$) alkylene glycol having a number average molecular weight (Mn) of less than 10,000 or a mixture thereof. Such poly($C_{2-3}$)alkylene glycols are also advantageous in the present invention in that they are generally liquid (or low melting point solid), non-toxic and therefore pharmaceutically acceptable, and both solubilize the compounds used therein and are themselves soluble in physiological fluids, thus having the potential to address both the solubility and permeability problems associated with these compounds. The active pharmaceutical ingredient is also sufficiently stable in certain poly($C_{2-3}$)alkylene glycols (particularly when in especially pure forms) thus removing the requirement for an additional stabilizer or allowing the use of a lower amount of a stabilizer.

The poly($C_{2-3}$) alkylene glycol may be a liquid or a solid. When the poly($C_{2-3}$) alkylene glycol is a solid, it is preferably soluble in polar protic solvents (particularly ethanol or 1,2-propanediol). In one embodiment, the poly($C_{2-3}$)alkylene glycol is a liquid.

In the described formulations, the poly($C_{2-3}$) alkylene glycol may be present at 1% to 99%, 90% to 99%, 10% to 90%, 30% to 70%, 40% to 60%, 45% to 55%, 60% to 75%, 72.7%, 62.5% or 52.5%. In one aspect, the poly($C_{2-3}$) alkylene glycol may be present at 90%-99%, to 55%, 60% to 75%, 72.7%, 62.5% or 52.5%. The above percentages are expressed by weight as a proportion of the total weight of all of the mixture of excipients (excluding the active ingredient). In one embodiment, the ($C_{2-3}$) alkylene glycol or a mixture thereof is the sole polar organic solvent present.

In this specification the term "polyethylene glycol" generally means a compound having the general formula:

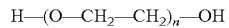

wherein n is at least 2. Typically, n ranges from 2 to 24, such as 4 to 22, such as 8 to 16, such as 8 to 10 or 12 to 14. In one embodiment the polyethylene glycol is linear. In another embodiment the polyethylene glycol is branched.

In this specification the term "polyethylene glycol", when followed by a number means a compound having the general formula above, wherein n is such that the number average molecular weight $M_n$ is the stated number in g/mol (with a typical tolerance of ±10%, preferably ±5%). For example, the term "polyethylene glycol 400" means polyethylene glycol (as defined above) having a number average molecular weight in the range 360 to 440 g/mol, preferably 380 to 420 g/mol, and the term "polyethylene glycol 600" means polyethylene glycol (as defined above) having a number average molecular weight in the range 540 to 660 g/mol, preferably 570 to 630 g/mol. The average molecular weight of the polyethylene glycol may range from 180 to 1050 g/mol, such as 280 to 720 g/mol, such as 360 to 660 g/mol, such as 380 to 420 g/mol or 570 to 630 g/mol.

Examples of polyethylene glycols suitable for use in the present invention include polyethylene glycol 200, polyethylene glycol 300, polyethylene glycol 400, polyethylene glycol 500, polyethylene glycol 600, polyethylene glycol 700, polyethylene glycol 800, polyethylene glycol 900, polyethylene glycol 1000 and mixtures thereof In one aspect; the poly($C_{2-3}$) alkylene glycol is a polyethylene glycol having a number average molecular weight (Mn) of 200 to 1000 and may be present at 1% to 99%, 90% to 99%, 10% to 90%, 30% to 70%, 40% to 60%, 45% to 55%, 60% to 75%, 72.7%, 62.5% or 52.5%. In another aspect, the polyethylene glycol having a number average molecular weight (Mn) of 200 to 1000 may be present at 90-99%, 45 to 55%, 60% to 75%, 72.7%, 62.5% or 52.5%. The above percentages are expressed by weight as a proportion of the total weight of all of the mixture of excipients (excluding the active ingredient).

In one embodiment, the polyethylene glycol has a number average molecular weight ($M_n$) of less than 8000. In one embodiment, the polyethylene glycol has a number average molecular weight ($M_n$) of less than 6000. In one embodiment, the polyethylene glycol has a number average molecular weight ($M_n$) of less than 4000. In one embodiment, the polyethylene glycol has a number average molecular weight ($M_n$) of less than 2000. In one embodiment, the polyethylene glycol has a number average molecular weight ($M_n$) of less than 1000.

When the composition contains a polyethylene glycol having a number average molecular weight ($M_n$) of greater than 1000, such polyethylene glycols typically comprise up to 75%, such as up to 50%, such as up to 40%, such as up to 30%, such as up to 25%, such as up to 20%, such as up to 15%, such as up to 10%, such as up to 5%, such as up to 4%, such as up to 3%, such as up to 2%, such as up to 1%, by weight of the total weight of the excipients (excluding the active ingredient).

In one embodiment, the polyethylene glycol may be the sole polar organic solvent present in the composition. In such an embodiment, the polyethylene glycol may comprise 40% to 65% by weight (expressed as a percentage of the total weight of the excipients excluding the active ingredient). In another embodiment, the polyethylene glycol may comprise 60% to 75% by weight (expressed as a percentage of the total weight of the excipients excluding the active ingredient). In another embodiment, the polyethylene glycol may comprise 70% to 80% by weight (expressed as a percentage of the total weight of the excipients excluding the active ingredient).

In another embodiment polyethylene glycol may be present as part of a mixture of polar organic solvents (especially a mixture of polar protic solvents). In one embodiment, the polyethylene glycol may be may be present as part of a mixture with $C_{3-6}$ diol, such as 1,2-propanediol. In this embodiment, the polyethylene glycol may comprise up to 99%, such as up to 98%, such as up to 97%, such as up to 96%, such as up to 95%, such as up to 90%, such as up to 85%, such as up to 80%, such as up to 75%, such as up to 70%, such as up to 65%, such as up to 60%, such as up to 55%, such as up to 50%, such as up to 45%, such as up to 40%, such as up to 35%, such as up to 30%, such as up to 25%, such as up to 20%, such as up to 15%, such as up to 10%, such as up to 5%, such as up to 4%, such as up to 3%, such as up to 2%, such as up to 1% of the mixture. These percentages are expressed by weight as a proportion of the total weight of all of the polar protic solvents present in the mixture (excluding the active ingredient and any other excipients). In this embodiment, the polyethylene glycol may comprise at least 1%, such as at least 2%, such as at least 3%, at least 4%, such as at least 5%, such as at least 10%, such at least 15%, such as at least 20%, such as at least 25%, such as at least 30%, such as at least 35%, such as at least 40%, such as at least 45%, such as at least 50%, such at least 55%, such as at least 60%, such as at least 65%, such as at least 70%, such as at least 75%, such as at least 80%, such as at least 85%, such as at least 90%, such at least 95%, such as at least 97%, such as at least 98%, or such as at least 99% of the mixture. In one embodiment, the mixture of polar organic solvents comprises 30% to 90% of polyethylene glycol. In one embodiment, the mixture of polar organic solvents comprises 90% to 99.9% of polyethylene glycol. In one embodiment, the mixture of polar organic solvents comprises 50% to 85% of polyethylene glycol. In one embodiment, the mixture of polar organic solvents comprises 40% to 65% of polyethylene glycol. In one embodiment, the mixture of polar organic solvents comprises 60% to 75% of polyethylene glycol. In one embodiment, the mixture of polar organic solvents comprises 75% to 95% of polyethylene glycol. In one embodiment, the mixture of polar organic solvents comprises 50% of polyethylene glycol. These percentages are expressed by weight as a proportion of the total weight of all of the polar protic solvents present in the mixture (excluding the active ingredient and any other excipients).

In one embodiment, the polyethylene glycol comprises or consists of a polyethylene glycol having a number average molecular weight ($M_n$) of less than 1000 or a mixture thereof. Examples of polyethylene glycols suitable for use in the present invention include polyethylene glycol 200, polyethylene glycol 300, polyethylene glycol 400, polyethylene glycol 500, polyethylene glycol 600, polyethylene glycol 700, polyethylene glycol 800, polyethylene glycol 900, and mixtures thereof. In one embodiment the polyethylene glycol is polyethylene glycol 400 or polyethylene glycol 600, or a mixture thereof. In one particular embodiment, the polyethylene glycol is polyethylene glycol 400. In one particular embodiment, the polyethylene glycol is polyethylene glycol 600.

In one particular embodiment, the polyethylene glycol is polyethylene glycol 600. It has surprisingly been found by the present inventors that polyethylene glycol 600, especially when part of a mixture of polar protic solvents, is capable of dissolving the compound 3-[2-(4-carbamimidoyl-phenylcarbamoyl)-5-methoxy-4-vinyl-phenyl]-6-(cyclopropylmethyl-carbamoyl)-pyridine-2-carboxylic acid at concentrations of up to 140 mg/ml. Dissolution at such high concentrations enables this active ingredient to be included in a liquid solution contained in a solid oral dosage forms (especially capsules, such as hard or soft gel capsules). Polyethylene glycol 600 is also soluble in physiological fluids. These properties of the solvent address both the solubility and absorption problems faced by this particular compound.

In one embodiment, the polyethylene glycol 600 may be the sole polar organic solvent present in the composition. In such an embodiment, the polyethylene glycol 600 may comprise 40% to 65% by weight (expressed as a percentage of the total weight of the excipients excluding the active ingredient). In another embodiment, the polyethylene glycol 600 may comprise 60% to 75% by weight (expressed as a percentage of the total weight of the excipients excluding the active ingredient). In another embodiment, the polyethylene glycol 600 may comprise 70% to 80% by weight (expressed as a percentage of the total weight of the excipients excluding the active ingredient).

In another embodiment polyethylene glycol 600 may be present as part of a mixture of polar organic solvents (especially a mixture of polar protic solvents). In one embodiment, the polyethylene glycol 600 may be may be present as part of a mixture with $C_{3-6}$ diol, such as 1,2-propanediol. In this embodiment, the polyethylene glycol may comprise up to 99%, such as up to 98%, such as up to 97%, such as up to 96%, such as up to 95%, such as up to 90%, such as up to 85%, such as up to 80%, such as up to 75%, such as up to 70%, such as up to 65%, such as up to 60%, such as up to 55%, such as up to 50%, such as up to 45%, such as up to 40%, such as up to 35%, such as up to 30%, such as up to 25%, such as up to 20%, such as up to 15%, such as up to 10%, such as up to 5%, such as up to 4%, such as up to 3%, such as up to 2%, such as up to 1% of the mixture. These percentages are expressed by weight as a proportion of the total weight of all of the polar protic solvents present in the mixture (excluding the active ingredient and any other excipients). In this embodiment, the polyethylene glycol 600 may comprise at least 1%, such as at least 2%, such as at least 3%, at least 4%, such as at least 5%, such as at least 10%, such at least 15%, such as at least 20%, such as at least 25%, such as at least 30%, such as at least 35%, such as at least 40%, such as at least 45%, such as at least 50%, such at least 55%, such as at least 60%, such as at least 65%, such as at least 70%, such as at least 75%, such as at least 80%, such as at least 85%, such as at least 90%, such at least 95%, such as at least 97%, such as at least 98%, such as at least 99% of the mixture. In one embodiment, the mixture of polar organic solvents comprises 30% to 90% of polyethylene glycol. In one embodiment, the mixture of polar organic solvents comprises 90% to 99.9% of polyethylene glycol 600. In one embodiment, the mixture of polar organic solvents comprises 50% to 85% of polyethylene glycol 600. In one embodiment, the mixture of polar organic solvents comprises 40% to 65% of polyethylene glycol 600. In one embodiment, the mixture of polar organic solvents comprises 60% to 75% of polyethylene glycol 600. In one embodiment, the mixture of polar organic solvents comprises 75% to 95% of polyethylene glycol 600. In one embodiment, the mixture of polar organic solvents comprises 50% of polyethylene glycol 600. These percentages are expressed by weight as a proportion of the total weight of all of the polar protic solvents present in the mixture (excluding the active ingredient and any other excipients).

When polyethylene glycol 600 is present as part of a mixture of polar organic solvents (especially a mixture of polar protic solvents) used to form liquid oral formulations (particularly oral solutions), the polyethylene glycol 600 may be used in a proportion of up to 99% of a mixture of solvents. The polyethylene glycol 600 may be used either as the sole polar organic solvent used to form liquid oral formulations (particularly oral solutions). When polyethylene glycol 600 is present as part of a mixture of polar organic solvents (especially a mixture of polar protic solvents) for liquid formulations contained in solid oral dosage forms (especially capsules, such as hard or soft gel capsules), the polyethylene glycol 600 may be used in a proportion of up to 80% (such as up to 75%) of a mixture of solvents. The polyethylene glycol 600 may be used either as the sole polar organic solvent used to form liquid formulations contained in solid oral dosage forms (especially capsules, such as hard or soft gel capsules). It has been found that solvent mixtures containing such proportions of polyethylene glycol 600 are particularly suitable for use in a solution for filling liquid filled capsules (particularly in a solution for filling soft gelatin capsules). In particular embodiments, the polyethylene glycol 600 is the sole polar organic solvent. In particular embodiments, the polyethylene glycol 600 comprises 20% to 80%, 1% to 99%, 25% to 75%, especially 40% to 75% of the mixture. These percentages are expressed by weight as a proportion of the total weight of all of the polar protic solvents present in the mixture (excluding the active ingredient and any other excipients). In particular, it has been found that, when present in these amounts, the polyethylene glycol 600, in addition to its ability to dissolve the compound 3-[2-(4-carbamimidoyl-phenylcarbamoyl)-5-methoxy-4-vinyl-phenyl]-6-(cyclopropylmethyl-carbamoyl)-pyridine-2-carboxylic acid, its hydrochloride salt and Form A, is both compatible with a soft gel formulation and (especially when present in high purity) minimizes the need for a stabiliser.

In one embodiment, the ($C_{2-3}$) alkylene glycols comprises or consists of a polypropylene glycol having an number average molecular weight ($M_n$) of less than 1000 or a mixture thereof. In this specification the term "polypropylene glycol" generally means a compound having the general formula:

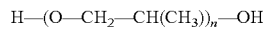

$$H-(O-CH_2-CH(CH_3))_n-OH$$

where n is at least 2. Typically n ranges from 2 to 18. In one embodiment the polypropylene glycol is linear. In another embodiment the polypropylene glycol is branched.

Similar to "polyethylene glycol" above, in this specification the term "polypropylene glycol", when followed by a number means a compound having the general formula above, wherein n is such that the number average molecular weight ($M_n$) is the stated number in g/mol (with a typical tolerance of ±10%, preferably 5%). Examples of polypropylene glycols suitable for use in the present invention include polypropylene glycol 200, polypropylene glycol 300, polypropylene glycol 400, polypropylene glycol 500, polypropylene glycol 600, polypropylene glycol 700, polypropylene glycol 800, polypropylene glycol 900, and mixtures thereof.

In one embodiment, the polypropylene glycol may be the sole polar organic solvent present in the composition. In such an embodiment, the polypropylene glycol may comprise 40% to 65% by weight (expressed as a percentage of the total weight of the excipients excluding the active ingredient). In another embodiment, the polypropylene glycol may comprise 60% to 75% by weight (expressed as a percentage of the total weight of the excipients excluding the active ingredient). In another embodiment, the polypropylene glycol may comprise 70% to 80% by weight (expressed as a percentage of the total weight of the excipients excluding the active ingredient).

In another embodiment polypropylene glycol may be present as part of a mixture of polar organic solvents (especially a mixture of polar protic solvents). In one embodiment, the polypropylene glycol may be may be present as part of a mixture with $C_{3-6}$ diol, such as 1,2-propanediol. In this embodiment, the polypropylene glycol may comprise up to 99%, such as up to 98%, such as up to 97%, such as up to 96%, such as up to 95%, such as up to 90%, such as up to 85%, such as up to 80%, such as up to 75%, such as up to 70%, such as up to 65%, such as up to 60%, such as up to 55%, such as up to 50%, such as up to 45%, such as up to 40%, such as up to 35%, such as up to 30%, such as up to 25%, such as up to 20%, such as up to 15%, such as up to 10%, such as up to 5%, such as up to 4%, such as up to 3%, such as up to 2%, such as up to 1% of the mixture. These percentages are expressed by weight as a proportion of the total weight of all of the polar protic solvents present in the mixture (excluding the active ingredient and any other excipients). In this embodiment, the polypropylene glycol may comprise at least 1%, such as at least 2%, such as at least 3%, at least 4%, such as at least 5%, such as at least 10%, such at least 15%, such as at least 20%, such as at least 25%, such as at least 30%, such as at least 35%, such as at least 40%, such as at least 45%, such as at least 50%, such at least 55%, such as at least 60%, such as at least 65%, such as at least 70%, such as at least 75%, such as at least 80%, such as at least 85%, such as at least 90%, such at least 95%, such as at least 97%, such as at least 98%, or such as at least 99% of the mixture. In one embodiment, the mixture of polar organic solvents comprises 30% to 90% of polypropylene glycol. In one embodiment, the mixture of polar organic solvents comprises 90% to 99.9% of polypropylene glycol. In one embodiment, the mixture of polar organic solvents comprises 50% to 85% of polypropylene glycol. In one embodiment, the mixture of polar organic solvents comprises 40% to 65% of polypropylene glycol. In one embodiment, the mixture of polar organic solvents comprises 60% to 75% of polypropylene glycol. In one embodiment, the mixture of polar organic solvents comprises 75% to 95% of polypropylene glycol. In one embodiment, the mixture of polar organic solvents comprises 50% of polypropylene glycol. These percentages are expressed by weight as a proportion of the total weight of all of the polar protic solvents present in the mixture (excluding the active ingredient and any other excipients).

The polar organic solvent or mixture of solvents may also contain water. In one embodiment, the water may comprise up to 10%, such as 9%, such as 8%, such as 7%, such as 6%, such as 5%, such as 4%, such as 3%, such as 2.5%, such as 2%, such as 1.5%, such as 1%, such as 0.5%, such as 0.2%, such as 0.1%, such as 0.05% of the mixture. These percentages are expressed by weight as a proportion of the total weight of all of the polar protic solvents present in the mixture (excluding the active ingredient and any other excipients).

In one embodiment, the polar organic solvent is selected from the group consisting of 1,2-propanediol, one or more polyethylene glycols having a number average molecular weight ($M_n$) of 200 to 800, and mixtures thereof, and optionally water. In one embodiment, the polar organic solvent is selected from the group consisting of one or more polyethylene glycols having a number average molecular weight ($M_n$) of 200 to 800 and optionally ethanol. In one embodiment, the polar organic solvent is selected from the group consisting of ethanol, 1,2-propanediol, one or more polyethylene glycols having a number average molecular weight ($M_n$) of 200 to 800, and mixtures thereof, and optionally water.

In one embodiment, the polar organic solvent comprises a mixture of 1,2-propanediol, one or more polyethylene glycols having a number average molecular weight ($M_n$) of 300 to 700 and optionally ethanol and water. In one embodiment, the polar organic solvent comprises a mixture of 1,2-propanediol, one or more polyethylene glycols having a number average molecular weight ($M_n$) of 300 to 700. In one embodiment, the polar organic solvent comprises a mixture of 1,2-propanediol and polyethylene glycol 400. In one embodiment, the polar organic solvent comprises a mixture of 1,2-propanediol, polyethylene glycol 400 and optionally ethanol and water. In one embodiment, the polar organic solvent comprises a mixture of 1,2-propanediol, polyethylene glycol 400, and ethanol and optionally water. In one embodiment, the polar organic solvent comprises a mixture of 1,2-propanediol and polyethylene glycol 600. In one embodiment, the polar organic solvent comprises a mixture of 1,2-propanediol, polyethylene glycol 600, and optionally ethanol and water. In one embodiment, the polar organic solvent comprises a mixture of 1,2-propanediol, polyethylene glycol 600, and ethanol and optionally water.

In one embodiment, the polar organic solvent comprises a mixture of a $C_{3-6}$ diol, such as 1,2-propanediol, one or more polyethylene glycols having a number average molecular weight ($M_n$) of 200 to 1000 as the sole polar organic solvents, wherein the $C_{3-6}$ diol is present at a maximum amount of 50%, 35%, 30%, 20% or 10%. These percentages are expressed by weight as a percentage of the total weight of the mixture of solvents (i.e. excluding the active ingredient and any other excipients). In one embodiment, the polar organic solvent comprises solely one or more polyethylene glycols having a number average molecular weight ($M_n$) of 200 to 1000.

In one embodiment, the polar organic solvent comprises a mixture of a $C_{3-6}$ diol, such as 1,2-propanediol, one or more polyethylene glycols having a number average molecular weight ($M_n$) of 200 to 800 at 20% to 99%, 20% to 50%, 50% to 95% or 60% to 90%, and optionally ethanol and/or water, wherein the solvent contains a maximum of 10% ethanol and 10% water. These percentages are expressed by weight as a percentage of the total weight of the mixture of solvents (i.e. excluding the active ingredient and any other excipients). In one embodiment, the polar organic solvent comprises solely one or more polyethylene glycols having a number average molecular weight ($M_n$) of 200 to 800. In one embodiment, the polar organic solvent comprises one or more polyethylene glycols having a number average molecular weight ($M_n$) of 200 to 800 at up to 100%, 20% to 99%, 20% to 50%, 50% to 95% or 60% to 90%, and optionally $C_{3-6}$ diol, such as 1,2-propanediol, ethanol and/or water, wherein the solvent contains a maximum of 20% or 50% $C_{3-6}$ diol, such as 1,2-propanediol, 10% ethanol and 10% water. These percentages are expressed by weight as a percentage of the total weight of the mixture of solvents (i.e. excluding the active ingredient and any other excipients).

In one embodiment, the polar organic solvent comprises a mixture of a $C_{3-6}$ diol, such as 1,2-propanediol, polyethylene glycol 600, wherein the $C_{3-6}$ diol is present at a maximum amount of 50%, 35%, 30%, 20% or 10%. These percentages are expressed by weight as a percentage of the total weight of the mixture of solvents (i.e. excluding the active ingredient and any other excipients). In one embodiment, the polar organic solvent comprises solely polyethylene glycol 600.

In one embodiment, the polar organic solvent comprises a mixture of a $C_{3-6}$ diol, such as 1,2-propanediol, polyethylene glycol 600 at 20% to 99%, 20% to 50%, 50% to 95% or 60% to 90%, and optionally ethanol and/or water, wherein the solvent contains a maximum of 10% ethanol and 10% water. These percentages are expressed by weight as a percentage of the total weight of the mixture of solvents (i.e. excluding the active ingredient and any other excipients).

In one embodiment, the polar organic solvent comprises polyethylene glycol 600 at up to 100%, 50% to 95% or 60% to 90%, and optionally $C_{3-6}$ diol, such as 1,2-propanediol, ethanol and/or water, wherein the solvent contains a maximum of 20% 1,2-propanediol, 10% ethanol and 10% water. These percentages are expressed by weight as a percentage of the total weight of the mixture of solvents (i.e. excluding the active ingredient and any other excipients).

In one embodiment, the mixture of polar organic solvents comprises 5% to 35% of 1,2-propanediol and 65% to 95% of polyethylene glycol 600. In one embodiment, the mixture of polar organic solvents comprises 15 to 30% of 1,2-propanediol and 70% to 85% of polyethylene glycol 600. In one embodiment, the mixture of polar organic solvents comprises up to 50% of 1,2-propanediol and 50% or more of polyethylene glycol 600. In one embodiment, the mixture of polar organic solvents comprises 50% of 1,2-propanediol and 50% of polyethylene glycol 600. These percentages are expressed by weight as a percentage of the total weight of the mixture of solvents (i.e. excluding the active ingredient and any other excipients).

In one embodiment, the mixture of polar organic solvents comprises 5% to 30% of 1,2-propanediol; 30% to 90% of polyethylene glycol 600; and 1% to 10% ethanol. In one embodiment, the mixture of polar organic solvents comprises 10% to 30% of 1,2-propanediol; 50 to 85% of polyethylene glycol 600; and 3% to 7% ethanol. In one embodiment, the mixture of polar organic solvents comprises 5% to 30% of 1,2-propanediol; 30% to 90% of polyethylene glycol 600; 1 to 10% ethanol; and 0 to 10% water. In one embodiment, the mixture of polar organic solvents comprises 10% to 30% of 1,2-propanediol; 50% to 85% of polyethylene glycol 600; 3% to 7% ethanol; and 0 to 10% water. These percentages are expressed by weight as a percentage of the total weight of the mixture of solvents (i.e. excluding the active ingredient and any other excipients).

In one embodiment, the mixture of polar organic solvents comprises 5% to 40% of 1,2-propanediol and 40% to 95% of one or more polyethylene glycols having a number average molecular weight (Mn) of 200 to 1000. In one embodiment, the mixture of polar organic solvents comprises 1% to 5% of 1,2-propanediol and 95% to 99% of one or more polyethylene glycols having a number average molecular weight (Mn) of 200 to 1000. In one embodiment, the mixture of polar organic solvents comprises 50% of 1,2-propanediol and 50% of one or more polyethylene glycols having a number average molecular weight (Mn) of 200 to 1000. In one embodiment, the mixture of polar organic solvents comprises up to 50% 1,2-propanediol and 50% or more of one or more polyethylene glycols having a number average molecular weight (Mn) of 200 to 1000. In one embodiment, the mixture of polar organic solvents comprises 15% to 35% of 1,2-propanediol and 40% to 65% of one or more polyethylene glycols having a number average molecular weight (Mn) of 200 to 1000.

In one embodiment, the mixture of polar organic solvents comprises 5% to 30% of 1,2-propanediol, 40% to 95% of one or more polyethylene glycols having a number average molecular weight (Mn) of 200 to 1000 and 0.1% to 10% ethanol. In one embodiment, the mixture of polar organic solvents comprises up to 50% of 1,2-propanediol, 50% or more of one or more polyethylene glycols having a number average molecular weight (Mn) of 200 to 1000 and 0.1% to 10% ethanol. In one embodiment, the mixture of polar organic solvents comprises 1% to 5% of 1,2-propanediol, 95% to 99% of one or more polyethylene glycols having a number average molecular weight (Mn) of 200 to 1000 and 0.1% to 10% ethanol. In one embodiment, the mixture of polar organic solvents comprises 15% to 35% of 1,2-propanediol, 40% to 65% of one or more polyethylene glycols having a number average molecular weight (Mn) of 200 to 1000 and 0.1% to 10% ethanol.

Particular mixtures of polar organic solvents include the following:
100% polyethylene glycol 600;
20% 1,2-propanediol and 80% polyethylene glycol 600;
50% 1,2-propanediol and 50% polyethylene glycol 600;
up to 50% 1,2-propanediol and 50% or more polyethylene glycol 600
6% 1,2-propanediol and 94% polyethylene glycol 600;
26.5% 1,2-propanediol; 66.9% polyethylene glycol 600; and 6.6% ethanol;
25.8% 1,2-propanediol; 67.7% polyethylene glycol 600; and 6.5% ethanol;
20% 1,2-propanediol; 70% polyethylene glycol 600; and 10% ethanol;
20% 1,2-propanediol; 75% polyethylene glycol 600; and 5% ethanol;
10% 1,2-propanediol; 85% polyethylene glycol 600; and 5% ethanol;
these percentages being expressed as a percentage of the total weight of the mixture of polar solvents (i.e. excluding the active ingredient and any other excipients).

In one embodiment, the polar organic solvent is supplied to the mixture in a grade of purity which is greater than 95%, such as greater than 97%, such as greater than 99%, such as greater than 99.5%, such as greater than 99.9%, such as greater than 99.95%, such as greater than 99.99%, by weight. In one embodiment, the polar organic solvent is supplied to the mixture in a grade of purity substantially free from oxidizing impurities (such as peroxides): the low percentage of such impurities means the requirement for an antioxidant in the formulation is minimized or avoided. In particular, the polar organic solvent may supplied to the mixture in a grade of purity which obviates the need for antioxidants.

In one embodiment, the polar organic solvent (as defined and exemplified above, either in its broadest aspect or a preferred aspect, particularly: $C_{2-6}$ monoalcohols, $C_{3-6}$ diols, poly($C_{2-3}$)alkylene glycols having a number average molecular weight ($M_n$) of less than 1000) has an aldehyde content of less than 10 parts per million by weight. This avoids cross linking with soft gel capsules. In particular, when the polar organic solvent is a polyethylene glycol (such as polyethylene glycol 400, polyethylene glycol 600, or polyethylene glycol 800, especially polyethylene glycol 600), the polyethylene glycol has an aldehyde content of less than 10 parts per million by weight.

Co-Solvents

The formulations of the present invention may further comprise one or more co-solvents. As used in the present specification, the term co-solvent includes any other excipient present in the formulation other than the polar organic solvents described above. Specific co-solvents include absorption enhancers and stabilizers. As discussed above, alcohols may be considered co-solvents in certain embodiments as well.

Formulations of the present invention may comprise a single co-solvent or more than one co-solvent. Where a co-solvent is present, the co-solvent may comprise 1 to 35% or 1 to 50% by weight of the composition. In one embodiment, the co-solvent comprises 5 to 30% by weight of the composition. In one embodiment, the co-solvent comprises 20 to 40% by weight of the composition. In one embodiment, the co-solvent comprises 1 to 20% by weight of the composition. In one embodiment, the co-solvent comprises 10 to 20% by weight of the composition. These percentages are expressed as a percentage of the total weight of the mixture of excipients (i.e. excluding the active ingredient).

Absorption Enhancer

In certain embodiments, the co-solvents of the present invention may increase the absorption of the API in addition to having other beneficial properties. Therefore, such co-solvents may be act, at least in part, as an absorption enhancer. It has been unexpectedly found by the present inventors that use of a co-solvent that acts, at least in part, as an absorption enhancer enables the active pharmaceutical ingredients used in the present invention, when dosed in a dosage form (particularly although not exclusively a capsule, such as a hard gel or soft gel capsule) which can achieve therapeutic plasma levels when dosed at 1 to 4 times per day, 1 to 3 times per day and potentially even once or twice daily.

The mechanism by which the absorption enhancers achieve this effect is not critical to the present invention. Without wishing to be bound by theory, it is postulated by the present inventors that certain absorption enhancers may further increase the solubility of the active pharmaceutical ingredient in the polar organic solvent or mixture thereof, such that a greater proportion of the dissolved active ingredient is capable of passing through the gut wall to achieve a therapeutic concentration of the active in blood plasma. Such absorption enhancers may be referred to herein as "chemical absorption enhancers". Alternatively, and again without wishing to be bound by theory, it is postulated by the present inventors that certain absorption enhancers may have an effect on the intestinal cell surface resulting in a change that increases the epithelial cell's permeability to the active ingredient. Such absorption enhancers may be referred to herein as "physiological absorption enhancers" or "permeability enhancers". It is even possible that certain absorption enhancers may achieve this effect through both mechanisms.

Examples of suitable co-solvents that act, at least in part, as absorption enhancers usable in the composition of the present invention include vitamin E poly($C_{2-3}$)alkylene glycol dicarboxylic esters (as defined below), surfactants (as defined below), bile salts (such as sodium cholate/deoxycholate), polymers (such as chitosan, polycarbophil, starch and carrageenan), fatty acids (defined herein as $C_{4-30}$ carboxylic acids which may be saturated or unsaturated, unsaturated acids containing from 1 to 3 double bonds in the fatty acid chain) and salts thereof (particularly alkali metal salts such as sodium and potassium salts), particularly oleic acid, sodium octanoate and sodium decanoate).

In one embodiment, the absorption enhancer is present in combination with a mixture of solvents, particularly polar protic solvents, at 0 to 50%, 0.1 to 50%, 0 to 5%, 0.1 to 5%, 0.1 to 1%, 5 to 30%, 10 to 25%, 15 to 20%, 20 to 30%, 20 to 40%, 1%, 27.2% or 20%. One or more absorption enhancers may be present. A particular combination of absorption enhancers is a vitamin E poly($C_{2-3}$)alkylene glycol dicarboxylic ester (as defined below) and a surfactant (as defined below). The percentages are expressed by weight as a percentage of the total weight of the mixture of excipients (i.e. excluding the active ingredient).

In one embodiment, the co-solvent is a vitamin E poly ($C_{2-3}$)alkylene glycol dicarboxylic ester. These are dicarboxylic acids, typically ($C_{3-6}$)dicarboxylic acids, where one acid function is esterified by a poly($C_{2-3}$)alkylene glycol (i.e. a polyethylene glycol or a polypropylene glycol, typically having a number average molecular weight ($M_n$) of 600 to 1400) and the other acid function is esterified by the hydroxyl group of a form of vitamin E (i.e. a tocopherol or a tocotrienol, as defined below).

In one embodiment, the dicarboxylic acid moiety (i.e. the acyl component) of the vitamin E poly($C_{2-3}$)alkylene glycol dicarboxylic ester is a malonic acid (propane-1,3-dicarboxylic acid) moiety. In one embodiment, the dicarboxylic acid moiety is a succinic acid (butane-1,4-dicarboxylic acid) moiety. In one embodiment, the dicarboxylic acid moiety is a glutaric acid (pentane-1,5-dicarboxylic acid) moiety. In one embodiment, the dicarboxylic acid moiety is an adipic acid (hexane-1,6-dicarboxylic acid) moiety.

In the described formulations, the vitamin E poly($C_{2-3}$) alkylene glycol dicarboxylic ester may be present at 0 to 50%, 0 to 5%, 0.1% to 5%, 0.1% to 1%, 5% to 30%, 20 to 40%, 10% to 25%, 15% to 20%, 20 to 30%, 1%, 27.2%, 26.6% or 20%. In one aspect, the vitamin E poly($C_{2-3}$) alkylene glycol dicarboxylic ester may be present at 15 to 30%, 20 to 30%, 20 to 40%, 27.2% or 26.6%. These percentages are expressed by weight as a percentage of the total weight of the mixture of excipients (i.e. excluding the active ingredient).

The eight forms of vitamin E are divided into two groups; four are tocopherols and four are tocotrienols. They are identified by prefixes alpha- (α-), beta- (β-), gamma- (γ-), and delta- (δ-). In one embodiment, the vitamin E moiety of the vitamin E poly($C_{2-3}$)alkylene glycol dicarboxylic ester is an alpha-tocopherol moiety. In one embodiment, the vitamin E moiety is a beta-tocopherol moiety. In one embodiment, the vitamin E moiety is a gamma-tocopherol moiety. In one embodiment, the vitamin E moiety is a delta-tocopherol moiety. In one embodiment, the vitamin E moiety of the vitamin E poly($C_{2-3}$)alkylene glycol dicarboxylic ester is an alpha-tocotrienol moiety. In one embodiment, the vitamin E moiety is a beta-tocotrienol moiety. In one embodiment, the vitamin E moiety is a gamma-tocotrienol moiety. In one embodiment, the vitamin E moiety is a delta-tocotrienol moiety. In each of these embodiments, the vitamin E moiety may have the D or L configuration. The vitamin E moiety may be a single stereoisomer or a mixture of stereoisomers. Natural tocopherols occur in the (R),(R),(R)-configuration only. The synthetic form contains eight different stereoisomers and is called 'all-rac'-α-tocopherol. In one embodiment, the vitamin E moiety of the vitamin E poly($C_{2-3}$) alkylene glycol dicarboxylic ester is a D-α-tocopherol moiety.

In one embodiment, the poly($C_{2-3}$)alkylene glycol moiety of the vitamin E poly($C_{2-3}$)alkylene glycol dicarboxylic ester is a polyethylene glycol moiety. In one embodiment, the poly($C_{2-3}$)alkylene glycol moiety is a polyethylene glycol 800 moiety. In one embodiment, the poly($C_{2-3}$)alkylene glycol moiety is a polyethylene glycol 1000 moiety. In one embodiment, the poly($C_{2-3}$)alkylene glycol moiety is a polyethylene glycol 1200 moiety.

In a particularly preferred embodiment, the co-solvent is a D-α-tocopherol polyethylene glycol 1000 succinate (also known as Vitamin E polyethylene glycol 1000 succinate or vitamin E TPGS). This compound is advantageous in the present invention in that, in addition to its function as a co-solvent as discussed above, it is pharmaceutically acceptable (in particular, being compatible with soft gel formulations), and may aid in solubilizing the compounds used therein and is particularly active in enhancing the absorption of the compounds. In addition, the vitamin E moiety may also provide a stabilizing effect to the API, thus having the potential to address the solubility, absorption, and stability problems associated with these compounds.

In the described formulations, the vitamin E poly($C_{2-3}$) alkylene glycol dicarboxylic ester is D-α-tocopherol polyethylene glycol 1000 succinate may be present at 0 to 50%, 0 to 5%, 0.1% to 5%, 0.1% to 1%, 5% to 30%, 20 to 40%, 10% to 25%, 15% to 20%, 20 to 30%, 1%, 27.2%, 26.6% or 20%. In one aspect, the D-α-tocopherol polyethylene glycol 1000 succinate may be present at 15 to 30%, 20 to 30%, 20 to 40%, 27.2% or 26.6%. These percentages are expressed by weight as a percentage of the total weight of the mixture of excipients (excluding the active ingredient).

In one embodiment, the co-solvent is a surfactant or a mixture thereof. A surfactant is a compound containing both a water insoluble (or oil soluble) component and a water soluble component. A surfactant is typically an organic compound that is amphiphilic, meaning it contains both a hydrophobic group (usually referred to as the tail) and a hydrophilic group (usually referred to as the head). Where present, the surfactant may typically comprise 0.01% to 25%, such as 0.5% to 15%, such as 1% to 10%, such as 0.1% to 5%, such as 0.1% to 3% of the total weight of the excipients (excluding the active ingredient). In certain embodiments, a surfactant is not present.

In one embodiment, the surfactant is a nonionic surfactant. In another embodiment, the surfactant is an ionic surfactant, classes of which include cationic surfactants, anionic surfactants and zwitterionic surfactants. In particular, it is envisaged within the scope of the present invention that the surfactant may act as an absorption enhancer. In certain aspects, the surfactant may also act as a stabilizer.

One particularly preferred class of ionic surfactants usable in the present invention is phospholipids. The structure of the phospholipid molecule generally consists of hydrophobic tails and a hydrophilic head. Most phospholipids consist of a glycerol or sphingosine backbone having attached to it either one or two fatty acyl groups, a phosphate group, and a small organic molecule. One class of phospholipids is glycerophospholipids, which are defined herein as any derivative of sn-glycero-3-phosphoric acid that contains at least one (preferably 1 or 2)O-acyl, or O-alkyl, or O-alkenyl residue attached to the glycerol moiety and a polar head made of a nitrogenous base, a glycerol or an inositol unit. In these groups, the acyl, alkyl and alkenyl residues typically have 4 to 30 carbon atoms (particularly 8 to 24, such as 12 to 20, such as 14 to 18) and the alkenyl groups typically have 1 to 3 double bonds. Commercially available glycerophospholipids typically comprise a mixture of species having different numbers of carbon atoms.

Examples of glycerophospholipids include phosphatidic acid (phosphatidate), phosphatidylethanolamine (cephalin), phosphatidylcholine, phosphatidylserine, and phosphoinositides such as phosphatidylinositol, phosphatidylinositol phosphate, phosphatidylinositol bisphosphate, and phosphatidylinositol triphosphate, and mixtures thereof. Another class of phospholipids is phosphosphingolipids, examples of which include ceramide phosphorylcholine (sphingomyelin), ceramide phosphorylethanolamine and ceramide phosphoryllipids, and mixtures thereof.

In one embodiment, the phospholipid is lecithin. Commercially available lecithin is a mixture of phospholipids typically comprising at least 95%, such as 97%, such as 99% by weight (as a percentage of the total weight of the phospholipids) phosphatidylcholine and the balance typically comprising phosphatidylethanolamine and/or phosphosphingolipids. In particular, it has been found that lecithin (particularly when used in solution in a polyethylene glycol, especially polyethylene glycol 400) is particularly suitable for use in a solution for filling liquid filled capsules (particularly in a solution for filling soft gelatin capsules).

In this embodiment, the lecithin may be added to the mixture alone, but is typically and preferably added as a solution in a polar organic solvent (as defined and exemplified above), and particularly in a solution in a poly($C_{2-3}$) alkylene glycol having a number average molecular weight ($M_n$) of less than 1000 (such as polyethylene glycol 400 or polyethylene glycol 600, especially polyethylene glycol 400). The lecithin may be present in an amount of up to 25%, such as up to 20%, such as up to 15% by weight in the solution. In one embodiment, the lecithin is present in an amount of 0.5 to 20%, such as 5 to 15%, such as 8 to 12% of the solution.

One particularly preferred class of anionic surfactants usable in the present invention is hydrocarbyl sulphates, in which a hydrocarbyl group (typically having from 4 to 30 carbon atoms, and is typically a $C_{4-30}$ alkyl group or a $C_{4-30}$ alkenyl group containing 1 to 3 double bonds) is bonded to a sulphate ($-OSO_2O^-$) group. Suitable counterions include those listed and exemplified above in relation to pharmaceutically acceptable base addition salts of the compounds used in the present invention, and preferably are alkali metal ions such as lithium, sodium and potassium. Examples of suitable hydrocarbyl sulphates include $C_{6-24}$ alkyl sulphates, such as $C_{8-22}$ alkyl sulphates, such as $C_{10-18}$ alkyl sulphates and particularly $C_{10}$, $C_{12}$, $C_{14}$, $C_{16}$ and $C_{18}$ alkyl sulphates.

In the described formulations, the hydrocarbyl sulphates, including $C_{6-24}$ alkyl sulphates, may be present at 0.1% to 7.5%, 0.1% to 1%, 0.5% to 5%, 0.1% to 3% or 2.5%. In one aspect, the hydrocarbyl sulphates, including $C_{6-24}$ alkyl sulphates, may be present at 0.1 to 5%, 2.5% or 5%. These percentages are expressed by weight as a percentage of the total weight of the mixture of excipients (i.e. excluding the active ingredient).

A particularly preferred surfactant usable in the present invention is sodium dodecyl sulphate (also known as sodium lauryl sulphate). This compound is advantageous in the present invention in that it is pharmaceutically acceptable. In particular, it has been found that sodium dodecyl sulphate (particularly when used in solution in a polyethylene glycol, especially polyethylene glycol 600) is particularly suitable for use in a solution for filling liquid filled capsules (particularly in a solution for filling soft gelatin capsules).

In the described formulations, the sodium dodecyl sulphate may be present 0% to 7.5%, 0.1% to 1%, 0.5% to 5%, 0.1% to 3%, 2.5% or 5%. In one aspect, the sodium dodecyl sulphate may be present at 0.1 to 5%, 2.5% or 5%. In certain embodiments, the sodium dodecyl sulphate is absent. These percentages are expressed by weight as a percentage of the total weight of the mixture of excipients (i.e. excluding the active ingredient).

In this embodiment, the sodium dodecyl sulphate may be added to the mixture alone, but is typically and preferably added as a solution in water or a polar organic solvent (as defined and exemplified above), and particularly in a solution in a poly($C_{2-3}$)alkylene glycol having a number average molecular weight ($M_n$) of less than 1000 (such as polyethylene glycol 400 or polyethylene glycol 600, especially polyethylene glycol 600). The sodium dodecyl sulphate may be present in an amount of up to 5%, such as up to 3%, such as up to 2.5% by weight in the solution. In one embodiment, the sodium dodecyl sulphate is present in an amount of 0.1% to 5%, such as 0.5% to 3%, such as 1% to 2.5% of the solution.

Stabilizer

In one embodiment, the co-solvent acts, at least in part as a stabilizer. Therefore, the compositions of the present invention may also comprise one or more co-solvents that act, at least in part, as a stabilizer. It has been found by the present inventors that use of a co-solvent that acts, at least in part, as a stabilizer enables the compounds used in the present invention to be capable of being formulated into an oral dosage form (such as a hard gel or soft gel capsule) which is both stable (with respect to factors such as light degradation, oxidation and/or elevated temperatures) and can achieve therapeutic plasma levels when dosed at 1 to 4 times per day, 1 to 3 times per day and potentially even once or twice daily.

In one embodiment, the stabilizer (including the antioxidants described herein) is present in combination with a mixture of solvents, particularly polar protic solvents, at 0.1% to 5%, 0.1% to 2%, 0.1% to 1%, 0.1% to 3%, 0.7%, 1% or 5%. One or more stabilizers may be present. The percentages are expressed by weight as a percentage of the total weight of the mixture of excipients (i.e. excluding the active ingredient).

In one embodiment, the co-solvent is an antioxidant. An antioxidant is a substance that inhibits the oxidation of other substance, usually by being oxidized themselves. Many antioxidants therefore are reducing agents. Oxidation reactions typically involve a chain reaction involving free radicals. Many antioxidants terminate these chain reactions by removing free radical intermediates, and inhibit other oxidation reactions. Both water-soluble and water-insoluble antioxidants are commercially available, the choice of these being performed according to the nature of the formulation.

Examples of possible antioxidants suitable for use in the compositions of the present invention include ascorbic acid derivatives such as ascorbic acid and salts thereof (such as sodium ascorbate), citric acid and derivatives thereof, erythorbic acid; thiol derivatives such as thioglycerol, cysteine, acetylcysteine, cystine, dithioerythritol, dithiothreitol and glutathione; vitamin E in all its forms (tocopherols or tocotrienols) and derivatives thereof, such as those described and exemplified below; phenols, especially those substituted with at least one tertiary alkyl group (preferably a tert-butyl group) such as those described and exemplified below; sulfurous acid salts such as sodium sulfite, sodium bisulfite, acetone sodium bisulfite, sodium metabisulfite, sodium sulfite, sodium formaldehyde sulfoxylate, and sodium thiosulfate; and nordihydroguaiaretic acid. Antioxidants may also be employed in conjunction with chelating agents, e.g. ethylenediamine tetraacetic acid (EDTA), citric acid, that act to form complexes with heavy-metal ions and other ions that are normally involved in oxidative degradation of active pharmaceutical ingredients.

In one embodiment, the co-solvent is vitamin E or a vitamin E derivative. The compositions of the present invention may contain a single species of vitamin E or a vitamin E derivative or mixtures of the foregoing. The term vitamin E includes tocopherols and tocotrienols. α-tocopherol is the most abundant and active form of this family of compounds.

Tocopherol and tocotrienol are chemically similar to one another, with tocotrienols containing three unsaturated bonds in the alkyl tail. The generic structure of tocopherol and tocotrienol are given below, where $R_1$ to $R_3$ are each independently H or a $C_{1-3}$ alkyl. In certain embodiment, $R_1$ to $R_3$ are each independently H or a $CH_3$. Derivatives of tocopherol and tocotrienol are also included where the OH group of the tocopherol and tocotrienol is substituted with moieties including acetate, phosphate, succinate, nicotinate and linoleate.

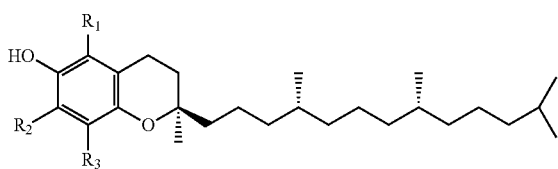

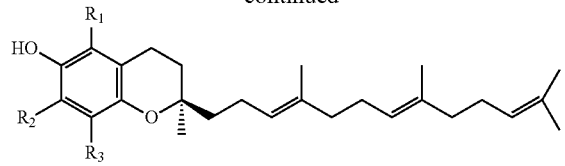
-continued

Tocopherols and/or tocotrienols each comprise a family of 4 compounds, identified by prefixes alpha- (α-), beta- (β-), gamma- (γ-), and delta- (δ-). In one embodiment, the co-solvent is alpha-tocopherol. In one embodiment, the co-solvent is beta-tocopherol. In one embodiment, the co-solvent is gamma-tocopherol. In one embodiment, the co-solvent is delta-tocopherol. In one embodiment, the co-solvent is alpha-tocotrienol. In one embodiment, the co-solvent is beta-tocotrienol moiety. In one embodiment, the co-solvent is gamma-tocotrienol moiety. In one embodiment, the co-solvent is delta-tocotrienol moiety. In each of these embodiments, the tocopherol and/or tocotrienol may have the D or L configuration. The tocopherol and/or tocotrienol may be a single stereoisomer or a mixture of stereoisomers. Natural tocopherols occur in the (R),(R),(R)-configuration only. The synthetic form contains eight different stereoisomers and is called 'all-rac'-α-tocopherol.

Therefore, vitamin E compounds useful in the composition of the present invention include the family of naturally occurring tocopherols and/or tocotrienols, as well as derivatives thereof. In one embodiment, the co-solvent is alpha-tocopherol.

In the described formulations, the vitamin E may be present at 0 to 50%, 0 to 10%, 10%, 0 to 5%, 0.1% to 5%, 0.1% to 2%, 0.1% to 1%, 0.1% to 3%, 30% to 70%, 0.7%, 1% or 5%. In one aspect, the vitamin E may be present at 0 to 5%, 0.1% to 1% or 0.1% to 2%. These percentages are expressed by weight as a percentage of the total weight of the mixture of excipients (i.e. excluding the active ingredient).

In a particularly preferred embodiment, the co-solvent is a D-α-tocopherol. This compound is advantageous in the present invention in that, in addition to its function of stabilizing the composition, it is pharmaceutically acceptable (in particular, being compatible with soft gel formulations), and may aid in solubilizing the compounds used therein, thus having the potential to address the solubility absorption, and stability problems associated with these compounds.

In the described formulations, the co-solvent is D-α-tocopherol and such compound may be present at 0 to 50%, 0 to 10%, 0 to 5%, 0.1% to 5%, 0.1% to 2%, 0.1% to 1%, 0.1% to 3%, 0.7%, 1% or 5%. In one aspect, the D-α-tocopherol may be present at 0 to 5%, 0.1% to 1%, 0.1% to 3% or 0.7%. These percentages are expressed by weight as a percentage of the total weight of the mixture of excipients (excluding the active ingredient).

In another embodiment, the co-solvent is a substituted phenol (i.e. a benzene ring substituted with 1 to 3 hydroxyl groups) which is further substituted with at least one tertiary alkyl group (preferably a tert-butyl group) or an alkyl ester (preferably a propyl ester) and, optionally, a ($C_{1-4}$) alkyl and/or a ($C_{1-4}$) alkoxy group. Examples of compounds in this class include phenols substituted with a single hydroxyl group further substituted with one tert-butyl group and a methoxy group, such as tert-butyl 4-hydroxyanisole (also known as butylated hydroxyanisole or BHA), which typically comprises a mixture of 2-tert-butyl-4-hydroxyanisole and 3-tert-butyl-4-hydroxyanisole and phenols substituted with a single hydroxyl group further substituted with one or two tert-butyl groups and a methyl group, such as 2,6-di-tert-butyl-4-methylphenol (also known as butylated hydroxytoluene, BHT).

Examples of compounds in this class include phenols substituted with a single hydroxyl group further substituted with a propyl ester group, such as propyl gallate. In one embodiment, the co-solvent is tert-butyl 4-hydroxyanisole. In one embodiment, the co-solvent is 2,6-di-tert-butyl-4-methylphenol. In one embodiment, the co-solvent is propyl gallate.

In the described formulations, the substituted phenol may be present at 0 to 20%, 0 to 15%, 0 to 10%, 0 to 5%, 0.1% to 5%, 0.1% to 1%, 1% to 20%, 0.1% to 3% or 0.7%. In one aspect, the substituted phenol may be present at 0.7%, 0.1% to 1% or 0.1% to 3%. These percentages are expressed by weight as a percentage of the total weight of the mixture of excipients (i.e. excluding the active ingredient).

In another embodiment, the co-solvent is a citric acid (2-hydroxypropane-1,2,3-trioic acid). In the described formulations, the citric acid may be present at 0 to 10%, 0 to 5%, 0.1% to 5%, 0.1% to 2%, 0.1% to 1%, 0.1% to 3%, 0.7%, 1% or 5%. In one aspect, the citric acid may be present at 0.7%, 0.1% to 1% or 0.1% to 3%. These percentages are expressed by weight as a percentage of the total weight of the mixture of excipients (i.e. excluding the active ingredient).

In a particular aspect, the citric acid may be substituted for the vitamin E component in the described formulations. In a particular aspect, the citric acid may be present at 0.1 to 2% and be substituted for the vitamin E component in a formulation comprising 60 to 80% of $(C_{2-3})$ alkylene glycols, such as polyethylene glycol, having a number average molecular weight (Mn) of 200 to 1000 and 20 to 40% of a vitamin E poly$(C_{2-3})$alkylene glycol dicarboxylic ester, such as D-α-tocopherol polyethylene glycol 1000 succinate. In a particular aspect, the citric acid may be present at 0.1 to 2% and be substituted for the vitamin E component in a formulation comprising up to 50% of a $C_{3-6}$ diol, such as 1,2-propanediol, 50% or more of a $(C_{2-3})$ alkylene glycols, such as polyethylene glycol, having a number average molecular weight (Mn) of 200 to 1000 and 20 to 40% of a vitamin E poly$(C_{2-3})$alkylene glycol dicarboxylic ester, such as D-α-tocopherol polyethylene glycol 1000 succinate. In a particular aspect, the citric acid may be present at 0.7% and be substituted for the vitamin E component in a formulation comprising 72.7% of polyethylene glycol 600, and 26.6% of D-α-tocopherol polyethylene glycol 1000 succinate. These percentages are expressed by weight as a percentage of the total weight of the mixture of excipients (i.e. excluding the active ingredient).

In one embodiment, the mixture of excipients comprises a $C_{3-6}$ diol, such as 1,2-propanediol, and a poly$(C_{2-3})$ alkylene glycol having a number average molecular weight (Mn) of 200 to 1000, such as polyethylene glycol having a number average molecular weight (Mn) of 200 to 1000 (or any subrange therein) at 1 to 99% and 1-50% of at least one co-solvent (as defined herein).

In another embodiment, the mixture of excipients comprises a combination of a $C_{3-6}$ diol, such as 1,2-propanediol, at 5-40% and a poly$(C_{2-3})$ alkylene glycol having a number average molecular weight (Mn) of 200 to 1000, such as polyethylene glycol having a number average molecular weight (Mn) of 200 to 1000 (or any subrange therein) at 20 to 95% and 1-50% of at least one co-solvent (as defined herein).

In another embodiment, the mixture of excipients comprises a combination of a $C_{3-6}$ diol, such as 1,2-propanediol, at 0 to 10% or 0 to 40%, and a poly$(C_{2-3})$ alkylene glycol having a number average molecular weight (Mn) of 200 to 1000, such as polyethylene glycol having a number average molecular weight (Mn) of 200 to 1000 (or any subrange therein) at 1 to 99% (for example 10 to 99%) and 1-50% of at least one co-solvent (as defined herein).

In another embodiment, the mixture of excipients comprises a combination of a $C_{3-6}$ diol, such as 1,2-propanediol, at 1 to 50% and a poly$(C_{2-3})$ alkylene glycol having a number average molecular weight (Mn) of 200 to 1000, such as polyethylene glycol having a number average molecular weight (Mn) of 200 to 1000 (or any subrange therein) at 1 to 90% and 1 to 50% of at least one co-solvent (as defined herein).

In another embodiment, the mixture of excipients comprises a combination of a $C_{3-6}$ diol, such as 1,2-propanediol, and a poly$(C_{2-3})$ alkylene glycol having a number average molecular weight (Mn) of 200 to 1000, such as polyethylene glycol having a number average molecular weight (Mn) of 200 to 1000 (or any subrange therein) at 30 to 80%, the $C_{3-6}$ diol being present at up to one-half the percentage of the polar protic solvent (for example up to a maximum of 40%) and 1-50% of at least one co-solvent (as defined herein).

In another embodiment, the mixture of excipients comprises a poly$(C_{2-3})$ alkylene glycol having a number average molecular weight (Mn) of 200 to 1000, such as polyethylene glycol having a number average molecular weight (Mn) of 200 to 1000 (or any subrange therein) at 1 to 99% (such as 1 to 99% or 50 to 90%) and 1-50% of at least one co-solvent (as defined herein).

In the foregoing paragraphs, the percentages of various compounds are expressed as a percentage of the total weight of the mixture of excipients (i.e. excluding the active ingredient).

In the foregoing paragraphs, the percentages of various compounds are expressed as a percentage of the total weight of the mixture of excipients (i.e. excluding the active ingredient).

In the foregoing descriptions of co-solvents, the vitamin E may be D-α-tocopherol, the alcohol may be ethanol, the $C_{10-18}$ alkyl sulphate may be sodium lauryl sulfate and the vitamin E poly$(C_{2-3})$alkylene glycol dicarboxylic ester may be D-α-tocopherol polyethylene glycol 1000 succinate.

In one aspect of the foregoing 6 embodiments, the co-solvent is a combination of one of the following:
i) the vitamin E may be present at 0 to 10%, the $C_{2-6}$ monoalcohol may be present at 0 to 7.5%, the a $C_{10-18}$ alkyl sulphate may be present at 0 to 5%, and the vitamin E poly$(C_{2-3})$alkylene glycol dicarboxylic ester may be present at 0 to 5% or 5 to 30%;
ii) the vitamin E may be present at 0.1% to 10%, the $C_{2-8}$ monoalcohol may be present at 0.1% to 7.5%, the a $C_{10-18}$ alkyl sulphate may be present at 0.1% to 5%, and the vitamin E poly$(C_{2-3})$alkylene glycol dicarboxylic ester may be present at 0 to 5% or 5 to 30%;
iii) the vitamin E may be present at 0 to 2%, the $C_{2-6}$ monoalcohol may be present at 0.1 to 6.0%, the a $C_{10-18}$ alkyl sulphate may be present at 0.1 to 3%, and the vitamin E poly$(C_{2-3})$alkylene glycol dicarboxylic ester may be present at 0 to 5% or 5 to 30%;
iv) the vitamin E may be present at 0.1 to 1%, the $C_{2-6}$ monoalcohol may be present at 2.0 to 6.0%, the a $C_{10-18}$ alkyl sulphate may be present at 1.0 to 4.0%, and the vitamin E poly$(C_{2-3})$alkylene glycol dicarboxylic ester may be present at 0 to 5% or 5 to 30%;

v) the vitamin E may be present at 0.1 to 2%, the $C_{2-6}$ monoalcohol may be present at 0.1 to 5%, the a $C_{10-18}$ alkyl sulphate may be present at 0.1 to 3%, and the vitamin E poly($C_{2-3}$)alkylene glycol dicarboxylic ester may be present at 5 to 30% or 20 to 40%;

vi) the vitamin E may be present at 0.1 to 2%, the $C_{2-6}$ monoalcohol is absent, the a $C_{10-18}$ alkyl sulphate may be present at 0.1 to 3%, and the vitamin E poly($C_{2-3}$) alkylene glycol dicarboxylic ester may be present at 5 to 30% or 20 to 40%; and vii) the vitamin E may be present at 0.1 to 2%, the $C_{2-6}$ monoalcohol is absent, the a $C_{10-18}$ alkyl sulphate is absent, and the vitamin E poly($C_{2-3}$)alkylene glycol dicarboxylic ester may be present at 5 to 30% or 20 to 40%.

Therefore, in another aspect of the foregoing 6 embodiments, the co-solvent is a combination of one of the following:

i) the D-α-tocopherol may be present at 0 to 10%, the ethanol may be present at 0 to 7.5%, the sodium lauryl sulfate may be present at 0 to 5%, and the D-α-tocopherol polyethylene glycol 1000 succinate may be present at 0 to 5% or 5 to 30%;

ii) the D-α-tocopherol may be present at 0.1% to 10%, the ethanol may be present at 0.1% to 7.5%, the sodium lauryl sulfate may be present at 0.1% to 5%, and the D-α-tocopherol polyethylene glycol 1000 succinate may be present at 0 to 5% or to 30%;

iii) the D-α-tocopherol may be present at 0 to 2%, the ethanol may be present at 0.1 to 6.0%, the sodium lauryl sulfate may be present at 0.1 to 3%, and the D-α-tocopherol polyethylene glycol 1000 succinate may be present at 0 to 5% or 5 to 30%;

iv) the D-α-tocopherol may be present at 0.1 to 1%, the ethanol may be present at 2.0 to 6.0%, the sodium lauryl sulfate may be present at 1.0 to 4.0%, and the D-α-tocopherol polyethylene glycol 1000 succinate may be present at 0 to 5% or or to 30%;

v) the D-α-tocopherol may be present at 0.1 to 2%, the ethanol may be present at 0.1 to 5%, the sodium lauryl sulfate may be present at 0.1 to 3%, and the D-α-tocopherol polyethylene glycol 1000 succinate may be present at 5 to 30% or 20 to 40%;

vi) the D-α-tocopherol may be present at 0.1 to 2%, the ethanol is absent, the sodium lauryl sulfate may be present at 0.1 to 3%, and the D-α-tocopherol polyethylene glycol 1000 succinate may be present at 5 to 30% or 20 to 40%; and vii) the D-α-tocopherol may be present at 0.1 to 2%, the ethanol is absent, the sodium lauryl sulfate is absent, and the D-α-tocopherol polyethylene glycol 1000 succinate may be present at 5 to 30% or 20 to 40%.

In the foregoing paragraphs, the percentages of various compounds are expressed as a percentage of the total weight of the mixture of excipients (i.e. excluding the active ingredient).

Furthermore, in one aspect of the foregoing 6 embodiments, the $C_{3-6}$ diol is 1,2-propanediol and the poly($C_{2-3}$) alkylene glycol having a number average molecular weight (Mn) of 200 to 1000 is polyethylene glycol 600.

Furthermore, in one aspect of the foregoing 6 embodiments, when the $C_{3-6}$ diol is present at 1 to 99%, 5 to 40%, 0 to 10%, 0 to 40%, 1 to 50% or up to 40%, the $C_{3-6}$ diol may be present at: 0%, 1 to 10%, 1 to 25%, 10 to 20%, 2.5 to 7.5%, 1% or 20%. When the $C_{3-6}$ diol is 1,2-propanediol the same ranges also apply.

Furthermore, in one aspect of the foregoing 6 embodiments, when the ($C_{2-3}$) alkylene glycol having a number average molecular weight (Mn) of 200 to 1000 is present at 1 to 99%, 20 to 95%, or 1 to 90% (whether alone or as a combination with a $C_{3-6}$ diol, the ($C_{2-3}$) alkylene glycol having a number average molecular weight (Mn) of 200 to 1000 may be present at: 90 to 99%, 10 to 90%, 30 to 70%, 40 to 60%, 45 to 55%, 60 to 75%, 72.7% 62.5% or 52.5%. When the ($C_{2-3}$) alkylene glycol having a number average molecular weight (Mn) of 200 to 1000 is polyethylene glycol 600, the same ranges apply.

Furthermore, in one aspect of the foregoing 6 embodiments, the co-solvent referred to may comprise a vitamin E (such as D-α-tocopherol), a $C_{2-6}$ monoalcohol (such as ethanol), $C_{10-18}$ alkyl sulphate (such as sodium lauryl sulfate) and a vitamin E poly($C_{2-3}$)alkylene glycol dicarboxylic ester (such as D-α-tocopherol polyethylene glycol 1000 succinate). Further, the co-solvent referred to may comprise a vitamin E (such as D-α-tocopherol), $C_{10-18}$ alkyl sulphate (such as sodium lauryl sulfate) and a vitamin E poly($C_{2-3}$) alkylene glycol dicarboxylic ester (such as D-α-tocopherol polyethylene glycol 1000 succinate). Further, the co-solvent referred to may comprise a vitamin E (such as D-α-tocopherol) and a vitamin E poly($C_{2-3}$)alkylene glycol dicarboxylic ester (such as D-α-tocopherol polyethylene glycol 1000 succinate)

In the co-solvent compositions described above, the vitamin E is present at 0.1% to 5%, 0.1% to 2%, 0.1% to 1%, 0.1% to 3%, 0.7%, 1% or 5%. In the co-solvent compositions described above, the vitamin E is D-α-tocopherol and is present at 0.1% to 5%, 0.1% to 2%, 0.1% to 1%, 0.1% to 3%, 0.7%, 1% or 5%.

In the co-solvent compositions described above, the $C_{2-8}$ monoalcohol is present at 0.1 to 10%, 0.1 to 1%, 0.5 to 7.5%, 0.5 to 2.5%, 2 to 6%, 3 to 5%, 2.5% or 5%. In the co-solvent compositions described above, the $C_{2-6}$ monoalcohol is ethanol and is present at 0.1 to 10%, 0.1 to 1%, 0.5 to 7.5%, 0.5 to 2.5%, 2 to 6%, 3 to 5%, 2.5% or 5%.

In the co-solvent compositions described above, the $C_{10-18}$ alkyl sulphate is present at 0.1 to 7.5%, 0.1 to 1%, 0.5 to 5%, 1 to 3% or 2.5%. In the co-solvent compositions described above, the $C_{10-18}$ alkyl sulphate is sodium dodecyl sulphate (also known as sodium lauryl sulphate) and is present at 0.1 to 7.5%, 0.1 to 1%, 0.5 to 5%, 1 to 3% or 2.5%.

In the co-solvent compositions described above, the vitamin E poly($C_{2-3}$)alkylene glycol dicarboxylic ester is present at 0 to 50%, 0.1 to 50%, 0 to 5%, 0.1 to 5%, 0.1 to 1%, 5 to 30%, 10 to 25%, 15 to 20%, 20 to 30%, 20 to 40%, 1%, 27.2% or 20%. In the co-solvent compositions described above, the vitamin E poly($C_{2-3}$)alkylene glycol dicarboxylic ester is D-α-tocopherol polyethylene glycol 1000 succinate (also known as Vitamin E polyethylene glycol 1000 succinate or vitamin E TPGS) and is present at 0 to 50%, 0.1 to 50%, 0 to 5%, 0.1 to 5%, 0.1 to 1%, 5 to 30%, 10 to 25%, 15 to 20%, 20 to 30%, 20 to 40%, 1%, 27.2% or 20%.

In one embodiment, the mixture of excipients comprises 70 to 75% of polyethylene glycol having a number average molecular weight (Mn) of 200 to 1000, 0 to 10% of a $C_{2-3}$ monoalcohol present, 0 to 5% of a $C_{10-18}$ alkyl sulphate, 0.1 to 5% of a vitamin E, citric acid or a combination thereof and 24 to 28% of a vitamin E poly($C_{2-3}$)alkylene glycol dicarboxylic ester.

In one embodiment, the mixture of excipients comprises 70 to 75% of polyethylene glycol having a number average molecular Weight (Mn) of 200 to 1000, 0.1 to 5% of a vitamin E, citric acid or a combination thereof and 24 to 28% of a vitamin E poly($C_{2-3}$)alkylene glycol dicarboxylic ester.

In one embodiment, the mixture of excipients comprises 70 to 75% of polyethylene glycol having a number average molecular weight (Mn) of 400 to 600, 0.1 to 5% of a D-α-tocopherol, citric acid or a combination thereof, and 24 to 28% of D-α-tocopherol polyethylene glycol 1000 succinate.

In one embodiment, the mixture of excipients comprises 20% of 1,2-propanediol, 52.5% of polyethylene glycol having a number average molecular weight (Mn) of 400 or 600, 5% of ethanol, 2.5% of sodium dodecyl sulphate and 20% of a D-α-tocopherol polyethylene glycol 1000 succinate.

In one embodiment, the mixture of excipients comprises 72.7% of polyethylene glycol having a number average molecular weight (Mn) of 400 or 600, 0.7% D-α-tocopherol and 26.6% of a D-α-tocopherol polyethylene glycol 1000 succinate.

In the foregoing paragraphs, the percentages of various compounds are expressed as a percentage of the total weight of the mixture of excipients (i.e. excluding the active ingredient).

In one embodiment, the excipients comprise a mixture of 1,2-propanediol, one or more polyethylene glycols having a number average molecular weight (Mn) of 200 to 800 (such as polyethylene glycol 400 or 600), a co-solvent and optionally ethanol and water. In one embodiment, the excipients comprise a mixture of 1,2-propanediol, one or more polyethylene glycols having a number average molecular weight (Mn) of 300 to 700 (such as polyethylene glycol 400 or 600) and a co-solvent. In one embodiment, the excipients comprise a mixture of 1,2-propanediol, one or more polyethylene glycols having a number average molecular weight ($M_n$) of 200 to 800 (such as polyethylene glycol 400 or 600), a co-solvent and ethanol and optionally water. In one embodiment, the excipients comprises a mixture of 1,2-propanediol, polyethylene glycol 400 and a co-solvent. In one embodiment, the excipients comprises a mixture of 1,2-propanediol, polyethylene glycol 400, a co-solvent and optionally ethanol and water. In one embodiment, the excipients comprises a mixture of 1,2-propanediol, polyethylene glycol 400, a co-solvent and ethanol and optionally water. In one embodiment, the excipients comprises a mixture of 1,2-propanediol, polyethylene glycol 600 and a co-solvent. In one embodiment, the excipients comprises a mixture of 1,2-propanediol, polyethylene glycol 600, a co-solvent and optionally ethanol and water. In one embodiment, the excipients comprises a mixture of 1,2-propanediol, polyethylene glycol 600, a co-solvent and ethanol and optionally water.

In the foregoing embodiments, the co-solvent may be a vitamin E, a vitamin E poly($C_{2-3}$)alkylene glycol dicarboxylic ester, a hydrocarbyl sulphate, a citric acid, a substituted phenol or a combination of the foregoing. In a particular embodiment, the co-solvent may be a vitamin E, a vitamin E poly($C_{2-3}$)alkylene glycol dicarboxylic ester or a combination of the foregoing. In another particular embodiment, the co-solvent may be a vitamin E poly($C_{2-3}$)alkylene glycol dicarboxylic ester, a, hydrocarbyl sulphate or a combination of the foregoing. In another particular embodiment, the co-solvent may be a vitamin E, a vitamin E poly($C_{2-3}$) alkylene glycol dicarboxylic ester, a, hydrocarbyl sulphate or a combination of the foregoing. In a particular embodiment, the co-solvent may be a citric acid, a vitamin E poly($C_{2-3}$)alkylene glycol dicarboxylic ester or a combination of the foregoing. In another particular embodiment, the co-solvent may be a citric acid, a vitamin E poly($C_{2-3}$) alkylene glycol dicarboxylic ester, a, hydrocarbyl sulphate or a combination of the foregoing. In a particular embodiment, the co-solvent may be a vitamin E, a citric acid, a vitamin E poly($C_{2-3}$)alkylene glycol dicarboxylic ester or a combination of the foregoing. In another particular embodiment, the co-solvent may be a vitamin E, a citric acid, a vitamin E poly($C_{2-3}$)alkylene glycol dicarboxylic ester, a, hydrocarbyl sulphate or a combination of the foregoing. Suitable ranges for the co-solvents are provided above.

In one embodiment, the polar organic solvent comprises solely one or more polyethylene glycols having a number average molecular weight ($M_n$) of 200 to 1000 (such as polyethylene glycol 400 or 600) and a co-solvent, wherein the co-solvent is present at a maximum amount of 40%.

In one embodiment, the excipients comprises a $C_{3-6}$ diol, such as 1,2-propanediol, one or more polyethylene glycols having a number average molecular weight ($M_n$) of 200 to 1000 (such as polyethylene glycol 400 or 600) at 1 to 99%, 5 to 80%, 20 to 99%, 50% to 95% or 60% to 90%, and a co-solvent, wherein the $C_{3-6}$ diol is present at a maximum amount of 30 to 40% and the co-solvent is present at a maximum amount of 40%. These percentages are expressed by weight as a percentage of the total weight of the mixture of excipients (i.e. excluding the active ingredient).

In one embodiment, the excipients comprise a $C_{3-6}$ diol, such as 1,2-propanediol, one or more polyethylene glycols having a number average molecular weight ($M_n$) of 200 to 700 (such as polyethylene glycol 400 or 600) at 1 to 99%, 5 to 80%, 20 to 99%, 50% to 95% or 60% to 90%, a co-solvent and optionally a $C_{2-6}$ monoalcohol and/or water, wherein the excipients contain a maximum of 30 to 40% $C_3$ diol, 10% $C_{2-6}$ monoalcohol, 10% water and 40% co-solvent. These percentages are expressed by weight as a percentage of the total weight of the mixture of excipients (i.e. excluding the active ingredient).

In one embodiment, the excipients comprise a $C_{3-6}$ diol, such as 1,2-propanediol, one or more polyethylene glycols having a number average molecular weight ($M_n$) of 200 to 700 (such as polyethylene glycol 400 or 600) at 1 to 99%, 5 to 80%, 20 to 99%, 50% to 95% or 60% to 90%, a co-solvent, a $C_{2-6}$ monoalcohol and optionally water, wherein the excipients contain a maximum of 30 to 40% $C_{3-6}$ diol, 10% $C_{2-6}$ monoalcohol, 10% water and 40% co-solvent. These percentages are expressed by weight as a percentage of the total weight of the mixture of excipients (i.e. excluding the active ingredient).

In one embodiment, the excipients comprise a $C_{3-6}$ diol, such as 1,2-propanedioldiol, one or more polyethylene glycols having a number average molecular weight (Mn) of 200 to 800 (such as polyethylene glycol 400 or 600) at 1 to 99%, 5 to 80%, 20 to 99%, 50% to 95% or 60% to 90% and optionally a co-solvent, a $C_{2-6}$ monoalcohol and/or water, wherein the excipients contains a maximum of 30 to 40% $C_{3-6}$ diol, 10% $C_{2-6}$ monoalcohol, 10% water and 40% co-solvent. These percentages are expressed by weight as a percentage of the total weight of the mixture of excipients (i.e. excluding the active ingredient).

In the above embodiments, when present the $C_{2-6}$ monoalcohol, such as ethanol, may comprise 1% to 10%, such as 1% to 5%. In the above embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a vitamin E, such as D-α-tocopherol, present at 0.1% to 10%, such as 0.1 to 1% or 0.1% to 5%, a citric acid present at 0.1% to 10%, such as 0.1 to 1% or 0.1% to 5%, a substituted phenol, such as BHA, BHT or propyl gallate, present at 0.1% to 10%, such as 0.1% to 5%, a $C_{10-18}$ alkyl sulphate, such as sodium dodecyl sulphate, present at 0.1% to 10%, such as 1% to 3% or a mixture of the foregoing. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30% and a C$_{10-18}$ alkyl sulphate, such as sodium dodecyl sulphate, present at 0.1% to 10%, such as 1% to 3%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30% and a vitamin E, such as D-α-tocopherol, present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a C$_{10-18}$ alkyl sulphate, such as sodium dodecyl sulphate, present at 0.1% to 10%, such as 1% to 3% and a vitamin E, such as D-α-tocopherol, present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30% and a citric acid present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a C$_{10-18}$ alkyl sulphate, such as sodium dodecyl sulphate, present at 0.1% to 10%, such as 1% to 3% and a citric acid present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a vitamin E, such as D-α-tocopherol and a citric acid, wherein the vitamin E and citric acid combined are present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a C$_{10-18}$ alkyl sulphate, such as sodium dodecyl sulphate, present at 0.1% to 10%, such as 1% to 3%, a vitamin E, such as D-α-tocopherol and a citric acid, wherein the vitamin E and citric acid combined are present at 0.1% to 10%, such as 0.1% to 1% or 0.1% to 5%. These percentages are expressed by weight as a percentage of the total weight of the mixture of excipients (i.e. excluding the active ingredient).

In one embodiment, the excipients comprise one or more polyethylene glycols having a number average molecular weight (Mn) of 200 to 800 (such as polyethylene glycol 400 or 600) at 1 to 99%, 5 to 80%, 20 to 99%, 50% to 95% or 60% to 90%, a co-solvent and optionally a C$_{2-6}$ monoalcohol and/or water, wherein the excipients contain a maximum of 10% C$_{2-8}$ monoalcohol, 10% water and 40% co-solvent. These percentages are expressed by weight as a percentage of the total weight of the mixture of excipients (i.e. excluding the active ingredient).

In one embodiment, the excipients comprise one or more polyethylene glycols having a number average molecular weight (Mn) of 200 to 800 (such as polyethylene glycol 400 or 600) at 1 to 99%, 5 to 80%, 20 to 99%, 50% to 95% or 60% to 90%, a co-solvent and optionally water, wherein the excipients contain a maximum of 10% water and 40% co-solvent. These percentages are expressed by weight as a percentage of the total weight of the mixture of excipients (i.e. excluding the active ingredient).

In the above embodiments, when present, the C$_{2-6}$ monoalcohol, such as ethanol, may comprise 1% to 10%, such as 1% to 5%. In the above embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a vitamin E, such as D-α-tocopherol, present at 0.1% to 10%, such as 0.1 to 1% or 0.1% to 5%, a citric acid present at 0.1% to 10%, such as 0.1 to 1% or 0.1% to 5%, a substituted phenol, such as BHA, BHT or propyl gallate, present at 0.1% to 10%, such as 0.1% to 5%, a C$_{10-18}$ alkyl sulphate, such as sodium dodecyl sulphate, present at 0.1% to 10%, such as 1% to 3% or a mixture of the foregoing. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30% and a C$_{10-18}$ alkyl sulphate, such as sodium dodecyl sulphate, present at 0.1% to 10%, such as 1% to 3%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30% and a vitamin E, such as D-α-tocopherol, present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a C$_{10-18}$ alkyl sulphate, such as sodium dodecyl sulphate, present at 0.1% to 10%, such as 1% to 3% and a vitamin E, such as D-α-tocopherol, present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30% and a citric acid present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a C$_{10-18}$ alkyl sulphate, such as sodium dodecyl sulphate, present at 0.1% to 10%, such as 1% to 3% and a citric acid present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a vitamin E, such as D-α-tocopherol and a citric acid, wherein the vitamin E and citric acid combined are present at 0.1% to 10%, such as 0.1 to 1% or 0.1% to 5%. Still further, in the above-embodiments, the co-solvent may be a vitamin E poly(C$_{2-3}$)alkylene glycol dicarboxylic ester, such as D-α-tocopherol polyethylene glycol 1000 succinate, present at 5% to 40%, such as 20% to 30%, a C$_{10-18}$ alkyl sulphate, such as sodium dodecyl sulphate, present at 0.1% to 10%, such as 1% to 3%, a vitamin E, such as D-α-tocopherol and a citric acid, wherein the vitamin E and citric acid combined are present at 0.1% to 10%, such as 0.1 to 1% or 0.1% to 5%. These percentages are expressed by weight as a percentage of the total weight of the mixture of excipients (i.e. excluding the active ingredient).

In one embodiment, the excipients comprise 1,2-propanediol, polyethylene glycol 600 at 1 to 99%, 5 to 80%, 20% to 99%, 50% to 95% or 60% to 90%, a co-solvent and optionally a C$_{2-6}$ monoalcohol and/or water, wherein the excipients contain a maximum of 40% 1,2-propanediol, 10% C$_{2-6}$ monoalcohol, 10% water and 40% co-solvent. These percentages are expressed by weight as a percentage of the total weight of the mixture of excipients (i.e. excluding the active ingredient).

In one embodiment, the excipients comprise 1,2-propanediol and polyethylene glycol 600 at 1 to 99%, 5 to 80%, 20% to 99%, 50% to 95% or 60% to 90%, a co-solvent, a $C_{2-6}$ monoalcohol and optionally water, wherein the excipients contain a maximum of 40% 1,2-propanediol, 10% $C_{2-6}$ monoalcohol, 10% water and 40% co-solvent. These percentages are expressed by weight as a percentage of the total weight of the mixture of excipients (i.e. excluding the active ingredient).

In one embodiment, the excipients comprise 1,2-propanediol, polyethylene glycol 600 at 1 to 99%, 5 to 80%, 20% to 99%, 50% to 95% or 60% to 90% and optionally a co-solvent, a $C_{2-6}$ monoalcohol and/or water, wherein the excipients contains a maximum of 40% 1,2-propanediol, 10% $C_{2-6}$ monoalcohol, 10% water and 40% co-solvent. These percentages are expressed by weight as a percentage of the total weight of the mixture of excipients (i.e. excluding the active ingredient).

In the above embodiments, when present, the $C_{2-6}$ monoalcohol, such as ethanol, may comprise 1% to 10%, such as 1% to 5%. In the above embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a vitamin E, such as D-α-tocopherol, present at 0.1% to 10%, such as 0.1% to 5%, a substituted phenol, such as BHA, BHT or propyl gallate, present at 0.1% to 10%, such as 0.1% to 5%, a $C_{10-18}$ alkyl sulphate, such as sodium dodecyl sulphate, present at 0.1% to 10%, such as 1% to 3% or a mixture of the foregoing. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a $C_{10-18}$ alkyl sulphate, such as sodium dodecyl sulphate, present at 0.1% to 10%, such as 1% to 3% or a mixture of the foregoing Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 30%, such as 20% to 40%, a vitamin E, such as D-α-tocopherol, present at 0.1% to 10%, such as 0.1% to 5% or a mixture of the foregoing. These percentages are expressed by weight as a percentage of the total weight of the mixture of excipients (i.e. excluding the active ingredient).

In one embodiment, the excipients comprise polyethylene glycol 600 at 1 to 99%, 5 to 80%, 20% to 99%, 50% to 95% or 60% to 90%, a co-solvent and optionally a $C_{2-6}$ monoalcohol and/or water, wherein the excipients contain a maximum of 10% $C_{2-6}$ monoalcohol, 10% water and 40% co-solvent. These percentages are expressed by weight as a percentage of the total weight of the mixture of excipients (i.e. excluding the active ingredient).

In one embodiment, the excipients comprise polyethylene glycol 600 at 1 to 99%, 5 to 80%, 20% to 99%, 50% to 95% or 60% to 90%, a co-solvent, a $C_{2-6}$ monoalcohol and optionally water, wherein the excipients contain a maximum of 10% $C_{2-6}$ monoalcohol, 10% water and 40% co-solvent. These percentages are expressed by weight as a percentage of the total weight of the mixture of excipients (i.e. excluding the active ingredient).

In one embodiment, the excipients comprise polyethylene glycol 600 at 1 to 99%, 5 to 80%, 20% to 99%, 50% to 95% or 60% to 90%, a co-solvent and optionally water, wherein the excipients contain a maximum of 10% water and 40% co-solvent. These percentages are expressed by weight as a percentage of the total weight of the mixture of excipients (i.e. excluding the active ingredient).

In the above embodiments, when present, the $C_{2-6}$ monoalcohol, such as ethanol, may comprise 1% to 10%, such as 1% to 5%. In the above embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a vitamin E, such as D-α-tocopherol, present at 0.1% to 10%, such as 0.1 to 1% or 0.1% to 5%, a citric acid present at 0.1% to 10%, such as 0.1 to 1% or 0.1% to 5%, a substituted phenol, such as BHA, BHT or propyl gallate, present at 0.1% to 10%, such as 0.1% to 5%, a $C_{10-18}$ alkyl sulphate, such as sodium dodecyl sulphate, present at 0.1% to 10%, such as 1% to 3% or a mixture of the foregoing. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30% and a $C_{10-18}$ alkyl sulphate, such as sodium dodecyl sulphate, present at 0.1% to 10%, such as 1% to 3%. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30% and a vitamin E, such as D-α-tocopherol, present at 0.1% to 10%, such as 0.1 to 1% or 0.1% to 5%. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a $C_{10-18}$ alkyl sulphate, such as sodium dodecyl sulphate, present at 0.1% to 10%, such as 1% to 3% and a vitamin E, such as D-α-tocopherol, present at 0.1% to 10%, such as 0.1 to 1% or 0.1% to 5%. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30% and a citric acid present at 0.1% to 10%, such as 0.1 to 1% or 0.1% to 5%. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a $C_{10-18}$ alkyl sulphate, such as sodium dodecyl sulphate, present at 0.1% to 10%, such as 1% to 3% and a citric acid present at 0.1% to 10%, such as 0.1 to 1% or 0.1% to 5%. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a vitamin E, such as D-α-tocopherol and a citric acid, wherein the vitamin E and citric acid combined are present at 0.1% to 10%, such as 0.1 to 1% or 0.1% to 5%. Still further, in the above-embodiments, the co-solvent may be a vitamin E poly($C_{2-3}$)alkylene glycol dicarboxylic ester, such as D-α-tocopherol polyethylene glycol 1000 succinate, present at 5% to 40%, such as 20% to 30%, a $C_{10-18}$ alkyl sulphate, such as sodium dodecyl sulphate, present at 0.1% to 10%, such as 1% to 3%, a vitamin E, such as D-α-tocopherol and a citric acid, wherein the vitamin E and citric acid combined are present at 0.1% to 10%, such as 0.1 to 1% or 0.1% to 5%. These percentages are expressed by weight as a percentage of the total weight of the mixture of excipients (i.e. excluding the active ingredient).

In one embodiment, the excipients comprise 5 to 25% of 1,2-propanediol; 30 to 90% of polyethylene glycol 600; 1 to 10% ethanol; 0.1% to 50% co-solvent. In one embodiment, the excipients comprise 5 to 25% of 1,2-propanediol; 30 to 90% of polyethylene glycol 600; 1 to 10% ethanol; 0.1 to 5% sodium dodecyl sulphate; and 1 to 50% D-α-tocopherol polyethylene glycol 1000 succinate. In one embodiment, the excipients comprise 5 to 20% of 1,2-propanediol; 30 to 70% of polyethylene glycol 600; 5 to 10% ethanol; 1 to 3% sodium dodecyl sulphate; and 5 to 35% D-α-tocopherol polyethylene glycol 1000 succinate. These percentages are expressed as a percentage of the total weight of the mixture of excipients (i.e. excluding the active ingredient).

In one embodiment, the excipients comprise 5 to 25% of 1,2-propanediol; 30 to 90% of polyethylene glycol 600; 0.1 to 5% sodium dodecyl sulphate; and 1 to 50% D-α-tocopherol polyethylene glycol 1000 succinate. In one embodiment, the excipients comprise 5 to 20% of 1,2-propanediol; 30 to 70% of polyethylene glycol 600; and 5 to 10% ethanol; 1 to 3% sodium dodecyl sulphate; and 5 to 35% D-α-tocopherol polyethylene glycol 1000 succinate.

These percentages are expressed as a percentage of the total weight of the mixture of excipients (i.e. excluding the active ingredient).

In one embodiment, the excipients comprise 80% of a mixture of polyethylene glycol 600 and 1,2-propanediol, wherein the 1,2-propanediol is present at a maximum of 40% and 0.1 to 50% co-solvent. In one embodiment, the excipients comprise 80% of a mixture of polyethylene glycol 600 and 1,2-propanediol, wherein the 1,2-propanediol is present at a maximum of 40%; 0.1% to 5% D-α-tocopherol (such as 0.1 to 1%); and 1% to 50% D-α-tocopherol polyethylene glycol 1000 succinate (such as 20 to 30%). In one embodiment, the excipients comprise 80% of a mixture of polyethylene glycol 600 and 1,2-propanediol, wherein the 1,2-propanediol is present at a maximum of 40%; 0.1% to 5% D-α-tocopherol (such as 0.1 to 1%); 1 to 3% sodium dodecyl sulphate; and 1% to 50% D-α-tocopherol polyethylene glycol 1000 succinate (such as 20 to 30%).

In one embodiment, the excipients comprise 80% of a mixture of polyethylene glycol 600 and 1,2-propanediol, wherein the 1,2-propanediol is present at a maximum of 40%; 0.1% to 5% citric acid (such as 0.1 to 1%); and 1% to 50% D-α-tocopherol polyethylene glycol 1000 succinate (such as 20 to 30%). In one embodiment, the excipients comprise 80% of a mixture of polyethylene glycol 600 and 1,2-propanediol, wherein the 1,2-propanediol is present at a maximum of 40%; 0.1% to 5% citric acid (such as 0.1 to 1%); 1 to 3% sodium dodecyl sulphate; and 1% to 50% D-α-tocopherol polyethylene glycol 1000 succinate (such as 20 to 30%). These percentages are expressed as a percentage of the total weight of the mixture of excipients (i.e. excluding the active ingredient).

In one embodiment, the excipients comprise 30 to 90% of polyethylene glycol 600 (such as 70 to 80%); and 0.1% to 50% co-solvent. In one embodiment, the excipients comprise 30% to 90% (such as 70 to 80%) of polyethylene glycol 600; 0.1% to 5% D-α-tocopherol (such as 0.1 to 1%); and 1% to 50% D-α-tocopherol polyethylene glycol 1000 succinate (such as 20 to 30%). In one embodiment, the excipients comprise 30% to 90% (such as 70 to 80%) of polyethylene glycol 600; 0.1% to 5% citric acid (such as 0.1 to 1%); and 1% to 50% D-α-tocopherol polyethylene glycol 1000 succinate (such as 20 to 30%). In one embodiment, the excipients comprise 30% to 90% (such as 70 to 80%) of polyethylene glycol 600; 0.1% to 5% D-α-tocopherol (such as 0.1 to 1%); 1 to 3% sodium dodecyl sulphate; and 1% to 50% D-α-tocopherol polyethylene glycol 1000 succinate (such as 20 to 30%). In one embodiment, the excipients comprise 30% to 90% (such as 70 to 80%) of polyethylene glycol 600; 0.1% to 5% citric acid (such as 0.1 to 1%); 1 to 3% sodium dodecyl sulphate; and 1% to 50% D-α-tocopherol polyethylene glycol 1000 succinate (such as 20 to 30%). These percentages are expressed as a percentage of the total weight of the mixture of excipients (i.e. excluding the active ingredient).

Particular mixtures of excipients include the following:

20% 1,2-propanediol; 70% polyethylene glycol 600; and 10% ethanol;

20% 1,2-propanediol; 75% polyethylene glycol 600; and 5% ethanol;

20% 1,2-propanediol; 75% polyethylene glycol 600; 2.5% ethanol; and 2.5% sodium dodecyl sulphate;

20% 1,2-propanediol; 77.5% polyethylene glycol 600; and 2.5% sodium dodecyl sulphate;

10% 1,2-propanediol; 85% polyethylene glycol 600; and 5% ethanol;

20% 1,2-propanediol; 52.5% polyethylene glycol 600; 5% ethanol; 2.5% sodium dodecyl sulphate; and 20% D-α-tocopherol polyethylene glycol 1000 succinate;

20% 1,2-propanediol; 72.5% polyethylene glycol 600; 5% ethanol; and 2.5% sodium dodecyl sulphate;

92% of a mixture comprising 20% 1,2-propanediol, 72.5% polyethylene glycol 600, 5% ethanol and 2.5% sodium dodecyl sulphate; and 8% water (typically added after dissolution of the active ingredient);

20% 1,2-propanediol; 67.5% polyethylene glycol 600; 5% ethanol; 2.5% sodium dodecyl sulphate; and 5% D-α-tocopherol polyethylene glycol 1000 succinate;

92% of a mixture comprising 20% 1,2-propanediol, 67.5% polyethylene glycol 600, 5% ethanol, 2.5% sodium dodecyl sulphate and 5% D-α-tocopherol polyethylene glycol 1000 succinate; and 8% water (typically added after dissolution of the active ingredient);

20% 1,2-propanediol; 62.5% polyethylene glycol 600; 5% ethanol; 2.5% sodium dodecyl sulphate; and 10% D-α-tocopherol polyethylene glycol 1000 succinate;

92% of a mixture comprising 20% 1,2-propanediol, 62.5% polyethylene glycol 600, 5% ethanol, 2.5% sodium dodecyl sulphate and 10% D-α-tocopherol polyethylene glycol 1000 succinate; and 8% water (typically added after dissolution of the active ingredient);

20% 1,2-propanediol; 52.5% polyethylene glycol 600; 5% ethanol; 2.5% sodium dodecyl sulphate; and 20% D-α-tocopherol polyethylene glycol 1000 succinate;

92% of a mixture comprising 20% 1,2-propanediol, 52.5% polyethylene glycol 600, 5% ethanol, 2.5% sodium dodecyl sulphate and 10% D-α-tocopherol polyethylene glycol 1000 succinate and 8% water (typically added after dissolution of the active ingredient);

20% 1,2-propanediol; 72.45% polyethylene glycol 600; 5% ethanol; 2.5% sodium dodecyl sulphate; 0.025% tert-butyl 4-hydroxyanisole and 0.025% 2,6-di-tert-butyl-4-methylphenol;

92% of a mixture comprising 20% 1,2-propanediol, 72.45% polyethylene glycol 600, 5% ethanol, 2.5% sodium dodecyl sulphate, 0.025% tert-butyl 4-hydroxyanisole and 0.025% 2,6-di-tert-butyl-4-methylphenol; and 8% water (typically added after dissolution of the active ingredient);

20% 1,2-propanediol; 72.45% polyethylene glycol 600; 5% ethanol; 2.5% sodium dodecyl sulphate; 0.025% tert-butyl 4-hydroxyanisole and 0.025% 2,6-di-tert-butyl-4-methylphenol;

92% of a mixture comprising 20% 1,2-propanediol, 72.45% polyethylene glycol 600, 5% ethanol, 2.5% sodium dodecyl sulphate, 0.025% tert-butyl 4-hydroxyanisole and 0.025% 2,6-di-tert-butyl-4-methylphenol; and 8% water (typically added after dissolution of the active ingredient);

72.1% polyethylene glycol 600, 27.2% D-α-tocopherol polyethylene glycol 1000 succinate and 0.7% D-α-tocopherol;

92% of a mixture comprising 72.1% polyethylene glycol 600, 27.2% D-α-tocopherol polyethylene glycol 1000 succinate and 0.7% D-α-tocopherol; and 8% water (typically added after dissolution of the active ingredient);

72.75% polyethylene glycol 600, 27.2% D-α-tocopherol polyethylene glycol 1000 succinate, 0.025% tert-butyl 4-hydroxyanisole and 0.025% 2,6-di-tert-butyl-4-methylphenol;

92% of a mixture comprising 72.75% polyethylene glycol 600, 27.2% D-α-tocopherol polyethylene glycol 1000 succinate, 0.025% tert-butyl 4-hydroxyanisole and 0.025% 2,6-di-tert-butyl-4-methylphenol; and 8% water (typically added after dissolution of the active ingredient);

72.7% polyethylene glycol 600; 26.6% D-α-tocopherol polyethylene glycol 1000 succinate and 0.7% D-α-tocopherol;

92% of a mixture comprising 72.7% polyethylene glycol 600; 26.6% D-α-tocopherol polyethylene glycol 1000 succinate and 0.7% D-α-tocopherol; and 8% water (typically added after dissolution of the active ingredient);

72.7% polyethylene glycol 600; 26.6% D-α-tocopherol polyethylene glycol 1000 succinate and 0.7% citric acid;

92% of a mixture comprising 72.7% polyethylene glycol 600; 26.6% D-α-tocopherol polyethylene glycol 1000 succinate and 0.7% citric acid; and 8% water (typically added after dissolution of the active ingredient);

The foregoing percentages being expressed as a percentage of the total weight of the mixture of excipients (i.e. excluding the active ingredient).

Dosage

The dosage of the compounds used in the present invention may vary depending on a number of factors such as the age, sex, weight and physiological condition of the subject to be treated. However, the formulations described herein enable for the first time the active compounds of formula (I) used in the present invention (particularly 3-[2-(4-carbamimidoyl-phenylcarbamoyl)-5-methoxy-4-vinyl-phenyl]-6-(cyclopropylmethyl-carbamoyl)-pyridine-2-carboxylic acid, its hydrochloride salt and Form A) to be formulated into an oral dosage form capable of delivering a therapeutically effective amount of the active compound to a subject.

The composition of the present invention, when formulated into a unit dose form, may provide a dose of, for example, between 1 mg and 8 g of the active ingredient. In one embodiment the composition provides a dose of between 5 mg and 5 g of the active ingredient. In one embodiment the composition provides a dose of between 10 mg and 3 g of the active ingredient. In one embodiment the composition provides a dose of between 50 mg and 2.5 g of the active ingredient. In one embodiment the composition provides a dose of between 100 mg and 1 g of the active ingredient. In one aspect, more than one unit dose form may be used to provide the specified ranges of active ingredient. Examples of specific compositions may include 100, 200, 300, 400, 500, 600, 700 or 800 mg of the active ingredient.

The compositions of the present invention may be administered at a dosing interval selected by the doctor depending on a number of factors such as the age, sex, weight and physiological condition of the subject to be treated. In one embodiment, the compositions are administered once a day. In one embodiment, the compositions are administered twice a day. In one embodiment, the compositions are administered three times a day. In one embodiment, the compositions are administered four times a day. A number of dose forms/compositions (preferably 1 to 4, more preferably 1 to 3, more preferably 1 or 2, and more preferably only one) may be administered at each dosing interval.

The daily dose of the compositions of the present invention may typically be between 1 mg/day and 8 g/day of the active ingredient. In one embodiment the daily dose of the composition may be between 5 mg/day and 5 g/day of the active ingredient. In one embodiment the daily dose of the composition may be between 10 mg/day and 3 g/day of the active ingredient. In one embodiment the daily dose of the composition may be between 50 mg/day and 2.5 g/day of the active ingredient. In one embodiment the daily dose of the composition may be between 100 mg/day and 1 g/day of the active ingredient.

Based on an average weight patient of 60 kg, the compositions of the present invention may typically provide between 0.016 mg/kg/day and 133.3 mg/kg/day of the active ingredient. In one embodiment the composition may provide between 0.083 mg/kg/day and 83.3 mg/kg/day of the active ingredient. In one embodiment the composition may provide between 0.166 mg/kg/day and 50 mg/kg/day of the active ingredient. In one embodiment the daily dose of the composition may provide between 0.833 mg/kg/day and 41.6 mg/kg/day of the active ingredient. In one embodiment the daily dose of the composition may be between 1.66 mg/kg/day and 16.6 mg/kg/day of the active ingredient.

Subjects

The compositions of the present invention may be administered to either a human or non-human subject. Examples of non-human subjects include companion animals such as cats, dogs, rabbits, hamsters, guinea pigs, gerbils, mice and rats, and livestock such as cows, sheep, goats, pigs and horses. In one embodiment, the subject is a human subject.

Method of Manufacture

The formulation may be prepared by procedures well known to those skilled in the art. When formulated as a liquid (particularly although not exclusively to fill capsules, such as soft gelatin capsules), the liquid may be a solution, suspension, emulsion or in other liquid forms. The drug in the liquid formulation may be dissolved, emulsified or suspended. The fill formulation may require heat to melt the drug or the excipients to form a liquid in order to fill the capsules. The formulation must exhibit physical and chemical stability during manufacturing and after encapsulation into the capsules.

In one embodiment, the composition is provided as a liquid, which is used to fill capsules, in particular hard gelatin or soft gelatin capsules.

A hard gel capsule is typically made in two parts by dipping metal pins in a gelling agent solution (such as gelatin). The gelatin is dried and removed from the pins. The two piece capsules are supplied as closed units to the pharmaceutical manufacturer. Before use, the two halves are separated, the lower half of the capsule is filled with powder, pellets or a liquid. The lower half of the capsule is pressed on. The powder, pellets or liquid inside the capsule contains the active ingredient(s) and any excipients. Powder excipients could include binders, disintegrants, fillers, glidant, and preservatives. Liquid excipients could include solvents, surfactants, suspending agents, preservatives and antioxidants.

A soft gel capsule is an oral dosage form for medicine similar to capsules. They consist of a shell (such as a gelatin based shell) surrounding a liquid fill. Softgel shells are typically a combination of gelatin, water, opacifier and a plasticiser such as glycerol and/or sorbitol(s).

Softgels are typically produced in a process known as encapsulation using the Rotary Die Encapsulation process. The encapsulation process has been described as a form/fill/seal process. Two flat ribbons of shell material are manufactured on the machine and brought together on a twin set of rotating dies. The dies contain recesses in the desired size and shape, which cut out the ribbons into a two dimensional shape, and form a seal around the outside. At the same time a pump delivers a precise dose of fill material through a nozzle incorporated into a filling wedge whose tip sits between the two ribbons in between two die pockets at the point of cut out. The wedge is heated to facilitate the sealing process. The wedge injection causes the two flat ribbons to expand into the die pockets, giving rise to the three dimensional finished product. After encapsulation, the softgels are dried for two days to two weeks depending on the product.

Medical Uses and Methods of Treatment

The present inventors have found for the first time that the compounds of formula (I), (I') and (II) can be used according to the present invention to treat hereditary angioedema and acquired angioedema (AAE) as well as other conditions. In this regard, the compounds of formula (I), (I') and (II) are preferably administered in the form of the oral compositions described herein. However, in this aspect of the present invention the use of the compounds of formula (I) is of general applicability and is not restricted to the oral compositions described herein: the compounds may therefore be dosed in any manner known to those skilled in the art, including orally (such as sublingually or transbuccally), parenterally (such as subcutaneously, intraadiposally, intraarticularly, intramuscularly, intrathecally, intraperitoneally, intravenously, or intraarterially), transdermally, rectally, intranasally, liposomally, via inhalation, vaginally, intraoccularly, or via local delivery (for example by catheter or stent).

Typical oral formulations include tablets, capsules, powders, solutions, elixirs, syrups, gels. Typical parenteral formulations include injections and infusions. Typical inhalation formulations include nasal sprays and nebulisers. Typical intraocular formulations include eye drops and ointments. Typical rectal formulations include suppositories. Examples of such methods of administration and suitable excipients for each of these modes of administration are well known to those skilled in the art.

In one embodiment, the hereditary angioedema is Type I hereditary angioedema. In another embodiment, the hereditary angioedema is Type II hereditary angioedema. In another embodiment, the hereditary angioedema is Type III hereditary angioedema.

Acquired Angioedema (AAE) (Caldwell J R, et al. Clin Immunol Immunopathol. 1972; 1:39-52) is characterized in several ways, including by acquired deficiency of C1 inhibitor (C1-INH), hyperactivation of the classical pathway of human complement and angioedema symptoms mediated by bradykinin released by inappropriate activation of the contact-kinin system. AAE may be present in two forms, AAE type 1 (which is normally associated with another disease) and AAE type II, which is normally associated with an autoimmune disease. AAE may be caused by a number of factors, including, but not limited to, autoimmune diseases (or example, the production of anti-C1INH antibodies) or by an acquired mutation in C1INH. Furthermore, the compounds of the formula (I), (I') and (II) may be used to treat side effects of angiotensin converting enzyme (ACE) inhibitor treatments. ACE inhibitors block the major pathway for breakdown of bradykinin. Inhibiting kallikrein formation through the use of the compounds of the formula (I), (I') and (II) reduces the formation of bradykinin.

In addition to the above use, the compounds of the formula (I') may also be used in the present invention to treat diseases other than HAE. For example, the compounds of formula (I') may be used to treat any disease or condition for which kallikrein (especially plasma kallikrein) contributes to the pathology or symptomatology of the disease state. In this aspect of the present invention the use of the compounds of formula (I') is of general applicability and is not restricted to the oral compositions described herein. The compounds of the formula (I') may therefore be used in the treatment of a disease or condition treatable via the mechanism of kallikrein (especially plasma kallikrein) inhibition.

In particular, the compounds of the formula (I') may be used to inhibit blood coagulation (particularly by inhibition of factor VIIa without directly inhibiting thrombin). The compounds can therefore be used to prevent intravascular blood clots or for anti-coagulant treatment. Examples of clinical situations in which anti-coagulant therapy would be beneficial are well known and include surgery (such as total hip replacement surgery, transluminal coronary angioplasty and treatment for myocardial infarction or crescendo angina).

Methods

XRPD Method

1. Transmission Mode XRPD

The X-ray powder diffraction pattern was collected with a PANalytical X'Pert PRO MPD diffractometer using an incident beam of Cu radiation produced using an Optix long, fine-focus source. An elliptically graded multilayer mirror was used to focus Cu Kα X-ray radiation through the specimen and onto the detector. Prior to the analysis, a silicon specimen (NIST SRM 640d) is analyzed to verify that the observed position of the Si (111) peak was consistent with the NIST-certified position. A specimen of the sample, after being powdered with a mortar and pestle, was sandwiched between 3-μm-thick films and analyzed in transmission geometry. A beam-stop, short anti-scatter extension, and anti-scatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror and the incident-beam anti-scatter slit (SS).

2. Reflection Mode XRPD

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a thin, circular layer centered on a silicon zero-background substrate. Anti-scatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

Differential Scanning Calorimetry (DSC) Method

DSC analyses were performed using a TA Instruments 2920 differential scanning calorimeter. Temperature calibration was performed using NIST-traceable indium metal. The sample was placed onto an aluminum DSC pan, covered with a lid, and the weight was accurately recorded. A weighed aluminum pan, T-zero hermetically sealed with manual pin hole (T0CHSMP), and configured as the sample pan, was placed on the reference side of the cell. The scanning method used for Form A was −30° C. to 275° C. at a rate of 10° C. per minute. The scanning method used for Form C was −30° C. to 250° C. at a rate of 10° C. per minute.

Thermogravimetric (TG) Analysis Method

TG analysis was performed using a TA Instruments 2950 thermogravimetric analyzer. Temperature calibration was performed using nickel and Alumel™. Each sample was placed in an aluminum pan and inserted into the TG furnace. The furnace was heated under a nitrogen purge. The data acquisition parameters for Form A were a temperature range from 0° C. to 250° C. at a rate of 10° C. per minute. The data acquisition parameters for Form C were a temperature range from 25° C. to 350° C. at a rate of 10° C. per minute.

EXAMPLES

Example 1—Synthesis of 3-[2-(4-carbamimidoyl-phenylcarbamoyl)-5-methoxy-4-vinyl-phenyl]-6-(cyclopropylmethyl-carbamoyl)-pyridine-2-carboxylic acid The synthesis of the above compound and intermediates is described below. In this section, the following abbreviations are used:

| | |
|---|---|
| Ac = acetyl | MEM = (2-methoxyethoxy)methyl |
| Bu = butyl | THF = tetrahydrofuran |
| Me = methyl | DME = 1,2-dimethoxyethane |
| Et = ethyl | TEA = triethylamine |
| Bn = benzyl | min = minute |
| DMSO = dimethyl sulfoxide | h = hour |
| MP = melting point | MS = mass spectrum |
| NMR = nuclear magnetic resonance spectrum | EDCI = 1-ethyl-3-(3-dimethylamino-propyl)-carbodiimide |
| IR = infra-red spectrum | TLC = thin layer chromatography |
| DMF = N,N-dimethylformamide | $R_f$ = retardation factor |
| Ether = diethyl ether | ES = electrospray ionisation |
| DIPEA = N,N-diisopropyl-ethylamine | DCC = N,N'-dicyclohexylcarbodiimide |

The synthesis of starting material, (4-(benzyloxy)-2-formyl-5-methoxyphenyl)boronic acid (1f) is described in Scheme 1.

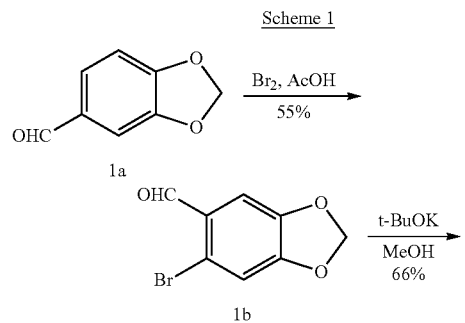

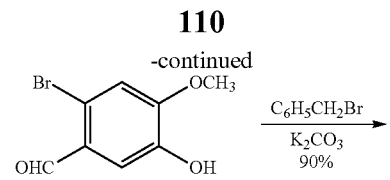

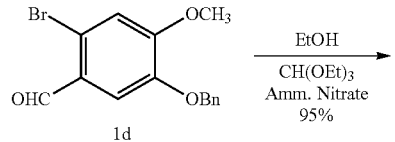

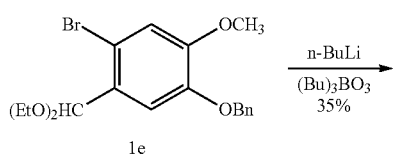

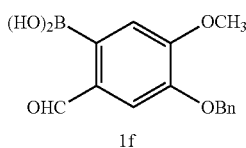

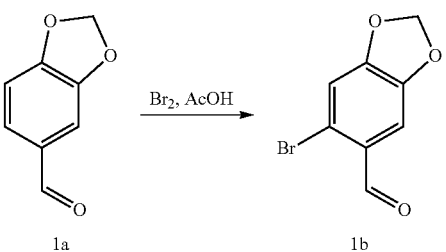 [SMILES: O=Cc1ccc2c(c1)OCO2 ; O=Cc1cc2c(cc1Br)OCO2]

Preparation of 6-bromobenzo[d][1,3]dioxole-5-carbaldehyde (1 b)

To a mixture of piperonal (1a) (498 g, 3.32 mol) in glacial acetic acid (1000 mL) was added a solution of bromine (200 mL, 3.89 mol) in glacial acetic acid (500 mL) over a period of 30 min and stirred at room temperature for 24 h. The reaction mixture was poured into water (2000 mL) and the solid that separated was collected by filtration. The solid was dissolved in boiling ethanol (4000 mL) and cooled to room temperature. The solid obtained on cooling was collected by filtration to furnish 6-bromobenzo[d][1,3]dioxole-5-carbaldehyde (1b) (365 g, 48%) as a white solid, MP 126° C.; $^1$HNMR (300 MHz, DMSO-d$_6$): δ 10.06 (s, 1H), 7.42 (s, 1H), 7.29 (s, 1H), 6.20 (d, J=12.3, 2H); IR (KBr) 3434, 2866, 1673, 1489, 1413, 1259, 1112, 1031, 925 cm$^{-1}$; Analysis calculated for $C_8H_5BrO_3 \cdot 0.25H_2O$: C, 41.15; H, 2.37; Found: C, 41.07; H, 2.11.

Preparation of 2-bromo-5-hydroxy-4-methoxybenzaldehyde (1c)

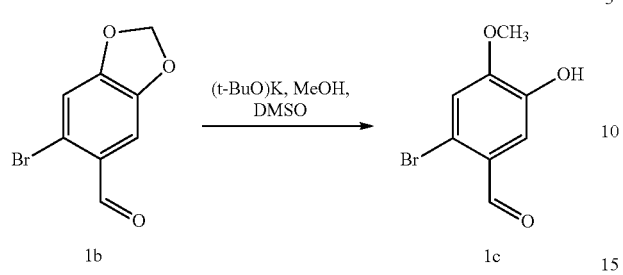

A solution of potassium tert-butoxide (397 g, 3.36 mol) in DMSO (1.5 L) was heated at 50° C. for 30 min. Methanol (1.5 L) was added to it and continued heating at 50° C. for additional 30 min. To the hot reaction mixture was added 6-bromo-benzo[d][1,3]dioxole-5-carbaldehyde (1 b) (350 g, 1.53 mol) and continued heating at 50° C. for 30 min. The reaction mixture was cooled to room temperature and quenched with water (2.3 L) and sodium hydroxide (61.2 g, 1.53 mol). The reaction mixture was washed with ether (2×1.5 L), acidified to pH 2 using conc. HCl and extracted with ethyl acetate (4×1 L). The ethyl acetate layers were combined and concentrated under vacuum to dryness. The residue obtained was treated with water (1.5 L) and ethyl acetate (1 L). The solid obtained was collected by filtration to furnish 2-bromo-5-hydroxy-4-methoxybenzaldehyde (1c) (97 g, 27.5% as a first crop). The layers from the filtrate were separated and aqueous layer was extracted with ethyl acetate (200 mL). The ethyl acetate layers were combined dried over MgSO$_4$ and concentrated under vacuum to dryness to furnish 2-bromo-5-hydroxy-4-methoxybenzaldehyde (1c) (192 g, 54.4%, second crop) as an orange solid, MP 108° C.; $^1$HNMR (300 MHz, DMSO-d$_6$): δ 10.00 (s, 1H), 9.92 (s, 1H), 7.27 (s, 1H), 7.26 (s, 1H), 3.93 (s, 3H); IR (KBr) 3477, 2967, 2917, 2837, 2767, 2740, 1657, 1595, 1428, 1270, 1210, 1164, 1022 cm$^{-1}$; Analysis calculated for C$_8$H$_7$BrO$_3$.H$_2$O: C, 38.58; H, 3.64: Found: C, 38.60; H, 3.60.

Preparation of 5-(benzyloxy)-2-bromo-4-methoxybenzaldehyde (1d)

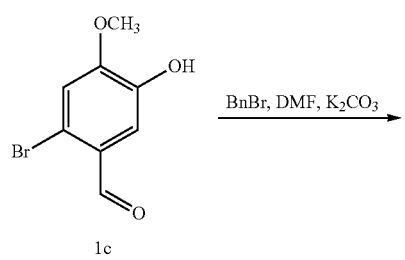

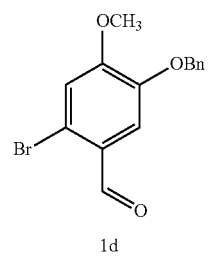

To a solution 2-bromo-5-hydroxy-4-methoxybenzaldehyde (1c) (120 g, 520 mmol) in DMF (1000 mL) was added potassium carbonate (79 g, 572 mmol) and benzyl bromide (68 mL, 572 mmol). The reaction mixture was stirred at room temperature overnight and quenched with water (3000 mL). The solid obtained was collected by filtration, washed with ether and dried under vacuum to furnish 5-(benzyloxy)-2-bromo-4-methoxybenzaldehyde (1d) (113.19 g, 67.9%) as a white solid, MP 144° C.; $^1$HNMR (300 MHz, DMSO-d$_6$): δ 10.06 (s, 1H), 7.47-7.34 (m, 7H), 5.17 (s, 2H), 3.92 (s, 3H); IR (KBr) 2898, 2851, 1673, 1592, 1502, 1437, 1402, 1264, 1210, 1158, 1017, 754 cm$^{-1}$; Analysis calculated for C$_{15}$H$_{13}$BrO$_3$: C, 56.10; H, 4.08; Found: C, 55.44; H, 4.08.

Preparation of 1-(benzyloxy)-4-bromo-5-(diethoxymethyl)-2-methoxybenzene (1e)

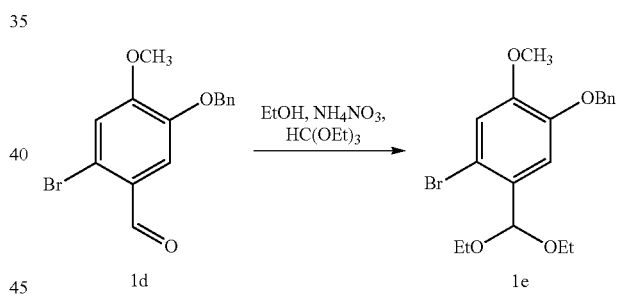

To a solution of 5-(benzyloxy)-2-bromo-4-methoxybenzaldehyde (1d) (100 g, 311 mmol) in ethanol (1500 mL) was added triethyl orthoformate (103 mL, 622 mmol), ammonium nitrate (7.5 g, 93.3 mmol) and stirred at room temperature overnight. The reaction mixture was treated with ether (1200 mL) and stirred for 15 min before filtration. The filtrate was concentrated under vacuum to dryness to give 1-(benzyloxy)-4-bromo-5-(diethoxymethyl)-2-methoxybenzene (1e) (134 g) as a brown syrup; The product was used in the next step without further purification; $^1$H NMR (300 MHz, DMSO-d$_6$) δ 7.45-7.37 (m, 4H), 7.36-7.33 (m, 1H), 7.17-7.14 (m, 1H), 7.10 (s, 1H), 5.10 (s, 2H), 3.80 (s, 3H), 3.58-3.33 (m, 5H), 1.13-1.07 (m, 6H); IR (KBr) 2974, 2879, 1601, 1503, 1377, 1260, 1163, 1060 cm; Analysis calculated for C$_{19}$H$_{23}$BrO$_4$: C, 57.73; H, 5.86; Found: C, 57.21; H, 5.94.

Preparation of (4-(benzyloxy)-2-formyl-5-methoxy-phenol)boronic acid (1f)

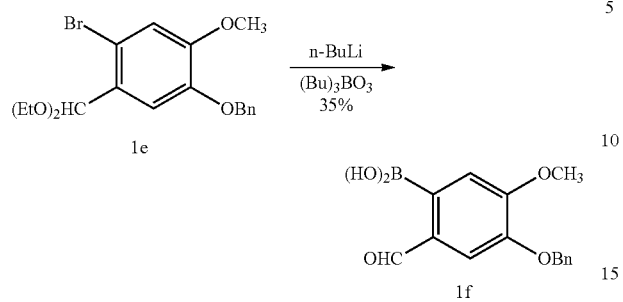

To a solution of 1-(benzyloxy)-4-bromo-5-(diethoxymethyl)-2-methoxybenzene (1e) (120 g, 300 mmol) in dry ether (1000 mL) at −78° C. was added n-butyllithium (1.6 M solution in hexanes, 244 mL, 390 mmol) over a period of 30 min and further stirred at −78° C. for 30 min. A solution of tri-n-butylborate (110 mL, 405 mmol) in dry ether (300 mL) was added to this solution at −78° C. over a period of 30 min. The reaction mixture was further stirred for 2 h at −78° C. and warmed to 0° C. The reaction mixture was quenched with 3N HCl (300 mL) at 0° C. and heated at reflux for 1 h. After cooling to room temperature, the solid obtained was collected by filtration washed with water (250 mL) dried in vacuum to afford (4-(benzyloxy)-2-formyl-5-methoxyphenyl)boronic acid (1f) (30.85 gm, 37.6% as a white solid. The organic layer from above filtrate was extracted with 1.5 N NaOH (3×200 mL). The combined basic extracts were acidified with conc. HCl (pH about 4). The solid obtained was collected by filtration, washed with water and dried under vacuum to furnish a second crop of (4-(benzyloxy)-2-formyl-5-methoxyphenyl)boronic acid (1f) (22.3 g, 26%) as a light orange solid MP 158° C.; $^1$H NMR (300 MHz, DMSO-$d_6$) δ 10.08 (s, 1H), 7.52 (s, 1H), 7.48-7.33 (m, 5H), 7.24 (s, 1H), 5.18 (s, 2H), 3.89 (s, 3H); $^1$H NMR (300 MHz, DMSO-$d_6$/$D_2O$) δ 10.06 (s, 1H), 7.52 (s, 1H), 7.49-7.32 (m, 5H), 7.23 (s, 1H), 5.18 (s, 2H), 3.89 (s, 3H); MS (ES+) 309.1 (M+Na); IR (KBr) 3335, 2937, 1647, 1545, 1388, 1348, 1268, 1146, 1095 cm$^{-1}$; Analysis calculated for $C_{15}H_{15}BO_5$·0.25$H_2O$: C, 62.00; H, 5.38; Found: C, 61.77; H, 5.19.

Synthesis of methyl-6-(cyclopropylmethylcarbamoyl)-3-(trifluoromethylsulfonyloxy)-picolinate The synthesis of the intermediate methyl 6-(cyclopropylmethylcarbamoyl)-3-(trifluoromethyl sulfonyloxy)picolinate (2h) is described in Scheme 2.

Scheme 2

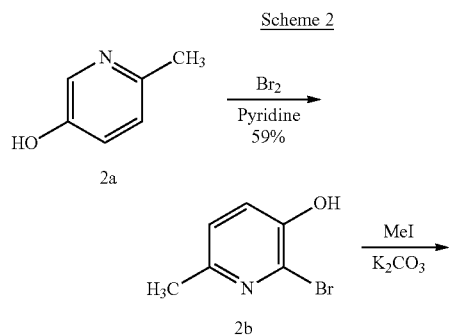

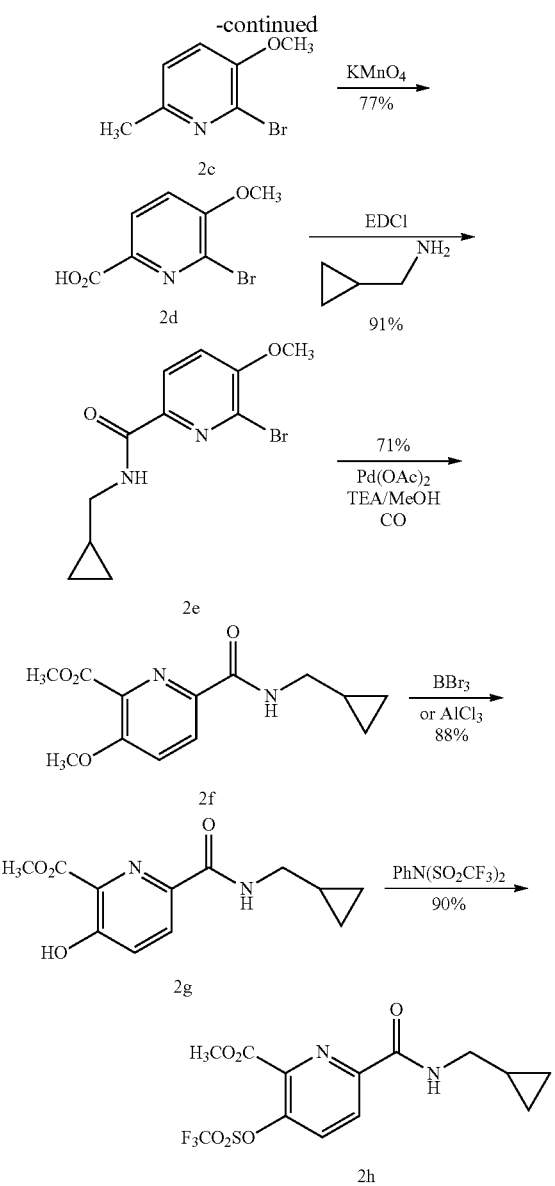

Preparation of 2-bromo-3-hydroxy-6-methylpyridine (2b)

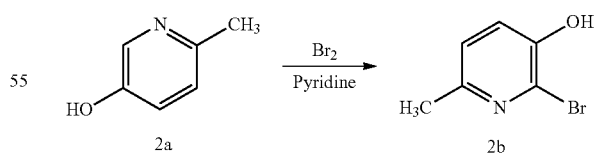

To a solution of 3-hydroxy-6-methylpyridine (2a) (3000 g, 27.5 mol) in pyridine (24 L) cooled to 15° C. was added a solution of bromine (4.83 kg, 1.55 L, 30.2 mol) in pyridine (3 L) over a period of 50 min maintaining the internal temperature between 20 to 25° C. After stirring for 19 h at room temperature the solvent was removed under vacuum and the residue was triturated with water. The solid separated was collected by filtration, washed with water and dried under vacuum to give 2-bromo-3-hydroxy-6-methylpyridine (2b) (3502 g, 67.7%) as a light brown solid which was used as such without further purification; ¹H NMR (300 MHz, DMSO-d₆) δ 10.43 (s, 1H), 7.18 (d, J=8.0 Hz, 1H), 7.08 (d, J=8.0 Hz, 1H), 2.33 (s, 3H); MS (ES+) 188.35, 186.36 (M+1).

Preparation of
2-bromo-3-methoxy-6-methylpyridine (2c)

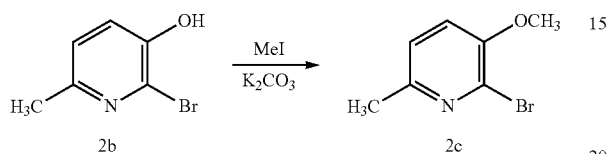

A mixture of 2-bromo-3-hydroxy-6-methylpyridine (2b) (3000 g, 15.96 mol), anhydrous potassium carbonate (3308 g, 23.94 mol), and iodomethane (2.491 kg, 1.09 L, 17.556 mol) in 30 L of acetone was heated at 40° C. overnight. The reaction mixture was cooled to room temperature and filtered through Celite. Evaporation of the solvent followed by silica gel chromatography (Hexane:ethyl acetate=7:3) afforded the desired compound, 2-bromo-3-methoxy-6-methylpyridine (2c) which was used as such for the next step; ¹H NMR (300 MHz, DMSO-d₆) δ 7.42 (dd, J=8.3, 1.5 Hz, 1H), 7.29-7.19 (m, 1H), 3.84 (d, J=1.6 Hz, 3H), 2.37 (d, J=1.7 Hz, 3H).

Preparation of
6-bromo-5-methoxy-2-pyridinecarboxylic acid (2d)

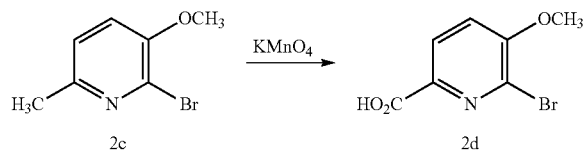

To a solution of 2-bromo-3-methoxy-6-methylpyridine (2c) (310 g, 1.53 mol) in 6000 mL of water at 60° C. was added KMnO₄ (725 g, 4.59 mol) in small portions over a 90 min period with vigorous mechanical stirring. A dark purple solution resulted. This solution was kept at 90° C. for a further 3 h and filtered through Celite while still hot to give a colourless filtrate. After cooling, the aqueous solution was acidified to pH 1-2 by adding 6 N HCl. The white solid obtained was collected by filtration to give on drying 6-bromo-5-methoxy-2-pyridinecarboxylic acid (2d) (302 g, 85%) of product, which was used as such in the next reaction without further purification. An analytical sample was obtained by recrystallization from methanol to give 6-bromo-5-methoxy-2-pyridinecarboxylic acid; ¹H NMR (300 MHz, DMSO-d₆) δ 7.40-7.28 (m, 1H), 7.17 (d, J=8.3 Hz, 1H), 3.83 (d, J=1.7 Hz, 3H).

Preparation of
6-bromo-N-(cyclopropylmethyl-5-methoxypicolinamide
(2e)

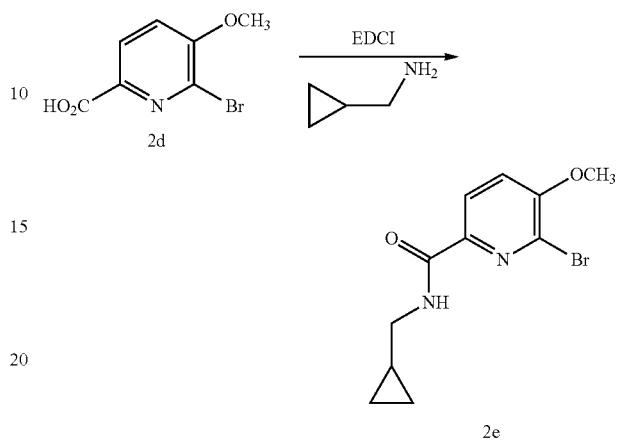

To a solution of 6-bromo-5-methoxy-2-pyridinecarboxylic acid (2d) (12 g, 52 mol) in pyridine (70 mL) was added EDCl (11.5 g, 59 mmol) and cyclopropylmethylamine (3.6 g, 52 mmol). The reaction mixture was stirred at room temperature overnight and then concentrated under vacuum. The reaction mixture was diluted with water (100 mL) and ethyl acetate (100 mL). The organic layer was separated and the water layer was extracted with ethyl acetate (2×100 mL). The organic layers were combined and washed with water (2×50 mL), brine (500 mL), dried over magnesium sulphate, filtered and concentrated under vacuum to furnish 10.43 g of crude product. The crude product was converted into a slurry (silica gel 20 g) and purified by flash column chromatography (silica gel 230 g, eluting with 0-100% ethyl acetate in hexane) to yield compound 6-bromo-N-(cyclopropylmethyl)-5-methoxypicolinamide (2e) (8.02 g, 54%) as off white solid, mp 67-70° C.; ¹HNMR (300 MHz, DMSO-d) δ 8.51 (t, J=5.8, 1H), 8.02 (d, J=8.4, 1H), 7.65 (d, J=8.5, 1H), 3.96 (s, 3H), 3.14 (t, J=6.5, 2H), 1.11-0.99 (m, 1H), 0.47-0.36 (m, 2H), 0.27-0.20 (m, 2H); MS (ES+) 307.0, 309.0 (100% M+Na)

Preparation of methyl
6-(cycloproplmethylcarbamoyl)-3-methoxypicolinate
(2f)

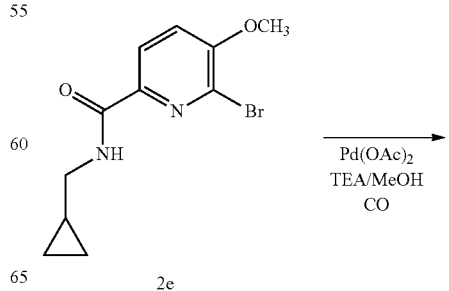

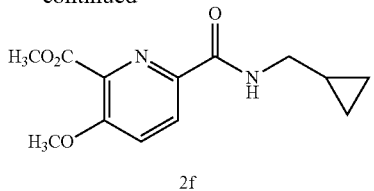

2f

To a solution of 6-bromo-N-(cyclopropylmethyl)-5-methoxypicolinamide (2e) (7.5 g, 27.6 mol) in methanol (300 mL) in a 2-L stainless steel bomb was added Pd(OAc)$_2$ (750 mg), 1,1-bis(diphenylphosphino)-ferrocene (750 mg), and triethylamine (3.9 mL, 27.6 mmol). The reaction mixture was vacuum flushed and charged with CO gas to 150 psi. The reaction mixture was and heated with stirring at 150° C. overnight and cooled to room temperature. The catalyst was filtered through a pad of celite, and concentrated to dryness to furnish crude product. The crude was purified by flash column chromatography (silica gel 150 g, eluting with, 0%, 5%, 10%, 20%, 30%, 50% ethyl acetate/hexanes (250 mL each) as eluents to give methyl 6-(cyclopropylmethyl-carbamoyl)-3-methoxypicolinate (2f) (6.29 g, 86.1%) as a salmon coloured solid, MP 107° C.; $^1$HNMR (300 MHz, DMSO-d) δ 8.28 (t, J=6.0, 1H), 7.91 (d, J=8.8, 1H), 7.55 (d, J=8.8, 1H), 3.68 (s, 3H), 3.64 (s, 3H), 2.90 (t, J=6.5, 2H), 0.89-0.68 (m, 1H), 0.26-0.09 (m, 2H), 0.08-0.00 (m, 2H); MS (ES+) 287.1 (M+Na); IR (KBr) 3316, 2921, 1730, 1659, 1534, 1472, 1432, 1315, 1272, 1228, 1189, 1099, 1003, 929, 846, 680 cm$^{-1}$; Analysis calculated for C$_{13}$H$_{16}$N$_2$O$_4$: C, 59.08; H, 6.10; N, 10.60; Found: C, 58.70; H, 5.97; N, 10.23.

Preparation of 6-(cyclopropylmethylcarbamoyl)-3-hydroxypicolinic acid (2 g)

carbamoyl)-3-hydroxypicolinic acid was added a solution of acetyl chloride (110 mL) in methanol (1.1 L). The reaction mixture was stirred for 12 h at room temperature and then concentrated to dryness in vacuo. After co-evaporating once with methanol, the compound was purified by flash-column chromatography (silica gel, 500 g, eluted with chloroform and 3% methanol in chloroform) to furnish 6-(cyclopropylmethylcarbamoyl)-3-hydroxypicolinic acid (2 g).

Boron Tribromide Method:

To a stirring solution of methyl 6-(cyclopropylmethylcarbamoyl)-3-ethoxypicolinate (2f) (58.0 g, 208 mmol) was added BBr$_3$ (79 mL, 834 mmol) in CH$_2$Cl$_2$ (1.3 L) at 0-5° C. The reaction mixture was allowed to warm to room temperature and stirred for 18 h. The reaction mixture was evaporated to dryness and anhydrous methanol (1 L) was added to the light yellowish solid residue. Insoluble solid was collected by filtration (36 g). Mother liquor was evaporated and co-evaporated with MeOH (2×200 mL). The insoluble solid (36 g) was treated with MeOH (500 mL) and acetyl chloride (50 mL) and stirred at room temperature for 18 h (at this point reaction mixture was clear). The mixture was evaporated to dryness and diluted with water and extracted with EtOAc. White solid that separated out from EtOAc layer was collected by filtration, washed with water (2×20 mL), dried in vacuo at 50° C. to afford 6-(cyclopropylmethylcarbamoyl)-3-hydroxypicolinic acid (2 g) (5.36 g, 10%) as a white solid, MP 92-95° C. $^1$HNMR (DMSO-ds) δ 11.04 (s, 1H, exchangeable with D$_2$O), 8.37 (t, J=6.0, 1 H, exchangeable with D$_2$O), 8.12 (d, J=8.7 Hz, 1H), 7.57 (d, J=8.7 Hz, 1H), 3.90 (m, 3H), 3.15 (m, 2H), 1.04 (m, 1H), 0.41 (m, 2H), 0.24 (m, 2H). IR (KBr): 3346, 3205, 1684 cm$^{-1}$; MS (ES+): 251.1 (M+1); Analysis calculated for C$_{12}$H$_{14}$N$_2$O$_4$·0.1H$_2$O: C, 57.18; H, 5.67; N, 11.14; Found: C, 57.11; H, 5.61; N, 11.09.

Preparation of methyl-6-(cyclopropylmethylcarbamoyl)-3-(trifluoromethylsulfonyloxy) picolinate (2h)

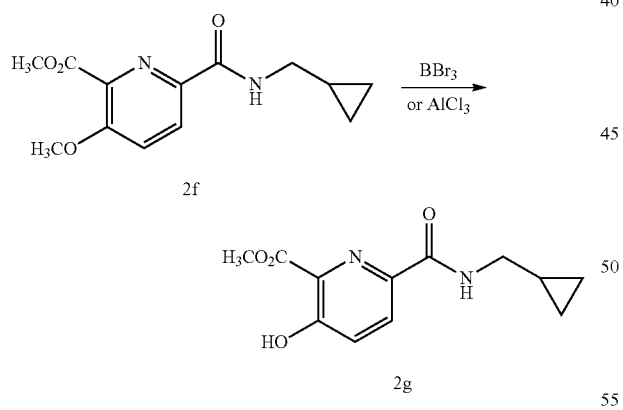

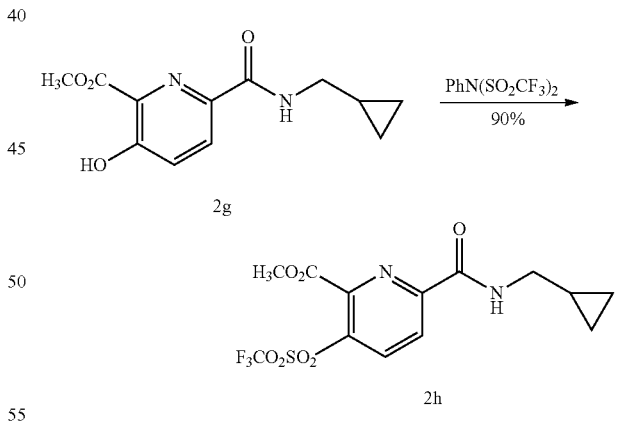

Aluminium Chloride Method:

To a solution of methyl 6-(cyclopropylmethylcarbamoyl)-3-methoxypicolinate (2f) (0.16 mmol) in dichloromethane (840 mL) was added AlCl$_3$ (193 g, 1.5 mol). The reaction mixture was heated at reflux for 12 h under nitrogen. After slowly adding ~2 L of 1 N HCl, the organic layer was separated. The aqueous layer was re-extracted several times with ethyl acetate/DME. The combined organic layer was washed with brine, dried (MgSO$_4$), and evaporated in vacuo to furnish crude 6-(cyclopropylmethylcarbamoyl)-3-hydroxypicolinic acid. To a solution of 6-(cyclopropylmethyl- To a solution of 6-(cyclopropylmethylcarbamoyl)-3-hydroxypicolinic acid (2 g) (28 mmol) in DMF (200 mL) were added triethylamine (12 mL, 84 mmol) and N-phenyl-bis(trifluoromethanesulfonimide) (12 g, 34 mmol). The reaction mixture was stirred for 1.5 h at room temperature and then poured into ice. After diluting with water and extracting with ethyl acetate, the aqueous phase was re-extracted, and then the combined organic layer was washed with water and concentrated under vacuum to give methyl-6-(cyclopropylmethylcarbamoyl)-3-(trifluoromethylsulfonyloxy)picolinate (2h), which was used in the next step without purification.

¹H NMR (300 MHz, CDCl₃) δ 8.50 (d, J=8.6, 1H), 8.07 (s, 1H), 7.88 (d, J=8.6, 1H), 4.09 (d, J=12.6, 3H), 3.48-3.24 (m, 2H), 1.18-1.01 (m, 1H), 0.69-0.44 (m, 2H), 0.42-0.20 (m, 2H). MS (ES⁺): 405.17, 100%, M+Na.

Synthesis of 3-[2-(4-carbamimidoyl-phenylcarbamoyl)-5-methoxy-4-vinyl-phenyl]-6-(cyclopropylmethyl-carbamoyl)-pyridine-2-carboxylic acid The synthesis of 3-[2-(4-carbamimidoyl-phenylcarbamoyl)-5-methoxy-4-vinyl-phenyl]-6-(cyclopropylmethyl-carbamoyl)-pyridine-2-carboxylic acid (3i) is described as shown in Scheme 3.

Scheme 3

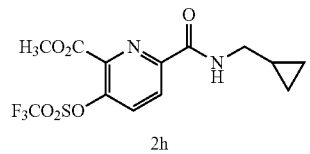
2h

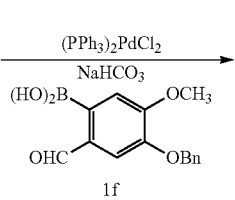
1f (PPh₃)₂PdCl₂
NaHCO₃
→

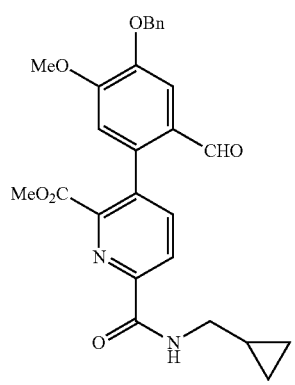
3a

NaClO₂
2-Methyl-2-butene
CH₃CN/t-BuOH
→

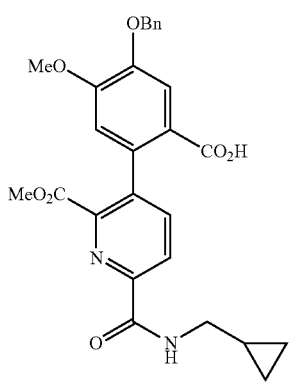
3b

MEM—Cl
DIPEA
→

-continued

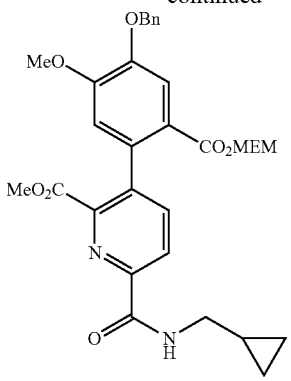
3c

H₂, Pd/C
→

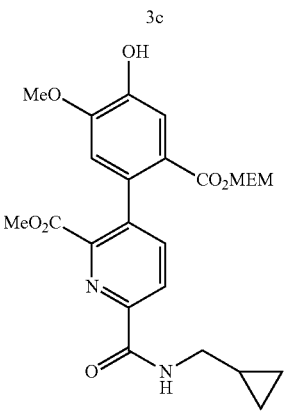
3d

Triflic acid
Pyridine
→

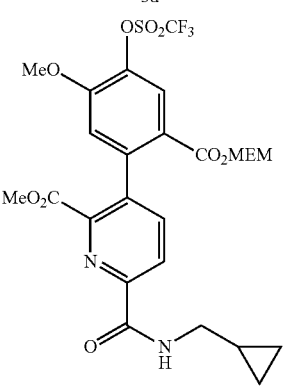
3e

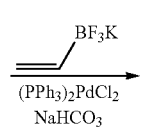
BF₃K (PPh₃)₂PdCl₂
NaHCO₃
→

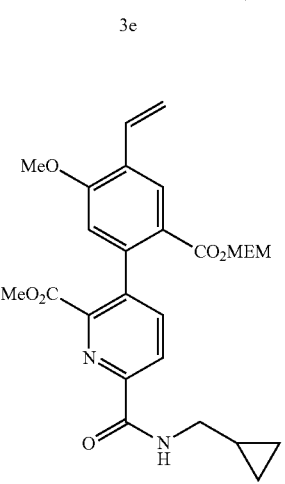
3f

HCl/DME
→

121
-continued

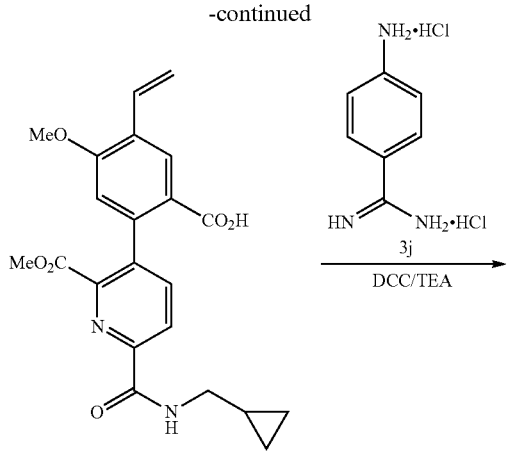

3g

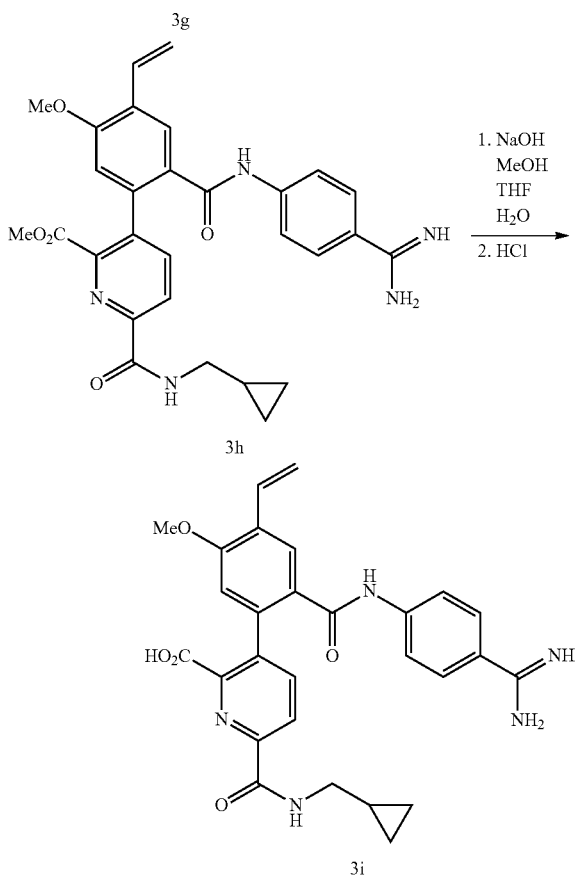

3-(4-Benzyloxy-2-formyl-5-methoxy-phenyl)-6-(cyclopropylmethyl-carbamoyl)-pyridine-2-carboxylic acid methyl ester (3a)

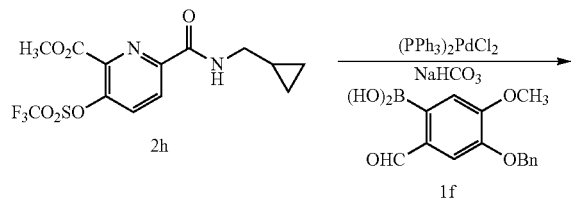

122
-continued

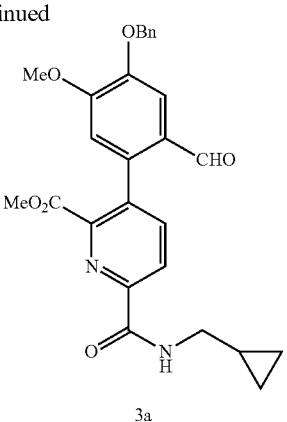

3a

To a solution of methyl-6-(cyclopropylmethylcarbamoyl)-3-(trifluoromethylsulfonyloxy) picolinate (2h) (24.3 g, 63 mmol) in DME (225 mL) were added water (25 mL), (4-(benzyloxy)-2-formyl-5-methoxyphenyl)boronic acid (1f) (27.3 g, 95 mmol), NaHCO$_3$ (15.9 g, 189 mmol), and bis(triphenylphosphine)palladium(II) chloride (0.885 g). The reaction mixture was stirred at 70° C. overnight under nitrogen. After extracting with ethyl acetate, the organic layer was washed with water and brine and dried (MgSO$_4$), and then concentrated under vacuum. The compound was purified by flash-column chromatography (silica gel, 300 g, eluting with 10%, 20%, 30% and 40% ethyl acetate in hexane) to furnish 3-(4-benzyloxy-2-formyl-5-methoxyphenyl)-6-(cyclopropylmethyl-carbamoyl)-pyridine-2-carboxylic acid methyl ester (3a) (25 g, 83%) as off white solid, MP 48-50° C.: $^1$H NMR (300 MHz, DMSO-d$_6$) δ 9.61 (s, 1H), 8.40 (d, J=7.9 Hz, 1H), 8.14 (t, J=5.0 Hz, 1H), 7.87 (d, J=8.1 Hz, 1H), 7.58 (s, 1H), 7.54-7.30 (m, 5H), 6.71 (s, 1H), 5.24 (s, 2H), 3.93 (s, 3H), 3.70 (s, 3H), 3.45-3.34 (m, 2H), 1.19-1.05 (m, 1H), 0.64-0.54 (m, 2H), 0.37-0.30 (m, 2H); IR (KBr) 1735, 1678, 1594, 1513, 1437, 1283, 1217, 1141, 1092 cm$^{-1}$; MS (ES+) 497.29 (M+Na); Analysis calculated for C$_{27}$H$_{26}$N$_2$O$_6$: C, 68.34; H, 5.52; N, 5.90; Found; C, 68.16; H, 5.62; N, 5.80.

2-(6-(Cyclopropylmethylcarbamoyl)-2-(methoxycarbonyl)pyridin-3-yl)-4-methoxy-5-vinylbenzoic acid (3b)

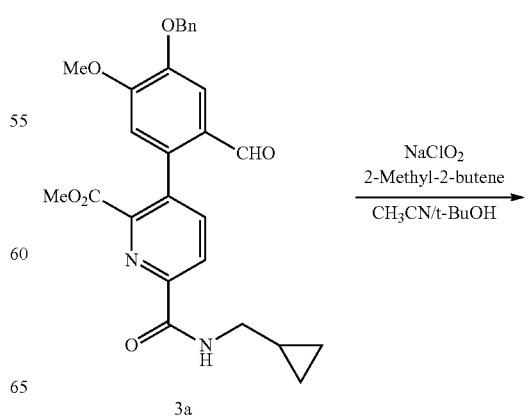

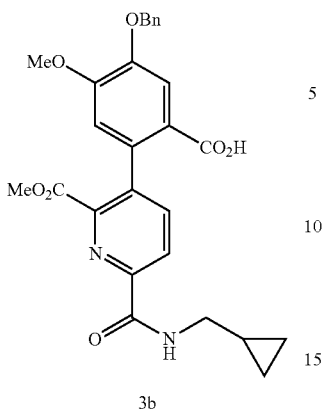

3b

To a solution of 3-(4-benzyloxy-2-formyl-5-methoxy-phenyl)-6-(cyclopropylmethyl-carbamoyl)-pyridine-2-carboxylic acid methyl ester (3a) (24 g, 50.6 mmol) in acetonitrile (50 mL), 2-methyl-2-propanol (350 mL), and water (125 mL) were added sodium dihydrogen phosphate (12.5 g) and 2-methyl-2-butene (55 mL, 519 mmol). The reaction mixture was cooled in an ice bath and then sodium chlorite (28 g) was added. After stirring for 1 h, the reaction mixture was extracted with ethyl acetate and washed with water. The aqueous layer was re-extracted and then the combined organic layers were dried (MgSO$_4$). The solvent was evaporated in vacuo to furnish 5-(benzyloxy)-2-(6-((cyclopropylmethyl)carbamoyl)-2-(methoxycarbonyl)pyridin-3-yl)-4-methoxybenzoic acid (3b) (29 g) which was used for the next step. MS (ES$^+$): 513.24, (M+Na(; (ES$^-$): 489.26, M−1.

Methyl 3-(4-(benzyloxy)-5-methoxy-2-(((2-methoxyethoxy)methoxy)carbonyl)phenyl)-6-(cyclopropylmethylcarbamoyl)picolinate (3c)

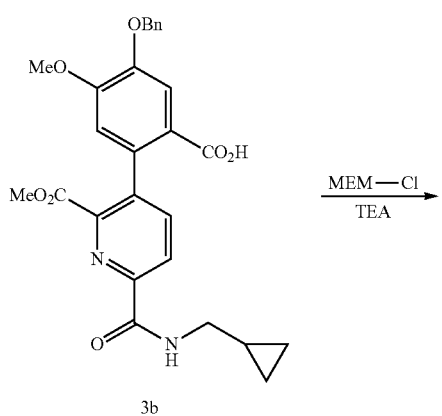

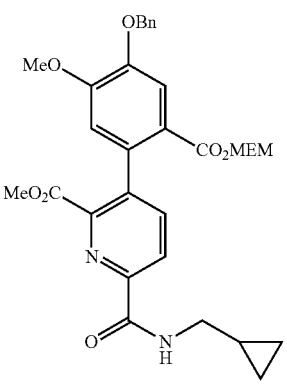

3c

To a mixture of 5-(benzyloxy)-2-(6-(cyclopropylmethyl-carbamoyl)-2-(methoxy-carbonyl)pyridin-3-yl)-4-methoxybenzoic acid (3b) (31 g, 63.2 mmol), and triethylamine (17.7 mL, 126.4 mmol) in dichloromethane (300 mL), was added MEM-chloride (9.03 mL, 79 mmol), and stirred at room temperature overnight. The reaction mixture was diluted with water and extracted with ethyl acetate. The organic layer was washed with water and dried over MgSO4, filtered and concentrated in vacuo. The residue was purified by flash column chromatography (silica gel, 40 g) to furnish methyl 3-(4-(benzyloxy)-5-methoxy-2-(((2-methoxyethoxy)methoxy)carbonyl)phenyl)-6-(cyclopropylmethylcarbamoyl)picolinate (3c) (32.8 g, 89%) as a thick gum; $^1$H NMR (300 MHz, CDCl$_3$) δ 8.35 (d, J=8.0 Hz, 1H), 8.15 (t, J=5.7 Hz, 1H), 7.78 (d, J=8.0 Hz, 1H), 7.71 (s, 1H), 7.49 (d, J=6.8 Hz, 2H), 7.36 (ddd, J=7.5, 14.8, 22.4 Hz, 3H), 6.66 (s, 1H), 5.37-5.13 (m, 4H), 3.90 (s, 3H), 3.69 (s, 3H), 3.60-3.49 (m, 2H), 3.49 (s, 2H), 3.39 (dd, J=4.4, 8.4 Hz, 2H), 3.34 (s, 3H), 1.19-1.00 (m, 1H), 0.57 (q, J=5.6 Hz, 2H), 0.38-0.25 (m, 2H). MS (ES$^+$): 601.24 (M+Na); (ES): 577.27 (M−1); $^1$H NMR (300 MHz, DMSO-de) δ 8.69 (t, J=6.1 Hz, 1H), 8.20 (d, J=8.0 Hz, 1H), 7.97 (d, J=8.0 Hz, 1H), 7.63 (s, 1H), 7.41 (m, 5H), 6.92 (s, 1H), 5.20 (m, 4H), 3.83 (s, 3H), 3.57 (s, 3H), 3.44 (m, 2H), 3.33 (m, 2H), 3.21 (m, 5H), 1.14 (m, 1H), 0.44 (m, 2H), 0.27 (m, 2H). IR (KBr): 1732, 1671 cm$^{-1}$. MS (ES+): 601.1 (M+Na); Analysis calculated for C$_{31}$H$_{34}$N$_2$O$_9$: C, 64.35; H, 5.92; N, 4.84; Found: C, 64.27; H, 6.04; N, 4.79.

Methyl 6-(cyclopropylmethylcarbamoyl)-3-(4-hydroxy-5-methoxy-2-(((2-methoxyethoxy)methoxy)carbonyl)phenyl)picolinate (3d)

6-(Cyclopropylmethylcarbamoyl)-3-(5-methoxy-2-(((2-methoxyethoxy)methoxy)-carbonyl)-4-(trifluoromethylsulfonyloxy)phenyl)picolinate (3e)

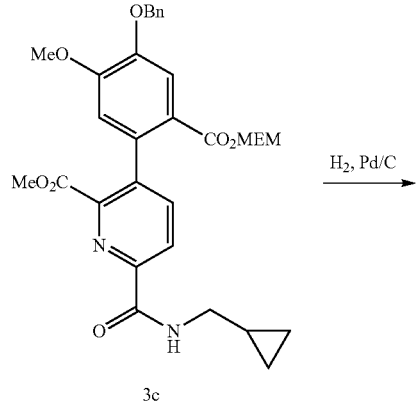

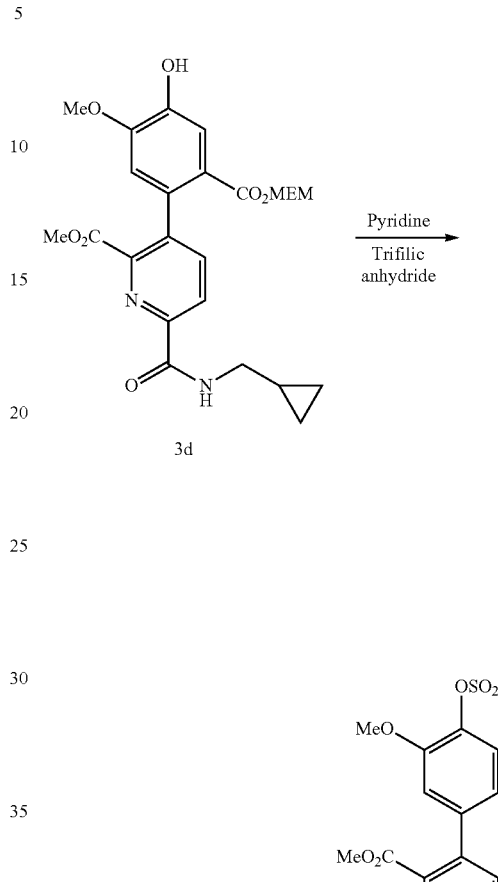

To a solution of methyl 3-(4-(benzyloxy)-5-methoxy-2-(((2-methoxyethoxy)methoxy)-carbonyl)phenyl)-6-(cyclopropylmethylcarbamoyl)picolinate (3c) (32.8 g, 56.68 mmol) in ethanol (650 mL) was added 10% Pd/C (4 g) and hydrogenated at 45 psi for 5 h. The catalyst was removed by filtration through Celite and the filtrate was concentrated under vacuum to yield methyl 6-(cyclopropylmethylcarbamoyl)-3-(4-hydroxy-5-methoxy-2-(((2-methoxyethoxy)methoxy)carbonyl)phenyl)picolinate (3d) (31.87 g, 86%), which was pure enough to be used as such for the next step. An analytical sample of methyl 6-(cyclopropylmethylcarbamoyl)-3-(4-hydroxy-5-methoxy-2-(((2-methoxyethoxy)methoxy)carbonyl)phenyl)picolinate (3d) was obtained by purification of 350 mg of above crude using flash column chromatography (silica gel, eluting with ethyl acetate in hexane) to afford methyl 6-(cyclopropylmethyl-carbamoyl)-3-(4-hydroxy-5-methoxy-2-(((2-methoxyethoxy)methoxy)carbonyl)-phenyl)picolinate (3d) as a clear gum; $^1$HNMR (300 MHz, DMSO-$d_6$) δ 9.74 (s, 1H), 8.68 (t, J=6.1 Hz, 1H), 8.18 (d, J=8.0 Hz, 1H), 7.95 (d, J=8.0 Hz, 1H), 7.47 (s, 1H), 6.83 (s, 1H), 5.19 (s, 2H), 3.77 (m, 3H), 3.58 (s, 3H), 3.44 (m, 2H), 3.34 (m, 2H), 3.21 (m, 5H), 1.04 (m, 1H), 0.44 (m, 2H), 0.27 (m, 2H); IR (KBr): 1731, 1664 cm$^{-1}$. MS (ES$^+$): 489.0 (M+1); Analysis calculated for $C_{24}H_{28}N_2O_9$: C, 59.01; H, 5.78; N, 5.73; Found: C, 58.92; H, 6.15; N, 5.29.

To a solution of methyl 6-(cyclopropylmethylcarbamoyl)-3-(4-hydroxy-5-methoxy-2-(((2-methoxyethoxy) methoxy) carbonyl)phenyl)picolinate (3d) (14.3 g, 29.3 mmol) in dichloromethane (150 mL) were added pyridine (12 mL, 146 mmol) and triflic anhydride (7.5 mL g, 44 mmol). After stirring overnight at room temperature under $N_2$, the reaction mixture was poured into ice water and then extracted twice with dichloromethane. After washing the combined organic extracts with water and drying (MgSO$_4$), the solvent was evaporated in vacuo. The compound was purified by flash chromatography over silica gel column using ethyl acetate: hexane to afford methyl 6-(cyclopropylmethylcarbamoyl)-3-(5-methoxy-2-(((2-methoxyethoxy)methoxy)-carbonyl)-4-(trifluoromethylsulfonyloxy)phenyl)picolinate (3e) (17 g, 93%); $^1$H NMR (300 MHz, CDCl$_3$) δ 8.41 (d, J=8.0, 1H), 8.17 (s, 1H), 8.03 (s, 1H), 7.79 (d, J=8.0, 1H), 6.82 (s, 1H), 5.32 (q, J=6.1, 2H), 3.97 (s, 3H), 3.74 (s, 3H), 3.67-3.57 (m, 2H), 3.55-3.45 (m, 2H), 3.41 (dd, J=8.2, 14.5, 2H), 3.34 (s, 3H), 1.36-1.17 (m, 1H), 0.58 (d, J=7.1, 2H), 0.33 (d, J=5.1, 2H).

Methyl 6-(cyclopropylmethylcarbamoyl)-3-(5-methoxy-2-(((2-methoxyethoxy)-methoxy)carbonyl)-4-vinylphenyl)picolinate (3f)

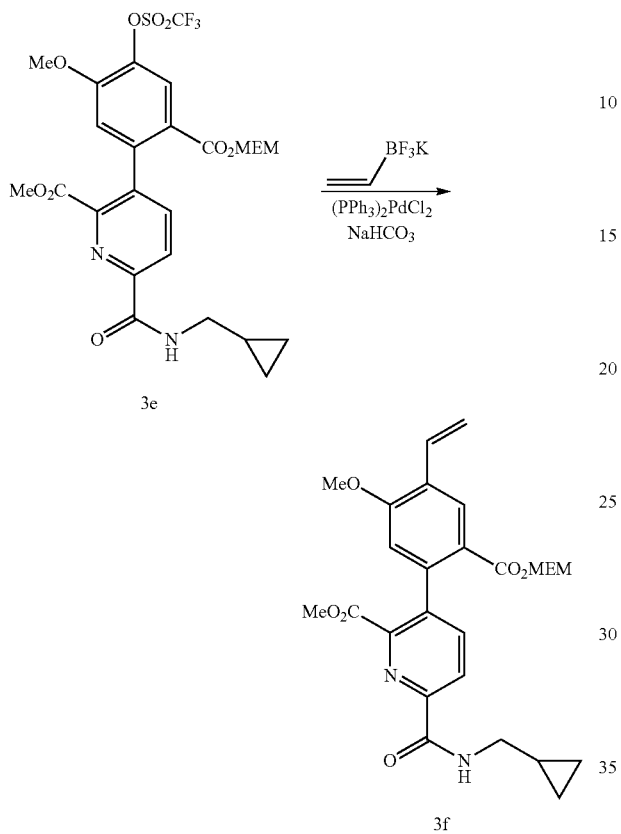

To a solution of methyl 6-(cyclopropylmethylcarbamoyl)-3-(5-methoxy-2-(((2-methoxyethoxy)methoxy)carbonyl)-4-(trifluoromethylsulfonyloxy)phenyl)picolinate (3e) (37.4 g, 60.30 mmol) and potassium vinyltrifluoroborate (16.87 g, 120.6 mmol) in DMF (450 mL) and water (45 mL) was bubbled $N_2$ for 5 min. To this mixture was added $NaHCO_3$ (20.26 g, 241.2 mmol) and dichloro-bis(triphenylphosphine) palladium (11) (6.34 g, 9.0 mmol). The reaction mixture was stirred at 70° C. for 20 h under $N_2$ (reaction progress was checked by $^1H$ NMR because product and starting material had same $R_f$ in TLC). The reaction mixture was cooled down to room temperature and diluted with ethyl acetate. The organic layer was separated, washed with water, brine, dried ($MgSO_4$) and filtered. The filtrate was concentrated under vacuum to yield crude methyl 6-(cyclopropylmethyl-carbamoyl)-3-(5-methoxy-2-(((2-methoxyethoxy)methoxy) carbonyl)-4-vinylphenyl)-picolinate (3f). The crude product was purified by flash column chromatography (silica gel, 1 kg, eluting with 0-100% ethyl acetate in hexane) to afford methyl 6-(cyclopropylmethylcarbamoyl)-3-(5-methoxy-2-(((2-methoxyethoxy)methoxy) carbonyl)-4-vinylphenyl)picolinate (3f) (26.54 g, 88%) as an amber gum; $^1H$ NMR (300 MHz, DMSO-$d_6$) δ 8.70 (t, J=6.1 Hz, 1H), 8.23 (d, J=8.0 Hz, 1H), 8.12 (s, 1H), 8.00 (d, J=8.0 Hz, 1H), 6.98 (m, 2H), 5.94 (dd, J=1.2, 17.8 Hz, 1H), 5.43 (d, J=12.5 Hz, 1H), 5.21 (d, J=6.5 Hz, 2H), 3.88 (s, 3H), 3.64 (s, 3H), 3.48 (d, J=3.1 Hz, 2H), 3.35 (m, 5H), 3.22 (m, 2H), 1.11 (s, 1H), 0.44 (dt, J=4.9, 5.5 Hz, 2H), 0.28 (q, J=4.8 Hz, 2H). IR (KBr): 1732, 1670 cm$^{-1}$. MS (ES+) 499.1 (M+1).

2-(6-(cyclopropylmethylcarbamoyl)-2-(methoxycarbonyl)pyridin-3-yl)-4-methoxy-5-vinylbenzoic acid (3q)

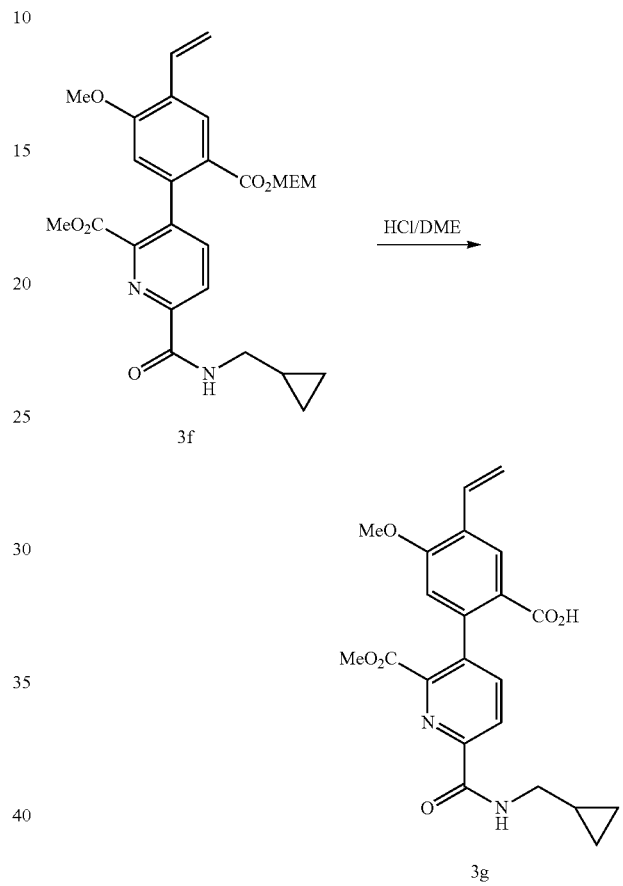

A mixture of methyl 6-(cyclopropylmethylcarbamoyl)-3-(5-methoxy-2-(((2-methoxyethoxy)methoxy) carbonyl)-4-vinylphenyl)picolinate (3f) (27.4 mmol) in DME (160 mL) and 6N HCl (40 mL) was stirred at room temperature for 6 h or till TLC showed complete conversion. The solvent was removed under vacuum. The residue obtained was suspended in water, the solid separated out was collected by filtration, washed with water and dried under vacuum to give 2-(6-(cyclopropylmethylcarbamoyl)-2-(methoxycarbonyl) pyridin-3-yl)-4-methoxy-5-vinylbenzoic acid (3 g) (7.0 g, 63%) as a white solid MP 40-42° C.; $^1H$ NMR (300 MHz, DMSO-$d_6$) δ 8.69 (t, J=6.0 Hz, 1H, NH), 8.20 (d, J=7.9 Hz, 1H), 8.09 (s, 1H), 7.95 (d, J=8.1 Hz, 1H), 6.97 (dd, J=18.0, 11.3 Hz, 1H), 6.88 (s, 1H), 5.92 (d, J=7.9 Hz, 1H), 5.38 (d, J=11.1 Hz, 1H), 3.85 (s, 3H), 3.63 (s, 3H), 3.27-3.17 (m, 2H), 1.15-1.05 (m, 1H), 0.48-0.40 (m, 2H), 0.31-0.24 (m, 2H); IR (KBr): 3084, 1728, 1650, 1533, 1212, 1143 cm-1; MS (ES+) 433.26 (M+Na); (ES-): 409.28 (M−1); Analysis calculated for $C_{22}H_{22}N_2O_6 \cdot 0.25H_2O$; C, 63.68; H, 5.47; N, 6.75; Found C, 63.75; H, 5.56; N, 6.65.

Methyl-3-(2-(4-carbamimidoylphenylcarbamoyl)-5-methoxy-4-vinylphenyl)-6-(cyclopropylmethylcarbamoyl)picolinate (3h)

3-[2-(4-carbamimidoyl-phenylcarbamoyl)-5-methoxy-4-vinyl-phenyl]-6-(cyclopropylmethylcarbamoyl)-pyridine-2-carboxylic acid (3l)

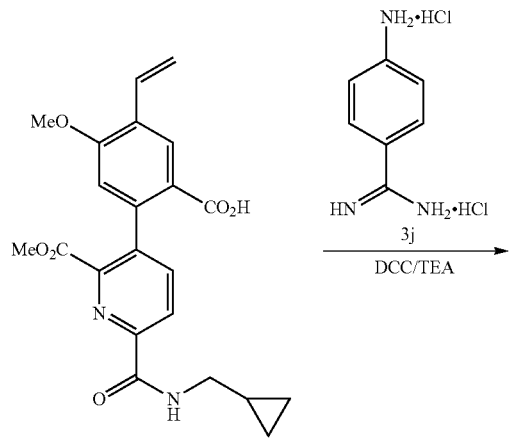

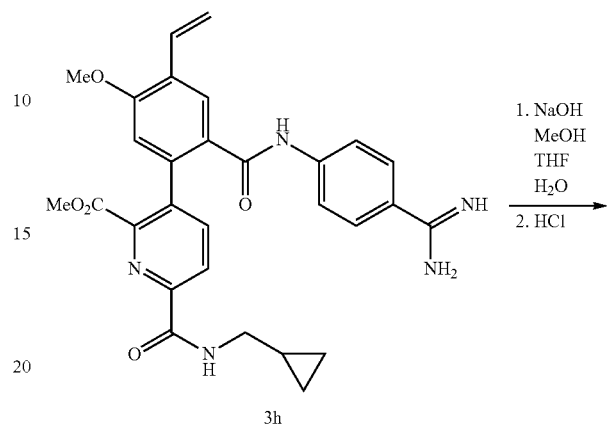

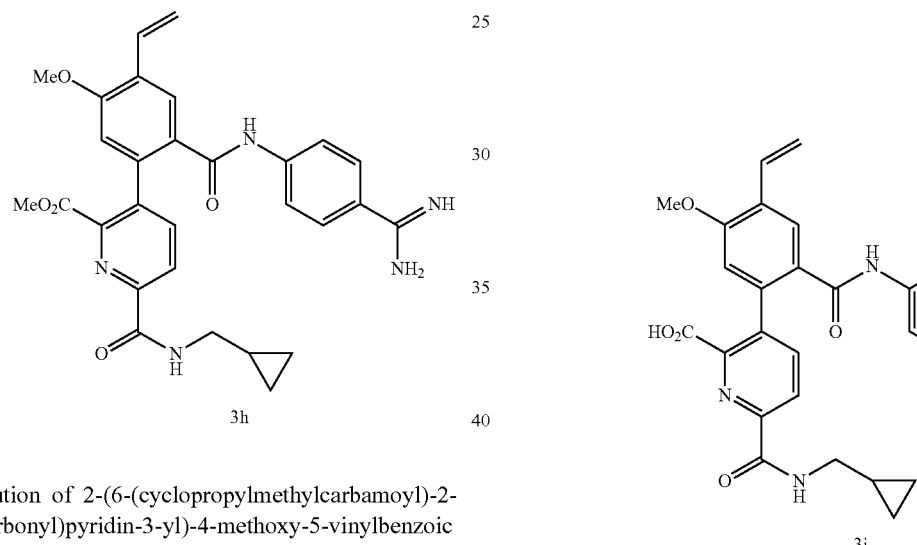

To a solution of 2-(6-(cyclopropylmethylcarbamoyl)-2-(methoxycarbonyl)pyridin-3-yl)-4-methoxy-5-vinylbenzoic acid (3 g) (2.35 g, 5.7 mmol) and 4-aminobenzimidamide dihydrochloride (3j) (1.79 g, 8.6 mmol) in DMF (20 mL) and pyridine (30 mL) at 0° C. was added EDCl (1.65 g, 8.6 mmol) and allowed to warm to room temperature overnight. The reaction mixture was quenched with 6N HCl (60 mL) and extracted with chloroform (3×60 mL). The organic layer was dried over MgSO4, filtered and purified by flash column chromatography (silica gel, 110 g, eluting with 0 to 100% chloroform in CMA 80 in CMA 50) yielding methyl-3-(2-(4-carbamimidoylphenyl-carbamoyl)-5-methoxy-4-vinylphenyl)-6-(cyclopropylmethylcarbamoyl)picolinate (3h) (2.2 g, 65%) as a white solid MP 266° C.; $^1$H NMR (300 MHz, DMSO-$d_6$) δ 10.78 (s, 1H), 9.26 (s, 2H), 9.03 (s, 2H), 8.67 (t, J=6.1, 1H), 8.22 (d, J=8.0, 1H), 8.06 (d, J=8.0, 1 H), 7.96 (s, 1H), 7.89-7.74 (m, 4H), 7.13-6.96 (m, 2H), 6.07 (d, J=17.7, 1H), 5.45 (d, J=12.4, 1H), 3.91 (s, 3H), 3.61 (s, 3H), 3.20 (s, 2H), 1.09 (dd, J=4.7, 8.2, 1H), 0.43 (dt, J=4.9, 5.4, 2H), 0.34-0.21 (m, 2H); MS (ES+) 528.1 (M+1); Analysis calculated for $C_{29}H_{29}N_5O_5 \cdot (H_2O)_{1.5} \cdot$ (HCl): C, 58.93; H, 5.63; N, 11.85; Found: C, 58.75; H, 5.65; N, 11.92.

To a solution of methyl-3-(2-(4-carbamimidoylphenylcarbamoyl)-5-methoxy-4-vinylphenyl)-6-(cyclopropylmethylcarbamoyl)picolinate (3h) (1 g, 1.9 mmol) in methanol (10 mL) and THF (10 mL) was added 2 N NaOH (10 mL). The reaction mixture was stirred at room temperature for 3 h, and concentrated in vacuo to remove methanol and THF. The aqueous layer was acidified with 6N HCl to pH 6-7 and the solid obtained was collected by filtration washed with water and ether to furnish on drying 3-[2-(4-carbamimidoyl-phenylcarbamoyl)-5-methoxy-4-vinyl-phenyl]-6-(cyclopropylmethyl-carbamoyl)-pyridine-2-carboxylic acid (3i)(0.775 g, 80%) as the hydrochloride salt as an off white solid.

$^1$H NMR (300 MHz, DMSO-d) δ 12.67 (s, 1H), 9.11 (s, 2H), 8.97 (s, 2H), 8.74 (s, 1H), 7.90 (d, J=7.8, 1H), 7.80 (s, 1H), 7.72-7.58 (m, 4H), 6.99 (dd, J=11.3, 17.7, 1H), 6.78 (s, 1H), 5.95 (d, J=17.2, 1H), 5.38 (d, J=11.9, 1H), 3.82 (s, 3H), 3.18 (s, 2H), 1.06 (s, 1H), 0.43 (d, J=7.9, 2H), 0.25 (d, J=4.7, 2H); MS (ES+) 514.0 (M+1); Analysis calculated for $C_{28}H_{27}N_5O_5 \cdot HCl \cdot H_2O$: C, 59.21; H, 5.32; N, 12.33; Found: C, 59.43; H, 5.21; N, 12.06.

Example 1A—Preparation of 3-[2-(4-Carbamimidoylphenylcarbamoyl)-5-methoxy-4-vinylphenyl]-6-(cyclopropylmethylcarbamoyl)pyridine-2-carboxylic acid hydrochloride in Form C

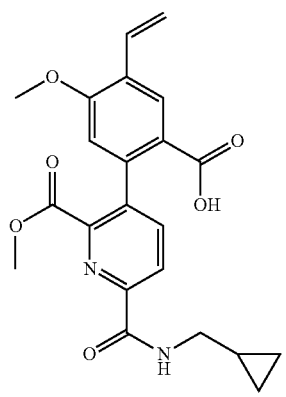

BCX4189

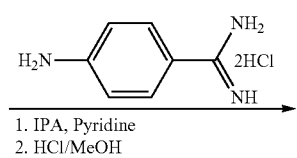

1. IPA, Pyridine
2. HCl/MeOH

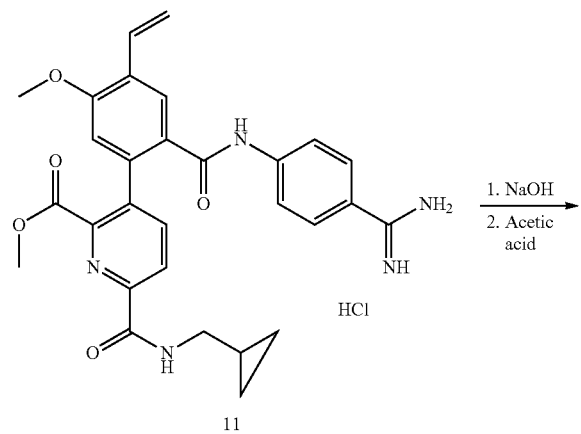

11

1. NaOH
2. Acetic acid

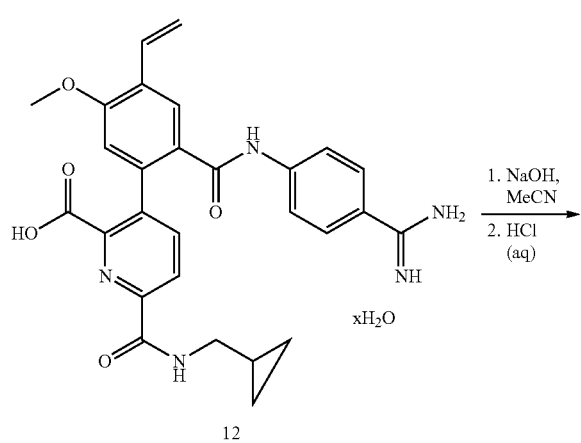

12

1. NaOH, MeCN
2. HCl (aq)

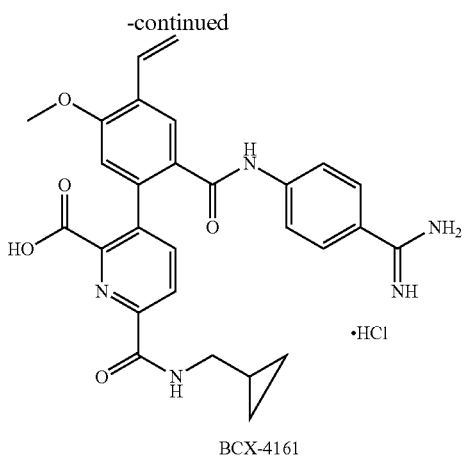

BCX-4161

The jacket of a 10 L glass reactor was set to −5° C. To the reactor was charged 2-(6-((cyclopropylmethyl)carbamoyl)-2-(methoxycarbonyl)-pyridin-3-yl)-4-methoxy-5-vinylbenzoic acid (6d) prepared in Step (11) of Example 1 (500 g, 1.22 mol), 4-amino-benzamidine.2HCl (280 g, 1.34 mol), and 2-propanol (4.05 kg). The mixture was cooled to 0.3° C., and pyridine (210 g, 2.62 mol) followed by EDCl-HCl (310 g, 1.61 mol) was added. The mixture was stirred at −1.1 to −0.3° C. for 22 hrs followed by addition of the second portion of EDCl.HCl (58 g, 0.30 mol). The temperature of jacket was set to 14.0° C., and the mixture was stirred for 89 hrs. The precipitate was filtered, and washed with 1.32 kg of 2-propanol.

The wet product (8a) was recharged to the reactor followed by addition of acetonitrile (1.6 kg) and water (0.57 kg). The mixture was heated to 46° C. Smopex-234 (21 g) and Acticarbone 2SW (10 g) were added and the mixture was stirred at this temperature for 1 hr. The solution was filtered, and filtrate was returned back to the reactor. The jacket of the reactor was set to −5° C., and the mixture was cooled to −0.2° C. NaOH solution (256 g 46% NaOH, 2.95 mol, in 960 g water) was added in 25 min keeping the temperature <3° C. The mixture was stirred at 0.2-2.0° C. for 1 hr 40 min and then quenched with conc. acetic acid (40 g, 0.66 mol). Diluted acetic acid (80 g, 1.33 mol AcOH in 1000 g water) was added during 1 hr 20 min (temperature 1.7-3.0° C.), followed by 1250 g water (30 min). The suspension was stirred at 0-3.0° for 1 hr, and filtered at 0-5° C. (ice mantle around the filter). The reactor and product (8d) was rinsed with 3.5 kg water.

The wet product (8d) was recharged to the reactor followed by 0.65 kg water and 1.69 kg acetonitrile. The mixture was heated to 57-60° C., and stirred at this temperature for 14.5 hrs. The mixture was cooled to −2.2° C. ($T_{jacket}$=−5° C.), and a solution of NaOH (163 g 46%, 1.87 mol, in 580 g water) was added during 15 min. The temperature rose to −0.4° C. Hydrochloric acid (407 g 37% HCl, 4 mol) was added in 10 min, the temperature rose to 7.5° C. The suspension was agitated at −3-0° C. for 19 hrs. The product was filtered and the filter cake was rinsed with 2.87 kg water, compressed and pulled dry. The wet product (1.30 kg) was dried at 40-43° C. and 50 mbar for 117 hrs to furnish 3-[2-(4-carbamimidoylphenylcarbamoyl)-5-methoxy-4-vinylphenyl]-6-(cyclopropylmethylcarbamoyl)pyridine-2-carboxylic acid hydrochloride (7b) (484 g) as Form C.

Example-1B: Preparation of 3-[2-(4-Carbamim-idoylphenylcarbamoyl)-5-methoxy-4-vinylphenyl]-6-(cyclopropylmethylcarbamoyl)pyridine-2-carboxylic acid hydrochloride in Form A The procedure was carried out in an identical manner to Example 1A, with the exception that after the final filtration the filter cake was rinsed with 2.87 kg methyl tert-butyl ether instead of 2.87 kg water, and pulled dry. The product was dried at 40-43° C. and 50 mbar to furnish 3-[2-(4-carbamimidoylphenylcarbamoyl)-5-methoxy-4-vinylphenyl]-6-(cyclopropylmethylcarbamoyl)pyridine-2-carboxylic acid hydrochloride (7b) as Form A.

Example 2—Physicochemical Studies

Physicochemical Properties of the Compound of Example 1

The $pK_a$ experiments have been performed by both UV-metric (in aqueous) and potentiometric method (in methanol cosolvents). Nine titrations have been performed for the compound, all from low to high pH (2.0-12.0).

The determined lower $pK_a$ is 2.31±0.15 by UV-metric method, and no lower $pK_a$ was observed by potentiometric method, and this lower $pK_a$ is thus reported as <3.0. The determined higher $pK_a$ is 11 0.38±0.15 by UV-metric method, and no higher $pK_a$ was observed by potentiometric method, and this higher $pK_a$ is thus reported as >11.0.

The octanol-PBS pH 7.4 partition coefficient (log $D_{7.4}$) assay was performed with the compound of Example 1. A 1 μL volume of a 1 mM stock solution of the compound in dimethyl sulfoxide (DMSO) was added to 500 μL 0.01 M phosphate buffer pH 7.4 (saturated with octanol) and 500 μL of octanol (saturated with 0.01 M phosphate buffer). Samples were mixed on a rotary mixer for 24 hours and the ratio of compound in each phase was determined by LC/MS/MS and the log D7.4 calculated. Samples were prepared in triplicate. Dexamethasone and ketoconazole were used as reference compounds. The results are shown in Table 3.

TABLE 3

| Compound | Log $D_{7.4}$ |
|---|---|
| Example 1 | 1.9 |
| Dexamethasone | 1.5 |
| Ketoconazole | 3.3 |

Permeability

The Caco-2 bi-directional permeability of the compound of Example 1 was evaluated in the absence and presence of a known P-gp inhibitor, verapamil. The compound was observed to be a low permeability compound and does not appear to be a substrate of P-gp. The results are shown in Table 4.

TABLE 4

| Condition | $P_{app}$ (A-B) × $10^{-6}$ cm/s | $P_{app}$ (B-A) × $10^{-6}$ cm/s | Efflux Ratio |
|---|---|---|---|
| Example 1 | 0.5 | 0.5 | 0.9 |
| Example 1 with P-gp inhibitor present | 0.5 | 0.4 | 0.9 |

Example 3—Solubility Studies

Aqueous Solubility

Aqueous solubility assays were performed with the compound of Example 1 in 0.1 M potassium phosphate pH 7.4, fasted and fed-state simulated gastric fluid, and fasted and fed-state simulated intestinal fluid (FaSSGF, FeSSGF, FaSSIF, FeSSIF). The target concentration in each solution was 100 μM. A 10 mM stock solution of the compound of Example 1 in DMSO was dispensed to a 96-well plate (10 μL per well) and dried under nitrogen. The aqueous solutions were added (1 mL) to the dried samples and mixed at 400 rpm at 37° C. on an orbital plate shaker. After 24 hours, the samples were centrifuged at 3,220 rcf (relative centrifugal force) for 10 minutes, and 10 μL of the resulting supernatants were removed and diluted for analysis by LC/MS/MS. Quantitation was performed by comparison to a single point standard of 100 μM of the compound of Example 1 in DMSO diluted identically to the test samples. Samples were prepared in triplicate. Testosterone and verapamil were used as reference compounds. The results are shown in Table 5.

TABLE 5

| | Observed Solubility (μM), Target 100 μM | | | | |
|---|---|---|---|---|---|
| Compound | 0.1M phosphate buffer pH 7.4 | Fasted-State SGF | Fasted-State SIF | Fed-State SGF | Fed-State SIF |
| Example 1 | 118 | 109 | 111 | 99 | 119 |
| Testosterone | 42 | 43 | 35 | 27 | 36 |
| Verapamil | 109 | 100 | 105 | 83 | 102 | pH Solubility

A pH-solubility curve was generated for the compound of Example 1 in citrate-phosphate buffers to evaluate the effect of pH on solubility of the free base material. The results are shown in FIG. 1. There is not a significant effect on aqueous solubility by adjusting the pH.

Solubility in Organic Solvents

The solubility of the compound of Example 1 in a range of organic solvents was measured. Solubility assays were performed by the sequential addition of the compound of Example 1 to an appropriate organic solvent while stirring vigorously until a precipitate is formed. The resulting suspension is then shaken for 24 hours at room temperature, filtered and the resulting solution was analyzed by appropriate analytical method. Quantitation was performed by comparison of the concentrations of the resulting solution of the compound of Example 1 to a single point calibration curve using a solution of the reference standard. The results are shown in Table 6.

TABLE 6

| Solvent | % Solvent in Water | Saturated concentration of Example 1, mg/mL |
|---|---|---|
| Ethanol | 40 | 5.9 |
| | 60 | 21.8 |
| Dimethyl acetamide | 100 | 23.9 |
| | 40 | 12.9 |
| | 60 | 24.8 |
| N-Methyl-2-pyrrolidone | 100 | >11 (not saturated) |
| Glycerol | 100 | 5.5 |

TABLE 6-continued

| Solvent | % Solvent in Water | Saturated concentration of Example 1, mg/mL |
|---|---|---|
| Polyethylene glycol 400 | 40 | 11.9 |
|  | 60 | 18.6 |
|  | 100 | 21.2 |
| Propylene glycol | 40 | 2.67 |
|  | 60 | 27.9 |
|  | 100 | >55 |

Solubility in Surfactant Solutions

The solubility of the compound of Example 1 in a range of surfactants was measured. Solubility assays were performed by the sequential addition of the compound of Example 1 to an appropriate organic solvent while stirring vigorously until a precipitate is formed. The resulting suspension is then shaken for 24 hours at room temperature, filtered and the resulting solution was analyzed by appropriate analytical method. Quantitation was performed by comparison of the concentrations of the resulting solution of the compound of Example 1 to a single point calibration curve using a solution of the reference standard. The results are shown in Table 7.

TABLE 7

| Surfactant | % Concentration in Aqueous Solutions | Saturated concentration of Example 1 (mg/ml) |
|---|---|---|
| Lecithin | 2 (in water) | 1.2 |
|  | 4 (in water) | 2.2 |
|  | 10 (in water) | 3.1 |
|  | 4 (in PEG 400) | 3.3 |
|  | 10 (in PEG 400) | 10.6 |
| D-alpha-tocopheryl-polyethylene glycol 1000 succinate | 20 (in PEG 400) | 20.8 |
|  | 12.3 (in PEG 400) | 7.8 |
| Octadecyl amine | 1 (in PEG 400) | 7.8 |
|  | 1 (in PEG400) | 7.1 |
| Palmitoyl-carnitine chloride | 0.10 (in water) | 0.3 |
| sulfuric acid monododecyl ester sodium salt (sodium lauryl sulphate) | 1 (in water) | 2.4 |
|  | 2 (in water) | 4.7 |
|  | 5 (in water) | 10 |
| 3-[(3-Chloamidopropyl)-dimethylamino]-1-propanesulfate | 1% | 0.66 |
| dioctyl sodium sulfosuccinate | 1% in PEG400 | 1.72 |

Further Solubility Studies

The solubility of the compound of Example 1 in a range of organic solvents, mixtures thereof, and some including surfactants, was measured. Aqueous solubility assays were performed by the sequential addition of the compound of Example 1 to an appropriate organic solvent while stirring vigorously until a precipitate is formed. The resulting suspension is then shaken for 24 hours at room temperature, filtered and the resulting solution was analyzed by appropriate analytical method. Quantitation was performed by comparison of the concentrations of the resulting solution of the compound 1 to a single point calibration curve using a solution of the reference standard. The results are shown in Table 8, in which all percentages are expressed by weight of the total weight of excipients, i.e. excluding the active and the following abbreviations are used:
PEG=polyethylene glycol
PG=1,2-propanediol
EtOH=ethanol
SLS=sodium n-dodecyl sulphate
Tween 80=polyoxyethylene (20) sorbitan monooleate

TABLE 8

| Solvent | Example 1 Solubility After 24 hrs (mg/ml) |
|---|---|
| Propylene Glycol | >150 |
| 2.5% SLS in 97.5% PEG400 | 31.3 |
| 20% PG in 80% PEG400 | 52.9 |
| 10% EtOH in 90% PEG400 | 61.4 |
| 2.5% SLS in 97.5% PEG600 | 25.9 |
| 20% PG in 80% PEG600 | 52.4 |
| 10% EtOH in 90% PEG600 | 61.4 |
| 8% EtOH/10% PG in 82% PEG600 | 61.0 |
| 2.5% SLS/8% EtOH/10% PG in 79.5% PEG600 | 57.3 |
| 2.5% SLS in 97.5% PG | >100 |
| 10% EtOH with 90% PG | >100 |
| 6% EtOH/15% glycerin/79% water | 0.07 |
| 6% EtOH/15% glycerin/79% water containing 0.3% Tween80 | 0.3 |

The results show the compound of Example 1 is most soluble in propylene glycol (PG) (150 mg/ml). Some mixtures composed of 90% or more propylene glycol were also very soluble (>100 mg/ml). Mixtures with propylene glycol and PEG were studied because these liquid ingredients are used in oral pharmaceutical products. Some of these PG/PEG mixtures dissolved a sufficient amount of the compound of Example 1 (50-60 mg/ml) for further investigation as an oral pharmaceutical product.

Additional solubility studies were undertaken using cyclodextrins, including α-cyclodextrin and a polyanionic β-cyclodextrin derivative with a sodium sulfonate salt separated from the lipophilic cavity by a butyl ether or sulfobutylether spacer group) (referred to herein as Captisol) in combination with a variety of co-agents.

Test samples were prepared with the indicated cyclodextrins and the compound of Example 1, both with and without additional agents. The test solutions were sonicated in a Fisher model 55 dismembrator (small probe) at its maximum setting of 5 for 90 seconds. The samples were rotated overnight at room temperature to allow equilibration. Quantitation was performed by comparison of the concentrations of the resulting solution of the compound 1 to a single point calibration curve using a solution of the reference standard. The results are shown in Table 9. The results show that the compound of Example 1 is not soluble in cyclodextrins and that the addition of a variety of co-agents did not increase this solubility.

TABLE 9

| Cyclodextrin (150 mM) | Co-solvent | Solubility (mg/ml) |
|---|---|---|
| Captisol | — | 7.61 |
| α-cyclodextrin | — | 10.00 |
| Captisol | HPMC E-5[#] | 4.16 |
| α-cyclodextrin | HPMC E-5[#] | 9.95 |
| Captisol | Polyethylene glycol 400* | 5.46 |
| α-cyclodextrin | Polyethylene glycol 400* | 5.00 |
| Captisol | Propylene glycol* | 3.30 |
| α-cyclodextrin | Propylene glycol* | 4.98 |
| Captisol | Ethanol* | 3.55 |
| α-cyclodextrin | Ethanol* | 0.27 |
| Captisol | DMSO* | 3.98 |
| α-cyclodextrin | DMSO* | 11.08 |
| Captisol | Sodium dodecyl sulphate[1] | 0.24 |
| α-cyclodextrin | Sodium dodecyl sulphate[1] | 10.0 |

HPMC E-5- hydroxypropyl methyl cellulose E5
[#]indicates compound added at 0.25% (expressed as a percentage of the total weight of the mixture (i.e. including the active ingredient)
*indicates compound added at 10% (expressed as a percentage of the total weight of the mixture (i.e. including the active ingredient)
[1]indicates compound added at 100 mg Example 4—Absorption Enhancement Studies in the Rat The objective of these studies was to evaluate the bioavailability of Example 1 in various combinations of excipients. Based on the solubility data that was reported previously, combinations of solvents were evaluated to study the effect of formulation composition on oral absorption. The following criteria were used to select solvents and enhancers for further formulation studies:

- The solubility of the compound of Example 1 had to be sufficient to deliver a therapeutic dose
- The permeability of the compound of Example 1 across the intestinal mucosa had to be sufficient to deliver an acceptable plasma concentration
- The formulation will use pharmaceutically acceptable excipients in concentrations and/or amounts that are found in current oral commercial pharmaceutical products
- The formulation had to exhibit acceptable physicochemical stability to meet global regulatory requirements
- The oral formulation could be manufactured and packaged with common pharmaceutical equipment and processes Following an initial screening of surfactant solutions and solvents, the materials showing improvements in absorption were combined to form solutions that would be amenable to a dosage form. Combinations of solvents and surfactants were evaluated in rat, dog and nonhuman primate models at levels appropriate for a potential human oral pharmaceutical product.

Once suitable solvents and enhancers were identified, combinations of these were made in concentrations allowed by the FDA inactive ingredient list. Additionally, solutions made using excipients suitable for an oral liquid and for a softgel capsule formulation were further pursued.

The solubility of the compound of Example 1 is low in aqueous/physiological fluids (0.1 mg/ml). The early studies in rats used aqueous dosing solutions. Gastrointestinal (GI) absorption was very low or zero. Initial rat studies (n=4) with intragastric (IG) dosing at 5 mg/Kg resulted in low plasma concentrations of the compound of Example 1 with some rats exhibiting no plasma concentrations. This indicates little or none of the compound of Example 1 was absorbed after IG administration. An example of the plasma concentrations observed is in Table 10.

Plasma Concentrations (Ng/Ml) after Intragastric Dosing in Rats Using Aqueous Dosing Solutions (Ng/Ml)

TABLE 10

|  | 0 min | 30 min | 1 hr | 2 hr | 4 hr | 8 hr |
|---|---|---|---|---|---|---|
| Rat 1 | 0 | 108 | 88 | 123 | 134 | 48 |
| Rat 2 | 0 | <10 | <10 | <10 | <10 | <10 |
| Rat 3 | 0 | 188 | 130 | 87 | 99 | 30 |
| Rat 4 | 0 | 23 | 30 | 27 | 24 | <10 |

Solubility studies identified solvents that were pharmaceutically acceptable for oral administration and could solubilize the compound of Example 1. These preparations (5 mg/kg compound of Example 1) were dosed in rats (n=4 for each condition and results presented as mean of the 4 values). The maximum plasma concentrations ($C_{max}$) increased and all rats exhibited the compound of Example 1 in the plasma, ie, there were no rats that did not absorb the compound of Example 1. Liquid mixtures that demonstrated an increase in $C_{max}$ are shown in Table 11.

Plasma Concentrations of the Compound of Example 1 in Rats Dosed Intragastrically

TABLE 11

| Formulation | $C_{max}$ at 5 mg/kg dose (ng/mL) |
|---|---|
| 20% ethanol in water | 80 |
| 2.5% sodium lauryl sulfate in water | 770 |
| 100% propylene glycol | 1380 |
| 10% ethanol/90% propylene glycol | 1585 |

Further rat absorption studies were performed with mixtures that would be appropriate for a liquid oral dosage form. These mixtures were formulated within the criteria noted above, namely that the solubility of the compound of Example 1 had to be sufficient to deliver a therapeutic dose; the permeability of the compound of Example 1 across the intestinal mucosa had to be sufficient to deliver an acceptable plasma concentration; the formulation composition used pharmaceutically acceptable excipients in concentrations and/or amounts that are found in current oral commercial pharmaceutical products; The formulation of the compound of Example 1 had to exhibit acceptable physicochemical stability to meet global regulatory requirements; and the oral formulation could be manufactured and packaged with common pharmaceutical equipment and processes.

These formulations included a variety of solvents and co-solvents for evaluation to maximize absorption and form a physicochemically stable liquid. Unless otherwise indicated, the percentages are expressed by weight as a proportion of the total weight of all excipients present in the mixture (i.e. excluding the active ingredient). These formulations were dosed intragastrically (IG) in rats at 5 mg/kg (Tables 12-14) or 300 mg/kg (Table 15) of the compound of Example 1 and blood samples were obtained from the rats at the indicated times. The plasma concentration (ng/ml) of the compound of Example 1 was determined for each condition (n=4 for each condition, presented as the mean of the 4 values) at each time point and are shown in Tables 12-15.

A number of co-solvents were evaluated. Table 12 shows exemplary results from these experiments using Poloxamer (polyoxypropylene (poly(propylene oxide)) flanked by two hydrophilic chains of polyoxyethylene (poly(ethylene oxide)), Tween 80 (polyethylene sorbitol ester), Cremphor (polyethylene glycol 1100 mono(hexadecyl/octadecyl) ether), Solutol (polyethylene glycol 660,12-hydroxy stearate) and sodium dodecyl sulfate at the indicated concentrations in water. As can be seen from Table 12, of the co-solvents evaluated, the sodium dodecyl sulfate containing formulation yielded the highest plasma concentration.

TABLE 12

| Formulation | 0 min | 30 min | 1 hr | 2 hr | 4 hr | 8 hr |
|---|---|---|---|---|---|---|
| 15% Poloxamer/85% water | 0 | 49 | 61 | 58 | 36 | 15 |
| 20% Tween80/80% water | 0 | 49 | 61 | 58 | 36 | 15 |
| 10% Cremophor/90% Water | 0 | 31 | 39 | 55 | 44 | 18 |
| 10% Solutol/90% Water | 0 | 142 | 154 | 165 | 102 | 29 |
| 2.5% Sodium Dodecyl Sulfate/97.5% Water | 0 | 538 | 617 | 770 | 686 | 183 |

A number of solvents were also evaluated. Table 13 shows exemplary results from these experiments showing the effect of propylene glycol (1,2-propanediol), polyethylene glycol and ethanol. Notably, the formulation containing polypropylene glycol at 100% showed high plasma concentrations of the compound of Example 1. However, this concentration of polypropylene glycol is higher than the concentrations and/or amounts that are typically used in oral commercial pharmaceutical products, including soft gelatin capsules. Formulations containing polyethylene glycol 400 (PEG 400) present at 100% and 20% ethanol were also tested but the results were significantly inferior to the formulation containing polypropylene glycol at 100%.

TABLE 13

| Formulation | 0 min | 30 min | 1 hr | 2 hr | 4 hr | 8 hr |
|---|---|---|---|---|---|---|
| 100% Propylene Glycol | 0 | 1380 | 1330 | 1313 | 687 | 209 |
| 100% PEG 400 | 0 | 153 | 200 | 231 | 197 | 53.2 |
| 20% Ethanol/80% Water | 0 | 148 | 109 | 105 | 117 | 39 |

Additional experiments using propylene glycol (1,2-propanediol) were conducted in the presence of co-solvents in order to identify a formulation with a lower propylene glycol percentage that still yielded high plasma concentrations (ng/ml) of the compound of Example 1. Representative experiments are shown in Table 14. The use of polyethylene glycol as a solvent in combination with propylene glycol were further explored. As can be seen, formulations containing decreasing amounts of propylene glycol in the presence of ethanol and/or polyethylene glycol yielded formulations with high plasma concentrations of the compound of Example 1.

TABLE 14

| Formulation | 0 min | 30 min | 1 hr | 2 hr | 4 hr | 8 hr |
|---|---|---|---|---|---|---|
| 10% Ethanol/90% Propylene Glycol | 0 | 1665 | 1648 | 1113 | 668 | 221 |
| 10% Ethanol/40% Propylene Glycol/50% water | 0 | 924 | 1045 | 822 | 440 | 129 |
| 10% Ethanol/50% Propylene Glycol/40% water | 0 | 287 | 843 | 1451 | 1398 | 803 |
| 5% Ethanol/75 PEG 600/20% propylene Glycol | 0 | 458 | 871 | 1112 | 1111 | 765 |
| 80% PEG 600/20% Propylene Glycol | 0 | 453 | 456 | 470 | 325 | 113 |

The combination of propylene glycol (1,2-propanediol), polyethylene glycol and ethanol was further explored in additional experiments using a variety of co-solvents, including D-α-tocopherol polyethylene glycol 1000 succinate (TPGS) and sodium dodecyl sulfate (SLS). Representative experiments are shown in Table 15. In these experiments, rates were dosed at 300 mg/kg. As can be seen in Table 15, the formulations containing D-α-tocopherol polyethylene glycol 1000 succinate, sodium dodecyl sulfate, ethanol, polyethylene glycol 600 and polypropylene glycol yielded formulations that resulted in high plasma concentrations of the compound of Example 1, with the 20% D-α-tocopherol polyethylene glycol 1000 succinate/2.5% sodium dodecyl sulfate/5% ethanol/52.5% polyethylene glycol 600/20% polypropylene glycol (1,2-propanediol) being the most effective. Notably, the amounts of each excipient present in the mixture is compatible with a variety of oral dosage forms, including, but not limited to, hard and soft gelatin capsules. The improvements in absorption and characteristics of the 20% D-α-tocopherol polyethylene glycol 1000 succinate/2.5% sodium dodecyl sulfate/5% ethanol/52.5% polyethylene glycol 600/20% polypropylene glycol (1,2-propanediol) were considered acceptable to proceed into Phase 1 human clinical trials described in Example 6 below.

TABLE 15

| Formulation | 0 min | 30 min | 1 hr | 2 hr | 4 hr | 8 hr | 24 hr |
|---|---|---|---|---|---|---|---|
| 5% TPGS/2.5% SLS/5% Ethanol/67.5% PEG 600/20% PG | 0 | 2489 | 5810 | 11365 | 9243 | 5930 | 147 |
| 20% TPGS/2.5% SLS/5% Ethanol/52.5% PEG 600/20% PG | 0 | 3658 | 7518 | 16950 | 10918 | 5855 | 1179 |

Example 5—Stability Studies

The chemical stability of the compound of Example 1 has been studied under various stressed conditions (elevated temperatures). This is a standard practice in the pharmaceutical industry in order to accelerate any chemical reactions that may occur due to environmental conditions (temperature, oxygen, light). Chemical stability is also studied under accelerated conditions to determine the compatibility or stability of the formulation ingredients with the compound of Example 1. If the stability data from the stress studies indicates a potential stability challenge, then further studies are required to identify the stability issue and resolve it.

Figure 2:
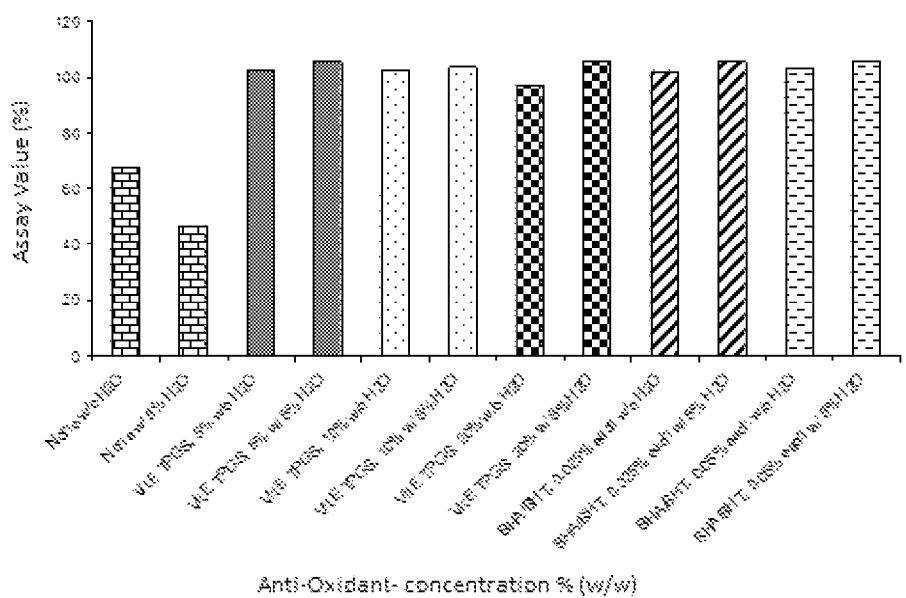
FIG. 2 illustrates assay values on formulations of the compound of Example 1 with various antioxidants.

Initial stability studies were conducted under accelerated conditions. It was determined the compound of Example 1, when combined with the candidate formulations, underwent degradation when exposed to light, oxygen and elevated temperatures. The route of degradation was determined to be oxidation of the vinyl substituent in the compound in Example 1. Several antioxidants were identified for study. These antioxidants are pharmaceutically acceptable for use in human oral dosage forms and are compatible with the gelatin composition in a soft gelatin capsule. The data indicates D-α-tocopherol polyethylene glycol 1000 succinate (Vitamin E-TPGS), tert-butyl 4-hydroxyanisole (butylated hydroxyanisole or BHA), and 2,6-di-tert-butyl-4-methylphenol (BHT) were effective antioxidants. The data is shown in FIG. 2.

Figure 3:
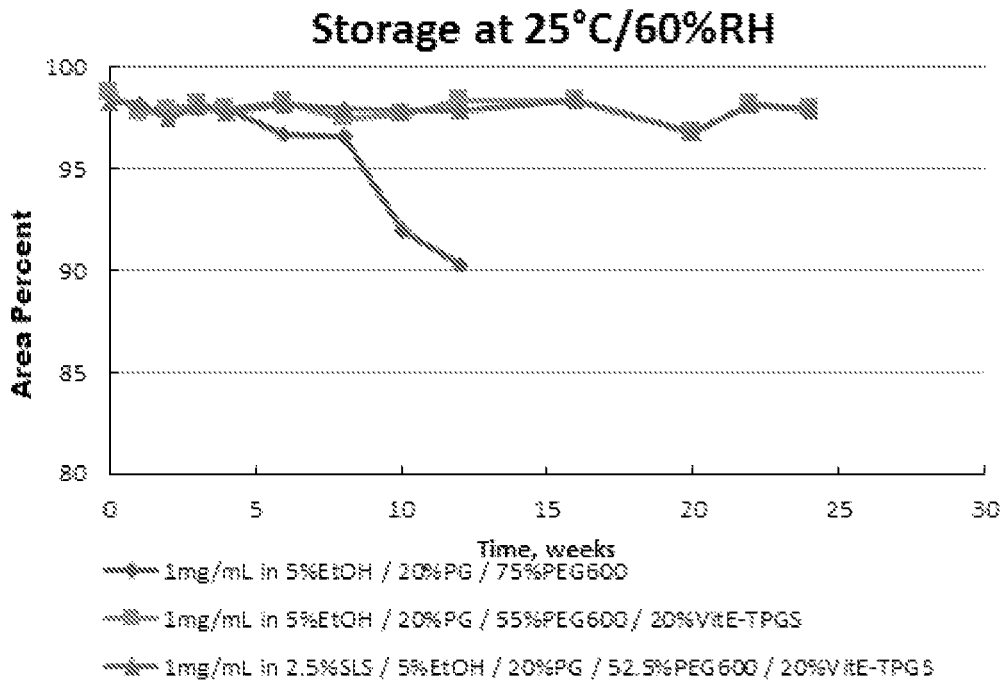
FIG. 3 illustrates the room temperature stability of various oral liquid formulations of the compound of Example 1 following storage at 25° C. and 60% relative humidity.

D-α-tocopherol polyethylene glycol 1000 succinate (vitamin E-TPGS) is commonly used in softgel formulations and it was selected for further study as a potential antioxidant in the formulations. The data indicates Vitamin E-TPGS is very effective in reducing or eliminating oxidation over the time period studied and at ambient temperature and humidity conditions. The formulations studied and the results obtained are illustrated in FIG. 3.

Figure 4:
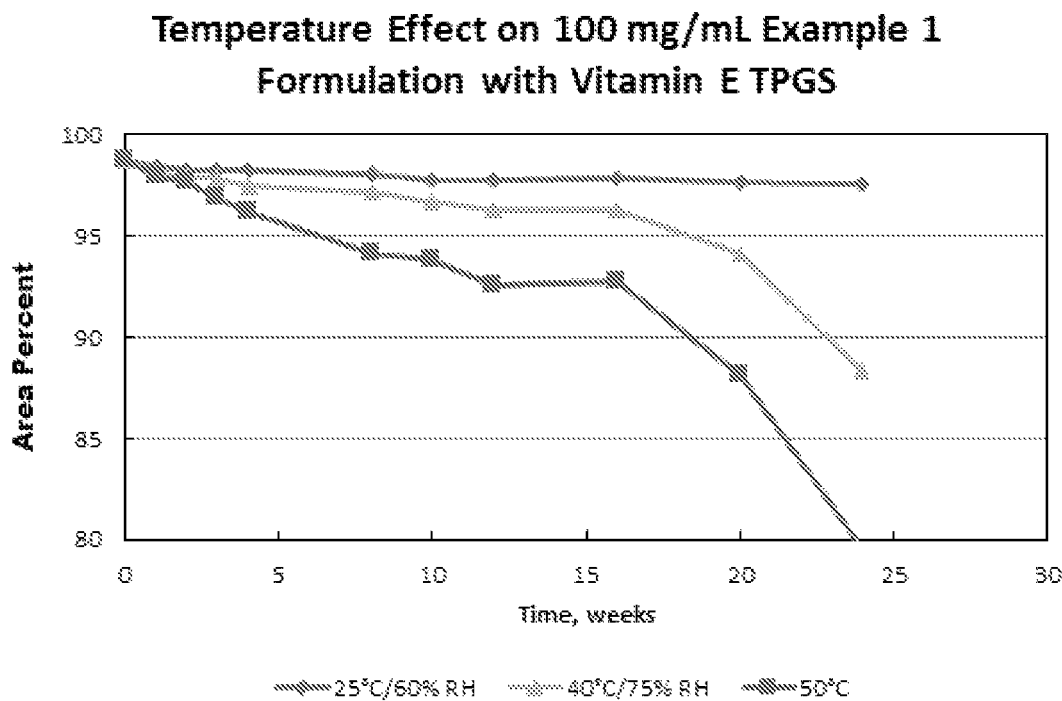
FIG. 4 illustrates the effect of temperature on the stability of an oral liquid formulation of the compound of Example 1 following storage under various conditions.

Additional studies investigated the effectiveness of the antioxidant at higher temperatures. The effectiveness of the antioxidant decreased as temperature was increased. This is shown in FIG. 4.

Figure 5:
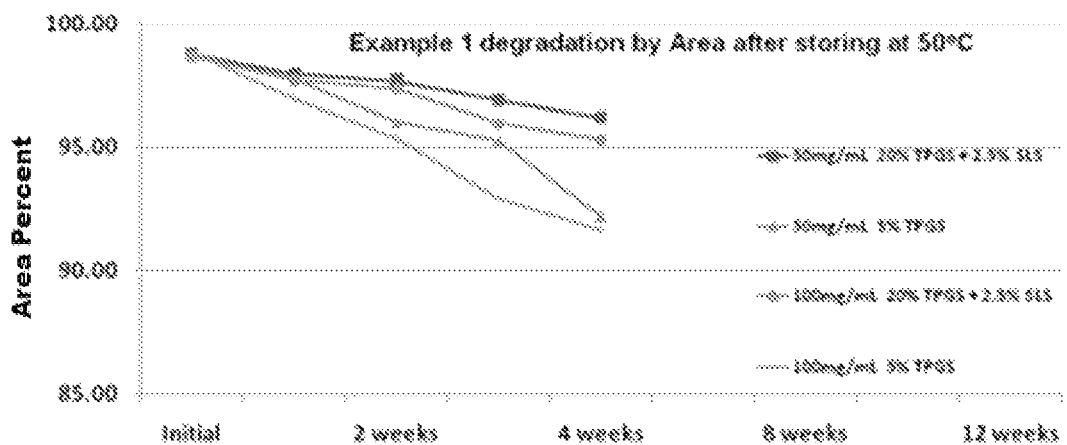
FIG. 5 illustrates the chemical stability of various oral liquid formulations of the compound of Example 1 following storage.

Additional formulation components were investigated and sodium lauryl sulfate, when combined with Vitamin E-TPGS, was found to have an improved antioxidant effect at 50° C. The data is shown in FIG. 5.

Figure 6:
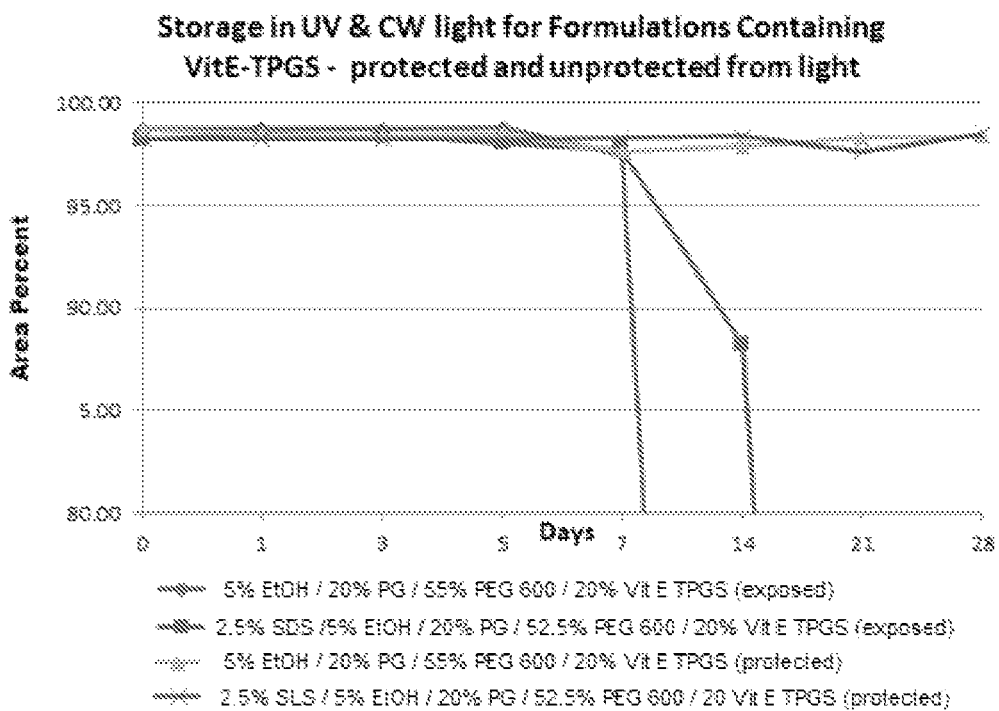
FIG. 6 illustrates the photostability of various oral liquid formulations of the compound of Example 1.

The compound of Example 1 also demonstrated photo-degradation when exposed to ultraviolet (UV) or white (CW) light. This degradation was noted in the final formulation candidates. Stability studies were performed with formulations that were protected from light and formulations exposed to light. In this study, the compound of Example 1 (1 mg/ml) was studied in 5% ethanol/20% propylene glycol/55% PEG 600120% vitamin E TPGS or 2.5% sodium dodecyl sulfate/5% ethanol/20% propylene glycol/52.5% PEG 600/20% vitamin E TPGS (with each formulation being exposed to or protected from exposure to light). The formulations protected from light did not exhibit degradation. The 5% ethanol/20% propylene glycol/55% PEG 600/20% vitamin E TPGS showed 80% degradation at around day 7 while the 2.5% sodium dodecyl sulfate/5% ethanol/20% propylene glycol/52.5% PEG 600/20% vitamin E TPGS showed 80% degradation around day 14. The data are in FIG. 6.

Certain formulations may require protection from light exposure. This can be accomplished through the use of industry standard packaging which is light resistant, e.g., amber glass bottles, high density amber plastic bottles and blister packages that have amber high density plastic or foil on the top and bottom of the blister package.

The compound of Example 1 exhibits degradation when exposed to increased temperature, light and oxygen. These degradation issues were resolved through a unique combination of ingredients and packaging as described above. In addition, the novel formulations required for resolution of these degradation issues also meets the criteria stated in Example 4, namely that the compound of Example 1 must be sufficiently soluble to deliver a therapeutic dose; its permeability across the intestinal mucosa must be sufficient to deliver an acceptable plasma concentration; the formulation uses pharmaceutically acceptable excipients in concentrations and/or amounts that are found in current oral commercial pharmaceutical products; it has to exhibit acceptable physicochemical stability to meet global regulatory requirements; and the oral formulation could be manufactured and packaged with common pharmaceutical equipment and processes.

Example 6—Human Pharmacokinetics and Kallikrein Inhibition Data with Hard Gelatin Capsules A two-part, Phase 1, double-blind, placebo-controlled study of the compound of Example 1 was conducted in healthy subjects. Part 1 of the study assessed the safety, tolerability and the pharmacokinetic (PK) and pharmacodynamic (PD) properties of the compound of Example 1 following a single ascending dose. Subjects were enrolled in five sequential cohorts and received the compound of Example 1 (50 mg, 125 mg, 250 mg, 500 mg or 1000 mg; n=6/cohort) or placebo (n=2/cohort) under fasting conditions. To enable a food-effect assessment on exposure, subjects enrolled in Cohort 4 (500 mg or placebo) subsequently received a second dose of the compound of Example 1 following a high-fat breakfast.

Part 2 of the study evaluated the safety, tolerability, PK, and PD of multiple ascending doses of the compound of Example 1. Twelve subjects were administered a 7-day course of the compound of Example 1 (n=10 subjects/cohort received the API and n=2 subjects/cohort received matching placebo) according to the following dose regimens: 100 mg of the compound of Example 1 or placebo every 8 hours (q8h) in Cohort 1; 200 mg of the compound of Example 1 or placebo q8h in Cohort 2; 400 mg of the compound of Example 1 or placebo q8h in Cohort 3 and 800 mg of the compound of Example 1 or placebo q8h in Cohort 4.

For Part 1 and Part 2 of the study, the compound of Example 1 was generally safe and well tolerated. There were no serious adverse events and no dose-limiting adverse events.

Results of Part 1

A total of 41 subjects were enrolled in Part 1 and 40 subjects completed the study. One subject in Cohort 5 who received the compound of Example 1 withdrew for non-compliance and was subsequently replaced.

Figure 7:
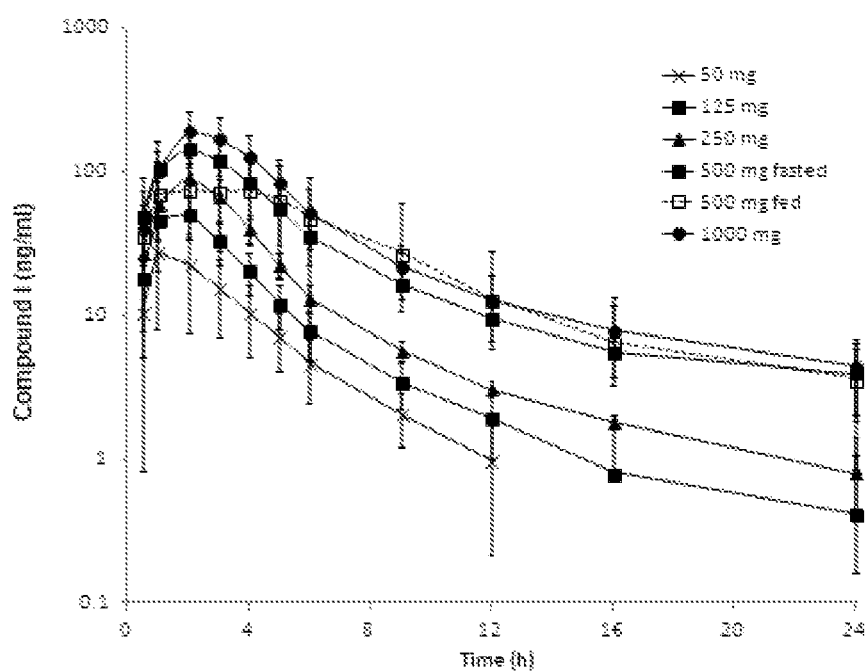
FIG. 7 illustrates the mean plasma concentration in subject over time following single oral doses of the compound of Example 1.

A summary of the pharmacokinetic parameters for fasting, single oral doses of 50 to 1000 mg of the compound of Example 1 (Part 1) is presented in Table 16. Mean concentrations of the compound of Example 1 by cohort are shown in FIG. 7. This data is also presented for a single oral dose of 500 mg administered after a high-fat breakfast.

Following single oral doses of the compound of Example 1 (in capsules form as described in Example 8) up to a dose of 1000 mg of the compound of Example 1 administered under fasting conditions, $C_{max}$ was reached approximately 2 hours after dosing. Compound concentrations then declined biphasically and were quantifiable through 9 hours postdose in Cohort 1 (50 mg) and 24 hours postdose in Cohorts 4 and 5 (500 and 1000 mg). The terminal half-life of the compound of Example 1 ranged from approximately 3 hours (Cohort 1) to 15 hours (Cohort 4); this apparent increase in $t_{1/2}$ with increasing dose is likely artefactual and due to more points being quantifiable in the terminal (versus initial distribution) phase. Examination of point estimates for dose-normalized (DN) $C_{max}$ indicates that $C_{max}$ increases in a less than dose-proportional manner over the 50 to 1000 mg dose range; 95% confidence interval (CI) ranges suggest reasonable dose-proportionality over the 125 to 500 mg range. Consideration of point estimates and associated CIs of DN $AUC_{inf}$ indicate that AUC is relatively dose-proportional with doses between 50 and 500 mg.

TABLE 16

Summary of Preliminary Plasma Pharmacokinetic Parameters Following Single Oral Doses of the Compound of Example 1

| Dose | Statistic | $T_{max}{}^a$ (h) | $C_{max}$ (ng/mL) | DN $C_{max}{}^b$ (ng/mL/mg) | $AUC_{last}$ (h * ng/mL) | $AUC_{0\text{-}inf}$ (h * ng/mL) | DN $AUC_{0\text{-}inf}{}^b$ (h * ng/mL/mg) | $t_{1/2}$ (h) |
|---|---|---|---|---|---|---|---|---|
| 50 mg | GM | 1.0 | 26.4 | 0.528 | 89.6 | 96.8 | 1.94 | 2.98 |
|  | CV % | (0.5, 2.0) |  | (0.30, 0.93) |  |  | (1.3, 3.0) |  |
|  | GM |  | 59 |  | 44 | 43 |  | 59 |
| 125 mg | GM | 2.0 | 54.0 | 0.432 | 188 | 197 | 1.58 | 4.66 |
|  | CV % | (1.0, 2.0) |  | (0.33, 0.57) |  |  | (1.1, 2.3) |  |
|  | GM |  | 27 |  | 35 | 36 |  | 82 |

TABLE 16-continued

Summary of Preliminary Plasma Pharmacokinetic Parameters Following Single Oral Doses of the Compound of Example 1

| Dose | Statistic | $T_{max}^a$ (h) | $C_{max}$ (ng/mL) | DN $C_{max}^b$ (ng/mL/mg) | $AUC_{last}$ (h * ng/mL) | $AUC_{0-inf}$ (h * ng/mL) | DN $AUC_{0-inf}^b$ (h * ng/mL/mg) | $t_{1/2}$ (h) |
|---|---|---|---|---|---|---|---|---|
| 250 mg | GM | 2.0 | 85.9 | 0.344 | 336 | 353 | 1.41 | 6.50 |
|  | CV % | (1.0, 2.0) |  | (0.22, 0.54) |  |  | (1.1, 1.9) |  |
|  | GM |  | 45 |  | 32 | 28 |  | 56 |
| 500 mg FASTED | GM | 2.0 | 155 | 0.311 | 760 | 802 | 1.60 | 15.4 |
|  | CV % | (1.0, 3.0) |  | (0.25, 0.38) |  |  | (1.2, 2.2) |  |
|  | GM |  | 21 |  | 32 | 29 |  | 75 |
| 500 mg FED$^c$ | GM | 2.5 | 82.1 |  | 586 | 642 |  | 18.9 |
|  | CV % | (1.0, 4.0) |  |  |  |  |  |  |
|  | GM |  | 36 |  | 68 | 76 |  | 49 |
| 1000 mg$^c$ | GM | 2.0 | 193 | 0.193 | 981 | 983 | 0.983 | 12.3 |
|  | CV % | (2.0, 4.0) |  | (0.12, 0.31) |  |  | (0.55, 1.7) |  |
|  | GM |  | 48 |  | 47 | 50 |  | 88 |

Figure 8:
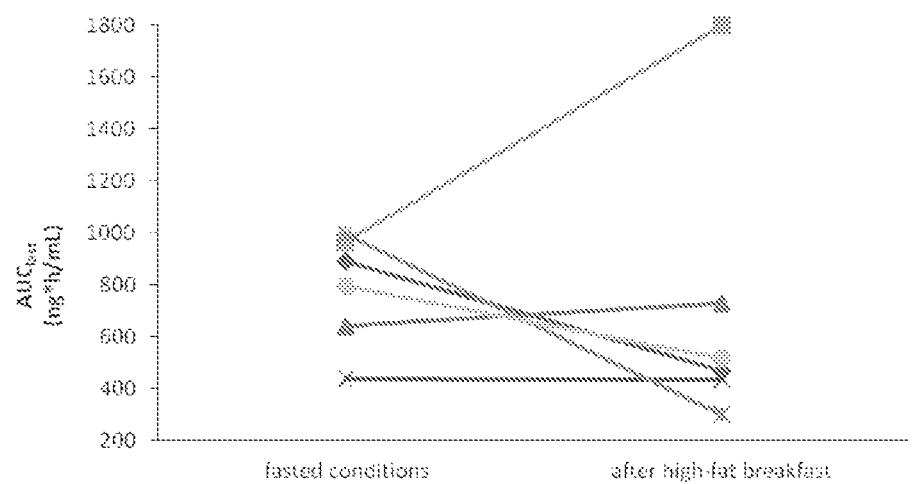
FIG. 8 illustrates $AUC_{last}$ values following administrate of a single 500 mg oral dose of the compound of Example 1 to a subject after an overnight fast and a high fat meal

$^a T_{max}$ summary is provided as median (minimum, maximum)
$^b$DN PK parameter summary is provided as GM (lower, upper limit of the 95% confidence interval for the GM)
$^c t_{1/2}$ and all $t_{1/2}$-derived parameters represent data from n = 5 subjects based upon the inability to accurately predict $t_{1/2}$ in one study subject; $t_{1/2}$ determined from sampling out to 96 hours postdose After a high-fat breakfast, geometric mean $C_{max}$ is reduced 47% as compared with the value obtained under fasting conditions. $AUC_{inf}$ and $AUC_{last}$ were more modestly reduced with food (23% and 20% reduction as compared with the fasting values, respectively). In addition, examination of within-subject differences in exposure following the two treatments do not always indicate that food reduces AUC of the compound of Example 1 (see FIG. 8). Moreover, within-subject differences in concentrations achieved near the end of the projected dosing interval that may be necessary to maintain clinical benefit were not pronounced. Therefore, the compound of Example 1 may be taken with food.

Figure 9:
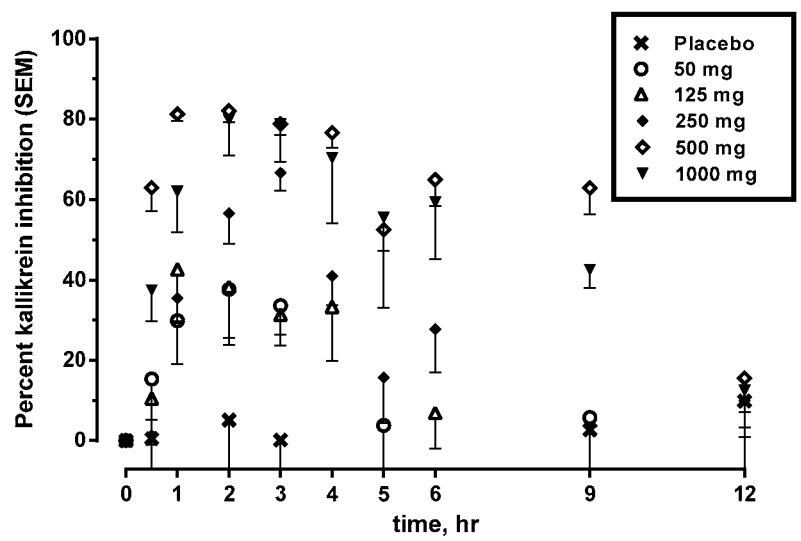
FIG. 9 illustrates the percent of plasma kallikrein inhibition over time after administration of various doses of the compound of Example 1 to a subject.

Plasma kallikrein activity was assessed in subject samples with an exploratory contact activation assay using a fluorogenic artificial substrate for kallikrein. In this assay, the contact pathway is activated by addition of ellagic acid, and amidolytic activity is measured. Results are expressed as percent inhibition compared to subject baseline samples and reflect inhibition additional to that resulting from the activity of normal levels of C1INH present in healthy subject plasma samples. Analysis of plasma kallikrein activity following single doses of the compound of Example 1 was performed through 12 hours postdose. As demonstrated in FIG. 9, meaningful inhibition of plasma kallikrein was achieved at the highest doses, with 70 to 80% inhibition achieved relative to pre-dose baseline at 500 and 1000 mg single doses. Samples from subjects receiving intermediate doses of 50-250 mg showed modest but real changes in comparison to placebo subject samples. The time course of inhibition generally followed the plasma pharmacokinetics of the compound. The greatest effect was seen around the time of $C_{max}$. Plasma kallikrein inhibition largely returned to baseline at 12 hours postdose, when plasma concentrations of the compound of Example 1 were low (generally <10 ng/mL).

Results of Part 2

Figure 10A:
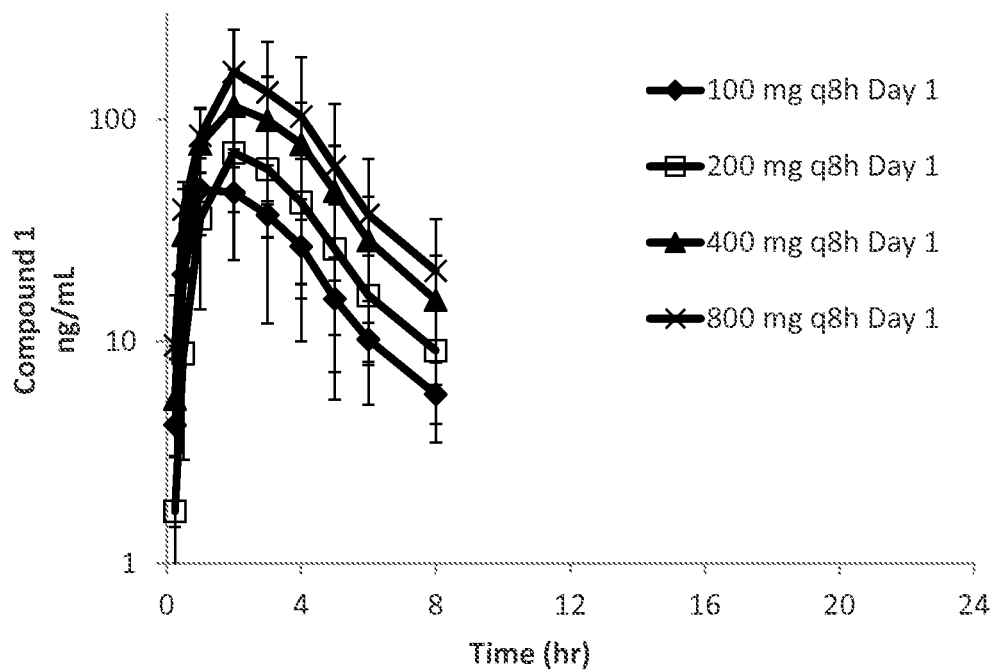
FIG. 10A illustrates mean plasma concentration in subject over time following the first dose of the compound of Example 1 on Day 1.
Figure 10B:
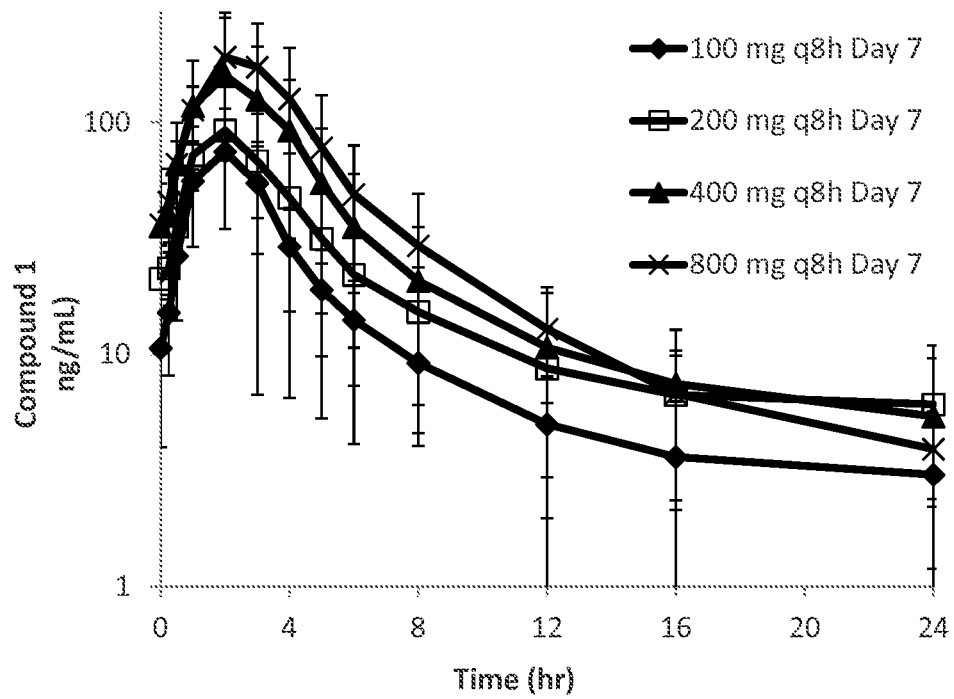
FIG. 10B illustrates mean plasma concentration in subject over time following the last dose of the compound of Example 1 on Day 7.

A total of 48 subjects were enrolled in Part 2 of the Study and 47 subjects completed the study. A summary of pharmacokinetic parameters for the compound of Example 1 for the first dose on Day 1 and last dose on Day 7 is presented in Table 17. Mean concentrations of the compound of Example 1 are shown in FIGS. 10A and B. Across dosing days and cohorts, maximal concentrations were achieved at approximately 2 hours postdose. Concentrations then declined biexponentially with a terminal elimination half-life of approximately 10 hours (calculated over a 24 hour period). The compound of Example 1 exhibited time-independent pharmacokinetics with repeated dosing, as within-subject Day 1 $AUC_{inf}$ and Day 7 $AUC_{tau}$ values were generally similar. After repeated dosing, there was accumulation in $C_{max}$ and AUC of approximately 30% compared to the first day of dosing. Day 7 geometric mean exposure ($AUC_{tau}$ and $C_{max}$) did increase with increasing dose. Drug exposure was dose proportional through 400 mg three times a day. At 400 mg three times a day, pre-dose geometric mean drug levels and coefficient of variation (CV) on day 7 were 28.6 ng/ml and 77% and post-dose geometric mean maximum drug levels and CV were 152 ng/ml and 57%. Plasma concentrations of the compound of Example 1 over 25 ng/ml are expected to be efficacious in treating conditions such as, but not limited to, HAE and AAE.

Figure 11:
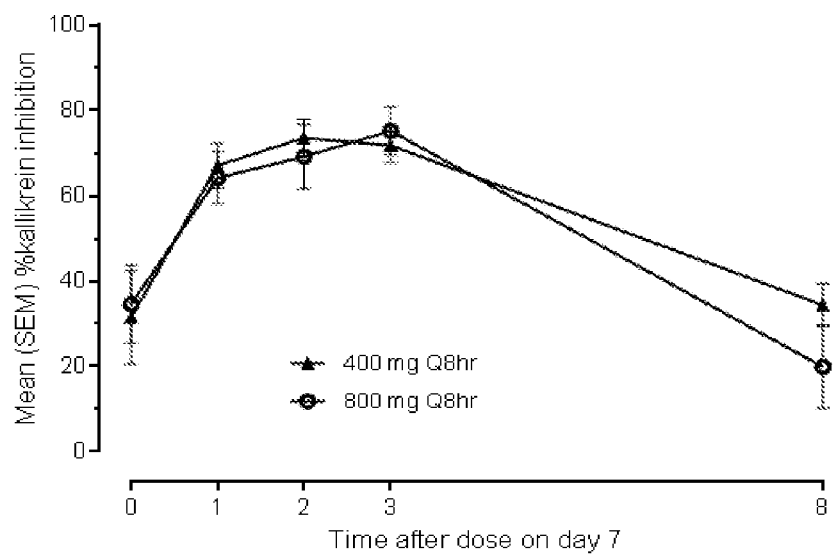
FIG. 11 illustrates the percent of plasma kallikrein inhibition over time after administration of 400 mg and 800 mg of the compound of Example 1 to a subject on day 7 of dosing.
Figure 12:
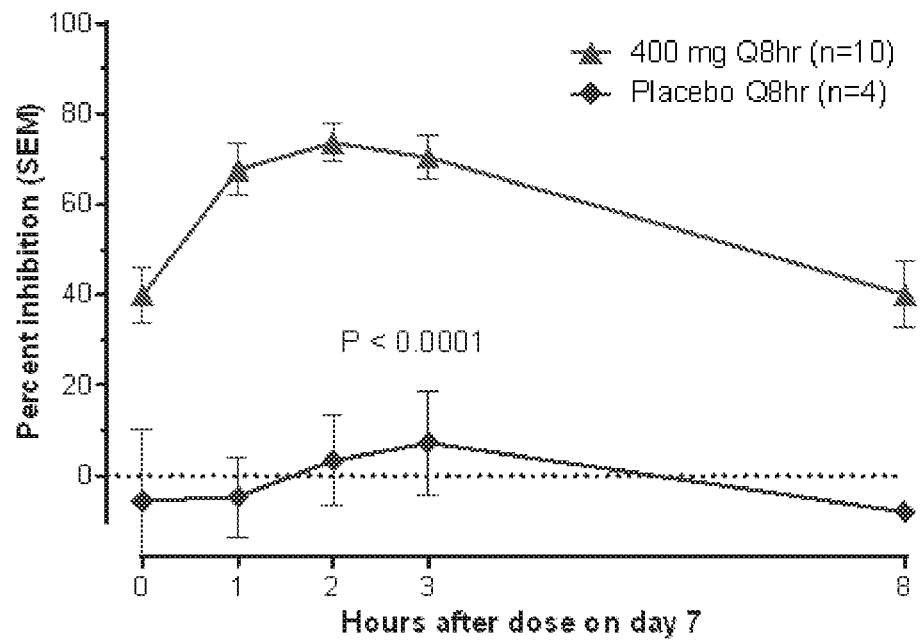
FIG. 12 illustrates the percent of plasma kallikrein inhibition over time after administration of 400 mg of the compound of Example 1 or placebo to a subject on day 7 of dosing.

Plasma kallikrein activity profiles were measured in Part 2 subjects on day 7 of dosing and the results were expressed as percent inhibition compared to the activity present in the Day 1 predose plasma sample. As demonstrated in FIG. 11 with data from the two highest dose cohorts, the degree and temporal pattern of inhibition observed after 7 days of dosing was similar to that observed after single doses. Kallikrein inhibition of 30-40% was seen at the beginning and end of the dosing interval on Day 7, with maximum inhibition observed around the time of $C_{max}$. The kallikrein inhibition seen with the both of the two highest dose cohorts was highly statistically significantly greater than with placebo (p<0.0001, ANOVA). FIG. 12 shows the plasma kallikrein activity profile of the 400 mg dose and placebo does as measured in Part 2 subjects on day 7 expressed as percent inhibition. Kallikrein inhibition was observed through the last dosing interval on day 7 compared to placebo (p<0.0001). No significant inhibition of plasma kallikrein activity was observed in the placebo group.

TABLE 17

| Treatment | | Day 1 PK values | | | Day 7 PK values | | | | | | | |
|---|---|---|---|---|---|---|---|---|---|---|---|---|
| | | AUC$_{0-8}$ (h * ng/mL) | C$_{max}$ (ng/mL) | T$_{max}$ (hr) | AUC$_{tau}$ (h * ng/mL) | C$_{max}$ (ng/mL) | DN AUC$_{tau}$[a] (ng * h/mL/mg) | T$_{max}$ (hr) | t$_{1/2}$[b] (h) | C$_{tau}$ (ng/mL) | Rac[c] AUC | Rac[c] Cmax |
| 100 mg q 8 h | Min | 85.0 | 36.9 | 1 | 91.9 | 29.8 | | 0.5 | 7.92 | 4.16 | 0.782 | 0.732 |
| | Median | 185 | 49.4 | 1 | 246 | 71.2 | | 2 | 11.5 | 7.92 | 1.24 | 1.33 |
| | Max | 357 | 92.3 | 3 | 469 | 140 | | 3 | 19.8 | 20.1 | 3.44 | 2.74 |
| | Geometric Mean (GM) | 173 | 54.5 | | 237 | 72.6 | 2.37 | | 12.4 | 8.34 | 1.37 | 1.33 |
| | CV % GM | 49 | 34 | | 52 | 53 | (1.67, 3.36) | | 28 | 47 | 44 | 45 |
| 200 mg q 8 h[d] | Min | 79.4 | 31.1 | 1 | 129 | 34.5 | | 1 | 7.23 | 3.71 | 0.407 | 0.478 |
| | Median | 251 | 89.7 | 2 | 385 | 92.3 | | 2 | 13.5 | 13.0 | 1.46 | 1.19 |
| | Max | 381 | 103 | 4 | 671 | 216 | | 2 | 18.4 | 30.1 | 3.04 | 3.51 |
| | GM | 236 | 72.0 | | 316 | 83.6 | 1.58 | | 12.6 | 12.9 | 1.34 | 1.16 |
| | CV % GM | 54 | 47 | | 62 | 64 | (1.05, 2.37) | | 32 | 71 | 76 | 63 |
| 400 mg q 8 h | Min | 203 | 71.3 | 1 | 265 | 89.8 | | 1 | 8.63 | 9.15 | 0.606 | 0.637 |
| | Median | 395 | 124 | 2 | 463 | 129 | | 2 | 12.7 | 14.6 | 1.34 | 1.30 |
| | Max | 753 | 208 | 4 | 1543 | 478 | | 3 | 25.6 | 53.4 | 2.41 | 2.30 |
| | GM | 421 | 119 | | 534 | 152 | 1.34 | | 13.0 | 17.4 | 1.27 | 1.28 |
| | CV % GM | 50 | 39 | | 62 | 57 | (0.890, 2.01) | | 33 | 65 | 48 | 43 |
| 800 mg q 8 h | Min | 176 | 65.2 | 1 | 226 | 61.4 | | 1 | 4.83 | 6.78 | 0.925 | 0.879 |
| | Median | 581 | 153 | 2 | 835 | 240 | | 2 | 8.03 | 30.3 | 1.25 | 1.16 |
| | Max | 1268 | 305 | 3 | 1407 | 372 | | 4 | 10.7 | 76.7 | 3.51 | 3.44 |
| | GM | 504 | 143 | | 678 | 187 | 0.847 | | 7.46 | 23.7 | 1.34 | 1.31 |
| | CV % GM | 77 | 66 | | 70 | 66 | (0.540, 1.33) | | 28 | 83 | 42 | 45 |

[a]DN AUC$_{tau}$ summary is provided as GM (lower, upper limit of the 95% confidence interval for the GM)
[b]Half-life on Day 1 was determined over a sampling time of 8 hours postdose; Day 7 half-life was determined through 24 hours postdose.
[c]Rac = accumulation ratio, calculated as AUC$_{tau}$ Day 7/AUC$_{0-8}$ Day 1 or C$_{max}$ Day 7/C$_{max}$ Day 1
[d]t$_{1/2}$ derived parameters for one subject in on active in Cohort 2 were excluded as this parameter could not be accurately determined

Example 7—Human Pharmacokinetics and Kallikrein Inhibition Data with Soft Gelatin Capsules A single dose, randomized, 3-period crossover study was conducted to evaluate the relative bioavailability of the compound of Example 1 formulated as a soft gelatin capsule to the compound of Example 1 formulated as a hard gelatin capsule and to determine the effect of food on the pharmacokinetics of the compound of Example 1. The goals of this study were to ascertain the relative bioavailability and pharmacokinetics of the compound of Example 1 in soft gelatin capsules to hard gelatin capsules when administered following an overnight fast in healthy subjects. In addition, the study estimated the effect of a high-fat meal upon the pharmacokinetics of the compound of Example 1 following single dose administration of 400 mg of the compound of Example 1 in a soft gelatin capsules to healthy subjects. Hard and soft gelatin capsules were prepared as in Example 8 and 9, respectively, below.

The study was a single-dose, open-label, randomized, 3-way cross-over design. During each treatment period, eighteen subjects will receive a single dose of one of the following treatments in a randomized sequence:

Treatment A: BCX4161 400 mg as 4×100 mg hard gelatin capsules following an overnight fast Treatment B: BCX4161 400 mg as 4×100 mg soft gelatin capsules following an overnight fast Treatment C: BCX4161 400 mg as 4×100 mg soft gelatin capsules following a high fat meal Subjects were admitted to the Clinical Research Unit (CRU) on Day-1 of each treatment period and remained in the CRU until the morning of Day 2 after the collection of the 24 hour pharmacokinetic (PK) sample and all assessments are complete. Each subject received either a single oral dose of the compound of Example 1 in a hard gelatin capsules or a single oral dose of the compound of Example 1 in a soft gelatin capsules (with and without a high fat meal) on the first day of each study period, and underwent safety and pharmacokinetic evaluations for the following 24 hours. Fourteen blood samples for the measurement of plasma concentrations of the compound of Example 1 were collected at predose on Day 1 and 0.5, 1, 1.5, 2, 2.5, 3, 4, 6, 8, 10, 12, 16 and 24 hours post dose in each dosing period. There was a minimum washout period of 7 days between doses based upon the elimination half-life for the compound.

The Table below outlines the dosing sequence used for a William's Latin Square design.

| | |
|---|---|
| 1 | ABC |
| 2 | BCA |
| 3 | CAB |
| 4 | CBA |
| 5 | ACB |
| 6 | BAC |

The results of the study are shown in Table 19. As can be seen in Table 19, the compound of Example 1 in the soft gelatin capsules (prepared as in Example 9) showed a geometric mean Cmax of approximately 80% as compared to the compound of Example 1 in hard gelatin capsules (prepared as in Example 8). Following single oral doses of the compound of Example 1 (in capsules form as described above) at a dose of 400 mg of the compound of Example 1 administered under fasting conditions, C$_{max}$ was reached approximately 2 hours after dosing as observed above. Compound concentrations then declined biphasically and were quantifiable through 12-15 hours postdose. Using the soft gelatin capsule formulation of the compound of Example 1, plasma concentrations over 25 ng/ml are expected. Such plasma levels of the compound of Example 1 are expected to be efficacious in treating conditions such as, but not limited to, HAE and AAE. Therefore, the compound of Example 1 formulated in a soft gelatin capsule displayed good bioavailability.

After a high-fat breakfast, geometric mean C$_{max}$ is reduced as compared with the value obtained under fasting conditions using the compound of Example 1 administered as a soft-gelatin capsule. AUC$_{inf}$ and AUC$_{last}$ were more modestly reduced with food.

TABLE 19

|  | GLSMR | lower 90% CI | upper 90% CI |
|---|---|---|---|
| Soft-Gelatin v. Hard Gelatin Capsules | | | |
| Cmax | 80.0127 | 63.930209 | 100.1409 |
| AUClast | 75.0791 | 61.06393 | 92.310895 |
| AUCinf | 72.1522 | 57.895868 | 89.919029 |
| Fed v. Fasting with Soft Gelatin Capsules | | | |
| Cmax | 52.313141 | 41.606344 | 65.775179 |
| AUClast | 62.423949 | 50.554206 | 77.080617 |
| AUCinf | 63.941649 | 51.09829 | 80.013138 |

Example 8—Dosage Form for Hard Gelatin Capsules

In one embodiment, 100 mgs of the compound of Example 1 (as a hydrochloride salt) is formulated into a compounded solution consisting of the excipients: sodium dodecyl sulfate, ethanol, polyethylene glycol 600, 1,2-propanediol, and D-α-tocopherol polyethylene glycol 1000 succinate filled into a white opaque, size 00, hard gelatin capsule according to the method described below. The components of the formulation, their function, and quality/compendial standards are provided in Table 19.

TABLE 19

| Component | Quantitative Composition (wt) | Function |
|---|---|---|
| 3-[2-(4-carbamimidoyl-phenyl-carbamoyl)-5-methoxy-4-vinyl-phenyl]-6-(cyclopropylmethyl-carbamoyl)-pyridine-2-carboxylic acid* | 11.7 | Compound of Example 1 |
| Sodium Dodecyl Sulfate, NF | 2.2 | Surfactant |
| Ethanol 200 Proof (Dehydrated Alcohol), USP | 4.4 | Solvent |
| Polyethylene Glycol 600, NF | 46.3 | Solvent |
| 1,2-Propanediol, USP | 17.7 | Solvent |
| D-α-tocopherol polyethylene glycol 1000 succinate, NF (Vitamin E TPGS) | 17.7 | Stabilizer/Absorption Enhancer |
| Total | 100.0 | |

*content by weight of the active species, excluding that of the counterion

Manufacture of the Dosage Form
Manufacture of the Fill Formulation

1. The Polyethylene Glycol 600 (PEG600) and Vitamin E TPGS were heated in an oven at 55±5° C. to melt the ingredients. The final temperatures of the melted ingredients and the start/stop times/dates for heating were recorded.
2. A magnetic stir bar was placed in the labelled Amber Glass jar with lid.
3. The sodium dodecyl sulfate was dispensed into a weigh boat.
4. The PEG600, previously heated in Step 1, was dispensed into a clean polypropylene beaker.
5. The lid from the labelled Amber Glass Jar containing the stir bar from Step 2, was removed and retained and placed on the magnetic stir plate.
6. The sodium dodecyl sulfate was charged into the Amber Glass jar.
7. The PEG600 (Step 9) was charged into the Amber Glass jar containing the Sodium Lauryl Sulfate (Step 6), and stirring initiated to create a small vortex in the liquid without the incorporation of air. The time and the final mixing speed setting were recorded.
8. Propylene glycol was dispensed into a clean polypropylene beaker.
9. The propylene glycol was dispensed into the Amber Glass Jar from Step 7 and mixing continued, adjusting stirring to maintain a small vortex in the liquid without the incorporation of air.
10. The heating setting on the magnetic stir plate was adjusted to heat the contents of the jar to 45° C. (±5° C.) and the initial and final temperature of the contents and the heating start and stop times below recorded.
11. Vitamin E TPGS, previously heated in Step 1, was dispensed into a clean polypropylene beaker.
12. The Vitamin E TPGS was charged into the Amber Glass jar from Step 15 and stirring adjusted to maintain a small vortex in the liquid without the incorporation of air. The heating setting on the magnetic stir plate was adjusted to maintain the contents of the jar at 45° C. (±5° C.) and the initial and final temperature of the contents and the mixing start and stop times below recorded. Mixing was continued until a clear solution is obtained.
13. Heating the contents of the Amber Glass jar from Step 12 was discontinued and the solution allowed to cool to ambient temperature (≤27° C.) while mixing. Stirring was adjusted to maintain a small vortex in the liquid without the incorporation of air. The cooling start and stop time, mixing speed setting, and the solution final temperature below were recorded.
14. Ethanol was dispensed into a clean polypropylene beaker.
15. The ethanol was charged into the Amber Glass jar from Step 13 and the Amber Glass Jar capped and closed with the lid. Mixing the solution was continued for not less than 10 minutes and stirring adjusted to maintain a small vortex in the liquid without the incorporation of air. The mixing start and stop times below were recorded.
16. The compound of Example 1 was dispensed into a weigh boat.
17. The Amber Glass jar (Step 15) was opened the compound of Example 1 (Step 16) slowly discharged into the Amber Glass Jar. The Amber Glass Jar was capped and closed with the lid and mixing continued until a clear solution is obtained, adjusting stirring to maintain a small vortex in the liquid without the incorporation of air. The mixing start and stop times below were recorded.

Filling of the Hard Gelatin Capsules

1. Empty hard gelatin capsules were weighed the average empty capsule weight determined.
2. The solution of the compound of Example 1 (Step 17) was used to manually fill empty capsules using disposable transfer pipettes and the following procedure:
   a) Tare the balance.
   b) Obtain an empty capsule then separate the capsule cap from the capsule body, placing both pieces on the balance and ensuring that the capsule body is maintained in an upright orientation.
   c) Record the empty capsule weight.
   d) Fill a sufficient quantity of the solution of the compound of Example 1 into the capsule body to ensure that the capsule gross weight is within the fill limits.
   e) Record the final gross capsule weight.
   f) Retrieve the filled capsule body and cap from the balance.

g) Place the capsule cap on the capsule body and manually close. Manually compress the capsule cap and body until the cap "snaps" closed. Do not crush the capsule. If the capsule is damaged during the filling and closing process, collect the capsule into a waste bag.
h) Repeat the filling process with a new empty capsule shell.
i) Place the filled and closed capsule into an empty Screw Top Vial in an upright orientation (i.e. capsule cap is up towards top of vial/closure). Place the closure on the vial and manually tighten.
j) Repeat until the required number of capsules has been filled and vialed or until the solution of the compound of Example 1 is exhausted.

Example 9—Dosage Form with Soft Gelatin Capsules

In another embodiment, 100 mg of the compound of Example 1 (as a hydrochloride salt) is formulated into a compounded solution consisting of the excipients: polyethylene glycol 600, D-α-tocopherol and D-α-tocopherol polyethylene glycol 1000 succinate filled into a white opaque, size 00, soft gelatin capsule according to the method described below. The components of the formulation, their function, and quality/compendial standards are provided in Table 20.

TABLE 20

| Component | Quantitative Composition (wt %) | Function |
| --- | --- | --- |
| 3-[2-(4-carbamimidoyl-phenyl-carbamoyl)-5-methoxy-4-vinyl-phenyl]-6-(cyclopropylmethyl-carbamoyl)-pyridine-2-carboxylic acid* | 13.5 | Compound of Example 1 |
| Polyethylene Glycol 600, NF | 62.4 | Solvent |
| D-α-tocopherol polyethylene glycol 1000 succinate, NF (Vitamin E TPGS) | 23.5 | Stabilizer/Absorption Enhancer |
| D-α-tocopherol | 0.6 | Stabilizer |
| Total | 100.0 | |

*content by weight of the active species, excluding that of the counterion

Example 10—Second Dosage Form With Soft Gelatin Capsules

In another embodiment, 100 mg of the compound of Example 1B (Form A) is formulated into a compounded solution consisting of the excipients: polyethylene glycol 600, D-α-tocopherol and D-α-tocopherol polyethylene glycol 1000 succinate filled into a white opaque, size 00, soft gelatin capsule according to the method described below. The components of the formulation, their function, and quality/compendial standards are provided in Table 21.

TABLE 21

| Component | Quantitative Composition (wt %) | Function |
| --- | --- | --- |
| 3-[2-(4-carbamimidoyl-phenyl-carbamoyl)-5-methoxy-4-vinyl-phenyl]-6-(cyclopropylmethyl-carbamoyl)-pyridine-2-carboxylic acid hydrochloride (Form A) | 11.76 | Compound of Example 1A |

TABLE 21-continued

| Component | Quantitative Composition (wt %) | Function |
| --- | --- | --- |
| Polyethylene Glycol 600, NF | 64.15 | Solvent |
| D-α-tocopherol polyethylene glycol 1000 succinate, NF (Vitamin E TPGS) | 23.50 | Stabilizer/Absorption Enhancer |
| D-α-tocopherol | 0.59 | Stabilizer |
| Total | 100.0 | |

*content by weight of the active species, excluding that of the counterion

What is claimed is:

1. An oral unit dosage form composition for use in a method of treating a disease or condition treatable via a mechanism of plasma kallikrein inhibition in a human subject, the method comprising orally administering to the human subject a therapeutically effective amount of a compound of formula I:

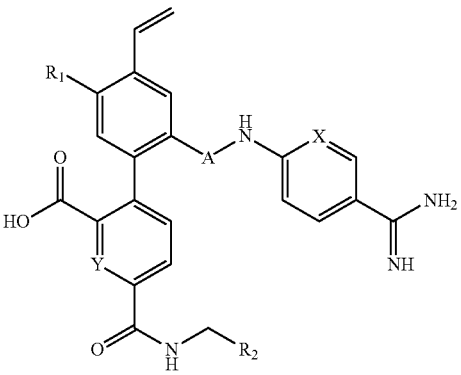

wherein:
X is CH or N;
Y is CH or N;
A is C=O or $CH_2$;
$R_1$ is hydrogen or a $C_{1-4}$ alkoxy group; and
$R_2$ is a $C_{1-4}$ alkyl group or a $C_{3-6}$ cycloalkyl group, optionally substituted by 1 or 2 hydroxyl groups;
or a pharmaceutically acceptable salt, solvate, ester or prodrug thereof and wherein the compound of formula I is administered in an excipient mixture comprising 50% to 80% of a polyethylene glycol having a number average molecular weight of 200 to 1000, 0.1% to 1% of a vitamin E and 20% to 30% of a vitamin E poly($C_{2-3}$)alkylene glycol dicarboxylic ester, the percentages expressed by weight of the total weight of the excipients.

2. The oral unit dosage form composition of claim 1, wherein the disease or condition is hereditary angioedema, type I hereditary angioedema, type II hereditary angioedema or acquired angioedema.

3. The oral unit dosage form composition of claim 1, wherein the therapeutically effective amount is administered according to a dosing interval of once a day or twice a day.

4. The oral unit dosage form composition of claim 1, wherein the therapeutically effective amount is administered according to a dosing interval of once a day or twice a day and a single unit dosage form is administered at each dosing interval.

5. The oral unit dosage form composition of claim 1, wherein the unit dose form provides an amount of a compound of formula I between 100 mg and 1000 mg.

6. The oral unit dosage form composition of claim 1, wherein the pharmaceutically acceptable salt is a hydrochloride salt.

7. The oral unit dosage form composition of claim 1, wherein the oral unit dose form is a solid oral dosage form.

8. The oral unit dosage form composition of claim 1, wherein the oral unit dose form is a tablet, capsule, powder, solution, elixir, syrup or gel.

9. The oral unit dosage form composition of claim 1, wherein the oral unit dose form is a capsule containing a pharmaceutically acceptable excipient comprising 1% to 99% of at least one polar protic solvent and one or more co-solvents, the percentages expressed by weight of the total weight of the excipients.

10. The oral unit dosage form composition of claim 1, wherein the polyethylene glycol having a number average molecular weight of 200 to 1000 is polyethylene glycol 600, the vitamin E is D-α-tocopherol and the vitamin E poly($C_{2-3}$)alkylene glycol dicarboxylic ester is D-α-tocopherol polyethylene glycol 1000 succinate.

11. The oral unit dosage form composition of claim 1, comprising 70% to 75% of polyethylene glycol having a number average molecular weight (Mn) of 200 to 1000, 0.1% to 5% of a vitamin E, citric acid or a combination thereof, and 24% to 28% of a vitamin E poly($C_{2-3}$)alkylene glycol dicarboxylic ester, the percentages expressed by weight of the total weight of the excipients.

12. The oral unit dosage form composition of claim 11, wherein the polyethylene glycol having a number average molecular weight of 200 to 1000 is polyethylene glycol 600, the vitamin E is D-α-tocopherol and the vitamin E poly($C_{2-3}$)alkylene glycol dicarboxylic ester is D-α-tocopherol polyethylene glycol 1000 succinate.

13. The oral unit dosage form composition of claim 1, wherein the compound of formula I is:

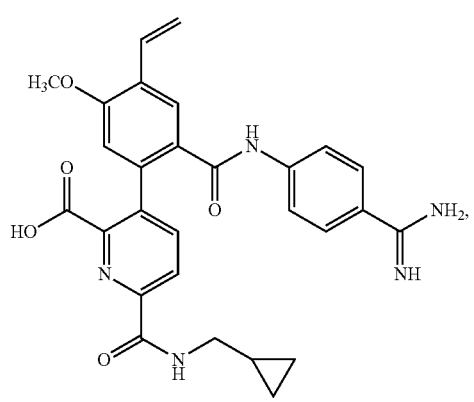

-continued

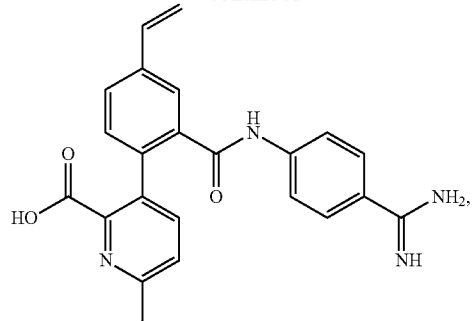

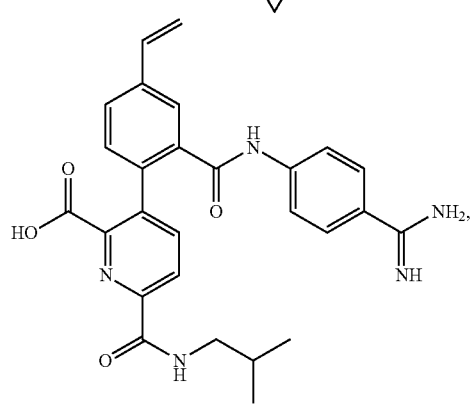

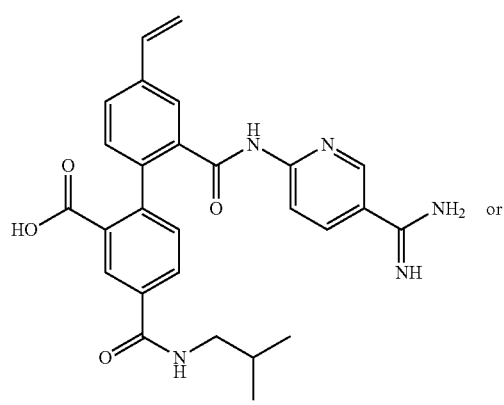 or

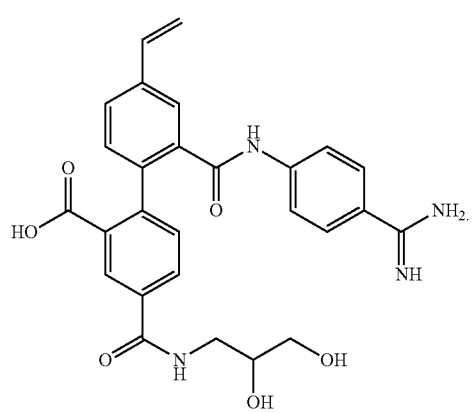 [SMILES: C=Cc1ccc(-c2ccc(C(=O)NCC(O)CO)cc2C(=O)O)c(C(=O)Nc2ccc(C(=N)N)cc2)c1]

14. The oral unit dosage form composition of claim 1, wherein the compound of formula I is:

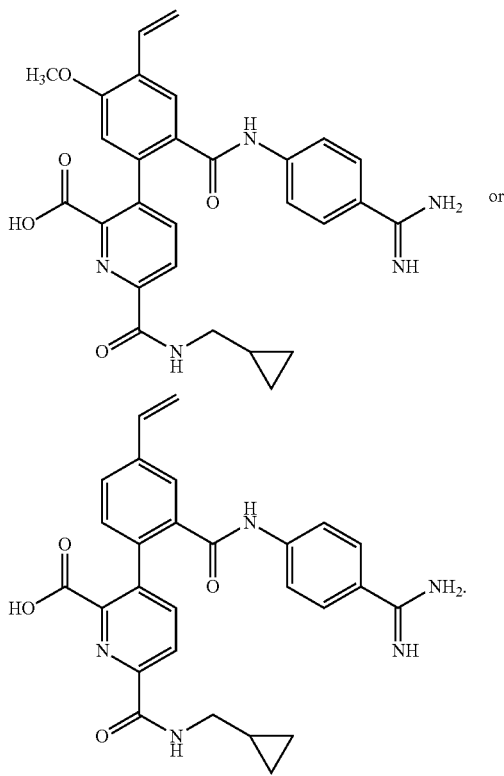

15. An oral unit dose form composition comprising an effective amount of a compound of the formula (I):

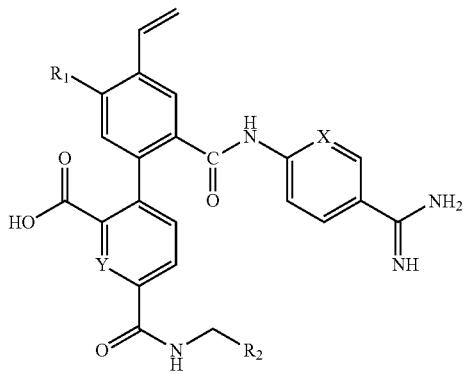

wherein
X is CH or N;
Y is CH or N;
$R_1$ is hydrogen or a $C_{1-4}$ alkoxy group and
$R_2$ is a $C_{1-4}$ alkyl group or a $C_{3-6}$ cycloalkyl group, optionally substituted by 1 or 2 hydroxyl groups;
or a pharmaceutically acceptable salt, solvate, ester or prodrug thereof and wherein the compound of formula I is administered in an excipient mixture comprising 50% to 80% of a polyethylene glycol having a number average molecular weight of 200 to 1000, 0.1% to 1% of a vitamin E and 20% to 30% of a vitamin E poly($C_{2-3}$)alkylene glycol dicarboxylic ester, the percentages expressed by weight of the total weight of the excipients.

16. The oral unit dose form composition of claim 15, wherein the unit dose form provides an amount of a compound of formula I between 100 mg and 1000 mg.

17. The oral unit dose form composition of claim 15, wherein the unit dose form provides an amount of a compound of formula I of 100 mg, 200 mg, 300 mg, 400 mg, 500 mg, 600 mg, 700 mg or 800 mg.

18. The oral unit dose form composition of claim 15, wherein the pharmaceutically acceptable salt is a hydrochloride salt.

19. The oral unit dose form composition of claim 15, wherein the oral unit dose form is a solid oral dosage form.

20. The oral unit dose form composition of claim 15, wherein the oral unit dose form is a tablet, capsule, powder, solution, elixir, syrup or gel.

21. The oral unit dose form composition of claim 15, wherein the oral unit dose form is a capsule containing a pharmaceutically acceptable excipient comprising 1% to 99% of at least one polar protic solvent and one or more co-solvents, the percentages expressed by weight of the total weight of the excipients.

22. The oral unit dose form composition of claim 15, wherein the polyethylene glycol having a number average molecular weight of 200 to 1000 is polyethylene glycol 600, the vitamin E is D-α-tocopherol and the vitamin E poly($C_{2-3}$)alkylene glycol dicarboxylic ester is D-α-tocopherol polyethylene glycol 1000 succinate.

23. The oral unit dose form composition of claim 15, comprising 70% to 75% of polyethylene glycol having a number average molecular weight (Mn) of 200 to 1000, 0.1% to 5% of a vitamin E, citric acid or a combination thereof, and 24% to 28% of a vitamin E poly($C_{2-3}$)alkylene glycol dicarboxylic ester, the percentages expressed by weight of the total weight of the excipients.

24. The oral unit dose form composition of claim 23, wherein the polyethylene glycol having a number average molecular weight of 200 to 1000 is polyethylene glycol 600, the vitamin E is D-α-tocopherol and the vitamin E poly($C_{2-3}$)alkylene glycol dicarboxylic ester is D-α-tocopherol polyethylene glycol 1000 succinate.

25. The oral unit dose form composition of claim 15, wherein the compound of formula I is:

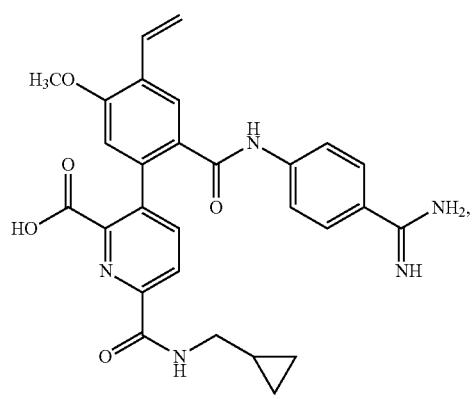

-continued
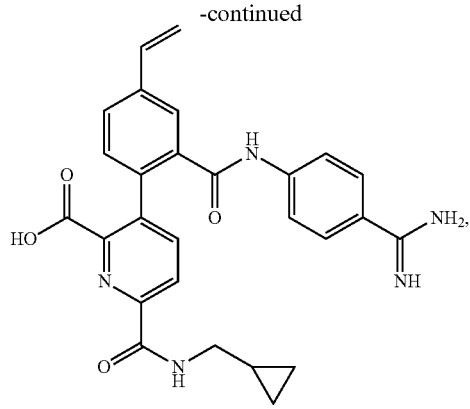
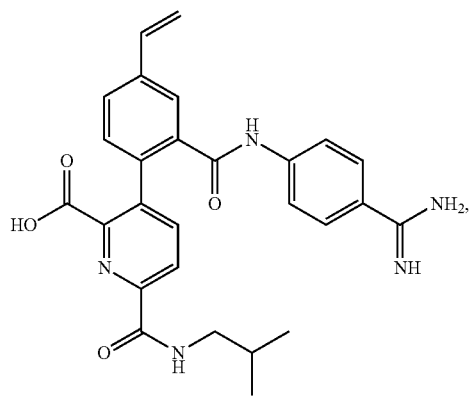
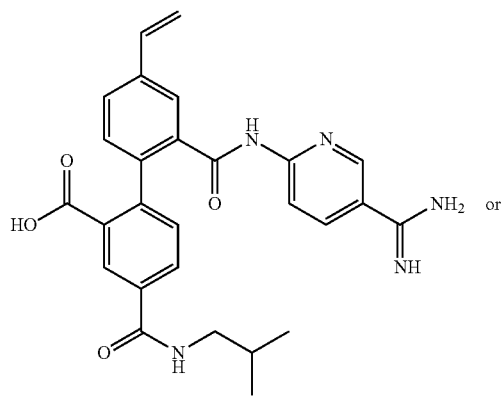
-continued
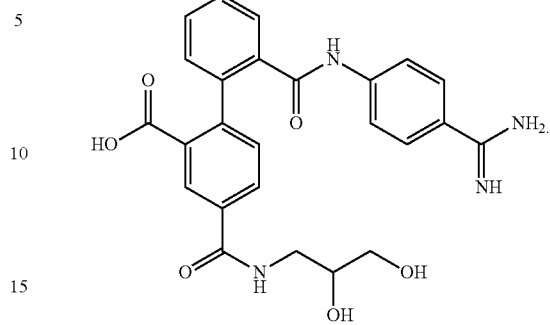
26. The oral unit dose form composition of claim 15, wherein the compound of formula I is:
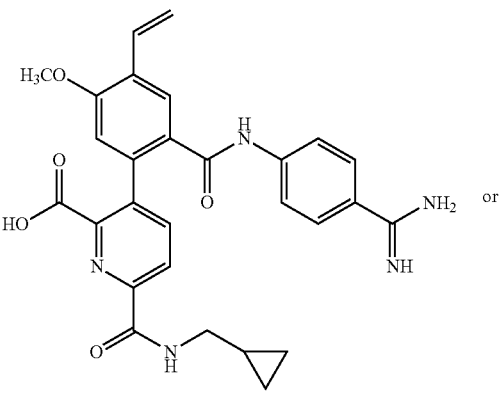
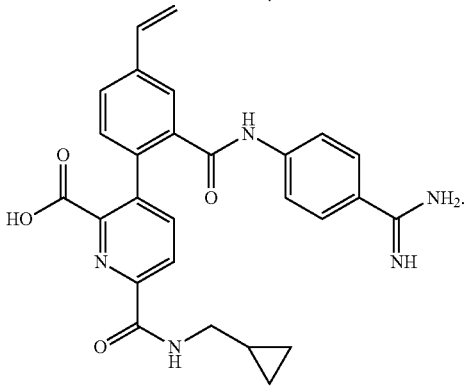
* * * * *